US012751965B2

(12) United States Patent
Schuberth-Wagner et al.

(10) Patent No.: US 12,751,965 B2
(45) Date of Patent: Oct. 6, 2026

(54) METHOD FOR OPTIMIZED RIG-I LIGANDS

(71) Applicants: Christine Schuberth-Wagner, Furstenfeldbruck (DE); Micha Feld, Emsdetten (DE)

(72) Inventors: Christine Schuberth-Wagner, Furstenfeldbruck (DE); Micha Feld, Emsdetten (DE)

(73) Assignees: Micha Feld, Emsdetten (DE); Christine Schuberth-Wagner, Emmering (DE)

( * ) Notice: Subject to any disclaimer, the term of this patent is extended or adjusted under 35 U.S.C. 154(b) by 1144 days.

(21) Appl. No.: 17/619,743

(22) PCT Filed: Jun. 25, 2020

(86) PCT No.: PCT/EP2020/067968

§ 371 (c)(1),
(2) Date: Dec. 16, 2021

(87) PCT Pub. No.: WO2020/260547

PCT Pub. Date: Dec. 30, 2020

(65) Prior Publication Data

US 2023/0147979 A1 May 11, 2023

Related U.S. Application Data

(60) Provisional application No. 62/867,453, filed on Jun. 27, 2019.

(51) Int. Cl.
*C07H 21/02* (2006.01)
*A61K 31/7088* (2006.01)
*C12N 15/11* (2006.01)

(52) U.S. Cl.
CPC ........ *A61K 31/7088* (2013.01); *C12N 15/111* (2013.01); *C12N 2310/14* (2013.01); *C12N 2310/31* (2013.01); *C12N 2310/315* (2013.01); *C12N 2310/321* (2013.01); *C12N 2310/322* (2013.01); *C12N 2310/344* (2013.01); *C12N 2310/3521* (2013.01)

(58) Field of Classification Search
CPC .......................... C12N 15/113; C12N 2310/14
See application file for complete search history.

(56) References Cited

U.S. PATENT DOCUMENTS 7,488,802 B2 2/2009 Collins et al.
7,521,051 B2 4/2009 Collins et al.
7,655,785 B1 2/2010 Bentwich
8,008,449 B2 8/2011 Korman et al.
8,168,757 B2 5/2012 Finnefroch et al.
8,354,509 B2 1/2013 Carven et al.
8,383,796 B2 2/2013 Korman et al.
9,439,962 B2 9/2016 Honjo et al.
2008/0025979 A1 1/2008 Honjo et al.
2009/0111765 A1 4/2009 Hartmann et al.
2011/0271358 A1 11/2011 Freeman et al.
2013/0037977 A1 2/2013 Burke et al.
2016/0152983 A1 6/2016 Goldeck et al.

FOREIGN PATENT DOCUMENTS

EP 3045536 A1 7/2016
WO 2004004771 A1 1/2004
WO 2004056875 A1 7/2004
WO 2004072286 A1 8/2004
WO 2008017473 A2 2/2008
WO 2009060281 A2 5/2009
WO 2009141146 A1 11/2009
WO 2010027827 A2 3/2010
WO 2010077634 A1 7/2010
WO 2011066342 A2 6/2011
WO 2012130886 A1 10/2012
(Continued)

OTHER PUBLICATIONS

Elbashir et al. (The EMBO Journal, vol. 20, No. 23, pp. 6877-6888, 2001).*
Ablasser, Andrea et al., RIG-I-dependent sensing of poly(dA:dT) through the induction of an RNA polymerase III-transcribed RNA intermediate, Nature Immunology, 2009, 1065-1072, 10(10).
Bruns, Annie M. et al., Activation of RIG-I-like receptor signal transduction, Critical Reviews in Biochemistry and Molecular Biology, 2011, 194-206, 47(2).
(Continued)

*Primary Examiner* — Amy Rose Hudson

(74) *Attorney, Agent, or Firm* — Leydig, Voit & Mayer, Ltd.

(57) ABSTRACT

Disclosed herein are double-stranded polyribonucleotides comprising a sense strand with 24 to 30 nucleotides in length and an antisense strand with 24 to 30 nucleotides in length, wherein the sense strand and the antisense strand form a fully complementary region of at least 24 base pairs with a blunt end at the 5'-end of the sense strand and the 3'-end of the antisense strand; and wherein the first 24 ribonucleotides at 5'-end of the sense strand further have at least one 2'-flourine modification at a ribonucleotide at a position selected from the group consisting of position number 2, 4, 6, 9, 10, 16, 21, 22, and 24, and no 2'-flourine modification at a ribonucleotide at a position selected from the group consisting of position number 1, 3, 8, and 14, and/or wherein the last 24 ribonucleotides at 3'-end of the antisense strand further have at least one 2'-flourine modification at a ribonucleotide at a position selected from the group consisting of position number 5, and 13, and no 2'-flourine modification at a ribonucleotide at a position selected from the group consisting of position 18 and 23; wherein all positions are counted from 5' to 3'.

4 Claims, 21 Drawing Sheets

Specification includes a Sequence Listing.

(56) References Cited

FOREIGN PATENT DOCUMENTS

| | | | |
|---|---|---|---|
| WO | 2013019906 | A1 | 2/2013 |
| WO | 2014049079 | A1 | 4/2014 |
| WO | 2014159990 | A1 | 10/2014 |
| WO | 2016179034 | A2 | 11/2016 |
| WO | 2017173427 | A1 | 10/2017 |
| WO | 2018172546 | A1 | 9/2018 |
| WO | 2019204743 | A1 | 10/2019 |

OTHER PUBLICATIONS

Chen, Y. Grace et al., Sensing Self and Foreign Circular RNAs by Intron Identity, Molecular Cell, 2017, 228-238 (e1-e5), 67(2).
Chiang, Cindy, Sequence-Specific Modifications Enhance the Broad-Spectrum Antiviral Response Activated by RIG-I Agonists, Journal of Virology, 2015, 8011-8025, vol. 89, No. 15.
Civril, Filiz et al., The RIG-I ATPase domain structure reveals insights into ATP-dependent antiviral signalling, EMBO reports, 2011, 1127-1134, 12(11).
Devarkar, Swapnil C. et al., Structural basis for m7G recognition and 2'-0-methyl discrimination in capped RNAs by the innate immune receptor RIG-I, PNAS, 2016, 596-601, 113(3).
Duewell, P. et al., RIG-I-like helicases induce immunogenic cell death of pancreatic cancer cells and sensitize tumors toward killing by CD8+ T cells, Cell Death and Differentiation, 2014, 1825-1837, 21(12).
Durbin, Ann Fiegen et al., RNAs Containing Modified Nucleotides Fail To Trigger RIG-I Conformational Changes for Innate Immune Signaling, mBio, 2016, 1-11, 7(5): e00833-16.
Elion, David L. et al., Therapeutically Active RIG-I Agonist Induces Immunogenic Tumor Cell Killing in Breast Cancers, Cancer Research, 2018, 6183-6195, N/A.
Fitzgerald, Megan E. et al., Selective RNA targeting and regulated signaling by RIG-I is controlled by coordination of RNA and ATP binding, Nucleic Acids Research, 2017, 1442-1454, 45(3).
Goubau, Delphine et al., Antiviral immunity via RIG-I-mediated recognition of RNA bearing 5'-diphosphates, Nature, 2014, 372-375, 514.
Goulet, Marie-Line et al., Systems Analysis of a RIG-I Agonist Inducing Broad Spectrum Inhibition of Virus Infectivity, PLoS Pathogens, 2013, 1-19, 9(4):e1003298.
Jiang, Fuguo et al., Structural basis of RNA recognition and activation by innate immune receptor RIG-I, Nature, 2011, 423-427, 479.
Junt, Tobias et al., Translating nucleic acid-sensing pathways into therapies, Nat Rev Immunol, 2015, 529-544, 15(9).
Kasumba, Dacquin M. et al., Therapeutic Targeting of RIG-I and MDA5 Might Not Lead to the Same Rome, Trends Pharmacol Sci, 2019, 116-127, 40(2).
Kowalinski, Eva et al., Structural Basis for the Activation of Innate Immune Pattern-Recognition Receptor RIG-I by Viral RNA, Cell, 2011, 423-435, 147.
Lee, Janghyun et al., Retraction—Systematic editing of synthetic RIG-I ligands to produce effective antiviral and anti-tumor RNA immunotherapies, Nucleic Acids Research, 2018, 1635-1647, 46(4).
Lee, Mi-Kyung et al., Structural features of influenza A virus panhandle RNA enabling and activation of RIG-I independently of 5'-triphosphate, Nucleic Acids Research, 2016, 8407-8416, 44(17).
Lee, Youngju et al., 2'Fluoro Modification Differentially Modulates the Ability of RNAs to Activate Pattern Recognition Receptors, Nucleic Acid Therapeutics, 2016, 173-182, vol. 26, No. 3.
Linehan, Melissa M. et al., A minimal RNA ligand for potent RIG-I activation in living mice, Science Advances, 2018, 1-10, 4: e1701854.
Louber, Jade et al., Kinetic discrimination of self/non-self RNA by the ATPase activity of RIG-I and MDA5, BMC Biology, 2015, 1-16, 13:54.
Ludwig, János et al., Rapid and Efficient Synthesis of Nucleoside 5'-O-(1-Thiotriphosphates), 5'-Triphosphates and 2',3'-Cyclophosphorothioates Using 2-Chloro-4H-1,3,2-benzodioxaphosphorin-4-one, J. Org. Chem., 1989, 631-635, 54.
Luo, Dahai et al., Structural Insights into RNA Recognition by RIG-I, Cell, 2011, 409-422, 147.
Nabet, Barzin Y. et al., Exosome RNA Unshielding Couples Stromal Activation to Pattern Recognition Receptor Signaling in Cancer, Cell, 2017, 352-366, 170(2).
Patel, Jenish R. et al., Activation and regulation of pathogen sensor RIG-I, Cytokine & Growth Factor Reviews, 2014, 513-523, 25.
Pichlmair, Andreas et al., RIG-I-Mediated Antiviral Responses to Single-Stranded RNA Bearing 5'-Phosphates, Science, 2006, 997-1001, 314.
Ranoa, Diana Rose E. et al., Cancer therapies activate RIG-I-like receptor pathway through endogenous non-coding RNAs, Oncotarget, 2016, 26496-26515, 7(18).
Reikine, Stephanie et al., Pattern recognition and signaling mechanisms of RIG-I and MDA5, Frontiers in Immunology, 2014, 1-7, vol. 5 | Article 342.
Schlee, Martin et al., Recognition of 5' Triphosphate by RIG-I Helicase Requires Short Blunt Double-Stranded RNA as Contained in Panhandle of Negative-Strand Virus, Immunity, 2009, 25-34, 31.
Schlee, Martin, Master sensors of pathogenic RNA—RIG-I like receptors, Immunobiology, 2013, 1322-1335, 218 (11).
Schuberth-Wagner, Christine et al., A Conserved Histidine in the RNA Sensor RIG-I Controls Immune Tolerance to N1-2'0-Methylated Self RNA, Immunity, 2015, 41-51, 43.
Shah, Neelam et al., Combined roles of ATP and small hairpin RNA in the activation of RIG-I revealed by solution-based analysis, Nucleic Acids Research, 2018, 3169-3186, 46(6).
Uzri, Dina et al., Nucleotide Sequences and Modifications That Determine RIG-I/RNA Binding and Signaling Activities, Journal of Virology, 2009, 4174-4184, vol. 83, No. 9.
Wang, Yanli et al., Structural and functional insights into 5'-ppp RNA pattern recognition by the innate immune receptor RIG-I, Nature Structural & Molecular Biology, 2010, 781-787, 17(7).
Wu, Wenxin et al., RIG-I and TLR3 are both required for maximum interferon induction by influenza virus in human lung alveolar epithelial cells, Virology, 2015, 181-188, 482.
Xue, Feng et al., SRSF1 Facilitates Cytosolic DNA-Induced Production of Type I Interferons Recognized by RIG-I, PLoS One, 2015, 1-15, 10(2):e0115354.

* cited by examiner

Figure 2

| | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | |
|---|---|---|---|---|---|---|---|---|---|---|---|---|---|---|---|---|---|---|---|---|---|---|---|---|---|---|
| Seq 1 | 5'- | G | A | C | G | C | U | G | A | C | C | C | U | G | A | A | G | U | U | C | A | U | C | U | U | |
| | 3'- | C | U | G | C | G | A | C | U | G | G | G | A | C | U | U | C | A | A | G | U | A | G | A | A | |
| Seq 2 | 5'- | G | U | U | C | U | G | C | A | A | U | C | A | G | C | U | A | A | A | C | G | U | U | A | U | |
| | 3'- | C | A | A | G | A | C | G | U | U | A | G | U | C | G | A | U | U | U | G | C | A | A | U | A | (AA) |
| Seq 3 | 5'- | G | U | U | C | U | A | A | A | A | G | C | A | A | A | G | A | U | U | C | C | A | U | A | A | |
| | 3'- | C | A | A | G | A | U | U | U | U | C | G | U | U | U | C | U | A | A | G | G | U | A | U | U | |
| Seq 4 | 5'- | G | G | U | C | C | G | C | U | G | U | G | A | U | U | U | U | U | G | G | A | U | U | U | G | |
| | 3'- | C | C | A | G | G | C | G | A | C | A | C | U | A | A | A | A | A | C | C | U | A | A | A | C | (AA) |
| | | 24 | 23 | 22 | 21 | 20 | 19 | 18 | 17 | 16 | 15 | 14 | 13 | 12 | 11 | 10 | 9 | 8 | 7 | 6 | 5 | 4 | 3 | 2 | 1 | |

N 2'-oMe modifications w/o adverse effect on RIG-I agonism that establish receptor selectivity Allowed consensus 2'-oMe selectivity pattern depending on the availability of a purine (3 out of 4)

Mod in sense or anti-sense strand at the purine

Seq 1: 5'-GACGCUGACCCUGAAGUUCAUCUU-3'
Seq 1: 3'-CUGCGACUGGGACUUCAAGUAGAA-5'

Seq 2: 5'-GUUCUGCAAUCAGCUAAACGUUAU-3'
Seq 2: 3'-CAAGACGUUAGUCGAUUUGCAAUA (AA)-5'

Seq 3: 5'-GUUCUAAAAGCAAAGAUUCCAUAA-3'
Seq 3: 3'-CAAGAUUUUCGUUUCUAAGGUAUU-5'

Seq 4: 5'-GGUCCGCUGUGAUUUUUGGAUUUG-3'
Seq 4: 3'-CCAGGCGACACUAAAAACCUAAAC (AA)-5'

Figure 4

| | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | |
|---|---|---|---|---|---|---|---|---|---|---|---|---|---|---|---|---|---|---|---|---|---|---|---|---|---|---|
| Seq 1 | 5'- | G | A | C | G | C | U | G | A | C | C | C | U | G | A | A | G | U | U | C | A | U | C | U | U | |
| | 3'- | C | U | G | C | G | A | C | U | G | G | G | A | C | U | U | C | A | A | G | U | A | G | A | A | |
| Seq 2 | 5'- | G | U | U | C | U | G | C | A | A | U | C | A | G | C | U | A | A | A | C | G | U | U | A | U | |
| | 3'- | C | A | A | G | A | C | G | U | U | A | G | U | C | G | A | U | U | U | G | C | A | A | U | A | (AA) |
| Seq 3 | 5'- | G | U | U | C | U | A | A | A | A | G | C | A | A | A | G | A | U | U | C | C | A | U | A | A | |
| | 3'- | C | A | A | G | A | U | U | U | U | C | G | U | U | U | C | U | A | A | G | G | U | A | U | U | |
| Seq 4 | 5'- | G | G | U | C | C | G | C | U | G | U | G | A | U | U | U | U | U | G | G | A | U | U | U | G | |
| | 3'- | C | C | A | G | G | C | G | A | C | A | C | U | A | A | A | A | A | C | C | U | A | A | A | C | (AA) |
| | | 24 | 23 | 22 | 21 | 20 | 19 | 18 | 17 | 16 | 15 | 14 | 13 | 12 | 11 | 10 | 9 | 8 | 7 | 6 | 5 | 4 | 3 | 2 | 1 | |

N 2'-F modifications that promote RIG-I agonism, are tolerated or decrease RIG-I activation by less than 20%

N (underlined) indicates 2'-F positions that compromise RIG-I agonism (decrease >20%)

Allowed consensus 2'-F pattern (3 out of 4)

Prohibited consensus 2'-F mod sites (3 out of 4)

Seq 1: 5'-GACGCUGACCCUGAAGUUCAUCUU-3'
Seq 1: 3'-CUGCGACUGGGACUUCAAGUAGAA-5'

Seq 2: 5'-GUUCUGCAAUCAGCUAAACGUUAU-3'
Seq 2: 3'-CAAGACGUUAGUCGAUUUGCAAUA (AA)-5'

Seq 3: 5'-GUUCUAAAAGCAAAGAUUCCAUAA-3'
Seq 3: 3'-CAAGAUUUUCGUUUCUAAGGUAUU-5'

Seq 4: 5'-GGUCCGCUGUGAUUUUUGGAUUUG-3'
Seq 4: 3'-CCAGGCGACACUAAAAACCUAAAC (AA)-5'

Figure 5

| | | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | |
|---|---|---|---|---|---|---|---|---|---|---|---|---|---|---|---|---|---|---|---|---|---|---|---|---|---|---|
| Seq 1 | 5'- | G | A | C | G | C | U | G | A | C | C | C | U | G | A | A | G | U | U | C | A | U | C | U | U | |
| | 3'- | C | U | G | C | G | A | C | U | G | G | G | A | C | U | U | C | A | A | G | U | A | G | A | A | |
| Seq 2 | 5'- | G | U | U | C | U | G | C | A | A | U | C | A | G | C | U | A | A | A | C | G | U | U | A | U | |
| | 3'- | C | A | A | G | A | C | G | U | U | A | G | U | C | G | A | U | U | U | G | C | A | A | U | A | (AA) |
| Seq 3 | 5'- | G | U | U | C | U | A | A | A | A | G | C | A | A | A | G | A | U | U | C | C | A | U | A | A | |
| | 3'- | C | A | A | G | A | U | U | U | U | C | G | U | U | U | C | U | A | A | G | G | U | A | U | U | |
| Seq 4 | 5'- | G | G | U | C | C | G | C | U | G | U | G | A | U | U | U | U | U | G | G | A | U | U | U | G | |
| | 3'- | C | C | A | G | G | C | G | A | C | A | C | U | A | A | A | A | A | C | C | U | A | A | A | C | (AA) |
| | | 24 | 23 | 22 | 21 | 20 | 19 | 18 | 17 | 16 | 15 | 14 | 13 | 12 | 11 | 10 | 9 | 8 | 7 | 6 | 5 | 4 | 3 | 2 | 1 | |

N indicates RIG-I activation above parent

2'-mod mediated boost over parent (at least 3 out of 4)

2'-mod mediated boost over parent depending on the presence of AA overhangs (>10%)

Seq 1: 5'-GACGCUGACCCUGAAGUUCAUCUU-3'
Seq 1: 3'-CUGCGACUGGGACUUCAAGUAGAA-5'

Seq 2: 5'-GUUCUGCAAUCAGCUAAACGUUAU-3'
Seq 2: 3'-CAAGACGUUAGUCGAUUUGCAAUA (AA)-5'

Seq 3: 5'-GUUCUAAAAGCAAAGAUUCCAUAA-3'
Seq 3: 3'-CAAGAUUUUCGUUUCUAAGGUAUU-5'

Seq 4: 5'-GGUCCGCUGUGAUUUUUGGAUUUG-3'
Seq 4: 3'-CCAGGCGACACUAAAAACCUAAAC (AA)-5'

Figure 6

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | |
|---|---|---|---|---|---|---|---|---|---|---|---|---|---|---|---|---|---|---|---|---|---|---|---|---|---|
| 5'- | **$N^1$** | N | **$N^3$** | N | N | N | **$N^2$** | **$N^1$** | **$N^2$** | **$N^4$** | N | **$N^6$** | N | **$N^1$** | **$N^7$** | N | N | N | N | **$N^6$** | N | N | N | N | |
| 3'- | N | **$N^1$** | **$N^8$** | N | **$N^2$** | N | **$N^1$** | N | N | N | N | N | N | N | **$N^7$** | N | N | N | N | N | N | **$N^6$** | **$N^5$** | **$N^5$** | (AA) |
| | 24 | 23 | 22 | 21 | 20 | 19 | 18 | 17 | 16 | 15 | 14 | 13 | 12 | 11 | 10 | 9 | 8 | 7 | 6 | 5 | 4 | 3 | 2 | 1 | |

$N^1$ 2'-oMe and 2'-F are not allowed

$N^2$ 2'-oMe is not allowed

$N^3$ 2'-F is not allowed

$N^4$ 2'-F strengthens the RIG-I response

$N^5$ 2'-F strengthens the RIG-I response in the presence of an AA overhang

$N^6$ 2'-oMe establish RIG-I selectivity when purines are available

$N^7$ 2'-oMe establish RIG-I selectivity when purines are available (sense or antisense strand)

$N^8$ 2'-oMe in the anti-sense strand prevents TLR8 agonism of the ssRNA stand

Figure 7 (continued)

D

No 2´-o-methyl-related receptor selectivity

No 2´-o-methyl-related receptor selectivity

| | |
|---|---|
| DR2-151 | 5´-GUUCUGCAACUCAAAGUGCUAUUG-3´<br>3´-CAAGACGUUGAGUUUCACGAUAAC-5´ |

2´-o-methyl-induced receptor selectivity

No 2´-o-methyl-related receptor selectivity

| | |
|---|---|
| DR2-118 | 5´-GUUCCAAUAGUAGUCAUAGCUAUU-3´<br>3´-CAAGGUUAUCAUCAGUAUCGAUAA-5´ |

No 2´-o-methyl-related receptor selectivity

2´-o-methyl-induced receptor selectivity

| | |
|---|---|
| DR2-101 | 5´-GCUCCUGAAUGCUUGCUUCAUCUU-3´<br>3´-CGAGGACUUACGAACGAAGUAGAA-5´ |

A

Figure 8b 5-mer | Box 1 | Neutral Box | Box 2

| | | | | | | | | | | | | | | | | | | | | | | | | |
|---|---|---|---|---|---|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
| | | F | | F | | | | | F | F | | oM | | | oM | F | | | | oM | F | F | | F |
| 5'- | $N^1$ | N | $N^3$ | N | N | N | $N^2$ | $N^1$ | $N^2$ | $N^4$ | N | $N^6$ | N | $N^1$ | $N^7$ | N | N | N | N | $N^6$ | N | N | N | N |
| 3'- | N | $N^1$ | $N^8$ | N | $N^2$ | N | $N^1$ | N | N | N | N | N | N | N | $N^7$ | N | N | N | N | N | N | $N^6$ | $N^5$ | $N^5$ |
| | | | oM | | | | | | | | | F | | | | | | | | F | | | | |
| | 24 | 23 | 22 | 21 | 20 | 19 | 18 | 17 | 16 | 15 | 14 | 13 | 12 | 11 | 10 | 9 | 8 | 7 | 6 | 5 | 4 | 3 | 2 | 1 |

$N^1$ 2'-oMe and 2'-F are not allowed $N^2$ 2'-oMe is not allowed $N^3$ 2'-F is not allowed $N^4$ 2'-F strengthens the RIG-I response $N^5$ 2'-F strengthens the RIG-I response in the presence of an AA overhang $N^6$ 2'-oMe establish RIG-I selectivity when purines are available $N^7$ 2'-oMe establish RIG-I selectivity when purines are available (sense or antisense strand)

$N^8$ 2'oMe in the anti-sense strand prevents TLR8 agonism of the ssRNA strand

5´-GCUCCUGAAUG$C_{12}$UUGCUUC$A_{20}$UCUU

3´-CGAGGACUUAC$G_{12}$AACGAAG$U_{20}$AGAA

5′-GUUCCAAUAGU$A_{12}$GUCAUAG$C_{20}$UAUU

3′-CAAGGUUAUCA$U_{12}$CAGUAUC$G_{20}$AUAA

5′-GUUCUGCAACU$C_{12}$AAAGUGC$U_{20}$AUUG
3′-CAAGACGUUGA$G_{12}$UUUCACG$A_{20}$UAAC

5´-GCUCCUGAAUG$\mathbf{C}_{\mathbf{12}}$UUG$_{15}$CUUC$\mathbf{A}_{\mathbf{20}}$UC$_{22}$UU 3´-CGAGGACUUACG$_{\mathbf{12}}$AA$\mathbf{C}_{15}$GAAGU$_{\mathbf{20}}$A$\mathbf{G}_{\mathbf{22}}$AA 5´-GUUCCAAUAGU$\mathbf{A}_{12}$GU$\mathbf{C}_{15}$AUAG$\mathbf{C}_{20}$U$A_{22}$UU 3´-CAAGGUUAUCA$U_{12}$CA$\mathbf{G}_{15}$UAUC$G_{20}$A$\mathbf{U}_{22}$AA

5´-GUUCUGCAACUC$_{12}$AAA$_{15}$GUGCU$_{20}$AU$_{22}$UG

3´-CAAGACGUUGAG$_{12}$UUU$_{15}$CACGA$_{20}$UA$_{22}$AC

Figure 17

5-mer | Box 1 | Neutral Box | Box 2

| | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 |
|---|---|---|---|---|---|---|---|---|---|---|---|---|---|---|---|---|---|---|---|---|---|---|---|---|
| 5'- | $N^1$ | $N^2$ | $N^6$ | $N^5$ | N | $N^5$ | $N^4$ | $N^1$ | $N^7$ | $N^2$ | $N^2$ | $\underline{N}^2$ | $N^2$ | $N^1$ | $N^3$ | $N^2$ | $N^3$ | $N^2$ | $N^2$ | $\underline{N}^2$ | $N^2$ | $N^2$ | $N^2$ | $N^2$ |
| 3'- | $N^3$ | $N^1$ | $N^2$ | $N^2$ | $N^7$ | $N^5$ | $N^1$ | $N^5$ | $N^2$ | $N^3$ | $N^2$ | $N^5$ | $N^2$ | $N^5$ | $N^2$ | $N^5$ | $N^2$ | $N^5$ | $N^5$ | $N^2$ | $N^5$ | $\underline{N}^2$ | $N^2$ | $N^2$ |
| | 24 | 23 | 22 | 21 | 20 | 19 | 18 | 17 | 16 | 15 | 14 | 13 | 12 | 11 | 10 | 9 | 8 | 7 | 6 | 5 | 4 | 3 | 2 | 1 |

$N^1$ 2'-oMe and 2'-F are not allowed $N^2$ 2'-oMe and 2'-F are allowed $N^3$ 2'-oMe is allowed $N^4$ 2'-oMe is not allowed $N^5$ 2'-F allowed only $N^6$ 2'-oMe allowed, 2'-F is not allowed $N^7$ 2'-oMe not allowed, 2'-F is allowed $\underline{N}$ 2'-oMe established RIG-I selectivity (depends on availability of purines)

METHOD FOR OPTIMIZED RIG-I LIGANDS

CROSS-REFERENCE TO RELATED APPLICATIONS

This application is a National Stage application of International Patent Application No. PCT/EP2020/067968, filed Jun. 25, 2020, which claims the benefit of priority to U.S. Provisional Patent Application No. 62/867,453, filed Jun. 27, 2019, the contents of each of which are hereby incorporated by reference in their entireties.

REFERENCE TO SEQUENCE LISTING SUBMITTED ELECTRONICALLY

The sequence listing of the present application is submitted electronically via EFS-Web as an ASCII formatted sequence listing with a file name "24730-US-PCT_SL.txt", creation date of Aug. 16, 2022, and a size of 93,125 bytes. This sequence listing submitted via EFS-Web is part of the specification and is herein incorporated by reference in its entirety.

BACKGROUND OF THE INVENTION

The nature of the classical RNA ligand allows manipulation of the 2' ribose subunits. Although it could be demonstrated previously that 2'-O-methylation and 2'-fluorination can promote selectivity for RIG-I and/or stability, a systematic evaluation of a RIG-I-related 2'-modification pattern that depends on the availability of purines/pyrimidines or is independent of the sequence is lacking.

Accordingly, there is still a need in the art for a 2'-modification pattern in RIG-I ligands with general applicability. Such a pattern would simplify producing highly effective RIG-I ligands with a high RIG-I selectivity.

SUMMARY OF THE INVENTION

The cytosolic PAMP sensor RIG-I detects foreign RNA and mounts an anti-pathogenic immune response. Transfection of synthetic RNA can mimic a viral invasion and can trigger a type I interferon signature. To enhance RIG-I selectivity and to improve RNA stability, synthetic RNAs can be 2' modified. However, identification of an adequate 2' modification pattern for RIG-I selectivity remains elusive. Based on single nucleotide permutation screenings we revealed 2'-o-methylation sites that can provide RIG-I selectivity depending on the availability of purines or can hamper RIG-I agonism at RIG-I-relevant concentrations. Moreover, 2'-fluorination of defined pyrimidines was identified to boost RIG-I agonism at RIG-I-relevant concentrations. An RNA-wide 2'-methylation and 2'-fluorination pattern establishing RIG-I selectivity independent of the RNA sequence was identified. For the first time, we provide evidence for a design rule to identify suitable RIG-I ligands.

The present disclosure provides new 2'-modification patterns that have general applicability to enhancing RIG-I selectivity and boosting or abrogating RIG-I-driven immune responses. As demonstrated herein, the newly identified patterns can be used for designing ligands for RIG-I activation. New design rules for highly selective, potent RIG-I agonists are provided.

The present disclosure also provides double-stranded polyribonucleotides comprising a sense strand with 24 to 30 nucleotides in length and an antisense strand with 24 to 30 nucleotides in length, wherein the sense strand and the antisense strand form a fully complementary region of at least 24 base pairs with a blunt end at the 5'-end of the sense strand and the 3'-end of the anti-sense strand; and wherein the first 24 ribonucleotides at 5'-end of the sense strand further have at least one 2'-flourine modification at a ribonucleotide at a position selected from the group consisting of position number 2, 4, 6, 9, 10, 16, 21, 22, and 24, and no 2'-flourine modification at a ribonucleotide at a position selected from the group consisting of position number 1, 3, 8, and 14, and/or wherein the last 24 ribonucleotides at 3'-end of the antisense strand further have at least one 2'-flourine modification at a ribonucleotide at a position selected from the group consisting of position number 5, and 13, and no 2'-flourine modification at a ribonucleotide at a position selected from the group consisting of position 18 and 23; wherein all positions are counted from 5' to 3'. In embodiments, the first 24 nucleotides at the 5'-end of the sense strand are ribonucleotides and have at least one 2'-o-methyl modification at a purine ribonucleotide at a position selected from the group consisting of position number 12, 15, and 20, and/or the last 24 nucleotides at 3'-end of the antisense strand are ribonucleotides and have at least one 2'-o-methyl modification at a purine ribonucleotide at position number 3; wherein all positions are counted from 5' to 3'.

The present disclosure further provides a pharmaceutical composition comprising at least one polyribonucleotide of the present invention and a pharmaceutically acceptable carrier, as further defined in the claims.

The double-stranded polyribonucleotide or the pharmaceutical composition of the present invention can advantageously be applied in medicine or veterinary medicine, such as for use in preventing and/or treating a disease or condition selected from a tumor, an infection, an allergic condition, and an immune disorder; or as a vaccine adjuvant; as further defined in the in the specification and claims.

Further provided is an ex vivo method for inducing type I IFN production in a cell, comprising the step of contacting a cell expressing RIG-I with at least one polyribonucleotide according to the present invention, optionally in mixture with a complexation agent, as defined in the claims.

Finally, the present disclosure also provides a method for producing the double-stranded polyribonucleotide of the invention, methods for increasing the selectivity for RIG-I of a RIG-I agonist, and methods for increasing the type I IFN response of a RIG-I agonist, as defined in the claims and further disclosed herein.

BRIEF DESCRIPTION OF THE DRAWINGS

FIG. 2: 2'-o-methylation of selected nucleotide positions mediating RIG-I selectivity. Four independent basis sequences (Seq1-4; SEQ ID NOs: 1-8) were permuted for 2'-o-methylation of single nucleotides and transfected into PBMCs to either target RIG-I (cytosolic delivery) or TLR7/8 (endosomal delivery). The activation of RIG-I, TLR7 and TLR8 was monitored by means of IFNα and IL12p70 release, respectively. Nucleotide positions for 2'-oMe modifications without (w/o) adverse effect on RIG-I agonism that establish receptor selectivity were identified. All nucleotide positions are counted from 5' to 3' of the region of complementation (i.e., not including the 5' overhang of antisense strand (AA) if present).

Figure 3:
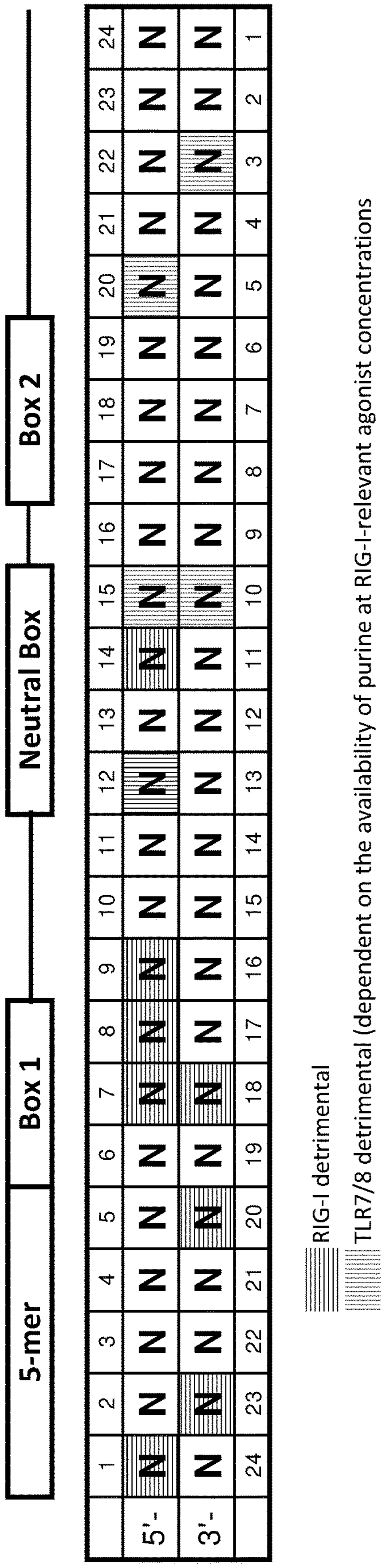

FIG. 3: Overview showing 2'-o-methyl modifications that are detrimental for RIG-I or TLR7/8.

FIG. 4: Detrimental effects of single 2'-F modifications. Four independent basis sequences (Seq1-4; SEQ ID NOs: 1-8) were permuted for 2'-fluorine of single nucleotides and transfected into PBMCs. On basis of the IFN-α levels released (data not shown) each RNA single 2'-o-fluorine position was classified as being detrimental (decrease≥20%) or being tolerated. All nucleotide positions are counted from 5' to 3' of the region of complementation (i.e., not including the 5' overhang of antisense strand (AA) if present).

FIG. 5: Defined 2'-fluorination elevates the RIG-I activation. Four independent basis sequences (Seq1-4; SEQ ID NOs: 1-8) were permuted for 2'-fluorine of single nucleotides and transfected into PBMCs. On basis of the IFN-α levels released (data not shown) one single 2'-o-fluorine position was found to increase RIG-I-related IFNα secretion independent of the RNA end configuration. Two additional 2'-fluorine positions were identified as promoting RIG-I agonism in proximity to a 5'-AA overhang. All nucleotide positions are counted from 5' to 3' of the region of complementation (i.e., not including the 5' overhang of antisense strand (AA) if present).

FIG. 6: Schematic overview of 2'-modifications and their contribution to selectivity, elevated RIG-I agonism and abrogation of RIG-I activation. All nucleotide positions are counted from 5' to 3' of the region of complementation (i.e., not including the 5' overhang of anti-sense strand (AA) if present).

Figure 7:
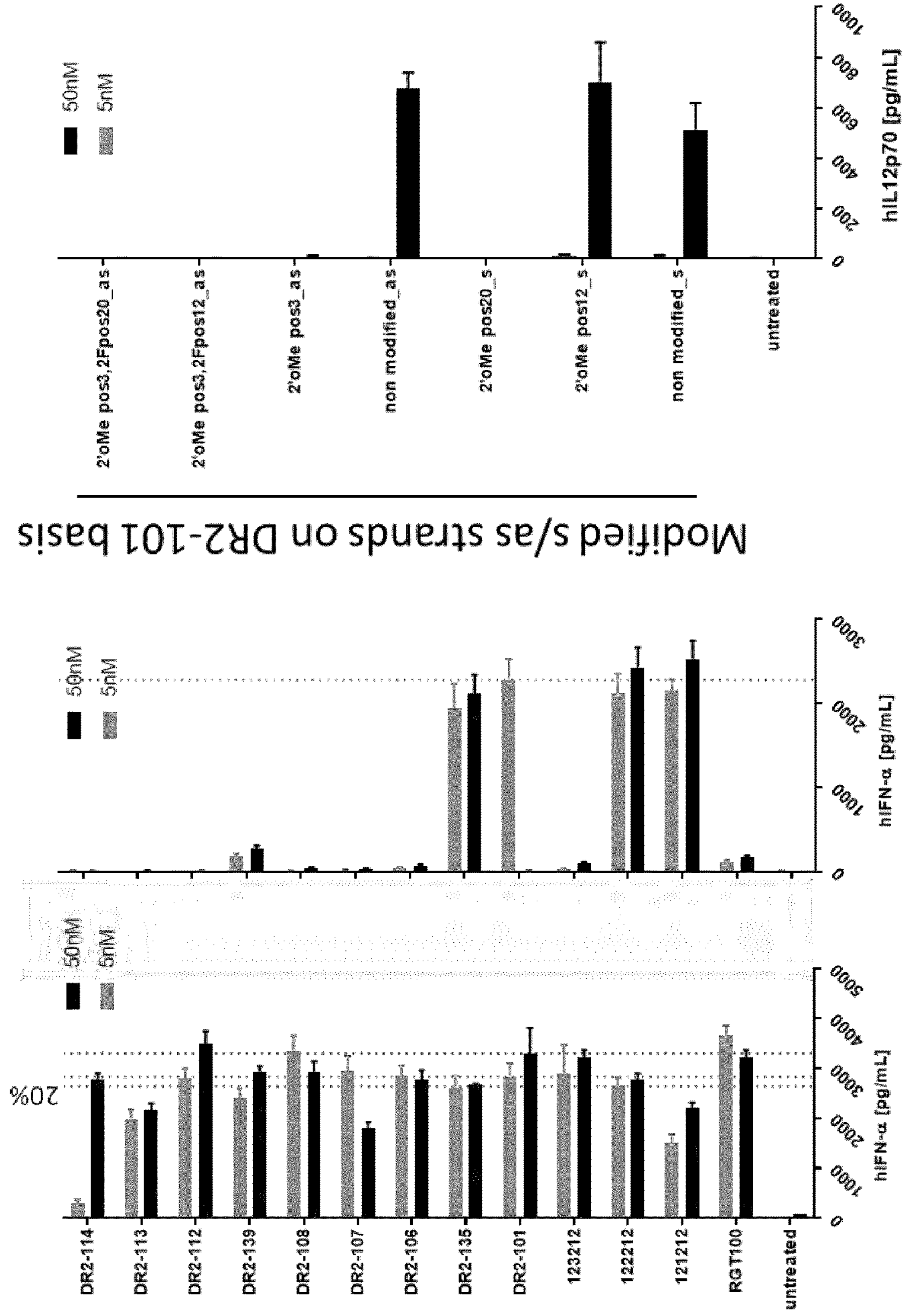
Figure 7:
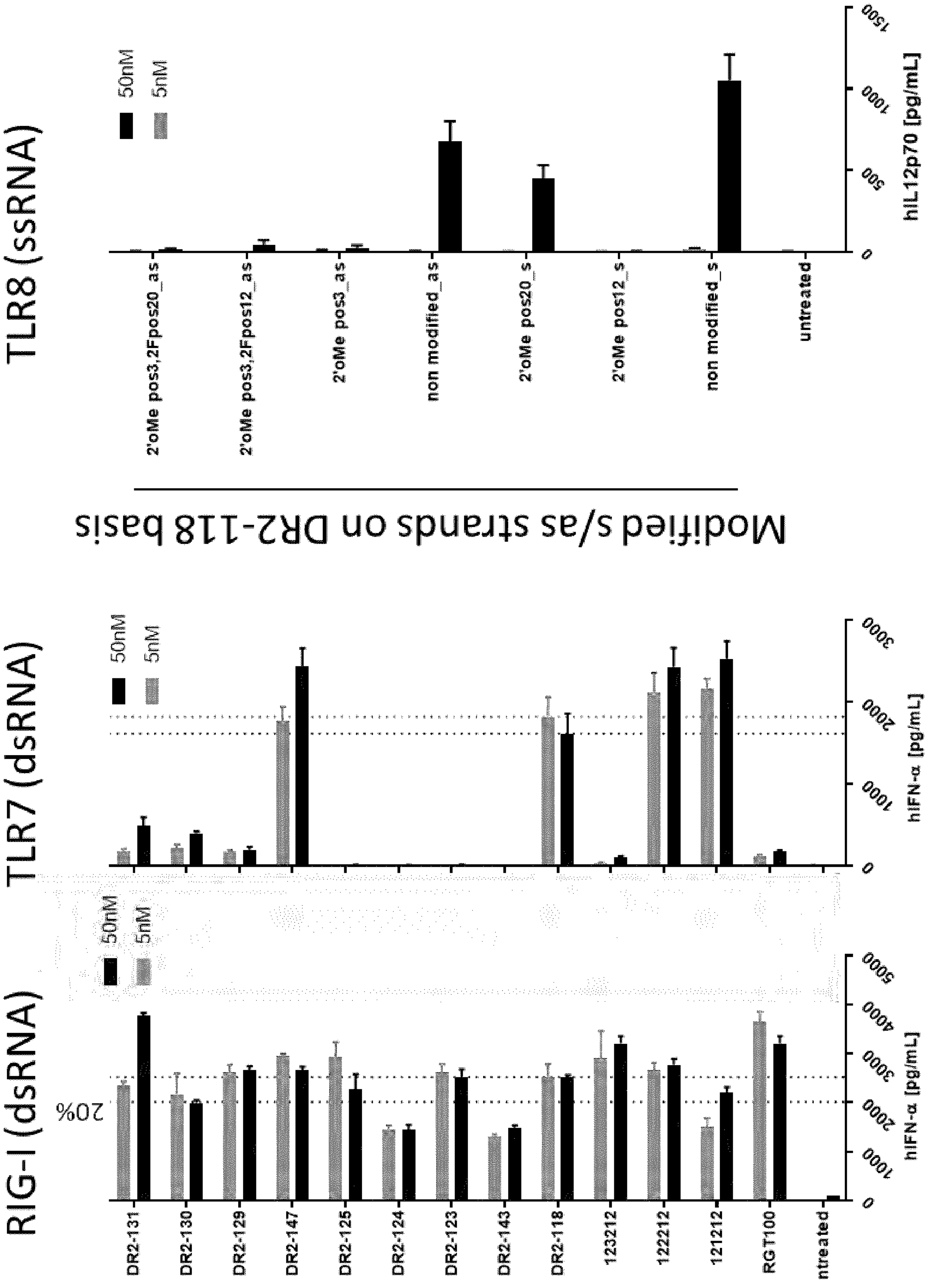
Figure 7:
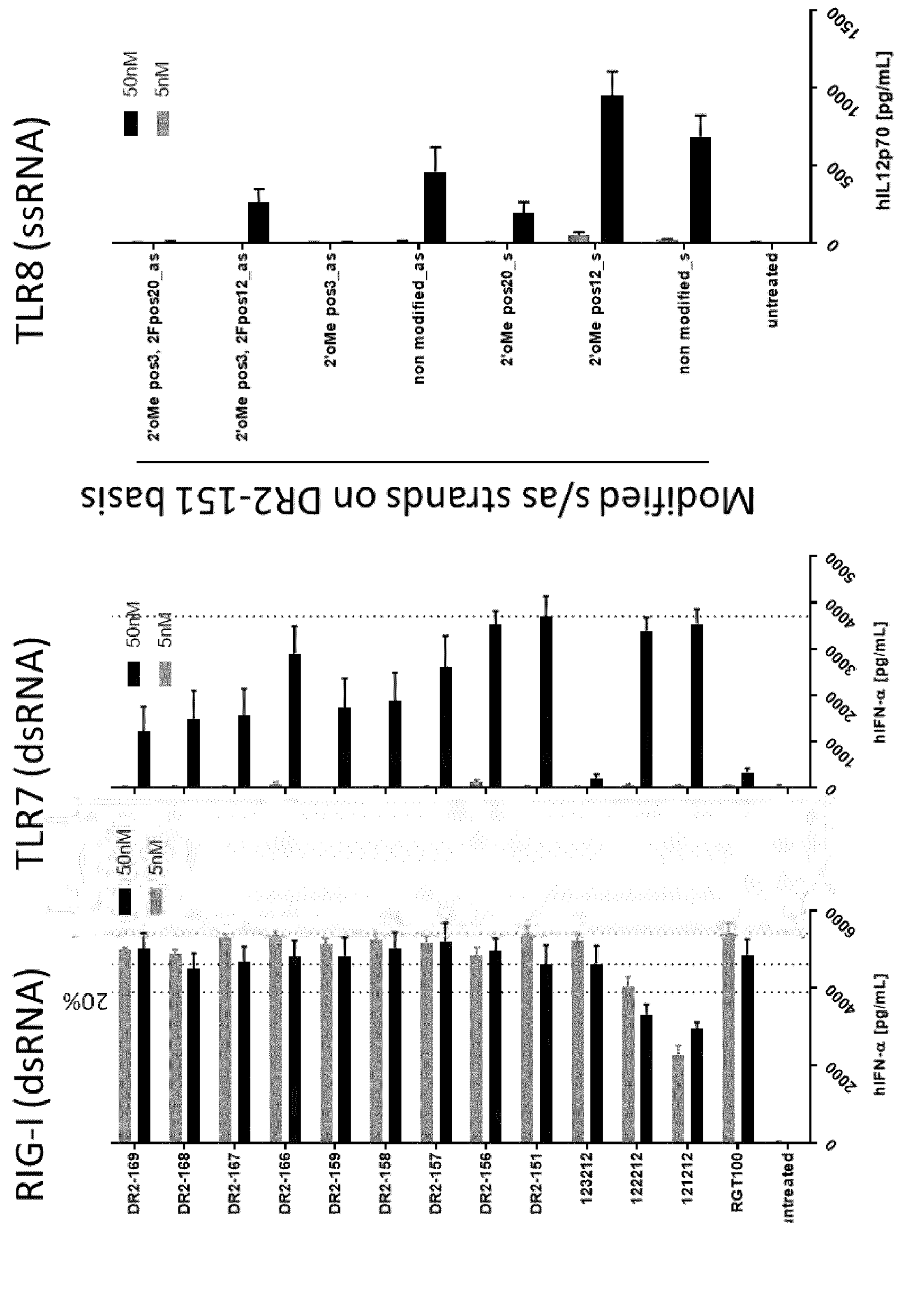

FIG. 7: Evaluation of the identified 2'-o-methylation sites to achieve receptor selectivity in 3 novel and independent basis sequences harboring the indicated modifications at the indicated positions (pos) in the sense(s) or antisense (as) strands (compare Table 1). RNAs were transfected into PBMCs to either target RIG-I (cytosolic delivery) or TLR7/8 (endosomal delivery). The activation of RIG-I, TLR7 and TLR8 was monitored by means of IFNα and IL12p70 release, respectively (A-C). The presence of a purine at the identified 2'-o-methylation positions appears to be crucial to establish receptor selectivity (D). Sense(s) and antisense (as) strands for DR-151 are SEQ ID NOs: 23 and 24 respectively. Sense(s) and antisense (as) strands for DR-118 are SEQ ID NOs: 16 and 17 respectively. Sense(s) and antisense (as) strands for DR-101 are SEQ ID NOs: 9 and 10 respectively.

Figure 8:
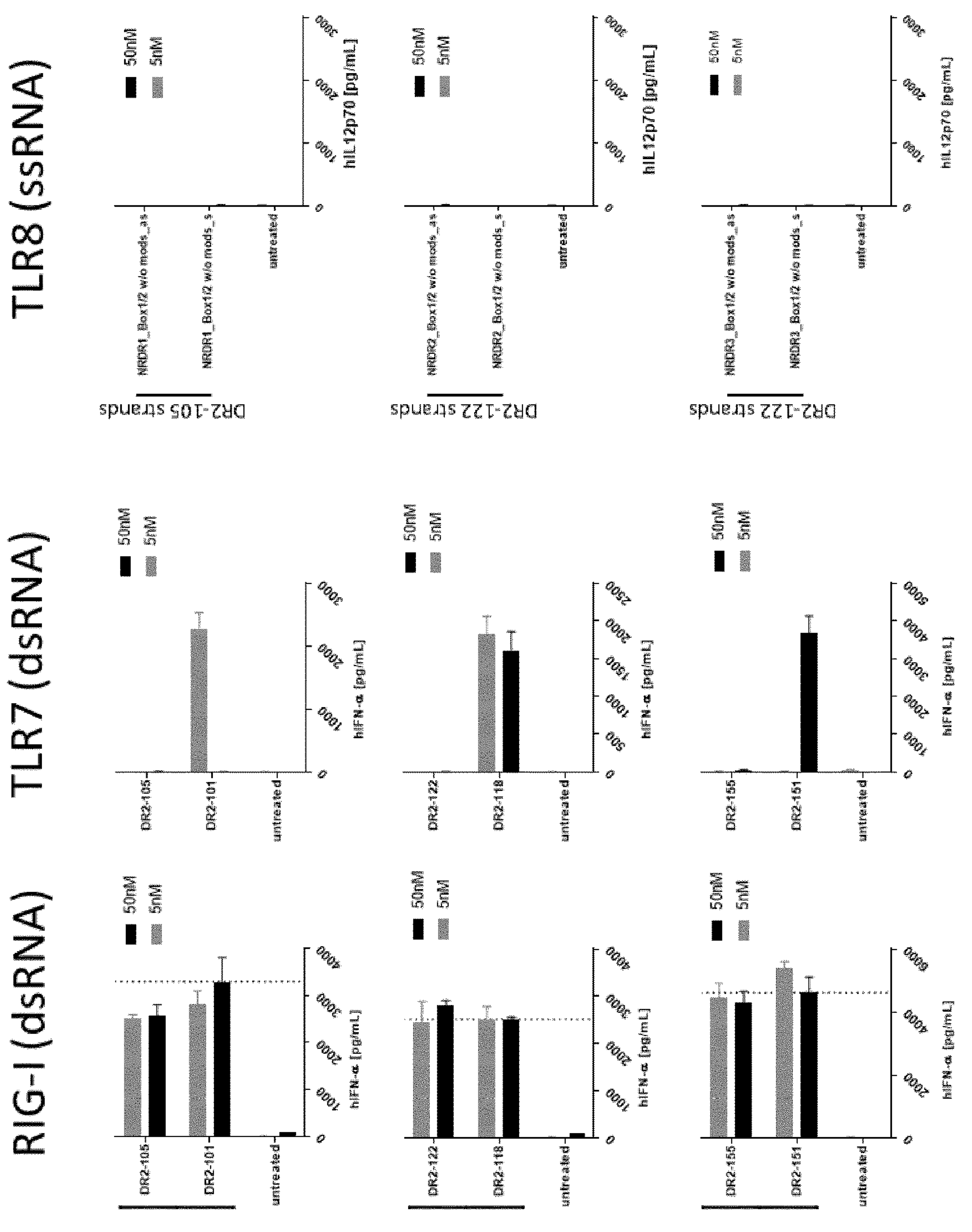

FIG. 8: Identification of a broad range 2'-modification pattern promoting receptor selectivity and ligand stabilization. Three independent basis sequences were modified with 2'-methyl and 2'-fluorine according to the modification pattern (compare Table 1). RNAs were transfected into PBMCs to either target RIG-I (cytosolic delivery) or TLR7/8 (endosomal delivery). The activation of RIG-I, TLR7 and TLR8 was monitored by means of IFNα and IL12p70 release, respectively. Application of the modification pattern led to receptor selectivity without having any detrimental effect on RIG-I agonism itself. (B) gives a schematic overview about the broad range modification pattern in conjunction with the proposed positional modification pattern.

Figure 9:
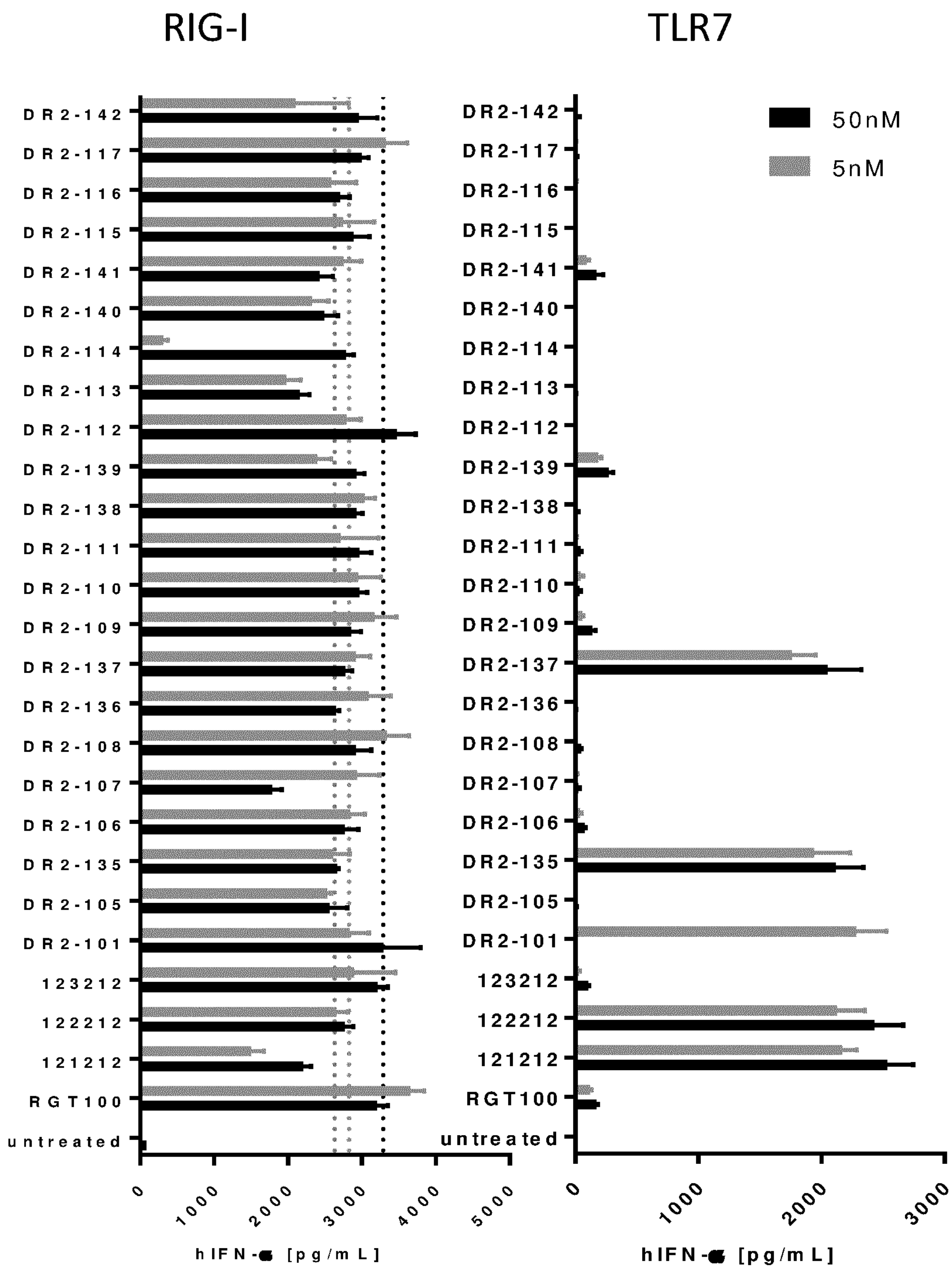

FIG. 9: Evaluation of 2'-o-methyl modification pattern in NRDR1 backbone. TLR7 agonization was tested at 50 nM agonist concentration. Sequences at bottom are the sense(s) and antisense (as) strands of DR2-101 (SEQ ID NOs: 9 and 10 respectively).

Figure 10:
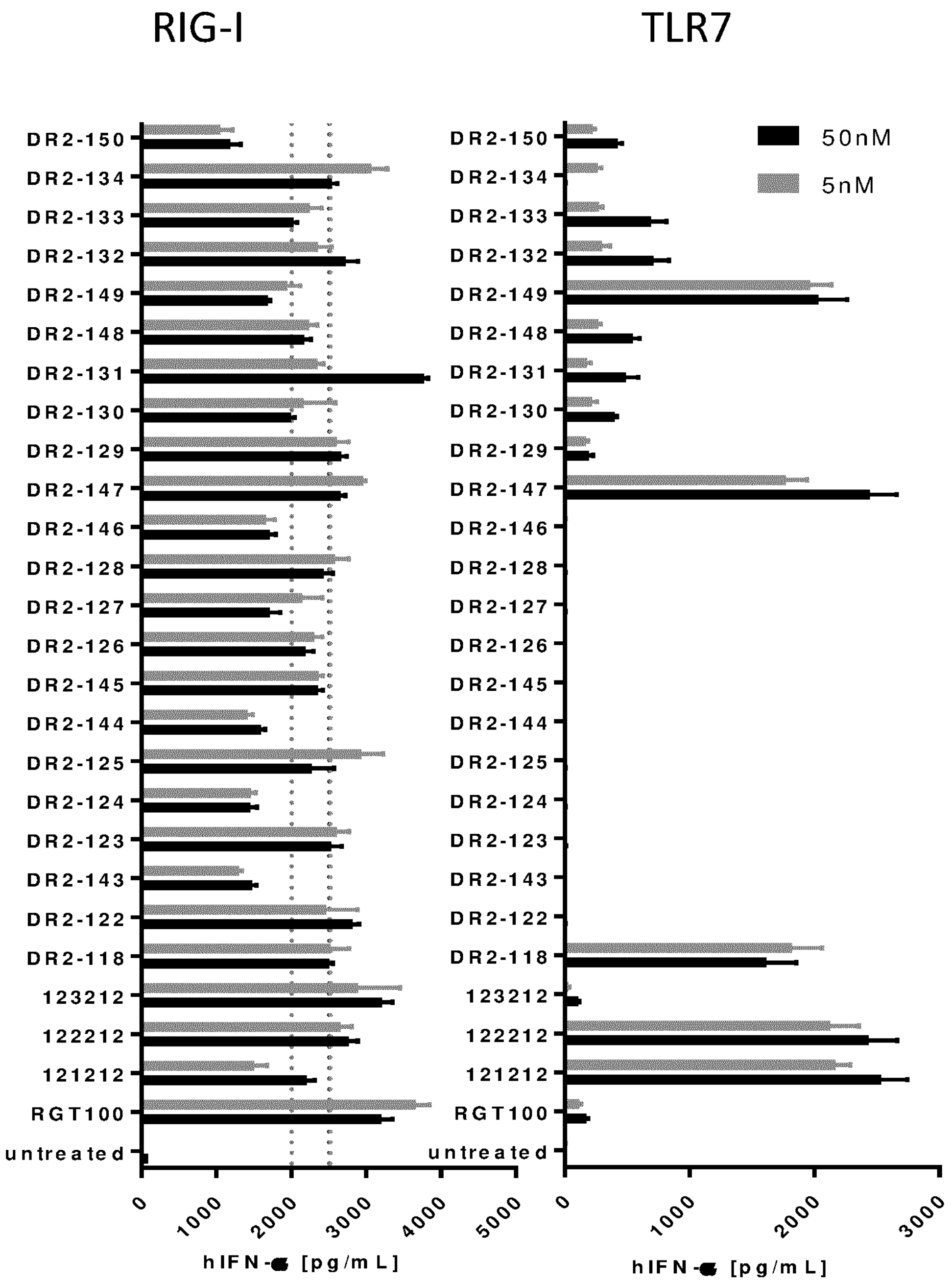

FIG. 10: Evaluation of 2'-o-methyl modification pattern in NRDR2 backbone. TLR7 agonization was tested at 50 nM agonist concentration. Sequences at bottom are the sense(s) and antisense (as) strands of DR2-118 (SEQ ID NOs: 16 and 17 respectively).

Figure 11:
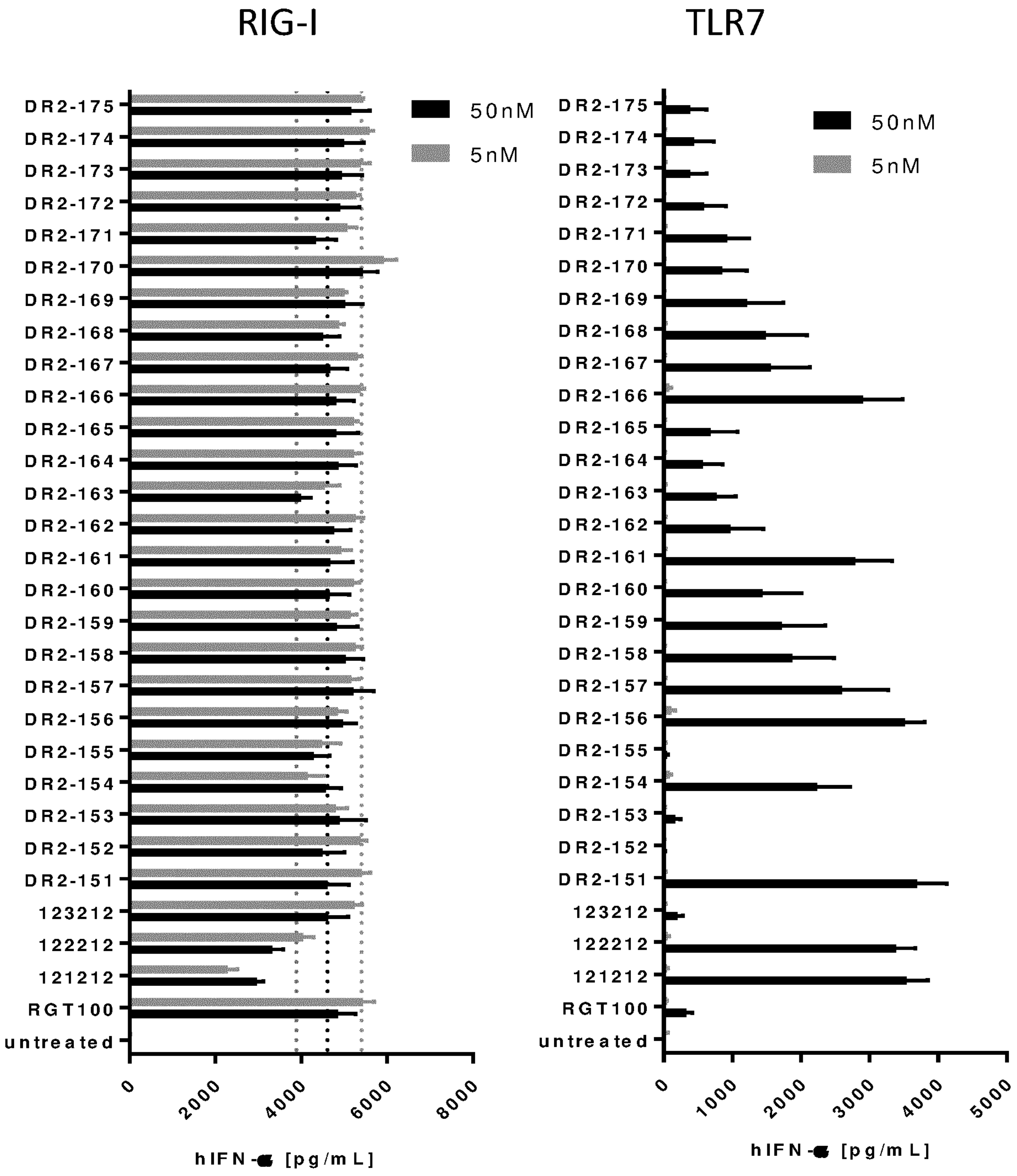

FIG. 11: Evaluation of 2'-o-methyl modification pattern in NRDR3 backbone. TLR7 agonization was tested at 50 nM agonist concentration. Sequences at bottom are the sense(s) and antisense (as) strands of DR2-151 (SEQ ID NOs: 23 and 24 respectively).

Figure 12:
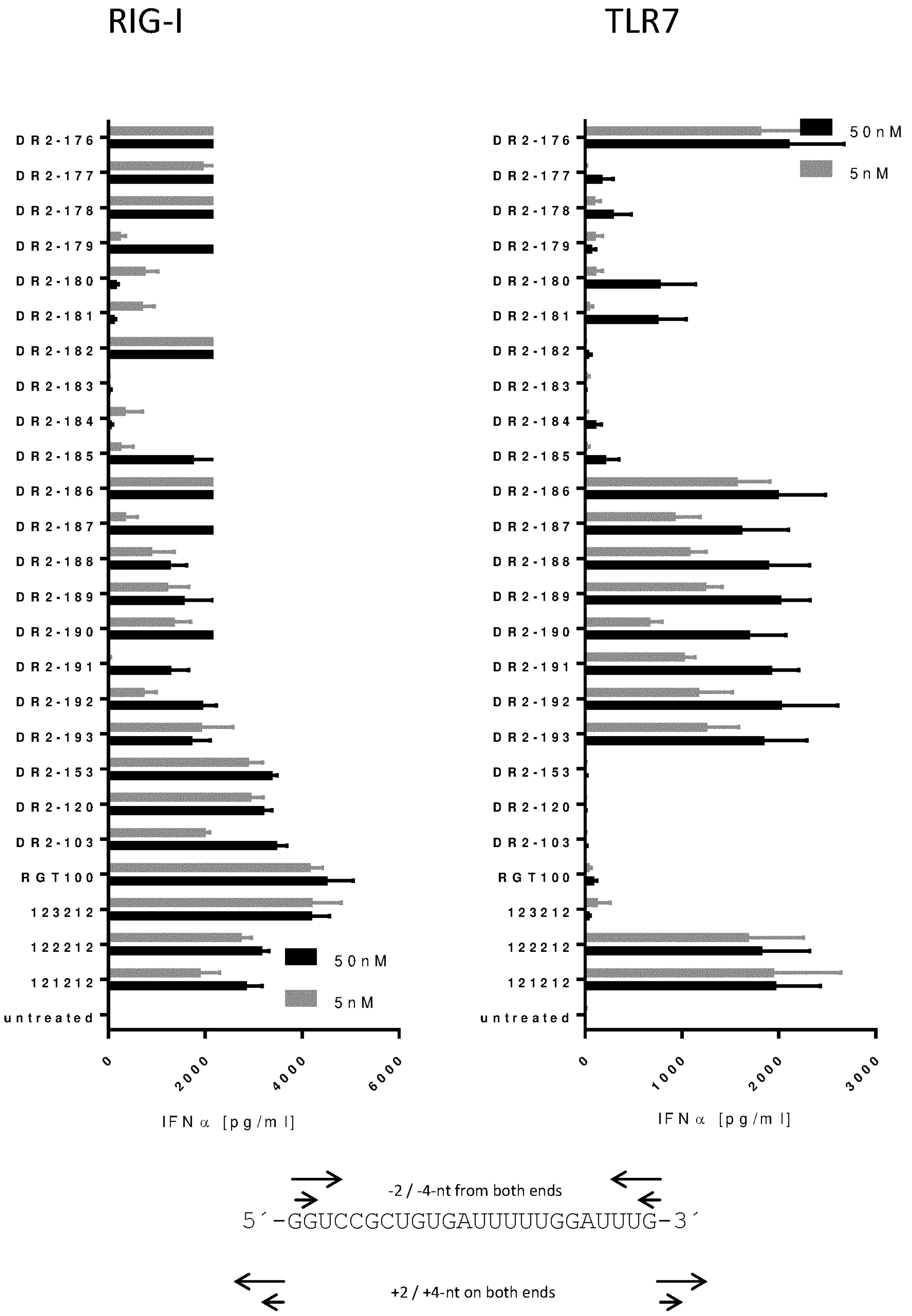

FIG. 12: Evaluation of 2'-o-methyl modification pattern in 24R80 #1.5 backbone with truncations or extensions to evaluate length independency. TLR7 agonization was tested at 50 nM agonist concentration. Sense(s) strand of 24R80 #1.5 shown at bottom (SEQ ID NO: 7).

Figure 13:
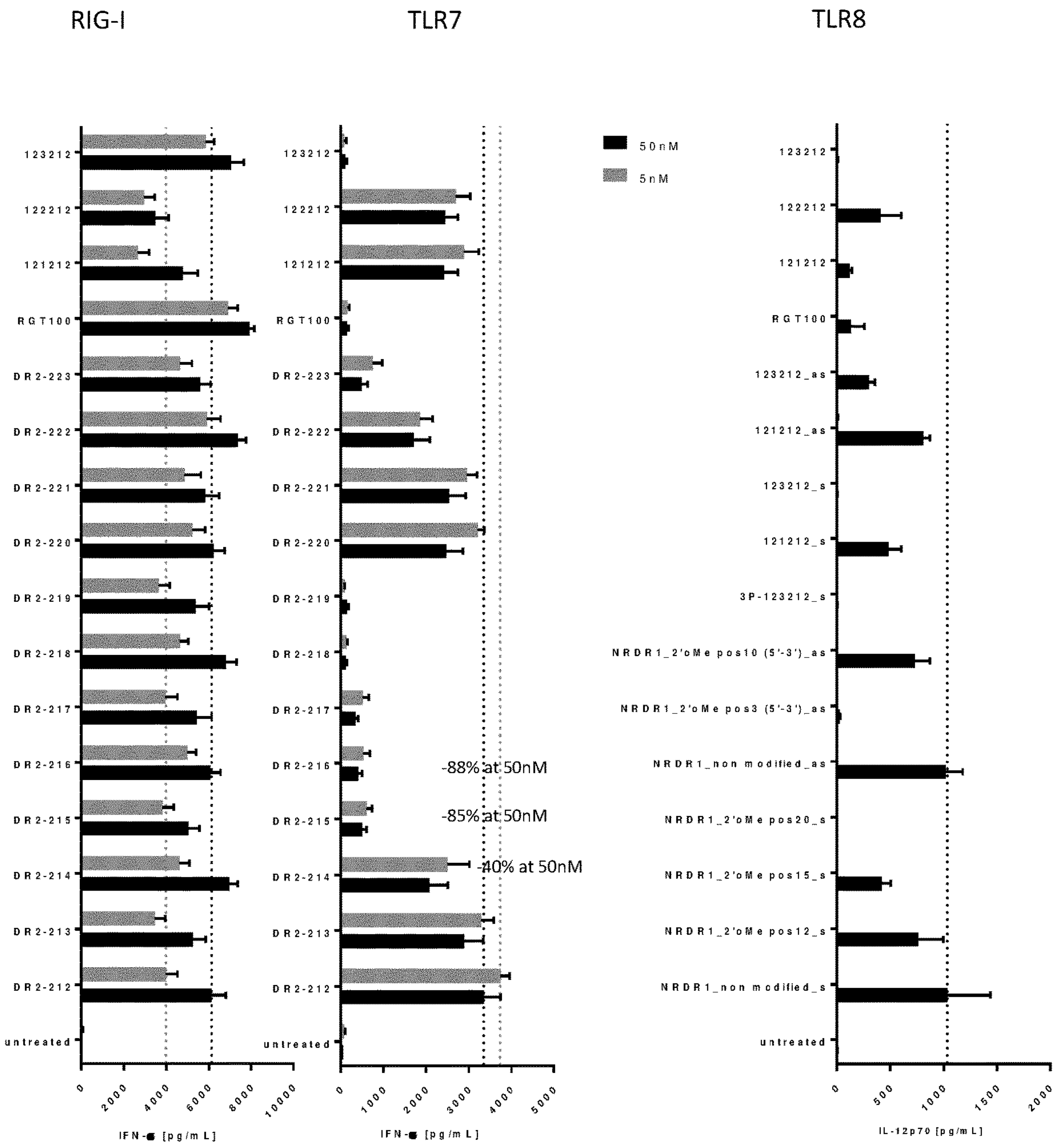

FIG. 13: Evaluation of all identified nucleotide positions that can confer receptor selectivity in NRDR1 backbone and their purine dependency. Sequences at bottom are the sense(s) and antisense (as) strands of DR2-101 (SEQ ID NOs: 9 and 10 respectively).

Figure 14:
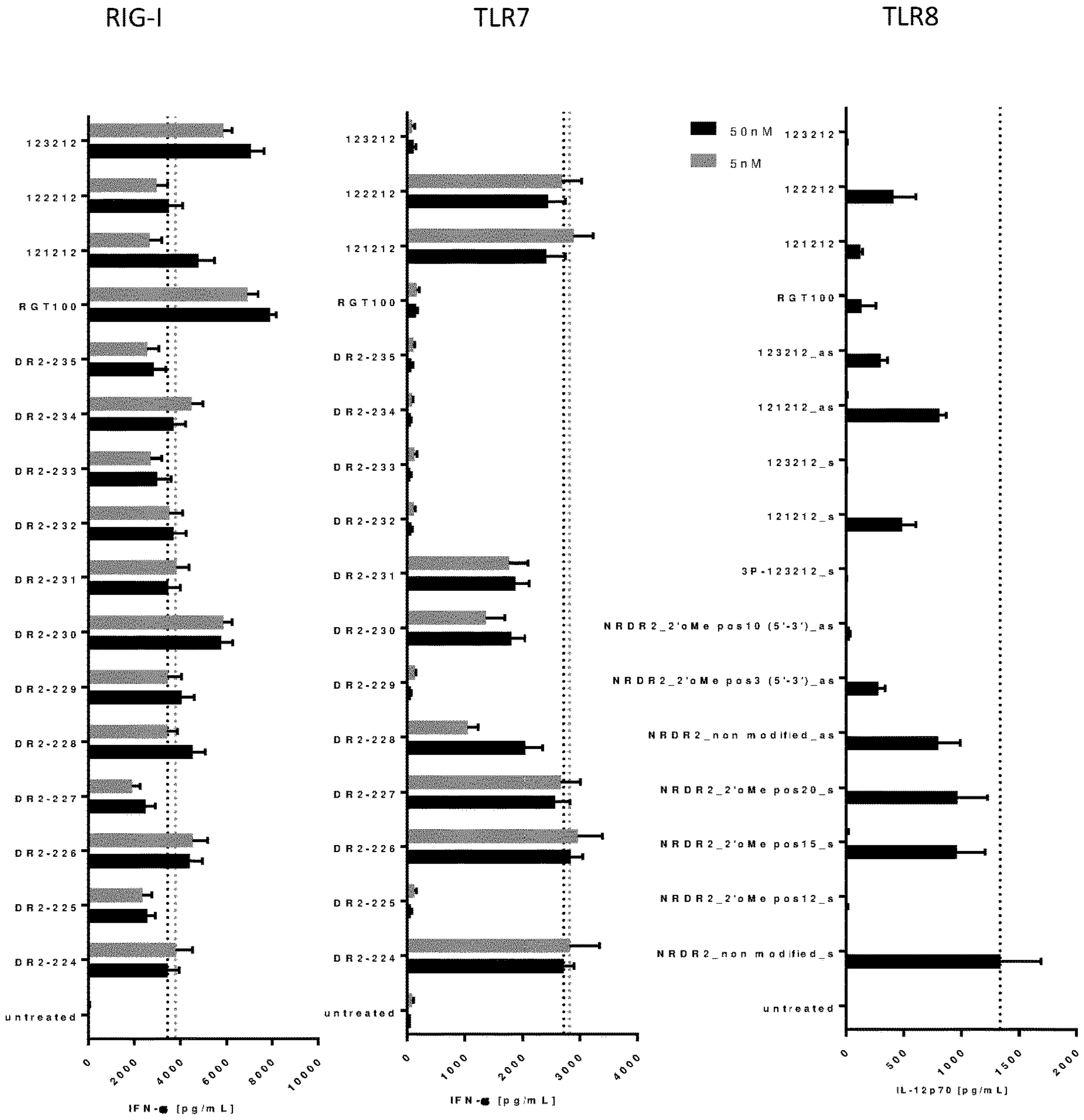

FIG. 14: Evaluation of all identified nucleotide positions that can confer receptor selectivity in NRDR2 backbone and their purine dependency. Sequences at bottom are the sense(s) and antisense (as) strands of DR2-118 (SEQ ID NOs: 16 and 17 respectively).

Figure 15:
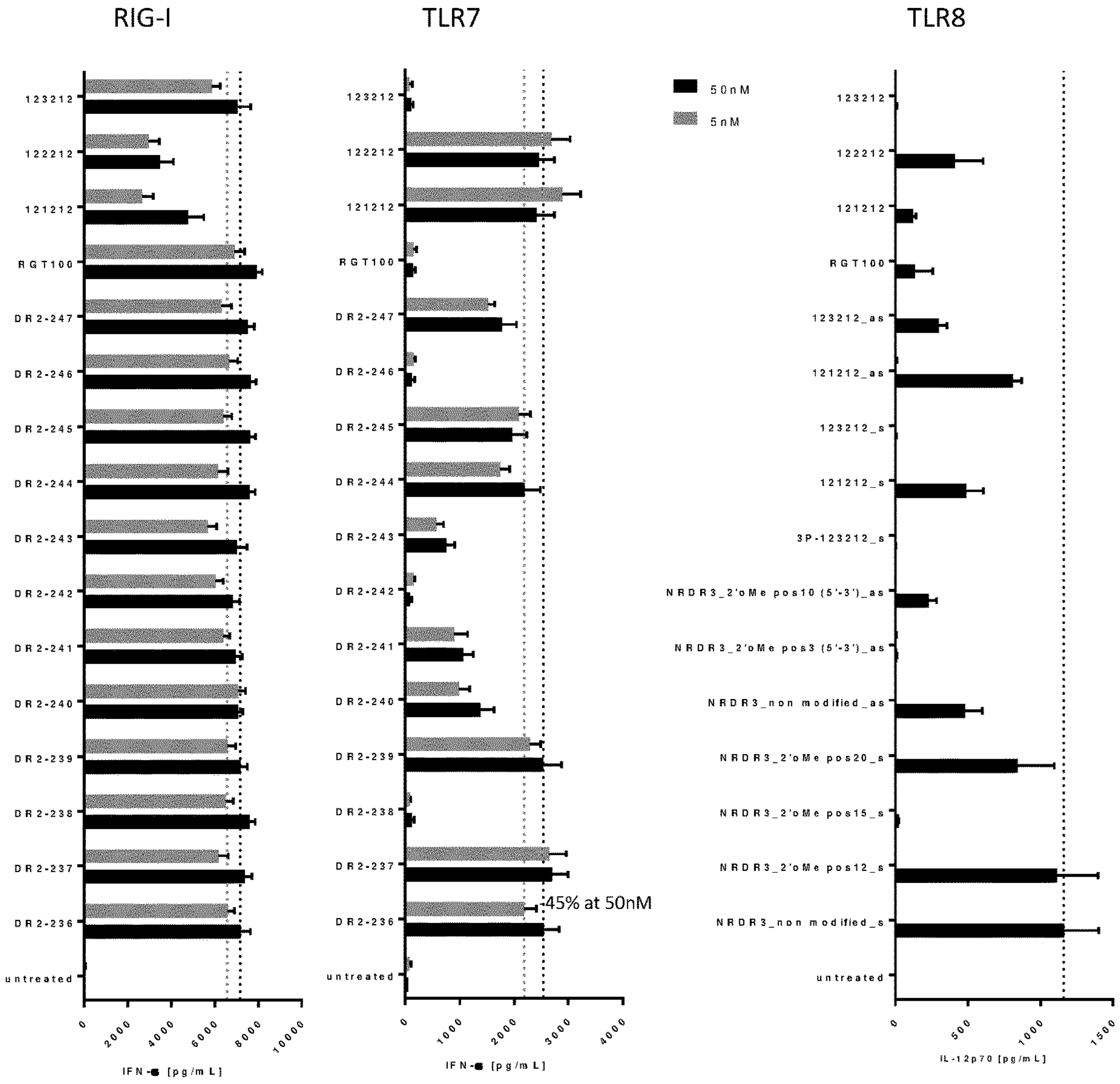

FIG. 15: Evaluation of all identified nucleotide positions that can confer receptor selectivity in NRDR3 backbone and their purine dependency. Sequences at bottom are the sense(s) and antisense (as) strands of DR2-151 (SEQ ID NOs: 23 and 24 respectively).

Figure 16:
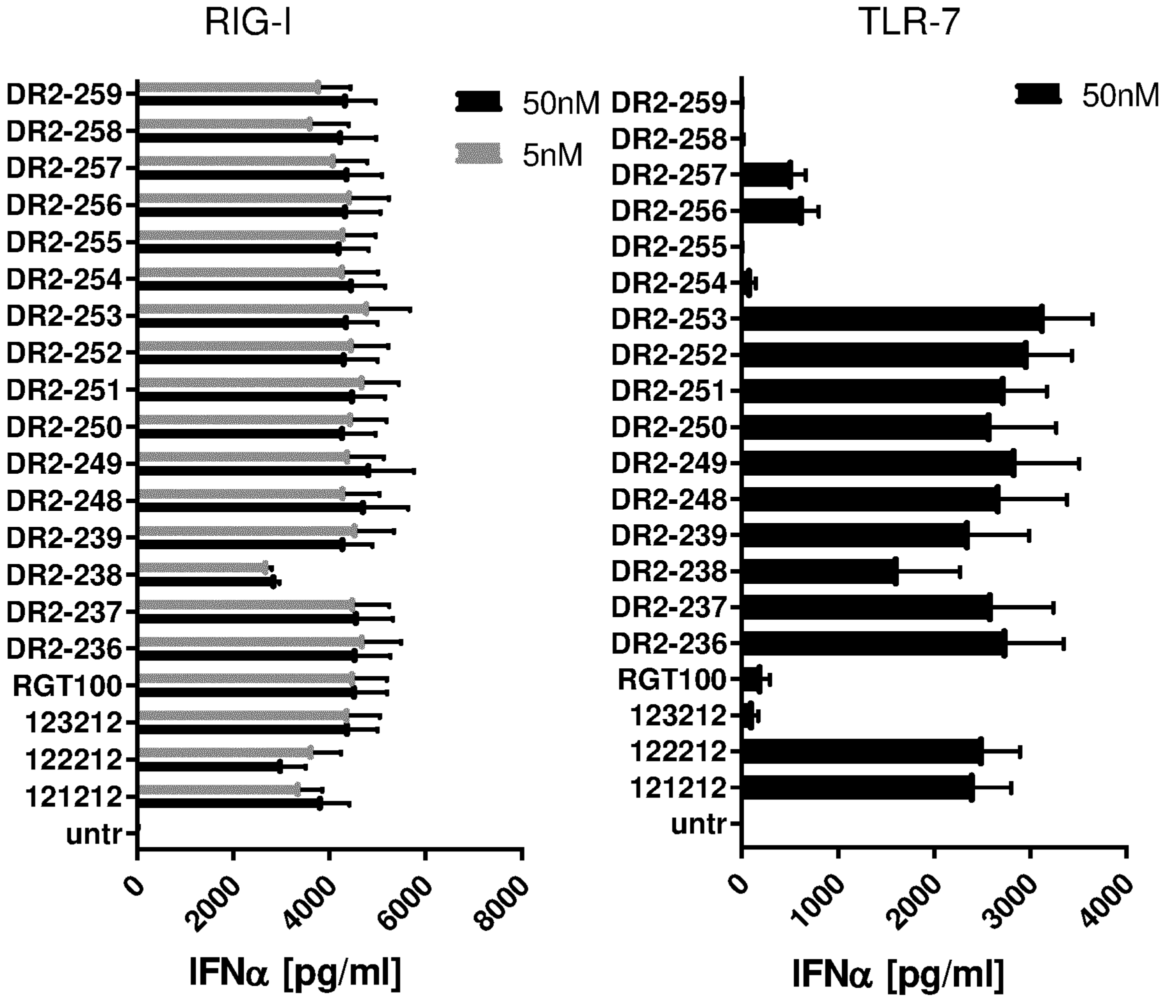

FIG. 16: Evaluation how exchanging pyrimidine nucleotides at positions 12 and 20 in the sense strand of NRDR3 base sequence for purines affects oligonucleotide's preferences for the RIG-I receptor and selectivity. TLR7/8 engagement was assessed at an agonist concentration of 50 nM.

FIG. 17: Schematic overview about the broad range modification pattern, summarizing the results of Example 3 shown in FIGS. 9-16 and Tables 6-10.

DETAILED DESCRIPTION OF THE INVENTION

The mammalian immune system has evolved a diverse array of pattern recognition receptors (PRRs) to detect invading pathogens and to clear infection (Goulet et al., PLOS Pathog. 2013; 9 (4): e1003298). During infection, foreign ribonucleic acids released from bacterial and viral threats are recognized by Toll-like receptors (TLRs) and RIG-I-like helicases (RLRs) (AmparoHagmann, PLOS 2013; 8 (4): e62872). The RLR-family comprises three DExD/H box RNA helicases RIG-I, MDA5 and LGP-2, all of which are located to the cytoplasm (Goulet et al., PLOS Pathog. 2013; 9 (4): e1003298). Interestingly, RLRs diverge in their pathophysiological action and have been suggested to trigger either anti-(LGP-2) or pro-inflammatory responses (MDA-5 and RIG-I) (Ranoa et al., Oncotarget 2016; 7 (18): 26496-26515). Consistently, gain-of-function mutations of the RIG-I encoding gene DDX58 are associated with rare inherited immune pathologies (Buers et al., Cyt Grow Fac Rev. 2016; 29:101-107; Jang et al., Am J Hum Genet. 2015; 96 (2): 266-274). Further, DDX58 177 C>T polymorphisms are implicated in the pathogenesis of classical Hodgkin lymphomas (Martin et al., Leuk Lymphoma 2016; 58:1686-1693).

Classically, RIG-I plays a crucial role in promoting the release of type I and type III interferons to fortify host's anti-viral immunity (Wu et al., Virology 2015; 482:181-188). Moreover, transcriptome analysis reveals a RIG-I-related signature covering the canonical pathway categories "IFN signaling", "activation of IRFs by cytosolic PRRs", "TNFR2 signaling" and "antigen presentation" indicating that RIG-I bridges the innate and adaptive immune system (Goulet et al., PLOS Pathog. 2013; 9 (4): e1003298). Intriguingly, RIG-I-induced immunogenic tumor cell death triggers adaptive immunity engaging dendritic cells and T-cells to kill tumors in vivo providing a second innate/adaptive immune system loop (Duewell et al., Cell Death Differ. 2014; 21 (12): 1825-1837). Of note, RIG-I-induced apoptosis is restricted to tumor-cells only (Duewell et al., Cell Death Differ. 2014; 21 (12): 1825-1837).

Recent studies report key structural features of optimal RIG-I ligands. Short length, doublestrandedness, 5'-triphosphorylation and blunt base pairing characterize the prototypic RNA-based RIG-I agonist (Schlee et al., Immunity 2009; 31:25-34; Pichlmair et al., Science 2006; 314:997-. 1001; Schlee, Immunobiology. 2013; 218 (11): 1322-1335; WO 2008/017473; WO 2009/141146; WO 2014/049079). Circular structures (Chen, et al., Molecular Cell, 2017, 1-11) and bent/KINK RNAs (Lee et al., Nucleic Acid Therapeutics 2016; 26 (3): 173-182) constitute another recently identified group of RIG-I ligands that do not require a tri-phosphate moiety. Nabet et al. (Cell 2017; 170 (2): 352-366.e13) reported that an unshielded endogenous RNA can activate RIG-I in tumor cells promoting aggressive features of cancer. Recent findings indicate also that endogenous small non-coding RNAs leaking to the cytoplasm can activate RIG-I during ionizing radiation therapy (Ranoa et al., Oncotarget 2016; 7 (18): 26496-26515). In addition, a hetero-trimeric complex of RIG-I/RNA polymerase III/serine-arginine-rich splicing factor 1 facilitates RIG-I activation in response to delocalized, cytosolic DNA via a 5' triphosphorylated RNA intermediate (Ablasser et al., Nat Immunol. 2009; 10 (10): 1065-1072; Xue et al., PLOS One 2015; 10 (2): e0115354).

Structural and functional analysis of RIG-I reveals that single amino acids and a lysine-rich patch located at the C-terminal domain (CTD) of RIG-I sense the structural properties of RNAs (Wang et al., Nat Struct & Mol Biol, 2010; 17 (7): 781-787). Remarkably, typical eukaryotic 2'-o-methylation pattern and 7-methyl guanosine capping of the 5'-triphosphate group of RNAs prevent binding to RIG-I and thus allow distinguishing host from pathogenic non-self RNA. Specifically, modifications at the very 5' end decrease RNA affinity, ATPase activity and production of pro-inflammatory cytokines (Schuberth-Wagner et al., Immunity. 2015; 43 (1): 41-51, Immunity; Devarkar et al., PNAS 2016; 113 (3): 596-601). Modified RNAs containing modified nucleotides m6A, Ψ, mΨ, 2FdU, 2FdC, 5mC, 5moC, and 5hmC appear to lack stimulatory activity (Durbin et al., mBio 2016; 7 (5), 1-11). Moreover, illegitimate RIG-I activation by endogenous RNA is controlled by fast ATPase turnover which leads to dissociation of the RIG-I/RNA complex (Louber et al., BMC Biol. 2015; 13:54). Interestingly, RIG-I mutations which correlate with a decreased ATPase activity appear to be constitutively active potentially due to signals from host RNA (Fitzgerald et al., Nucleic Acids Research 2016; gkw816).

PCT/EP2018/057531 identified functional boxes to RIG-I agonists that showed immune activation. In particular, a 5' 5-mer box harboring a G1 N(no A)$_2$ U$_3$ C$_4$ Ns motif (5-mer), and two additional regulatory boxes at positions 6-8 (box 1) and 17-19 (box 2) were identified.

All sequences provided herein are indicated in accordance with Appendix 2, Table 1 of the WIPO ST.25 standard. Accordingly, a nucleotide "b" means "g or c or u" (i.e. not a), a nucleotide "d" means "a or g or u" (i.e. not c), a nucleotide "w" means "a or u" (i.e. a weak interaction), a nucleotide "s" means "g or c" (i.e. a strong interaction), a nucleotide "v" means "a or g or c" (i.e. not u), and a nucleotide "n" means "a or g or c or u" (i.e. any).

Nucleic acid sensors efficiently trigger anti-viral and anti-cancer immune pathways to strengthen the body's defense mechanisms. Nucleic acid sensors such as TLRs and RIG-I have emerged as attractive targets for pharmacological activation in order to recover host homeostasis (Junt and Barchet, Nat Rev Immunol 2015; 15 (9): 529-544). Therefore, we set out to identify a structural design method to develop 2' modified RIG-I ligands having improved target receptor specificity and selectivity.

Figure 1:
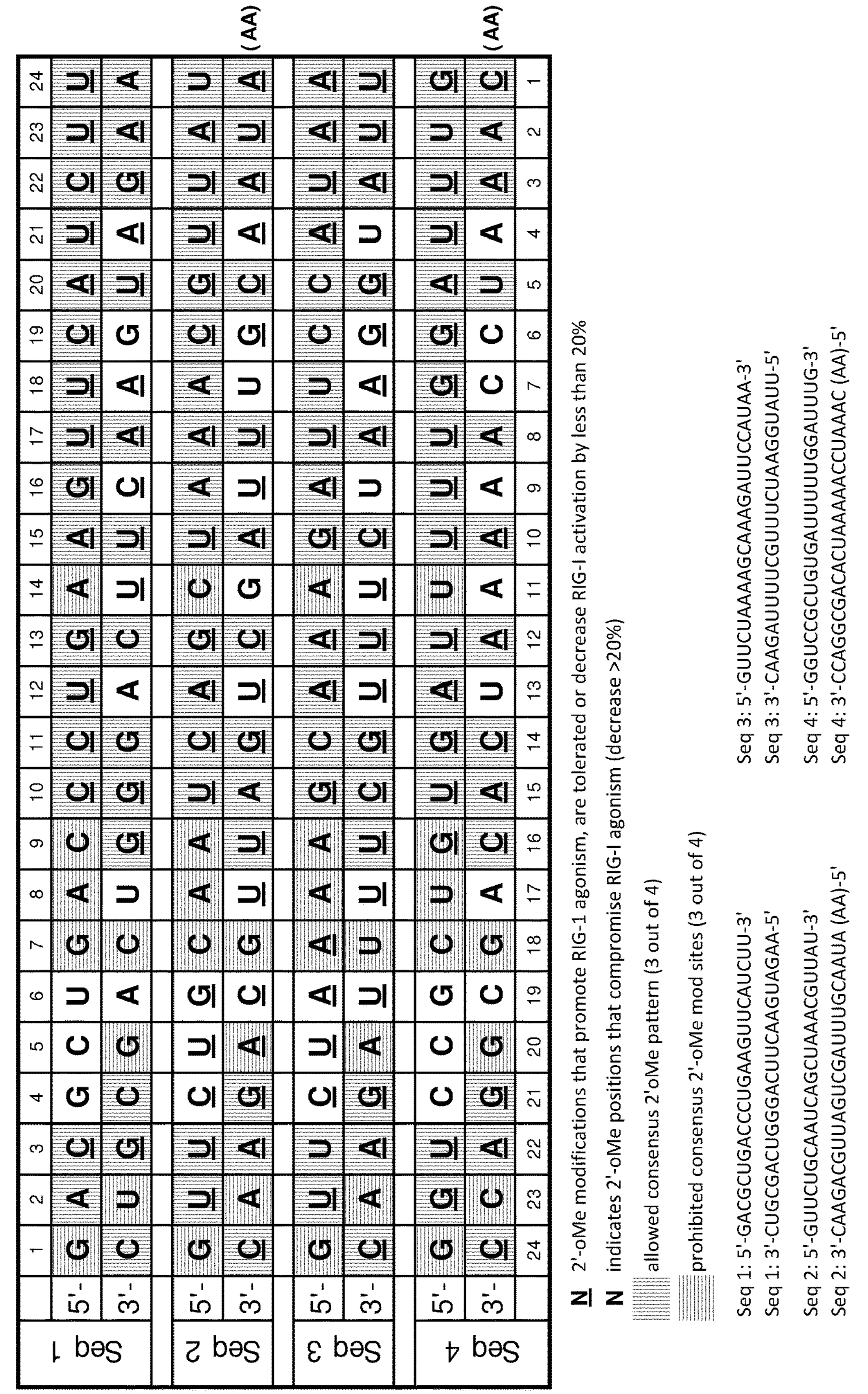
FIG. 1: Detrimental effects of single 2'-oMe modifications. Four independent basis sequences (Seq 1-4; SEQ ID NOs: 1-8) were permuted for 2'-o-methylation of single nucleotides ("N") and transfected into PBMCs. On basis of the IFNα levels released (data not shown) each single 2'-o-methylation position was classified as being detrimental (decrease≥20%) or being tolerated. All nucleotide positions are counted from 5' to 3' of the region of complementation (i.e., not including the 5' overhang of antisense strand (AA) if present).

Here we present the identification of a novel design rule providing a rationale to select single nucleotides for 2'-modifications to finetune the RNA/RIG-I interactions. We define single nucleotides that can be modified by 2'-o-methyl or 2'-fluorine to improve selectivity and boost RIG-I activity, respectively (FIGS. 2, 5, 8B, and 13). As there is a prerequisite for purines (2'-o-methyl) or pyrimidines (2'-fluorine) at these positions, this provides a rationale to choose appropriate nucleotides at defined positions when designing novel RIG-I ligands. Moreover, we identify sites where 2'-o-methyl and/or 2'-fluorine modification compromises RIG-I agonism (FIGS. 1 and 4). Indeed, crystal structural studies demonstrated that specific amino acids of RIG-I can sense distinct nucleotides and structural conformations of the dsRNA backbone to promote immune activation (Wang et al., Nat Struct & Mol Biol, 2010; 17 (7): 781-787). Of note, 2'-methylation of the very 5' nucleotide and capping of the 5'-triphosphate can prevent RIG-I activation (Schuberth-Wagner et al., Immunity. 2015; 43 (1): 41-51; Devarkar et al., PNAS 2016; 113 (3): 596-601). Durbin et al. (mBio 2016; 7 (5), 1-11) showed that RNAs fully modified for 2FdU are hyperstable and bind with high affinity to RIG-I. However, full 2FdU RNAs failed to induce a RIG-I-specific immune response. Furthermore, 2FdU modified polyU/UC also lost the ability to activate RIG-I, whereas the 2FdC modified polyU/UC triggered an immune response comparable to the non-modified parent RNA (Uzri & Gehrke, J Virol., 2009, 83 (9): 4174-4184). RNAs modified with one of the following nucleotides m6A, Ψ, mΨ, 5mC, 5moC, and 5hmC also may not activate RIG-I (Durbin et al., mBio 2016; 7 (5), 1-11), highlighting that a non-directed approach appears inadequate.

Accordingly, the present disclosure provides a double-stranded polynucleotide comprising a sense strand 24 to 30 nucleotides in length and an antisense strand 24 to 30 nucleotides in length, wherein the sense strand and the antisense strand form a fully complementary region of at least 24 base pairs with a blunt end at the 5'-end of the sense strand and the 3'-end of the antisense strand; and/or wherein the first 24 ribonucleotides at 5'-end of the sense strand further have at least one 2'-fluorine modification at a ribonucleotide at a position selected from the group consisting of position number 2, 4, 6, 9, 10, 16, 21, 22, and 24, and no 2'-fluorine modification at a ribonucleotide at a position selected from the group consisting of position number 1, 3, 8, and 14, and/or the last 24 ribonucleotides at 3'-end of the antisense strand further have at least one 2'-fluorine modification at a ribonucleotide at a position selected from the group consisting of position number 5 and 13, and no 2'-fluorine modification at a ribonucleotide at a position selected from the group consisting of position 18 and 23; wherein all positions are counted from 5' to 3'.

An embodiment of the invention wherein the first 24 ribonucleotides at 5'-end of the sense strand further have at least one 2'-fluorine modification at a ribonucleotide is realized when the ribonucleotide is a purine. Another embodiment of the invention wherein the first 24 ribonucleotides at 5'-end of the sense strand further have at least one 2'-fluorine modification at a ribonucleotide is realized when the ribonucleotide is a pyrimidine. Another embodiment of the invention wherein the last 24 ribonucleotides at 3'-end of the antisense strand further have at least one 2'-fluorine modification at a ribonucleotide is realized when the ribonucleotide is a purine. Another embodiment of the invention wherein the last 24 ribonucleotides at 3'-end of the antisense strand further have at least one 2'-fluorine modification at a ribonucleotide is realized when the ribonucleotide is a pyrimidine.

In embodiments, the first 24 nucleotides at the 5'-end of the sense strand are ribonucleotides and have at least one 2'-O-methyl modification at a purine ribonucleotide at a position selected from the group consisting of position number 12, 15, and 20, and no 2'-o-methyl modification at a ribonucleotide at a position selected from the group consisting of position number 1, 7, 8, 9, and 14, and/or wherein the last 24 nucleotides at the 3'-end of the antisense strand are ribonucleotides and have at least one 2'-o-methyl modification at a purine ribonucleotide at a position selected from the group consisting of position number 3, 10, and 22, and no 2'-o-methyl modification at a 20 ribonucleotide at a position selected from the group consisting of position 18, 20, and 23; wherein all positions are counted from 5' to 3'.

In specific embodiments, the double-stranded polyribonucleotide comprises at least one 2'-o-methylation at a purine ribonucleotide at a position selected from the group consisting of position number 12, 15, and 20 in the sense strand and at least one 2'-o-methylation at a purine ribonucleotide at a position selected from the group consisting of position number 3, 10, and 22 of the last 24 nucleotides of the antisense strand, wherein all positions are counted from 5' to 3'. In embodiments the double-stranded polyribonucleotide comprises at least one 2'-o-methylation and at least one 2'-fluorine modification, e.g., at least one 2'-o-methylation a purine ribonucleotide at a position selected from the group consisting of position number 12, 15, and 20 in the sense strand and at least one 2'-o-methylation at a purine ribonucleotide at a position selected from the group consisting of position number 3, 10, and 22 of the last 24 nucleotides of the antisense strand, wherein all positions are counted from 5' to 3'; and at least one 2'-fluorine modification at at a ribonucleotide at a position selected from the group consisting of position number 2, 4, 6, 9, 10, 16, 21, 22, and 24 of the sense strand and at least one 2'-fluorine modification at a ribonucleotide at a position selected from the group consisting of position number 5 and 13 of the last 24 nucleotides of the antisense strand, wherein all positions are counted from 5' to 3'. In embodiments, the remaining ribonucleotides at the other positions in the first 24 ribonucleotides at 5'-end of the sense strand and the last 24 ribonucleotides at 3'-end of the antisense strand are not modified at the ribose unit; wherein all positions are counted from 5' to 3'.

The above-indicated positions have been shown to be of importance. For example, it was surprisingly found that the double-stranded ribonucleotide exhibits increased RIG-I selectivity over TLR7 in embodiments wherein the double-stranded ribonucleotide has at least one 2'-o-methylated purine at a position selected from the group of positions consisting of positions 12, 15, and 20 in the first 24 ribonucleotides at 5'-end of the sense strand, and position 3 and 10 in the last 24 ribonucleotides at the 3'-end of the antisense strand, each counted from 5' to 3'. Position 15 in the sense strand and position 10 in the antisense strand are both purines, and a methylation in one position usually excludes the presence of a methylation in the other position. The presence of a 2'-o-methylation in position 22 of the antisense strand further prevents TLR8 agonism by the single strand. For example, the sense strand may have 2'-o-methyl modifications at one, at two, or at all three positions 12, 15, and 20, and the antisense strand may have a 2'-o-methylation at position 22.

In specific embodiments, the double-stranded ribonucleotide has at least one 2'-o-methylated purine at a position selected from the group of positions consisting of position 12 and 20 in the first 24 ribonucleotides at 5'-end of the sense strand, and position 3 in the last 24 ribonucleotides at the 3'-end of the antisense strand; wherein all positions are counted from 5' to 3'. Further combinations of 2'-o-methylations are exemplified by the compounds shown in Table 1, irrespective of the 2'-fluoro pattern.

The data in the examples further demonstrate good RIG-I activation in cases wherein the first 24 ribonucleotides at 5'-end of the sense strand have at least one 2'-fluorine modification at a ribonucleotide at a position selected from the group consisting of position number 2, 4, 6, 9, 10, 16, 21, 23, and 24, and/or wherein the last 24 ribonucleotides at 3'-end of the antisense strand have at least one 2'-fluorine modification at a ribonucleotide at a position selected from the group consisting of position number 1, 2, 5, and 13. For example, the double-stranded polyribonucleotide may have at least one 2'-fluorine modification at one or more- or even at every one—of position number 2, 4, 9, 10, 21, 23, and 24, and/or at a position selected from position number 5 and 13. Moreover, it was also surprisingly found that in embodiments wherein the double-stranded ribonucleotide has a 2'-fluorinated pyrimidine at position 10 at the 5'-end of the sense strand (counted from 5' to 3'), RIG-I activation and interferon induction could be boosted. Further combinations of 2'-fluoro modifications are exemplified by the compounds shown in Table 1, irrespective of their respective 2'-o-methylation pattern.

Generally, RIG-I agonists may have a length of 21-300 base pairs (cf. FIGS. 4B and 5 in Schlee et al., Immunity, 31 (1): 25-34 (2009); and page 2 in Reikine et al., Front Immunol. 2014; 5:324)). Moreover, Table 1 herein below provides several compounds showing potential to activate RIG-I, which compounds have a length of 20 (DR2-179) to 28 (DR2-185) base pairs. These compounds exemplify how the 24-base pair 2'modification pattern can be suitably applied to shorter and longer double-stranded ribonucleotides. Accordingly, in general, the sense strand and the antisense strand of the double-stranded polyribonucleotide may independently have a length of 20-300 nucleotides, 21-300 nucleotides, 22-300 nucleotides, 23-300 nucleotides, or 24-300 nucleotides. The sense and the antisense strand may independently from each other have a length of at most 250 nucleotides, preferably at most 200 nucleotides, more preferably at most 150 nucleotides, more preferably at most 100 nucleotides, more preferably at most 90 nucleotides, more preferably at most 80 nucleotides, more preferably at most 70 nucleotides, more preferably at most 60 nucleotides, more preferably at most 55 nucleotides, preferably at most 50 nucleotides, more preferably at most 45 nucleotides, more preferably at most 40 nucleotides, more preferably at most 38 nucleotides, such as 37 nucleotides, more preferably at most 36 nucleotides, such as 35 nucleotides, more preferably at most 34 nucleotides, such as 33 nucleotides, more preferably at most 32 nucleotides, such as 31 nucleotides. In embodiments of the invention, the sense strand and the anti-sense strand of the double-stranded polyribonucleotide may independently have a length of 24 to 30 nucleotides, such as 24 to 29 nucleotides, more preferably 24 to 28 nucleotides, such as 24 to 27 nucleotides, more preferably 24 to 26 nucleotides, such as 24 to 25 nucleotides, and most preferably both strands have a length of 24 nucleotides.

The fully complementary region formed by the sense and antisense strand may in principle have a length of up to 300 base pairs. In general, the fully complementary region may have a length of at most 250 base pairs, preferably at most 200 base pairs, more preferably at most 150 base pairs, more preferably at most 100 base pairs, more preferably at most 90 base pairs, more preferably at most 80 base pairs, more preferably at most 70 base pairs, more preferably at most 60 base pairs, more preferably at most 55 base pairs, preferably at most 50 base pairs, more preferably at most 45 base pairs, more preferably at most 40 base pairs, more preferably at most 38 base pairs, such as 37 base pairs, more preferably at most 36 base pairs, such as 35 base pairs, more preferably at most 34 base pairs, such as 33 base pairs, more preferably at most 32 base pairs, such as 31 base pairs. In embodiments of the invention, the fully complementary region has a length of at most 30 base pairs, such as 29 base pairs, more preferably at most 28 base pairs, such as 27 base pairs, more preferably at most 26 base pairs, such as 25 base pairs, and most preferably 24 base pairs.

In some embodiments, the complementary antisense strand has at most 2 nucleotides more in length than the sense strand; or at most 1 nucleotide more in length than the sense strand; or the complementary antisense strand has the same length than the sense strand. In some embodiments, the double-stranded polyribonucleotide of the present disclosure has two blunt ends, i.e. both strands have the same length. In certain embodiments, the double-stranded polyribonucleotide of the present disclosure has two blunt ends and a length of 24 nucleotides.

In an alternative embodiment, the antisense strand has a length of 26 ribonucleotides, and the sense strand has a length of 24 ribonucleotides. In such embodiments, the antisense strand will exhibit a two-nucleotide overhang at its 5'-end. It is demonstrated in the examples herein below that RIG-I activation can be boosted in embodiments wherein the antisense strand has an overhang of two adenine at the 5'-end, and a 2'-fluorinated ribonucleotide at position 1 or 2, or in both position 1 and 2, in the last 24 ribonucleotides at the 3'-end of the antisense strand; wherein the positions are counted from 5' to 3'.

In some embodiments, the sense strand, or the antisense strand, or both the sense strand and the antisense strand are selected from SEQ ID NO: 10-15, 18-22, 24-35, 44-45, 49-54, 60-62, 159-166, and 206-209.

In some embodiments, the sense strand, or the antisense strand, or both the sense strand and the antisense strand are selected from the group consisting of SEQ ID NOs: 7-64, 69-72, 77-80, 85-88, 92-99, 104-107, 112-115, 120-123, 127-169, and 206-209.

In embodiments, the double-stranded polyribonucleotide is selected from the doublestranded polyribonucleotides DR2-105, DR2-107 to DR2-111, DR2-113 to DR2-117, DR2-121 to DR2-122, DR2-124-DR2-128, DR2-130 to DR2-134, DR2-136 to DR2-138, DR2-140 to DR2-142, DR2-144 to DR2-146, DR2-148 to DR2-150, DR2-155, DR2-158 to DR2-165, DR2-168 to DR2-175, DR2-260 to DR2-265, and DR2-269 to DR2-270 shown in Table 1.

In particular embodiments, the double-stranded polyribonucleotide is selected from the group consisting of the double-stranded polyribonucleotides DR2-102 to DR2-117, DR2-119 to DR2-150, DR2-152 to DR2-175, DR2-213 to DR2-223, DR2-225 to DR2-235, DR2-237 to DR2-247, DR2-254 to DR2-265 and DR2-269 to DR2-270 shown in Table 1 herein below.

The present disclosure provides a novel design rule providing a rationale to select single nucleotides for 2'-modifications to finetune the RNA/RIG-I interactions. The present disclosure provides positions within a double-stranded polyribonucleotide, which can be modified by 2'-o-methyl or 2'-fluorine to achieve selectivity and boosting of RIG-I activity, respectively. These effects are to a large extent sequence independent (except for the presence or absence of purines or pyrimidines). PCT/EP2018/057531 describes sequence related design rules for designing RIGI agonists that have immune activation. In particular, PCT/EP2018/057531 identifies a 5' 5-mer box harboring a $G_1$ N(no $A)_2$ $U_3$ $C_4$ $N_5$ motif (5-mer), and two additional regulatory boxes at positions 6-8 (box 1) and 17-19 (box 2). Of course, the sequence independent rules disclosed herein can be combined with previously described, sequence-related design rules.

Hence, in certain preferred embodiments of the double-stranded polyribonucleotide, the sense strand starts at the 5' end with a sequence selected from the group consisting of:

```
                                    (SEQ ID NO: 170)
5'-gbucndnwnnnnnnnnwnsnn-3',

                                    (SEQ ID NO: 171)
5'-gucuadnwnnnnnnnnwnsnn-3',

                                    (SEQ ID NO: 172)
5'-guagudnwnnnnnnnnwnsnn-3',

                                    (SEQ ID NO: 173)
5'-gguaadnwnnnnnnnnwnsnn-3',

                                    (SEQ ID NO: 174)
5'-ggcagdnwnnnnnnnnwnsnn-3',

                                    (SEQ ID NO: 175)
5'-gcuucdnwnnnnnnnnwnsnn-3',

                                    (SEQ ID NO: 176)
5'-gcccadnwnnnnnnnnwnsnn-3',
and

                                    (SEQ ID NO: 177)
5'-gcgcudnwnnnnnnnnwnsnn-3'.
```

As noted above, there are also certain structural motifs by way of two boxes for the RNA sequence of the sense strand that are involved in IFNα inducing activity. For example, it could be demonstrated that selecting a cytosine at position 6, or cytosine or guanosine at position 8 in above sequences SEQ ID NO: 170-177 abrogates IFNα inducing activity. Likewise, lower IFNα inducing activity is found when selecting a nucleotide other than adenosine or uracil in the position indicated as position 17 in above sequences SEQ ID NO: 170-177, or when selecting an RNA sequence having an adenosine or uracil in the position indicated as position 19 in above sequences SEQ ID NO: 170-177.

Certain nucleotides at position 6-8 of the RNA sequence of SEQ ID NO: 170-177 showed particularly high IFNα inducing activity. This sequence is shown in FIG. 6 as "Box 1". An embodiment of the invention is realized when in the sequence of the sense strand at position 6 ("d" in SEQ ID NO: 170-177) is u, and/or the ribonucleotide at position 7 ("n" in SEQ ID NO: 170-177) is g, and/or the ribonucleotide at position 8 ("w" in SEQ ID NO: 170-177) is a. In another embodiment the ribonucleotide at position 6 ("d" in SEQ ID NO: 170-177) is g, and the ribonucleotide at position 7 ("n" in SEQ ID NO: 170-177) is c. Another embodiment is wherein in the RNA sequence of the sense strand the ribonucleotides at position 6-8 are UGA (Box 1). Another embodiment is wherein in the RNA sequence of the sense strand the ribonucleotides at position 6-8 are GCA (Box 1). In another embodiment, the ribonucleotide at position 6 ("d" in SEQ ID NO: 170-177) is u, the ribonucleotide at position 7 ("n" in SEQ ID NO: 170-177) is g, and the ribonucleotide at position 8 ("w" in SEQ ID NO: 170-177) is a. A guanosine at position 6 and a cytosine at position 7 is also well tolerated. Hence, in another embodiment the ribonucleotide at position 6 ("d" in in SEQ ID NO: 170-177) is g, the ribonucleotide at position 7 ("n" following "d" in SEQ ID NO: 170-177) is c.

In addition, an adenosine at position 9 is further associated with an increase in IFNα inducing activity of RIG-I agonists as disclosed herein. Hence, the ribonucleotide at position 9 can be "a" in the sequence of the sense strand (e.g., any one of SEQ ID NO: 170-177). Accordingly, another embodiment is wherein in the RNA sequence of the ribonucleotides of the sense strand at position 6-8 are GAA (Box 1), in particular wherein in the RNA sequence of the sense strand the ribonucleotides at position 6-9 are GAAA or GCAA.

Apart from Box1, also identified is another Box2 at positions 17-19. The nucleotide at position 17 is defined as adenosine or uracil ("w") in SEQ ID NO: 170-177. An embodiment is realized when "w" is uracil. Another embodiment is realized when "w" is adenosine. Other embodiments include those wherein the sequence at the 5'end of the sense strand of the doublestranded polyribonucleotide is selected from the group consisting of:

5'-gbucndnwnnnnnnnnunsnn-3' (SEQ ID NO: 178), (SEQ ID NO: 178)
5'-gbucndnwnnnnnnnnunsnn-3', (SEQ ID NO: 210)
5'-gbucndnwnnnnnnnnansnn-3', (SEQ ID NO: 179)
5'-gucuadnwnnnnnnnnunsnn-3', (SEQ ID NO: 180)
5'-guagudnwnnnnnnnnunsnn-3', (SEQ ID NO: 181)
5'-gguaadnwnnnnnnnnunsnn-3', (SEQ ID NO: 182)
5'-ggcagdnwnnnnnnnnunsnn-3', (SEQ ID NO: 183)
5'-gcuucdnwnnnnnnnnunsnn-3', (SEQ ID NO: 184)
5'-gcccadnwnnnnnnnnunsnn-3',
and (SEQ ID NO: 185)
5'-gcgcudnwnnnnnnnnunsnn-3'.

In another embodiment, in the sequence of the sense strand the ribonucleotide at position 18 (the "n" preceding "s" in SEQ ID NO: 170-177) is u, and/or the ribonucleotide at position 19 ("s" in SEQ ID NO: 170-177) is c. Along with the defined "u" at position 17 in SEQ ID NO: 170-177, the latter reflects a consensus sequence of Box2 "uuc". In another embodiment, this Box2 consensus sequence is "aac".

It follows from the foregoing that an embodiment is one which combines the previous embodiments. Such embodiments include those wherein the sequence at the 5'-end of the sense strand of the double-stranded polyribonucleotide is selected from the group consisting of:

(SEQ ID NO: 186)
5'-gbucnugaannnnnnnuucnn-3', (SEQ ID NO: 211)
5'-gbucngcaannnnnnnaacnn-3', (SEQ ID NO: 187)
5'-gucuaugaannnnnnnuucnn-3', (SEQ ID NO: 188)
5'-guaguugaannnnnnnuucnn-3', (SEQ ID NO: 189)
5'-gguaaugaannnnnnnuucnn-3', (SEQ ID NO: 190)
5'-ggcagugaannnnnnnuucnn-3', (SEQ ID NO: 191)
5'-gcuucugaannnnnnnuucnn-3', (SEQ ID NO: 192)
5'-gcccaugaannnnnnnuucnn-3',
and (SEQ ID NO: 193)
5'-gcgcuugaannnnnnnuucnn-3'.

In particular embodiments, the sequence at the 5'end of the sense strand is 5'-gbucnugaannnnnnnuucnn-3' (SEQ ID NO: 186), more specifically the sequence at the 5'-end of the sense strand may be 5'-gbucnugaaannnnnuuucnn-3' (SEQ ID NO: 194). In other embodiments, the sequence at the 5'end of the sense strand is 5'-gbucngcaannnnnnnaacnn-3' (SEQ ID NO: 211), more specifically 5'-gbucngcaaunnnnnaaacnn-3' (SEQ ID NO: 212).

The aforementioned 5-mer, Box1, adenosine at position 9, and Box2 can additionally be introduced into the complementary strand. For example, the ribonucleotides in Box1 can be selected in a way such that the complementary antisense strand comprises the "Box2" of UUC, UGC, or AAC. Still in another embodiment in the sequence of the sense strand, the ribonucleotide at position 6 ("d" in SEQ ID NO: 170-177) is g, and/or the ribonucleotide at position 7 ("n" following "d" in SEQ ID NO: 170-177) is a, and/or the ribonucleotide at position 8 ("w" in SEQ ID NO: 170-177) is a. In another embodiment, in the sequence of the sense strand, the ribonucleotide at position 6 ("d" in SEQ ID NO: 170-177) is g, the ribonucleotide at position 7 ("n" following "d" in SEQ ID NO: 170-177) is a, and the ribonucleotide at position 8 ("w" in SEQ ID NO: 170-177) is a. In this case, the complementary antisense strand will encompass a sequence which closely reflects the preferred consensus sequence of Box2 "uuc".

In order to introduce the adenosine at position 9 of the last 24 ribonucleotides at the 3' end of the antisense strand (counting from 5' to 3'), the ribonucleotide at position 16 in the sequence of the sense strand of the double-stranded polyribonucleotide is u. The adenine at position 9 has been shown to further increase type I IFN induction.

As noted above, a Box1 motif of GCA is well tolerated. Thus, in another embodiment, such Box1 motif is introduced into the complementary strand by way that in the sequence of the sense strand of the double-stranded polyribonucleotide, the ribonucleotide at position 17 is u, the ribonucleotide at position 18 is g, and the ribonucleotide at position 19 is c, in which case the complementary strand will comprise Box1 ($G6C_7A8$). Likewise, the last five ribonucleotides can be selected from any nucleotide. Accordingly, it can be selected such that the complementary strand comprises the 5-mer sequence for which high type-I IFN inducing activity could be demonstrated. In embodiments, in the sense strand the ribonucleotide sequence at positions 20-24 is selected from 5'-ngavc-3', 5'-uagac-3', 5'-acuac-3', 5'-uuacc-3', 5'-cugcc-3', 5'-gaagc-3', 5'-ugggc-3', 5'-guuau-3' and 5'-agcgc-3'. One particular embodiment is realized when the consensus sequence is 5'-ngavc-3'. Thus, in another embodiment, in the sense strand the sequence at position 6-24 is 5'-ugaannnnnnnuucngavc-3' (SEQ ID NO: 195; thereby comprising the consensus 5-mer sequence (and box 1) in the complementary antisense strand); 5'-ugaannnnnnuuucngavc-3' (SEQ ID NO: 196; thereby comprising the consensus 5-mer sequence, Box1, and a9 in the complementary anti-sense strand); 5'-gaaannnnnnuuucngavc-3' (SEQ ID NO: 197, thereby comprising the consensus 5-mer sequence, Box1, a9, and Box2 in the complementary antisense strand); or 5'-gaaannnnnnuuucngavc-3' (SEQ ID NO: 198), thereby comprising the consensus 5-mer, Box1, adenosine at position 9, and Box 2 in both strands.

In combination with the 5-mer of 5'-gbucn-3', an embodiment is realized with the following ribonucleotide sequences in the sense strand:

(SEQ ID NO: 199)
5'-gbucnugaannnnnnnnuucnnnnn-3', (SEQ ID NO: 213)
5'-gbucngcaannnnnnnnaacnnnnn-3', (SEQ ID NO: 200)
5'-gbucnugaannnnnnnnuucngavc-3', (SEQ ID NO: 201)
5'-gbucnugaannnnnnnnuucngavc-3', (SEQ ID NO: 202)
5'-gbucnugaannnnnnnuuucngavc-3', (SEQ ID NO: 203)
5'-gbucngaaannnnnnnnuucngavc-3', (SEQ ID NO: 204)
5'-gbucngaaannnnnnnnuucngavc-3',
or (SEQ ID NO: 205)
5'-gbucngaaannnnnnnuuucngavc-3'.

Another embodiment is realized with the following ribonucleotide sequences in the sense strand: 5'-gbucngcaannnnnnnaacguuau-3' (SEQ ID NO: 214).

The polyribonucleotide may have a 5'OH at its 5' end, or a monophosphate at its 5' end. However, the type-I IFN inducing activity is strongly increased if the polyribonucleotide exhibits a diphosphate, triphosphate or a di-/or triphosphate analogue.

Therefore, the sense strand may have a mono-, di-, or triphosphate or respective analogue attached to its 5' end. Likewise, the complementary antisense strand may have a mono-, di-, or triphosphate or respective analogue attached to its 5' end. Since the effect of monophosphate appears to be marginal (cf. FIG. **3*f*** in Goubau et al Nature 2014; 514:372-375), the sense strand can have a di-, or triphosphate or respective analogue attached to its 5' end, and/or the complementary antisense strand can have a di-, or triphosphate or respective analogue attached to its 5' end. In another embodiment the sense strand has a triphosphate or respective analogue attached to its 5' end, and/or the complementary antisense strand has a triphosphate or respective analogue attached to its 5' end. In another embodiment, both strands have a triphosphate or triphosphate analogue attached to the 5' end, in particular both strands have a triphosphate attached to the 5' end. Even though it was recently demonstrated that cap structures are tolerated (Schuberth-Wagner et al., Immunity 43 (1): 41-51 (2015)), the 5' triphosphate is preferably free of any cap structure.

The triphosphate/triphosphate analogue generally comprises the structure of formula (I)

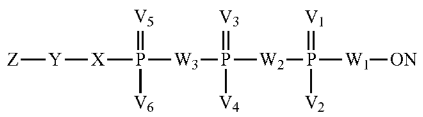

1

In this group, $V_1$, $V_3$ and $V_5$ are independently selected from O, S and Se. Preferably, $V_1$, $V_3$ and $V_5$ are O. $V_2$, $V_4$ and $V_6$ are in each case independently selected from OH, $OR^1$, SH, $SR^1$, F, $NH_2$, $NHR^1$, $N(R^1)_2$ and $BH_3^-M^+$. Preferably, $V_2$, $V_4$ and $V_6$ are OH. $R^1$ may be $C_1$-6 alkyl, $C_2$-6 alkenyl, $C_2$-6 alkynyl, $C_2$-6 acyl or a cyclic group, e.g., a $C_3$-8 cyclo (hetero)alkyl group, a $C_3$-8 cyclo (hetero) alkenyl group, phenyl or $C_5$-6 heteroaryl group, wherein heteroatoms are selected from N, O and S. Further, two $R^1$ may form a ring, e.g., a 5- or 6-membered ring together with an N-atom bound thereto. $R^1$ may also comprise substituents such as halo, e.g., F, Cl, Br or I, O (halo) $C_1$-2 alkyl and—in the case of cyclic groups-(halo) $C_{1-2}$ alkyl. $M^+$ may be an inorganic or organic cation, e.g., an alkali metal cation or an ammonium or amine cation. $W_1$ may be O or S. Preferably, $W_1$ is O. $W_2$ may be O, S, NH or $NR_2$. Preferably, $W_2$ is O. $W_3$ may be O, S, NH, $NR_2$, $CH_2$, CHHal or $C(Hal)_2$. Preferably, $W_3$ is O, $CH_2$ or CF2. $R^2$ may be selected from groups as described for $R^1$ above. Hal may be F, Cl, Br or I. As noted above, according to an especially preferred embodiment $V_1$, $V_2$, $V_3$, $V_4$, $V_5$, $V_6$, $W_1$, $W_2$ and $W_3$ are O. Further suitable triphosphate analogs are described in the claims of WO 2009/060281.

Durbin et al. (Durbin et al., mBio 2016; 7 (5), 1-11) presented evidence that RNAs modified with one of the following nucleotides m6A, Ψ, mΨ, 5mC, 5moC, and 5hmC also do not activate RIG-I. Accordingly, in a preferred embodiment, the double-stranded polyribonucleotide of the present disclosure is made up of the ribonucleotides a, g, c, u, and optionally inosine only; in particular the polyribonucleotide does not contain m6A, Ψ, mΨ, 5mC, 5moC, and 5hmC.

On the other hand, the double-stranded polyribonucleotide of the present disclosure may comprise at least one synthetic or modified internucleoside linkage, in order to improve the stability of the double-stranded polyribonucleotide against degradation. Suitable synthetic or modified internucleoside linkages are phosphodiester, phosphorothioate, $N_3$ phosphoramidate, boranophosphate, 2,5-phosphodiester, amide-linked, phosphonoacetate (PACE), morpholino, peptide nucleic acid (PNA), or a mixture thereof, provided the linkage(s) do not compromise the type I IFN-inducing activity of the polyribonucleotide. In embodiments realized in the examples, the polyribonucleotide comprises phosphorothioate linkage(s). In such embodiments, the phosphorothioate linkage(s) are located (i) between position 1 and 2, and position 2 and 3 of the sense strand;
(ii) between position 22 and 23, and position 23 and 24 of the antisense strand;
(iii) between position 22 and 23, and position 23 and 24 of the sense strand; and/or (iv) between position 1 and 2, and position 2 and 3 of the antisense strand.

Phosphorothioate-modified compounds having a modification at a terminal end of the oligonucleotide are preferred. During phosphorothioate modification the non-binding oxygen atom of the bridging phosphate is substituted for a sulfur atom in the backbone of a nucleic acid. This substitution reduces the cleavability by nucleases at this position significantly and results in a higher stability of the nucleic acid strand.

The following sugar modifications are known in the field, and can be introduced into the polyribonucleotide, preferably outside the 24 base pairs formed by the 5'-end of the sense strand and the 3'-end of the antisense strand, using routine measures only: RNA, DNA, 2'-O-ME, 2'FRNA, 2'F-ANA, 4'S-RNA, UNA, LNA, 4'S-FANA, 2'-O-MOE, 2'-O-allyl, 2'-O-ethylamine, 2'-O-cyanoethyl, 2'-O-acetalester, 4'-C-aminomethyl-2'-O-methyl RNA, 2'-azido, MC, ONA, tcDNA, CeNA, ANA, HNA and 2',4' bridged ribosides such as, but not limited to methylene-cLNA, N-MeO-amino BNA, N-Me-aminooxy BNA, 2',4'-BNANC.

Additional modified nucleotides which may be suitably used are 2'-deoxy-2'-fluoro modified nucleotide, abasic nucleotide, 2'-amino-modified nucleotide, 2'-alkyl-modified nucleotide, and non-natural base comprising nucleotide.

Further provided is a method for producing a RIG-I agonist, comprising the step of (a) preparing a sense strand as defined herein above;
(b) preparing a fully complementary antisense strand as defined herein above; and
(c) annealing the sense strand with the antisense strand, thereby obtaining a RIG-I agonist.

In addition, the present disclosure provides a method for increasing the selectivity for RIGI of a RIG-I agonist, comprising the steps of:

(a) providing a double-stranded polyribonucleotide comprising a sense strand with 24 to 30 nucleotides in length and an antisense strand with 24 to 30 nucleotides in length, wherein the sense strand and the antisense strand form a fully complementary region of at least 24 base pairs with a blunt end at the 5'-end of the sense strand and the 3'-end of the anti-sense strand; and wherein the first 24 nucleotides at the 5'-end of the sense strand are ribonucleotides; and wherein the sense strand has no 2'-o-methyl modification at a ribonucleotide at a position selected from the group consisting of position number 1, 7, 8, 9, and 14, and wherein the last 24 nucleotides at 3'-end of the antisense strand are ribonucleotides and wherein the antisense strand has in its last 24 nucleotides no 2'-o-methyl modification at a ribonucleotide at a position selected from the group consisting of position 18, 20, and 23; wherein all positions are counted from 5' to 3';
(b) identifying whether the polyribonucleotide of step (a) comprises a purine ribonucleotide at a position selected from the group consisting of position number 12, 15, and 20 in the sense strand, and position number 3 and 10 of the antisense strand, and
(c) introducing at least one 2'-o-methyl modification at a purine ribonucleotide identified in step (b).

In embodiments, the double-stranded ribonucleotide provided in step (a) has a purine at a position selected from the group of positions consisting of position 12, 15, and 20 in the first 24 ribonucleotides at 5'-end of the sense strand, and position 3 in the last 24 ribonucleotides at the 3'-end of the antisense strand. The selectivity for RIG-I can be further increased by introducing a 2'-o-methyl modification at the ribonucleotide at position 22 in the last 24 ribonucleotides at the 3'-end of the antisense strand. As explained above, such a modification is believed to hamper the activation of TLR-8. Otherwise, the polyribonucleotide provided in step (a) may be further characterized as disclosed above with regard to the polyribonucleotide of the present disclosure.

Moreover, the present disclosure also provides a method for increasing the type I IFN response of a RIG-I agonist, comprising the steps of:

(a) providing a double-stranded polyribonucleotide comprising a sense strand with 24 to 30 nucleotides in length and an antisense strand with 24 to 30 nucleotides in length, wherein the sense strand and the antisense strand form a fully complementary region of at least 24 base pairs with a blunt end at the 5'-end of the sense strand and the 3'-end of the antisense strand; and wherein the first 24 nucleotides at the 5'-end of the sense strand are ribonucleotides; and wherein the sense strand has no 2'-fluorine modification at a ribonucleotide at a position selected from the group consisting of position number 1, 3, 8, and 14, and wherein the last 24 nucleotides at 3'-end of the antisense strand are ribonucleotides and wherein the antisense strand has in its last 24 nucleotides no 2'-fluorine modification at a ribonucleotide at a position selected from the group consisting of position 18 and 23; wherein all positions are counted from 5' to 3'; and
(b) introducing at least one 2'-fluorine modification at a ribonucleotide at a position selected from the group consisting of position number 2, 4, 6, 9, 10, 16, 21, 22, and 24 of the sense strand, and position number 5, and 13 of the last 24 ribonucleotides of the antisense strand; wherein all positions are counted from 5' to 3'.

In embodiments, the method further comprises the step of identifying whether the polyribonucleotide of step (a) comprises a pyrimidine ribonucleotide at position 10 at the 5'-end of the sense strand and introducing a 2'-fluorine modification at position 10 at the 5'-end of the sense strand where said ribonucleotide is a pyrimidine ribonucleotide. It thus follows that the additional step of identifying whether the polyribonucleotide of step (a) comprises a pyrimidine ribonucleotide at position 10 at the 5'-end of the sense strand is carried out after step (a) and prior to step (b).

Furthermore, also disclosed is a method for increasing the type I IFN response of a RIG-I agonist, comprising the steps of:

(a) providing a double-stranded polyribonucleotide comprising a sense strand with 24 nucleotides in length and an antisense strand with 26 nucleotides in length, wherein the sense strand and the antisense strand form a fully complementary region with a blunt end at the 5'-end of the sense strand and the 3'-end of the antisense strand, and wherein the antisense strand has an overhang of two adenine at the 5'-end; and wherein the first 24 nucleotides at the 5'-end of the sense strand are ribonucleotides; and wherein the sense strand has no 2'-fluorine modification at a ribonucleotide at a position selected from the group consisting of position number 1, 3, 8, and 14, and wherein the last 24 nucleotides at 3'-end of the antisense strand are ribonucleotides and wherein the antisense strand has in its last 24 nucleotides no 2'-fluorine modification at a ribonucleotide at a position selected from the group consisting of position 18 and 23; wherein all positions are counted from 5' to 3'; and (b) introducing a 2'-fluorine modification at a ribonucleotide at a position selected from the group consisting of position number 1, 2, or in both positions 1 and 2 of the last 24 ribonucleotides of the antisense strand; wherein all positions are counted from 5' to 3'.

Finally, the present disclosure provides a method for increasing the type I IFN response of a RIG-I agonist, comprising the steps of:

(a) providing a double-stranded polyribonucleotide comprising a sense strand with 24 nucleotides in length and an antisense strand with 24 nucleotides in length, wherein the sense strand and the antisense strand form a fully complementary region with two blunt ends; and wherein the nucleotides of the sense strand are ribonucleotides; and wherein the sense strand has no 2'-fluorine modification at a ribonucleotide at a position selected from the group consisting of position number 1, 3, 8, and 14, and wherein the nucleotides of the antisense strand are ribonucleotides and wherein the antisense strand has no 2'-fluorine modification at a ribonucleotide at a position selected from the group consisting of position 18 and 23; wherein all positions are counted from 5' to 3'; and (b) introducing an overhang of two adenine at the 5'-end of the antisense strand; and (c) introducing a 2'-fluorine modification at a ribonucleotide at a position selected from the group consisting of position number 1, 2, or in both positions 1 and 2 of the last 24 ribonucleotides of the antisense strand; wherein all positions are counted from 5' to 3'.

In the above methods for increasing the type I IFN response of a RIG-I agonist, the polyribonucleotide provided in step (a) may be further characterized as disclosed above with regard to the polyribonucleotide of the present disclosure.

Of course, the methods steps and embodiments of the method for increasing the selectivity for RIG-I of a RIG-I agonist may be combined with the method steps and embodiments for increasing the type I IFN response of a RIG-I agonist, thereby providing a method for improving a RIG-I agonist.

Various methods for producing polyribonucleotides are known in the art. Chemical synthesis is one such method of preparation. It is preferred that the synthesized polyribonucleotides are purified and quality-controlled such that the polyribonucleotide preparation contains essentially a homogenous population of oligonucleotides having essentially the same chemical identity (or chemical composition), including the same nucleotide sequence, backbone, modifications, length, and end structures. In particular, the respective single-stranded as well as the annealed doublestranded polyribonucleotides may exhibit a purity of at least 85%, preferably of at least 90%, more preferably of at least 91%, more preferably of at least 92%, more preferably of at least 93%, more preferably of at least 94%, more preferably of at least 95%, more preferably of at least 96%, more preferably of at least 97%, more preferably of at least 98%, and most preferably of at least 99%.

The polyribonucleotides can be purified by any standard methods in the art, such as capillary gel electrophoresis and HPLC. Synthetic polyribonucleotides, either single-stranded or double-stranded, obtained from most commercial sources contain 5' OH. These synthetic oligonucleotides can be modified at the 5' end to bear a 5' triphosphate by any appropriate methods known in the art. The preferred method for 5' triphosphate attachment is that developed by János Ludwig and Fritz Eckstein (J. Org. Chem., 1989, 54 (3): 631-635), or the method described on pages 4-14 and FIG. 1 in WO 2012/130886, or on pages 15-21 and in Examples 1-4 of WO 2014/049079.

Alternatively, in vitro transcription can be employed. However, in order to obtain the single strands to prepare the double-stranded polyribonucleotide by in vitro transcription, measures need to be taken to ensure that each intended in vitro transcribed single strand is indeed single-stranded. Aberrant transcripts may be generated in vitro using an RNA polymerase. For example, it is hypothesized that an RNA transcript generated by an RNA polymerase in vitro may fold back onto itself and prime RNA-dependent RNA synthesis, leading to the generation of aberrant transcripts of undefined and/or non-uniform lengths and sequences. Therefore, in principle, any measure that would prevent RNA synthesis primed by the RNA transcript itself can be employed.

For example, a single stranded polyribonucleotide is designed to have a sequence X1-X2-X3 . . . . Xm-2-Xm-1-Xm, wherein m is the length of the oligonucleotide, wherein the sequence has no or minimal self-complementarity, wherein X1, X2, X3, . . . , Xm are chosen from 1, 2 or 3 of the 4 conventional nucleotides A, U, C and G, wherein at least one of the nucleotides that are complementary to any of Xm-2, Xm-1, and Xm, i.e., Ym-2, Ym-1, and Ym, is not among the 1, 2, or 3 nucleotides chosen for X1, X2, X3, . . . , Xm.

An appropriate DNA template for generating such an ssRNA oligonucleotide can be generated using any appropriate methods known in the art. An in vitro transcription reaction is set up using the DNA template and a nucleotide mixture which does not contain the complementary nucleotide(s) which is (are) not comprised in X1-X2-X3 . . . . Xm-2-Xm-1-Xm. Any appropriate in vitro transcription conditions known in the art can be used. Due to the absence of the complementary nucleotide, no aberrant RNA-primed RNA synthesis can take place. As a result, a single-stranded population of X1-X2-X3 . . . Xm can be obtained. The resulting ssRNA preparation can be purified by any appropriate methods known in the art and an equal amount of two purified ssRNA preparations with complementary sequence can be annealed to obtain an essentially homogenous population of a double-stranded RNA oligonucleotide of desired sequence.

It is also possible to synthesize the two strands forming the double-stranded oligonucleotide using different methods. For example, one strand can be prepared by chemical synthesis and the other by in vitro transcription. Furthermore, if desired, an in vitro transcribed ssRNA can be treated with a phosphatase, such as calf intestine phosphatase (CIP), to remove the 5' tri-phosphate.

The polyribonucleotide may contain any naturally-occurring, synthetic, modified nucleotides, or a mixture thereof, in order to increase the stability and/or delivery and/or the selectivity for RIG-I, and/or other properties of the polyribonucleotide. In doing so, it is at the same time generally attempted to minimize a reduction in the type I IFN-inducing activity of the polyribonucleotide. The polyribonucleotide may contain any naturally-occurring, synthetic, modified internucleoside linkages, or a mixture thereof, as long as the linkages do not compromise the type I IFN-inducing activity of the polyribonucleotide. The 5' phosphate groups of the polyribonucleotide may be modified as long as the modification does not compromise the type I IFN-inducing activity of the oligonucleotide. For example, one or more of the oxygens (O) in the phosphate groups may be replaced with a sulfur(S); the triphosphate group may be modified with the addition of one or more phosphate group(s).

The oligonucleotide may be modified covalently or non-covalently to improve its chemical stability, resistance to nuclease degradation, ability to cross cellular and/or sub-cellular membranes, target (organ, tissue, cell type, subcellular compartment)-specificity, pharmacokinetic properties, biodistribution, reduce its toxic side effects, optimize its elimination or any combinations thereof. For example, phosphorothioate linkage(s) and/or pyrophosphate linkage(s) may be introduced to enhance the chemical stability and/or the nuclease resistance of an RNA oligonucleotide. In another example, the RNA oligonucleotide may be covalently linked to one or more lipophilic group(s) or molecule(s), such as a lipid or a lipid-based molecule, preferably, a cholesterol, folate, anandamide, tocopherol, palmitate, or a derivative thereof. The lipophilic group or molecule is preferably not attached to the blunt end bearing the 5' monophosphate, diphosphate, or triphosphate groups. Preferably, the modification does not compromise the type I IFN-inducing activity of the oligonucleotide. Alternatively, a reduction in the type I IFN-inducing activity of the oligonucleotide caused by the modification is off-set by an increase in the stability and/or delivery and/or other properties as described above.

The polyribonucleotide may comprise further terminal and/or internal modifications, e.g., cell specific targeting entities covalently attached thereto. Those entities may promote cellular or cell-specific uptake and include, for example vitamins, hormones, peptides, oligosaccharides and analogues thereof. Targeting entities may e.g., be attached to modified nucleotide or non-nucleotidic building blocks by methods known to the skilled person. For example, a targeting moiety as described on pages 5-9 in WO 2012/039602 may be attached to the non-phosphorylated 5'-end of the polyribonucleotide. Moreover, nanostructure scaffolds comprising cell targeting moieties as described in Brunner et al., (Angew Chem Int Ed Engl. 2015; 54 (6): 1946-1949) may be linked to the non-tri-phosphorylated end of the polyribonucleotide.

The double-stranded polyribonucleotide of the present invention is intended to function as an improved RIG-I agonist. RIG-I agonistic activity can be measured by quantitation of IFNα or IP10 levels in cell culture supernatant using the human IFN alpha matched antibody pairs ELISA (eBioscience, San Diego, CA, USA) or IP10 using the human matched antibody pairs ELISA respectively (BD Biosciences, Franklin Lakes, NJ, USA), or by IFNβ-mRNA detection via pPCR. Here, IFNα levels in cell culture supernatant of PBMCs treated with the RIG-I agonist are compared to IFNα levels in cell culture supernatant of a control, e.g., untreated cells or cells treated with an irrelevant polyribonucleotide for which is known that it does not induce type I IFN secretion. For the treatment with the RIG-I agonist, RNA is transfected into cells using Lipofectamine 2000 according to manufacturer's instructions (Invitrogen).

For example, human primary peripheral blood mononuclear cells (PBMCs) are isolated from fresh buffy coats obtained from healthy volunteers according to standard protocols (Schuberth-Wagner et al., Immunity 43 (1): 41-51 (2015), the content of which is incorporated herein by reference). PBMCs ($2.6\times10^6$ cells/ml) are seeded in 96-well plates and maintained in RPMI1640 supplemented with 10% FCS, 1.5 mM L-glutamine and 1×penicillin/streptomycin. PBMCs are then stimulated once with 5 nM of the RIG-I agonist and conditioned medium is collected after 17 hrs and measured for IFNα levels using the human IFN alpha matched antibody pairs ELISA (eBioscience, San Diego, CA, USA). In order to prevent endosomal TLR activation, PBMCs can be pre-treated with 5 μg/ml chloroquine (Sigma Aldrich) for at least 1 hr. A RIG-I agonist is capable of inducing at least 50 μg/ml IFNα, more preferably at least 100 μg/ml IFNα, even more preferably at least 150 μg/ml IFNα. In even more preferred embodiments, the RIG-I agonist is capable of inducing at least 200 μg/ml IFNα, more preferably at least 250 μg/ml IFNα, even more preferably at least 500 μg/ml, still more preferably at least 1000 μg/ml IFNα, and in a most preferred embodiment at least 2000 μg/ml IFNα.

In some embodiments, the RIG-I agonist has one blunt end which bears a 5' tri-phosphate and one end with a 5' or 3' overhang, wherein the 5' or 3' overhang is composed of deoxyribonucleotides and contains defined sequence motifs recognized by TLR9 as known in the field. In preferred embodiments, the 5' or 3' overhang of the RIG-I agonist comprises one or more unmethylated CpG dinucleotides. The RIG-I agonist may contain one or more of the same or different structural motif(s) or molecular signature(s) recognized by TLR3, TLR7, TLR8 and TLR9 as known in the field.

By "fully complementary", it is meant that the annealed double-stranded polyribonucleotide is not interrupted by any single-stranded structures. A polyribonucleotide section is fully complementary when the two strands forming the section have the same length and the sequences of the two strands are 100% complementary to each other. As established in the art, two nucleotides are said to be complementary to each other if they can form a base pair, either a Watson-Crick base pair (A-U, G-C) or a wobble base pair (U-G, U-A, I-A, I-U, I-C). Mismatch of one or two nucleotides may be tolerated in the double-stranded section of the polyribonucleotide in that the IFN-inducing activity of the polyribonucleotide is not significantly reduced. The mismatch is preferably at least 6 bp, more preferably at least 12 bp, even more preferably at least 18pb away from the 5'-end bearing the 5-mer sequence.

In one embodiment, the double-stranded RNA oligonucleotide contains one or more GU wobble base pairs instead of GC or UA base pairing. In a preferred embodiment, at least 1, 2, 3, 4, 5%, preferably at least 10, 15, 20, 25, 30%, more preferably at least 35, 40, 45, 50, 55, 60%, even more preferably at least 70, 80, or 90% of the adenosine (A), uracil (U) and/or guanosine (G) in the oligonucleotide is replaced with inosine (I).

The present disclosure further provides use of a polyribonucleotide of the present invention in the manufacture of a medicament for the treatment to induce an immune response and/or to induce RIG-I-dependent type I interferon production. In one embodiment, the disease or disorder to be treated is a cell proliferation disorder. In another embodiment, the cell proliferation disorder is cancer. In another embodiment, the cancer is brain cancer, leukemia, skin cancer, breast, prostate cancer, thyroid cancer, colon cancer, lung cancer, or sarcoma. In another embodiment, the cancer is glioma, glioblastoma multiforme, paraganglioma, supratentorial primordial neuroectodermal tumors, acute myeloid leukemia, myelodysplastic syndrome, chronic myelogenous leukemia, melanoma, breast, prostate, thyroid, colon, lung, central chondrosarcoma, central and periosteal chondroma tumors, fibrosarcoma, and/or cholangiocarcinoma.

Pharmaceutical Composition

A further aspect of the present invention relates to a pharmaceutical composition comprisesing a RIG-I agonist of the present disclosure. The pharmaceutical composition described herein further comprises a pharmaceutically acceptable carrier.

The pharmaceutical composition may be formulated in any way that is compatible with its therapeutic application, including intended route of administration, delivery format and desired dosage. Optimal pharmaceutical compositions may be formulated by a skilled person according to common general knowledge in the art, such as that described in Remington's Pharmaceutical Sciences (18th Ed., Gennaro A R ed., Mack Publishing Company, 1990).

The pharmaceutical composition may be formulated for instant release, controlled release, timed-release, sustained release, extended release, or continuous release.

The pharmaceutical composition may be administered by any route known in the art, including, but not limited to, topical, enteral and parenteral routes, provided that it is compatible with the intended application. Topic administration includes, but is not limited to, epicutaneous, inhalational, intranasal, vaginal administration, enema, eye drops, and ear drops. Enteral administration includes, but is not limited to, oral, rectal administration and administration through feeding tubes. Parenteral administration includes, but is not limited to, intravenous, intraarterial, intramuscular, intracardiac, subcutaneous, intraosseous, intradermal, intrathecal, intraperitoneal, transdermal, transmucosal, intratumoral, and inhalational administration.

In a preferred embodiment, the RIG-I agonist or pharmaceutical composition of the present disclosure is for local (e.g., mucosa, skin) applications, such as in the form of a spray (i.e., aerosol) preparation. In another preferred embodiment, the RIG-I agonist or pharmaceutical composition of the present disclosure is for intratumoral administration in the treatment of visceral tumors. The pharmaceutical composition may, for example, be formulated for intravenous or subcutaneous administration, and therefore preferably comprises an aqueous basis (buffers, isotonic solutions etc.), one or more stabilizer, one or more cryoprotective, one or more bulking agent, one or more excipient like salt, sugar, sugar alcohol, one or more tonicity agent, and if needed one or more preserving agent. The pharmaceutical composition may also comprise one or more transfection reagent, which enables an effective and protected transport of the RIG-I agonist into the cytosol of the cell where the RIG-I receptor is located. Transfection or complexation reagents are also referred to as "carrier" or "delivery vehicle" in the art.

Buffer solutions are aqueous solutions of a mixture of a weak acid and its conjugate base, or vice versa. This buffer solution only causes slight pH changes when a small amount of a strong acid or base is added to the system. Buffer solutions are used as a means of keeping pH at a nearly constant value in a wide variety of chemical applications. Buffers used for a drug product formulation mainly contain liquids and substances that are listed in the Pharmacopoeia and which are non-toxic to the cell or mammal being exposed to at the dosages and concentrations employed. These buffer systems are also called "biological buffers" and often include, but are not limited to, substances like maleic-, phosphoric-, lactic-, malic-, citric-, succinic-, acetic-, formic-, pivalic-, boric- and picolinic acid; sodium acetate; sodium chloride; potassium chloride; acetone; ammonium sulfate; ammonium acetate; copper sulfate; phthalate; pyridine; piperazine; histidine; MES; Tris; HEPES; imidazole; MOPS; BES; DIPSO; TAPSO; TEA; glycine; ethanolamine; CAPSO; and piperidine.

Besides buffer systems also other solutions/liquids which are common for pharmaceutical use are also used for the formulation of the RIG-I agonist, e.g., sodium chloride (NaCl 0.9%), Glucose 5%, phosphate buffered saline, (Krebs-) Ringer solution or water for Injections (WFI). With regard to the pharmaceutical composition of the present disclosure, a trehalose based Trisphosphate buffer is preferred. Trehalose or other sugars or sugar alcohols like sucrose are very often used as cryoprotectants, especially if the final drug product is desired as a lyophilized formulation.

Moreover, anti-oxidants including ascorbic acid, low molecular weight (less than about 10 residues) polypeptides; proteins such as serum albumin, gelatine or immunoglobulins; hydrophilic polymers such as polyvinylpyrrolidone, amino acids such as glycine, glutamine, asparagine, arginine or lysine; monosaccharides, disaccharides and other carbohydrates including glucose, mannose or dextrin, gelating agents such as EDTA, sugar, alcohols such as mannitol or sorbitol; saltforming counterions such as sodium; and/or non-ionic surfactants such as TWEEN, polyethylene or polyethylene glycol are also often included to improve stability of final pharmaceutical composition.

The delivery vehicle in an oligonucleotide-based drug product formulation is a complexation reagent which forms a complex with the oligonucleotide and facilitates the delivery of the oligonucleotide into the cells.

Any delivery vehicle which is compatible with the intended use of the pharmaceutical composition can be employed. Examples of complexation reagents include a wide range of different polymers (branched and linear), liposomes, lipids, peptides and biodegradable microspheres. According to an especially preferred embodiment the compound of the invention is dissolved in sterile deionized water before it is complexed to a linear polyethylenimine or derivative (e.g., in vivojetPEI™ (PolyPlus)) which leads to a formation of polyplexes that facilitate the transfer and the uptake of the oligonucleotide into the cells. Other polymers like dendrimers, branched polymers, viromers or other modified polymers are also possible carrier systems for a RIG-I targeting oligonucleotide. Besides polymers also lipid-based transfection reagents are able to complex or encapsulate the oligonucleotide. This group of delivery vehicles include neutral or mono- and polycationic lipids, lipid nanoparticles (LNP), liposomes, virosomes, stable-nucleic-acid-lipid particles (SNALPs), SICOMATRIX® (CSL Limited), poly (D,L-lactide-co-glycoliic acid PLGA) and also modified lipid reagents. Furthermore, also polycationic peptides like poly-L-Lysine, poly-L-Arginine or protamine do have the ability to delivery oligonucleotides into cells.

In addition to being delivered by a delivery agent, the oligonucleotide and/or the pharmaceutical composition can be delivered into cells via physical means such as electroporation, shock wave administration, ultrasound triggered transfection, and gene gun delivery with gold particles.

The pharmaceutical composition may further comprise another reagent such as a reagent that only stabilizes the oligonucleotide. Examples of a stabilizing reagent include a protein that complexes with the oligonucleotide to form an iRNP, chelators such as EDTA, salts, and RNase inhibitors.

In another embodiment, the delivery agent is a virus, preferably a replication-deficient virus. The oligonucleotide to be delivered is contained in the viral capsule and the virus may be selected based on its target specificity. Examples of useful viruses include polymyxoviruses which target upper respiratory tract epithelia and other cells, hepatitis B virus which targets liver cells, influenza virus which targets epithelial cells and other cells, adenoviruses which targets a number of different cell types, papilloma viruses which targets epithelial and squamous cells, herpes virus which targets neurons, retroviruses such as HIV which targets $CD4^+$ T cells, dendritic cells and other cells, modified Vaccinia Ankara which targets a variety of cells, and oncolytic viruses which target tumor cells. Examples of oncolytic viruses include naturally occurring wild-type Newcastle disease virus, attenuated strains of reovirus, vesicular stomatitis virus (VSV), and genetically engineered mutants of herpes simplex virus type 1 (HSV-1), adenovirus, poxvirus and measles virus.

In another embodiment the delivery agent is a virus like particle. In a further preferred embodiment, the virus-like particle is a recombinant virus-like particle. Also preferred, the virus-like particle is free of a lipoprotein envelope. Preferably, the recombinant virus-like particle comprises, or alternatively consists of, recombinant proteins of Hepatitis B virus, measles virus, Sindbis virus, Rotavirus, Foot-and-Mouth-Disease virus, Retrovirus, Norwalk virus or human Papilloma virus, RNA-phages, Qβ-phage, GA-phage, fr-phage, AP205-phage and Ty.

In addition to being delivered by a delivery agent, the oligonucleotide and/or the pharmaceutical composition can be delivered into cells via physical means such as electroporation, shock wave administration, ultrasound triggered transfection, and gene gun delivery with gold particles.

The present disclosure further provides a pharmaceutical composition comprising at least one polyribonucleotide of the present invention and a pharmaceutically acceptable carrier for use in a therapy. The composition may be useful in a method of inducing an immune response and/or inducing RIG-I-dependent type I interferon production in a subject, such as a mammal in need of such inhibition, comprising administering an effective amount of the compound to the subject.

Non-limiting examples of uses for the double-stranded polyribonucleotide or pharmaceutical composition of the present invention include prevention and/or treatment of any disease, disorder, or condition in which inducing IFN production would be beneficial. For example, increased IFN production, by way of the nucleic acid molecule of the invention, may be beneficial to prevent or treat a wide variety of disorders, including, but not limited to, bacterial infection, viral infection, parasitic infection, immune disorders, respiratory disorders, cancer and the like.

Infections include, but are not limited to, viral infections, bacterial infections, anthrax, parasitic infections, fungal infections and prion infection.

Viral infections include, but are not limited to, infections by hepatitis C, hepatitis B, influenza virus, herpes simplex virus (HSV), human immunodeficiency virus (HIV), respiratory syncytial virus (RSV), vesicular stomatitis virus (VSV), cytomegalovirus (CMV), poliovirus, encephalomyocarditis virus (EMCV), human papillomavirus (HPV) and smallpox virus. In one embodiment, the infection is an upper respiratory tract infection caused by viruses and/or bacteria, in particular, flu, more specifically, bird flu.

Bacterial infections include, but are not limited to, infections by streptococci, staphylococci, *E. coli*, and *Pseudomonas*. In one embodiment, the bacterial infection is an intracellular bacterial infection which is an infection by an intracellular bacterium such as mycobacteria (tuberculosis), *chlamydia, mycoplasma, listeria*, and a facultative intracellular bacterium such as *Staphylococcus aureus*.

Parasitic infections include, but are not limited to, worm infections, in particular, intestinal worm infection, microeukaryotes, and vector-borne diseases, including for example Leishmaniasis.

In a preferred embodiment, the infection is a viral infection or an intracellular bacterial infection. In a more preferred embodiment, the infection is a viral infection by hepatitis C, hepatitis B, influenza virus, RSV, HPV, HSV1, HSV2, and CMV.

Immune disorders include, but are not limited to, allergies, autoimmune disorders, and immunodeficiencies.

Allergies include, but are not limited to, respiratory allergies, contact allergies and food allergies.

Autoimmune diseases or disorders include, but are not limited to, multiple sclerosis, diabetes mellitus, arthritis (including rheumatoid arthritis, juvenile rheumatoid arthritis, osteoarthritis, psoriatic arthritis), encephalomyelitis, myasthenia gravis, systemic lupus erythematosus, autoimmune thyroiditis, dermatitis (including atopic dermatitis and eczematous dermatitis), psoriasis, Sjogren's Syndrome, Crohn's Disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis.

Immunodeficiencies include, but are not limited to, spontaneous immunodeficiency, acquired immunodeficiency (including AIDS), drug-induced immunodeficiency or immunosuppression (such as that induced by immunosuppressants used in transplantation and chemotherapeutic agents used for treating cancer), and immunosuppression caused by chronic hemodialysis, trauma or surgical procedures.

Respiratory disorders include, but are not limited to, acute lung injury (ALI), acute respiratory distress syndrome (ARDS), asthma, chronic obstructive pulmonary disease (COPD), obstructive sleep apnea (OSA), idiopathic pulmonary fibrosis (IPF), tuberculosis, pulmonary hypertension, pleural effusion, and lung cancer.

Examples of cancers include, but are not limited to, Acute Lymphoblastic Leukemia; Acute Myeloid Leukemia; Adrenocortical Carcinoma; AIDS-Related Lymphoma; AIDS-Related Malignancies; Anal Cancer; Astrocytoma; Bile Duct Cancer; Bladder Cancer; Bone Cancer, Osteosarcoma/Malignant Fibrous Histiocytoma; Brain Stem Glioma; Brain Tumor, Cerebellar Astrocytoma; Brain Tumor, Cerebral Astrocytoma/Malignant Glioma; Brain Tumor, Ependymoma; Brain Tumor, Medulloblastoma; Brain Tumor, Supratentorial Primitive Neuroectodermal Tumors; Brain Tumor, Visual Pathway and Hypothalamic Glioma;

Breast Cancer; Bronchial Adenomas/Carcinoids; Carcinoid Tumor; Carcinoid Tumor, Gastrointestinal; Carcinoma, Adrenocortical; Carcinoma, Islet Cell; Central Nervous System Lymphoma, Primary; Cerebral Astrocytoma/Malignant Glioma; Cervical Cancer; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer; Cutaneous T-Cell Lymphoma; Endometrial Cancer; Ependymoma; Epithelial Cancer, Ovarian; Esophageal Cancer; Esophageal Cancer; Ewing's Family of Tumors; Extracranial Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer; Hodgkin's Lymphoma; Hypopharyngeal Cancer; Hypothalamic and Visual Pathway Glioma; Intraocular Melanoma; Islet Cell Carcinoma (Endocrine Pancreas); Kaposi's Sarcoma; Kidney Cancer; Laryngeal Cancer; Leukemia, Acute Lymphoblastic; Leukemia, Acute Myeloid; Leukemia, Chronic Lymphocytic; Leukemia, Chronic Myelogenous; Leukemia, Hairy Cell; Lip and Oral Cavity Cancer; Liver Cancer; Lung Cancer, Non-Small Cell; Lung Cancer, Small Cell; Lymphoblastic Leukemia; Lymphoma, AIDS-Related; Lymphoma, Central Nervous System (Primary); Lymphoma, Cutaneous T-Cell; Lymphoma, Hodgkin's; Lymphoma, Hodgkin's During Pregnancy; Lymphoma, Non-Hodgkin's; Lymphoma, Primary Central Nervous System; Macroglobulinemia, Waldenstrom's; Male Breast Cancer; Malignant Mesothelioma; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia; Myeloma, Multiple; Myeloproliferative Disorders, Chronic; Nasal Cavity and Paranasal Sinus Cancer; Nasopharyngeal Cancer; Neuroblastoma; Non-Hodgkin's Lymphoma; Non-Small Cell Lung Cancer; Oral Cancer; Oral Cavity and Lip Cancer; Oropharyngeal Cancer; steosarcoma/Malignant Fibrous Histiocytoma of Bone; Ovarian Epithelial Cancer; Ovarian Germ Cell Tumor; Ovarian Low Malignant Potential Tumor; Pancreatic Cancer; Paranasal Sinus and Nasal Cavity Cancer; Parathyroid Cancer; Penile Cancer; Pheochromocytoma; Pineal and Supratentorial Primitive Neuroectodermal Tumors; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer; Prostate Cancer; Rectal Cancer; Renal Cell (Kidney) Cancer; Renal Pelvis and Ureter, Transitional Cell Cancer; Retinoblastoma; Rhabdomyosarcoma; Salivary Gland Cancer; Sarcoma, Ewing's Family of Tumors; Sarcoma, Kaposi's; Sarcoma (Osteosarcoma)/Malignant Fibrous Histiocytoma of Bone; Sarcoma, Soft Tissue; Sezary Syndrome; Skin Cancer; Skin Cancer (Melanoma); Skin Carcinoma, Merkel Cell; Small Cell Lung Cancer; Small Intestine Cancer; Soft Tissue Sarcoma; Squamous Neck Cancer with Occult Primary, Metastatic; Stomach (Gastric) Cancer; Supratentorial Primitive Neuroectodermal Tumors; T-Cell Lymphoma, Cutaneous; Testicular Cancer; Thymoma, Malignant; Thyroid Cancer; Transitional Cell Cancer of the Renal Pelvis and Ureter; Trophoblastic Tumor, Gestational; Ureter and Renal Pelvis, Transitional Cell Cancer; Urethral Cancer; Uterine Sarcoma; Vaginal Cancer; Visual Pathway and Hypothalamic Glioma; Vulvar Cancer; Waldenstrom's Macro globulinemia; and Wilms' Tumor.

In one embodiment, the cancer is brain cancer, such as an astrocytic tumor (e.g., pilocytic astrocytoma, subependymal giant-cell astrocytoma, diffuse astrocytoma, pleomorphic xanthoastrocytoma, anaplastic astrocytoma, astrocytoma, giant cell glioblastoma, glioblastoma, secondary glioblastoma, primary adult glioblastoma, and primary pediatric glioblastoma); oligodendroglial tumor (e.g., oligodendroglioma, and anaplastic oligodendroglioma); oligoastrocytic tumor (e.g., oligoastrocytoma, and anaplastic oligoastrocytoma); ependymoma (e.g., myxopapillary ependymoma, and anaplastic ependymoma); medulloblastoma; primitive neuroectodermal tumor, schwannoma, meningioma, meatypical meningioma, anaplastic meningioma; and pituitary adenoma. In another embodiment, the brain cancer is glioma, glioblastoma multiforme, paraganglioma, or suprantentorial primordial neuroectodermal tumors (sPNET).

In another embodiment, the cancer is leukemia, such as acute myeloid leukemia (AML), myelodysplastic syndrome (MDS), chronic myelogenous leukemia (CML), myeloproliferative neoplasm (MPN), post-MPN AML, post-MDS AML, del (5q)-associated high risk MDS or AML, blast-phase chronic myelogenous leukemia, angioimmunoblastic lymphoma, and acute lymphoblastic leukemia.

In one embodiment, the cancer is skin cancer, including melanoma. In another embodiment, the cancer is prostate cancer, breast cancer, thyroid cancer, colon cancer, or lung cancer. In another embodiment, the cancer is sarcoma, including central chondrosarcoma, central and periosteal chondroma, and fibrosarcoma. In another embodiment, the cancer is cholangiocarcinoma.

In certain embodiments, the pharmaceutical composition further comprises one or more pharmaceutically active therapeutic agent(s). Alternatively, the RIG-I agonist or the pharmaceutical composition of the present disclosure are for use in a combination treatment with one or more pharmaceutically active therapeutic agent(s).

The pharmaceutical composition of the present disclosure may be administered in combination with one or more additional therapeutic agents. In embodiments, one or more pharmaceutical compositions of the present disclosure may be co-administered. The additional therapeutic agent(s) may be administered in a single dosage form with the pharmaceutical composition of the present disclosure, or the additional therapeutic agent(s) may be administered in separate dosage form(s) from the dosage form containing the pharmaceutical composition of the present disclosure. The additional therapeutic agent(s) may be one or more agents selected from the group consisting of anti-viral compounds, antigens, adjuvants, anti-cancer agents, CTLA-4, LAG-3 and PD-1 pathway antagonists, lipids, peptides, chemotherapeutic agents, immunomodulatory cell lines, checkpoint inhibitors, vascular endothelial growth factor (VEGF) receptor inhibitors, topoisomerase II inhibitors, smoothen inhibitors, alkylating agents, anti-tumor antibiotics, anti-metabolites, retinoids, and immunomodulatory agents including but not limited to anti-cancer vaccines. It will be understood the descriptions of the above additional therapeutic agents may be overlapping. It will also be understood that the treatment combinations are subject to optimization, and it is understood that the best combination to use of the pharmaceutical composition of the present disclosure and one or more additional therapeutic agents will be determined based on the individual patient needs.

A compound disclosed herein may be used in combination with one or more other active agents, including but not limited to, other anti-cancer agents that are used in the prevention, treatment, control, amelioration, or reduction of risk of a particular disease or condition (e.g., cell proliferation disorders). In one embodiment, a pharmaceutical composition of the present disclosure is combined with one or more other anti-cancer agents for use in the prevention, treatment, control amelioration, or reduction of risk of a particular disease or condition for which the compounds disclosed herein are useful. Such other active agents may be administered, by a route and in an amount commonly used therefor, contemporaneously or sequentially with a compound of the present disclosure.

When a pharmaceutical composition of the present disclosure is used contemporaneously with one or more other active agents, a composition containing such other active agents in addition to the compound disclosed herein is contemplated. Accordingly, the compositions of the present disclosure include those that also contain one or more other active ingredients, in addition to a compound disclosed herein. A compound disclosed herein may be administered either simultaneously with, or before or after, one or more other therapeutic agent(s). A compound disclosed herein may be administered separately, by the same or different route of administration, or together in the same pharmaceutical composition as the other agent(s).

Products provided as a combined preparation include a composition comprising a pharmaceutical composition of the present disclosure and one or more other active agent(s) together in the same pharmaceutical composition, or a pharmaceutical composition of the present disclosure and one or more other therapeutic agent(s) in separate form, e.g., in the form of a kit.

The weight ratio of a compound disclosed herein to a second active agent may be varied and will depend upon the effective dose of each agent. Generally, an effective dose of each will be used. Thus, for example, when a compound disclosed herein is combined with another agent, the weight ratio of the compound disclosed herein to the other agent will generally range from about 1000:1 to about 1:1000, such as about 200:1 to about 1:200. Combinations of a compound disclosed herein and other active agents will generally also be within the aforementioned range, but in each case, an effective dose of each active agent should be used. In such combinations, the compound disclosed herein and other active agents may be administered separately or in conjunction. In addition, the administration of one element may be prior to, concurrent to, or subsequent to the administration of other agent(s).

In one embodiment, this disclosure provides a composition comprising a pharmaceutical composition of the present disclosure and at least one other therapeutic agent as a combined preparation for simultaneous, separate or sequential use in therapy. In one embodiment, the therapy is the treatment of a cell proliferation disorder, such as cancer.

In one embodiment, the disclosure provides a kit comprising two or more separate pharmaceutical compositions, at least one of which contains a pharmaceutical composition of the present disclosure. In one embodiment, the kit comprises means for separately retaining said compositions, such as a container, divided bottle, or divided foil packet. An example of such a kit is a blister pack, as typically used for the packaging of tablets, capsules, and the like.

A kit of this disclosure may be used for administration of different dosage forms, for example, oral and parenteral, for administration of the separate compositions at different dosage intervals, or for titration of the separate compositions against one another. To assist with compliance, a kit of the disclosure typically comprises directions for administration.

Disclosed herein is a use of a pharmaceutical composition of the present disclosure for treating a cell proliferation disorder, wherein the medicament is prepared for administration with another active agent. The disclosure also provides the use of another active agent for treating a cell proliferation disorder, wherein the medicament is administered with a pharmaceutical composition of the present disclosure.

The disclosure also provides the use of a pharmaceutical composition of the present disclosure for treating a cell proliferation disorder, wherein the patient has previously (e.g., within 24 hours) been treated with another active agent. The disclosure also provides the use of another therapeutic agent for treating a cell proliferation disorder, wherein the patient has previously (e.g., within 24 hours) been treated with a pharmaceutical composition of the present disclosure. The second agent may be applied a week, several weeks, a month, or several months after the administration of a compound disclosed herein.

Anti-viral compounds that may be used in combination with the pharmaceutical composition of the present disclosure include hepatitis B virus (HBV) inhibitors, hepatitis C virus (HCV) protease inhibitors, HCV polymerase inhibitors, HCV NS4A inhibitors, HCV NS5A inhibitors, HCV NS5b inhibitors, and human immunodeficiency virus (HIV) inhibitors.

Antigens and adjuvants that may be used in combination with the pharmaceutical composition of the present disclosure include B7 costimulatory molecule, interleukin-2, interferon-y, GM-CSF, CTLA-4 antagonists, OX-40/OX-40 ligand, CD40/CD40 ligand, sargramostim, levamisol, vaccinia virus, Bacille Calmette-Guerin (BCG), liposomes, alum, Freund's complete or incomplete adjuvant, detoxified endotoxins, mineral oils, surface active substances such as lipolecithin, pluronic polyols, polyanions, peptides, and oil or hydrocarbon emulsions. Adjuvants, such as aluminum hydroxide or aluminum phosphate, can be added to increase the ability of the compound to trigger, enhance, or prolong an immune response. Additional materials, such as cytokines, chemokines, and bacterial nucleic acid sequences, like CpG, a toll-like receptor $(TLR)_9$ agonist as well as additional agonists for TLR 2, TLR 4, TLR 5, TLR 7, TLR 8, TLR9, including lipoprotein, LPS, monophosphoryl lipid A, lipoteichoic acid, imiquimod, resiquimod, stimulator of interferon genes (STING) agonists and in addition retinoic acid-inducible gene I (RIG-I) agonists such as poly I: C, used separately or in combination with the described compositions are also potential adjuvants.

CLTA-4 and PD-1 pathways are important negative regulators of immune response. Activated T-cells upregulate CTLA-4, which binds on antigen-presenting cells and inhibits T-cell stimulation, IL-2 gene expression, and T-cell proliferation; these anti-tumor effects have been observed in mouse models of colon carcinoma, metastatic prostate cancer, and metastatic melanoma. PD-1 binds to active T-cells and suppresses T-cell activation; PD-1 antagonists have demonstrated anti-tumor effects as well. CTLA-4 and PD-1 pathway antagonists that may be used in combination with the pharmaceutical composition of the present disclosure include ipilimumab, tremelimumab, nivolumab, pembrolizumab, CT-011, AMP-224, and MDX-1106.

"PD-1 antagonist" or "PD-1 pathway antagonist" means any chemical compound or biological molecule that blocks binding of PD-L1 expressed on a cancer cell to PD-1 expressed on an immune cell (T-cell, B-cell, or NKT-cell) and preferably also blocks binding of PD-L2 expressed on a cancer cell to the immune-cell expressed PD-1. Alternative names or synonyms for PD-1 and its ligands include: PDCD1, PD1, CD279, and SLEB2 for PD-1; PDCDIL1, PDL1, B7H1, B7-4, CD274, and B7-H for PD-L1; and PDCD1L2, PDL2, B7-DC, Btdc, and CD273 for PD-L2. In any of the treatment method, medicaments and uses of the present disclosure in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP 005009. Human PD-L1 and PD-L2 amino acid sequences can be found in NCBI Locus No.: NP 054862 and NP_079515, respectively.

PD-1 antagonists useful in any of the treatment method, medicaments and uses of the present disclosure include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody, or a chimeric antibody and may include a human constant region. In some embodiments, the human constant region is selected from the group consisting of IgG1, IgG2, IgG3, and IgG4 constant regions, and in preferred embodiments, the human constant region is an IgG1 or IgG4 constant region. In some embodiments, the antigen binding fragment is selected from the group consisting of Fab, Fab'-SH, $F(ab')_2$, scFv, and Fv fragments.

Examples of mAbs that bind to human PD-1, and useful in the treatment method, *medica*ments and uses of the present disclosure, are described in U.S. Pat. Nos. U.S. Pat. Nos. 7,488,802, 7,521,051, 8,008,449, 8,354,509, and 8,168,757, PCT International Patent Application Publication Nos. WO2004/004771, WO2004/072286, and WO2004/056875, and U.S. Patent Application Publication No. US2011/0271358.

Examples of mAbs that bind to human PD-L1, and useful in the treatment method, *medica*ments and uses of the present disclosure, are described in PCT International Patent Application Nos. WO2013/019906 and WO2010/077634 A1 and in U.S. Patent No. U.S. Pat. No. 8,383,796. Specific antihuman PD-L1 mAbs useful as the PD-1 antagonist in the treatment method, medicaments and uses of the present disclosure include MPDL3280A, BMS-936559, MEDI4736, MSB0010718C, and an antibody that comprises the heavy chain and light chain variable regions of SEQ ID NO:24 and SEQ ID NO:21, respectively, of WO2013/019906.

Other PD-1 antagonists useful in any of the treatment method, medicaments, and uses of the present disclosure include an immune-adhesion that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immune-adhesion molecules that specifically bind to PD-1 are described in PCT International Patent Application Publication Nos. WO2010/027827 and WO2011/066342. Specific fusion proteins useful as the PD-1 antagonist in the treatment method, medicaments, and uses of the present disclosure include AMP-224 (also known as B7-DCIg), which is a PD-L2-FC fusion protein and binds to human PD-1.

Thus, the invention further relates to a method of treating cancer in a human patient comprising administration of a pharmaceutical composition of the present disclosure and a PD-1 antagonist to the patient. The compound of the invention and the PD-1 antagonist may be administered concurrently or sequentially.

In particular embodiments, the PD-1 antagonist is an anti-PD-1 antibody, or antigen binding fragment thereof. In alternative embodiments, the PD-1 antagonist is an anti-PD-L1 antibody, or antigen binding fragment thereof. In some embodiments, the PD-1 antagonist is pembrolizumab (KEYTRUDA™, Merck & Co., Inc., Kenilworth, NJ, USA), nivolumab (OPDIVO™, Bristol-Myers Squibb Company, Princeton, NJ, USA), cemiplimab (LIBTAYO™, Regeneron Pharmaceuticals, Inc., Tarrytown, NY, USA), atezolizumab (TECENTRIQ™, Genentech, San Francisco, CA, USA), durvalumab (IMFINZI™, AstraZeneca Pharmaceuticals LP, Wilmington, DE), or avelumab (BAVENCIO™, Merck KGaA, Darmstadt, Germany).

In some embodiments, the PD-1 antagonist is pembrolizumab. In particular sub-embodiments, the method comprises administering 200 mg of pembrolizumab to the patient about every three weeks. In other sub-embodiments, the method comprises administering 400 mg of pembrolizumab to the patient about every six weeks.

In further sub-embodiments, the method comprises administering 2 mg/kg of pembrolizumab to the patient about every three weeks. In particular sub-embodiments, the patient is a pediatric patient.

In some embodiments, the PD-1 antagonist is nivolumab. In particular sub-embodiments, the method comprises administering 240 mg of nivolumab to the patient about every two weeks. In other sub-embodiments, the method comprises administering 480 mg of nivolumab to the patient about every four weeks.

In some embodiments, the PD-1 antagonist is cemiplimab. In particular embodiments, the method comprises administering 350 mg of cemiplimab to the patient about every 3 weeks.

In some embodiments, the PD-1 antagonist is atezolizumab. In particular sub-embodiments, the method comprises administering 1200 mg of atezolizumab to the patient about every three weeks.

In some embodiments, the PD-1 antagonist is durvalumab. In particular sub-embodiments, the method comprises administering 10 mg/kg of durvalumab to the patient about every two weeks.

In some embodiments, the PD-1 antagonist is avelumab. In particular sub-embodiments, the method comprises administering 800 mg of avelumab to the patient about every two weeks.

Examples of other cytotoxic agents include, but are not limited to, arsenic trioxide (sold under the tradename TRISENOX®), asparaginase (also known as L-asparaginase, and *Erwinia* Lasparaginase, sold under the tradenames ELSPAR® and KIDROLASE®).

Chemotherapeutic agents that may be used in combination with the pharmaceutical composition of the present disclosure include abiraterone acetate, altretamine, anhydrovinblastine, auristatin, bexarotene, bicalutamide, BMS 184476, 2,3,4,5,6-pentafluoro-N-(3-fluoro-4-methoxyphenyl)benzene sulfonamide, bleomycin, N,N-dimethyl-L-valyl-L-valyl-N-methyl-Lvalyl-L-proly-1-Lproline-tbutylamide, cachectin, cemadotin, chlorambucil, cyclophosphamide, 3',4'-didehydro-4'deoxy-8'-norvincaleukoblastine, docetaxol, doxetaxel, cyclophosphamide, carboplatin, carmustine, cisplatin, cryptophycin, cyclophosphamide, cytarabine, dacarbazine (DTIC), dactinomycin, daunorubicin, decitabine dolastatin, doxorubicin (adriamycin), etoposide, 5-fluorouracil, finasteride, flutamide, hydroxyurea and hydroxyureataxanes, ifosfamide, liarozole, lonidamine, lomustine (CCNU), MDV3100, mechlorethamine (nitrogen mustard), melphalan, mivobulin isethionate, rhizoxin, sertenef, streptozocin, mitomycin, methotrexate, taxanes, nilutamide, nivolumab, onapristone, paclitaxel, pembrolizumab, prednimustine, procarbazine, RPR109881, stramustine phosphate, tamoxifen, tasonermin, taxol, tretinoin, vinblastine, vincristine, vindesine sulfate, and vinflunine.

Examples of vascular endothelial growth factor (VEGF) receptor inhibitors include, but are not limited to, bevacizumab (sold under the trademark AVASTIN by Genentech/Roche), axitinib (described in PCT International Patent Publication No. WO01/002369), Brivanib Alaninate ((S)((R)-1-(4-(4-fluoro-2-methyl-1H-indol-5-yloxy)-5-methylpyrrolo[2,1-f][1,2,4]triazin-6-yloxy) propan-2-yl)$_2$-aminopropanoate, also known as BMS-582664), motesanib (N-(2,3-dihydro3,3-dimethyl-1H-indol-6-yl)-2-[(4-pyridinylmethyl)amino]-3-pyridinecarboxamide, and described in PCT International Patent Application Publication No. WO02/068470), pasireotide (also known as SO 230, and described in PCT International Patent Publication No. WO02/010192), and sorafenib (sold under the tradename NEXAVAR).

Examples of topoisomerase II inhibitors include, but are not limited to, etoposide (also known as VP-16 and Etoposide phosphate, sold under the tradenames TOPOSAR, VEPESID, and ETOPOPHOS), and teniposide (also known as VM-26, sold under the tradename VUMON).

Examples of alkylating agents, include but are not limited to, 5-azacytidine (sold under the trade name VIDAZA), decitabine (sold under the trade name of DECOGEN), temozolomide (sold under the trade names TEMODAR and TEMODAL by Schering-Plough/Merck), dactinomycin (also known as actinomycin-D and sold under the tradename COSMEGEN), melphalan (also known as L-PAM, L-sarcolysin, and phenylalanine mustard, sold under the tradename ALKERAN), altretamine (also known as hexamethylmelamine (HMM), sold under the tradename HEXALEN), carmustine (sold under the tradename BCNU), bendamustine (sold under the tradename TREANDA), busulfan (sold under the tradenames BUSULFEX® and MYLERAN®), carboplatin (sold under the tradename PARAPLATIN®), lomustine (also known as CCNU, sold under the tradename CEENU®), cisplatin (also known as CDDP, sold under the tradenames PLATINOL® and PLATINOL®-AQ), chlorambucil (sold under the tradename LEUKERAN®), cyclophosphamide (sold under the tradenames CYTOXAN® and NEOSAR®), dacarbazine (also known as DTIC, DIC and imidazole carboxamide, sold under the tradename DTIC-DOME®), altretamine (also known as hexamethylmelamine (HMM) sold under the tradename HEXALEN®), ifosfamide (sold under the tradename IFEX®), procarbazine (sold under the tradename MATULANE®), mechlorethamine (also known as nitrogen mustard, mustine and mechloroethamine hydrochloride, sold under the tradename MUSTARGEN®), streptozocin (sold under the tradename ZANOSAR®), thiotepa (also known as thiophosphoamide, TESPA and TSPA, and sold under the tradename THIOPLEX®.

Examples of anti-tumor antibiotics include, but are not limited to, doxorubicin (sold under the tradenames ADRIAMYCIN® and RUBEX®), bleomycin (sold under the tradename LENOXANE®), daunorubicin (also known as dauorubicin hydrochloride, daunomycin, and rubidomycin hydrochloride, sold under the tradename CERUBIDINE®), daunorubicin liposomal (daunorubicin citrate liposome, sold under the tradename DAUNOXOME®), mitoxantrone (also known as DHAD, sold under the tradename NOVANTRONE®), epirubicin (sold under the tradename ELLENCE™), idarubicin (sold under the tradenames IDAMYCIN®, IDAMYCIN PFS®), and mitomycin C (sold under the tradename MUTAMYCIN®).

Examples of anti-metabolites include, but are not limited to, claribine (2-chlorodeoxyadenosine, sold under the tradename LEUSTATIN®), 5-fluorouracil (sold under the tradename ADRUCIL®), 6-thioguanine (sold under the tradename PURINETHOL®), pemetrexed (sold under the tradename ALIMTA®), cytarabine (also known as arabinosylcytosine (Ara-C), sold under the tradename CYTOSAR-U®), cytarabine liposomal (also known as Liposomal Ara-C, sold under the tradename DEPOCYT™), decitabine (sold under the tradename DACOGEN®), hydroxyurea (sold under the tradenames HYDREA®, DROXIA™ and MYLOCEL™), fludarabine (sold under the tradename FLUDARA®), floxuridine (sold under the tradename FUDR®), cladribine (also known as 2-chlorodeoxyadenosine (2-CdA) sold under the tradename LEUSTATIN™), methotrexate (also known as amethopterin, methotrexate sodium (MTX), sold under the tradenames RHEUMATREX® and TREXALL™), and pentostatin (sold under the tradename NIPENT®).

Examples of retinoids include, but are not limited to, alitretinoin (sold under the tradename PANRETIN®), tretinoin (all-trans retinoic acid, also known as ATRA, sold under the tradename VESANOID®), isotretinoin (13-c/s-retinoic acid, sold under the tradenames ACCUTANE® AMNESTEEM®, CLARAVIS®, CLARUS®, DECUTAN®, ISOTANER, IZOTECH®, ORATANER, ISOTRET® and SOTRET®), and bexarotene (sold under the tradename TARGRETIN®). Further disclosed herein is a compound disclosed herein, or a pharmaceutically acceptable salt thereof, for use in therapy. In one embodiment, disclosed herein is the use of a compound disclosed herein, or a pharmaceutically acceptable salt, solvate or hydrate thereof, for the preparation of a medicament for use in therapy.

The pharmaceutical composition may be use for prophylactic and/or therapeutic purposes. For example, a spray (i.e., aerosol) preparation may be used to strengthen the anti-viral capability of the nasal and the pulmonary mucosa.

Such a composition and/or formulation according to the invention can be administered to a subject in need thereof, particularly a human patient, in a sufficient dose for the treatment of the specific conditions by suitable means or a healthy human for prophylaxis or adjuvant activity. For example, the composition and/or formulation according to the invention may be formulated as a pharmaceutical composition together with pharmaceutically acceptable carriers, diluents and/or adjuvants. Therapeutic efficiency and toxicity may be determined according to standard protocols. The pharmaceutical composition may be administered systemically, e.g., intraperitoneally, intramuscularly, or intravenously or locally such as intranasally, subcutaneously, intradermally or intrathecally. The dose of the composition and/or formulation administered will, of course, be dependent on the subject to be treated and on the condition of the subject such as the subject's weight, the subject's age and the type and severity of the disease or disorder to be treated, the manner of administration and the judgement of the prescribing physician.

In a preferred embodiment the pharmaceutical composition is administered intradermally. It is especially preferred that the composition is administered intradermally via tattooing, microneedling and/or microneedle patches.

The RIG-I agonist of the present disclosure is preferably dissolved and diluted to the desired concentration in sterile, deionized water (purified water) and is then applied on the shaved, ethanoldisinfected skin using a pipetting device, and subsequently tattooed into the skin. For tattooing, for example, the water-based pharmaceutical composition according to the invention is intradermally injected into the skin, using a (medical) tattoo device fitted with a multi-needle (single use) needle-tip (such as a 9-needle, single-use tip).

The typical tattooing procedure is as follows: After the water-based pharmaceutical composition is pipetted onto the shaved and ethanol cleaned skin, it is introduced into the tattoo machine's multi-needle tip by placing the running needle tip (running at a speed of, for example, 100-120 Hz, in particular at 100 Hz) gently on top of the droplet of water-based pharmaceutical composition. Once the droplet of water-based pharmaceutical composition is completely adsorbed in the running needle tip, and hence resides in between the running needles, the running tip is gently moved back and forth over the skin, by holding the now filled needle tip in a 90-degree angle to the skin. Using this method, the water-based pharmaceutical composition is completely tattooed into the skin. For instance, for 50-100 μl of water-based pharmaceutical composition this typically takes 10-15 seconds, over a skin area of 2-4 square centimeters. Potential benefits of this treatment over standard single intradermal bolus injection include that the water-based pharmaceutical composition is evenly injected over a larger area of skin and is more evenly and more precisely divided over the target tissue: By using a 9-needle tip at 100 Hz for 10 seconds, this method ensures 9000 evenly dispersed intradermal injections in the treated skin.

Of course, a person skilled in the art may deviate from and adjust the procedure, depending on the patient or part of the body to be treated. The microneedling procedure may be carried out in close analogy to the tattooing procedure. However, with microneedling the tattoo needle-tip is replaced by a microneedling tip, which ensures more superficial intradermal administration. The water-based pharmaceutical composition is in principle pipetted onto the shaved and ethanol cleaned skin and then administered intradermally using the microneedling tip, in analogy to the tattoo procedure. Microneedling does not have necessity to prior adsorption of the pharmaceutical composition in between the microneedling needles.

Additionally, it is envisioned that fractional laser technology (Gold, J Clin Aesthet Dermatol. 2010; 3 (12): 37-42) with, or otherwise harbouring, the pharmaceutical composition can be used for transdermal/intradermal delivery. This may have the specific advantage that the intradermal delivery of the pharmaceutical composition can be enhanced as the laser-generated cutaneous channels provide an enlarged cutaneous surface area suggesting that this might substantiate the efficacy.

In Vitro Applications

The present application provides the in vitro use of the RIG-I agonist described above. In particular, the present application provides the use of at least one RIG-I agonist of the present disclosure for inducing an anti-viral response, in particular, a type I IFN response, more specifically, an IFN-α/β or IP10 response, in vitro or ex vivo. The present application also provides the use of at least one RIG-I agonist obtainable by the methods of the present disclosure for inducing apoptosis of a tumor cell in vitro.

The present disclosure provides an in vitro method for stimulating an anti-viral response, in particular, a type I IFN response, more specifically, an IFN-α, IFN-β or IP10 response in a cell, comprising the steps of (a) mixing at least one RIG-I agonist of the present disclosure and as described above with a complexation agent; and (b) contacting a cell with the mixture of (a), wherein the cell expresses RIG-I.

The cells may express RIG-I endogenously and/or exogenously from an exogenous nucleic acid (RNA or DNA). The exogenous DNA may be a plasmid DNA, a viral vector, or a portion thereof. The exogenous DNA may be integrated into the genome of the cell or may exist extrachromosomally. The cells include, but are not limited to, primary immune cells, primary non-immune cells, and cell lines. Immune cells include, but are not limited to, peripheral blood mononuclear cells (PBMC), plasmacytoid dendritic cells (PDC), myeloid dendritic cells (MDC), macrophages, monocytes, B cells, natural killer cells, granulocytes, $CD4^+$ T cells, $CD8^+$ T cells, and NKT cells. Non-immune cells include, but are not limited to, fibroblasts, endothelial cells, epithelial cells such as keratinocytes, and tumor cells. Cell lines may be derived from immune cells or non-immune cells. Further examples of suitable cell lines can be found in the examples section below.

The present disclosure also provides an in vitro method for inducing apoptosis of a tumor cell, comprising the steps of: (a) mixing at least one RIG-I agonist obtainable by the methods of the present disclosure and as described above with a complexation agent; and (b) contacting a tumor cell with the mixture of (a). The tumor cell may be a primary tumor cell freshly isolated from a vertebrate animal having a tumor or a tumor cell line. Alternatively, the cell may also be a virus infected cell.

In Vivo Applications

The present application provides the in vivo use of the oligonucleotide preparation of the invention described above.

In particular, the present application provides a double-stranded polyribonucleotide of the present disclosure for use in medicine or veterinary medicine. The present application further provides a double-stranded polyribonucleotide of the present disclosure for use in inducing an anti-viral response, in particular, a type I IFN response, more specifically, an IFN-α and β response, in a vertebrate animal, in particular, a mammal. The present application further provides a doublestranded polyribonucleotide of the present disclosure for use in inducing apoptosis of a tumor cell in a vertebrate animal, in particular, a mammal. The present application additionally provides a double-stranded polyribonucleotide of the present disclosure for use in preventing and/or treating a disease and/or disorder in a vertebrate animal, in particular, a mammal, in medical and/or veterinary practice. The diseases and/or disorders include, but are not limited to, infections, tumors/cancers, and immune disorders.

Similarly, the present application provides a medical or veterinary therapeutic method comprising administering an effective amount of the double-stranded polyribonucleotide of the present disclosure to a subject in need thereof. The present application further provides a method for inducing an anti-viral response, in particular, a type I IFN response, more specifically, an IFN-α and β response, in a vertebrate animal, in particular, a mammal, comprising the step of administering an effective amount of the double-stranded polyribonucleotide of the present disclosure to said vertebrate animal/mammal. The present application further provides a method for inducing apoptosis of a tumor cell in a vertebrate animal, in particular, a mammal, comprising the step of administering an effective amount of the double-stranded polyribonucleotide of the present disclosure to said vertebrate animal/mammal. The present application additionally provides a method for preventing and/or treating a disease and/or disorder in a vertebrate animal, in particular, a mammal, comprising the step of administering the double-stranded polyribonucleotide of the present disclosure to a vertebrate animal/mammal. The diseases and/or disorders include, but are not limited to, infections, tumors/cancers, and immune disorders.

Infections include, but are not limited to, viral infections, bacterial infections, parasitic infections, fungal infections and prion infection. Viral infections include, but are not limited to, infections by hepatitis C, hepatitis B, influenza virus, herpes simplex virus (HSV), human immunodeficiency virus (HIV), respiratory syncytial virus (RSV), vesicular stomatitis virus (VSV), cytomegalovirus (CMV), poliovirus, encephalomyocarditis virus (EMCV), human papillomavirus (HPV), West Nile virus, zika virus, SARS, and smallpox virus. In one embodiment, the infection is an upper respiratory tract infection caused by viruses and/or bacteria, in particular, flu, more specifically, bird flu. Bacterial infections include, but are not limited to, infections by streptococci, staphylococci, *E. coli, B. anthracis*, and *pseudomonas*. In one embodiment, the bacterial infection is an intracellular bacterial infection. Such an intracellular bacterial infection can be, for example, an infection by an intracellular bacterium such as mycobacteria (tuberculosis), *chlamydia, mycoplasma, listeria*, or a facultative intracellular bacterium such as *Staphylococcus aureus*. Parasitic infections include, but are not limited to, worm infections, in particular, intestinal worm infection.

In a preferred embodiment, the infection is a viral infection or an intracellular bacterial infection. In a more preferred embodiment, the infection is a viral infection by hepatitis C, hepatitis B, influenza virus, RSV, HPV, HSV1, HSV2, and CMV.

In this context, the RIG-I agonist or pharmaceutical composition comprising same is also contemplated for use in the treatment of condylomata warts, which are HPV-related.

Tumors include both benign and malignant tumors (i.e., cancer). Cancers include, but are not limited to biliary tract cancer, brain cancer, breast cancer, cervical cancer, choriocarcinoma, colon cancer, endometrial cancer, esophageal cancer, gastric cancer, intraepithelial neoplasm, leukemia, lymphoma, liver cancer, lung cancer, melanoma, myelomas, neuroblastoma, oral cancer, ovarian cancer, pancreatic cancer, prostate cancer, rectal cancer, sarcoma, skin cancer, testicular cancer, thyroid cancer and renal cancer.

In certain embodiments, the cancer is selected from hairy cell leukemia, chronic myelogenous leukemia, acute lymphoblastic leukemia cutaneous T-cell leukemia, acute myeloid leukemia, chronic myeloid leukemia, non-Hodgkin's lymphoma, multiple myeloma, follicular lymphoma, malignant melanoma, squamous cell carcinoma, renal cell carcinoma, prostate carcinoma, bladder cell carcinoma, breast carcinoma, ovarian carcinoma, non-small cell lung cancer, small cell lung cancer, hepatocellular carcinoma, basal cell carcinoma, colon carcinoma, cervical dysplasia, head and neck cancer, mamma carcinoma, bile duct cancer, bone cancers, esophageal cancer, gastric cancer, lymphoma, Merkel cell carcinoma, mesothelioma, pancreatic cancer, parathyroid cancer, multiple myeloma, rectal cancer, testicular cancer, vaginal cancer and Kaposi's sarcoma (AIDS-related and non-AIDS related) as well as all metastatic variants thereof.

In this context, the RIG-I agonist or pharmaceutical composition comprising same is also contemplated for use in the treatment of precancer actinic keratosis (the current treatment of which is ingenol-mebutate via necrosis/apoptosis). Hence, also disclosed is a method for treating precancer actinic keratosis comprising the step of administering an effective amount of the RIG-I agonist or pharmaceutical composition disclosed herein to a subject in need thereof.

Immune disorders include, but are not limited to, allergies, autoimmune disorders, and immunodeficiencies. Allergies include, but are not limited to, respiratory allergies, contact allergies and food allergies, and may further encompass allergy related conditions such as asthma, in particular allergic asthma, dermatitis, in particular atopic dermatitis and eczematous dermatitis, and allergic encephalomyelitis. Autoimmune diseases include, but are not limited to, multiple sclerosis, diabetes mellitus, arthritis (including rheumatoid arthritis, juvenile rheumatoid arthritis, osteoarthritis, psoriatic arthritis and psoriasis), encephalomyelitis, myasthenia gravis, systemic lupus erythematosus, autoimmune thyroiditis, psoriasis, Sjogren's Syndrome, Crohn's disease, aphthous ulcer, iritis, conjunctivitis, keratoconjunctivitis, ulcerative colitis, systemic and cutaneous lupus erythematosus, scleroderma, vaginitis, proctitis, drug eruptions, leprosy reversal reactions, erythema nodosum leprosum, autoimmune uveitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Graves' disease, sarcoidosis, primary biliary cirrhosis, uveitis posterior, and interstitial lung fibrosis.

Immunodeficiencies include, but are not limited to, spontaneous immunodeficiency, acquired immunodeficiency (including AIDS), drug-induced immunodeficiency or immunosuppression (such as that induced by immunosuppressants used in transplantation and chemotherapeutic agents used for treating cancer), and immunosuppression caused by chronic hemodialysis, trauma or surgical procedures.

In a preferred embodiment, the immune disorder is multiple sclerosis.

In certain embodiments, the oligonucleotide is used in combination with one or more pharmaceutically active agents such as immunostimulatory agents, anti-viral agents, antibiotics, antifungal agents, anti-parasitic agents, anti-tumor agents, cytokines, chemokines, growth factors, anti-angiogenic factors, chemotherapeutic agents, antibodies, checkpoint-inhibitors, and gene silencing agents. Preferably, the pharmaceutically active agent is selected from the group consisting of an immunostimulatory agent, an anti-viral agent and an anti-tumor agent. The more than one pharmaceutically active agents may be of the same or different category.

The invention also provides a double-stranded polyribonucleotide as described herein above for use as a vaccine adjuvant. In some embodiments, the RIG-I agonist is used in combination with an anti-viral vaccine, an anti-bacterial vaccine, and/or an anti-tumor vaccine, wherein the vaccine can be prophylactic and/or therapeutic. Thus, also disclosed is a method for preparing a vaccine composition, comprising the step of combining the RIG-I agonist of the present disclosure with an anti-viral vaccine, an anti-bacterial vaccine, and/or an anti-tumor vaccine, wherein the vaccine can be prophylactic and/or therapeutic. The vaccine composition may be a vaccine in the field of oncology, immune disorders, autoimmune diseases, asthma, or allergy and infection.

The pharmaceutical composition may be used in combination with one or more prophylactic and/or therapeutic treatments of diseases and/or disorders such as infection, tumor, and immune disorders. The treatments may be pharmacological and/or physical (e.g., surgery, radiation, ultrasound treatment, and/or heat- or thermo-treatment).

Vertebrate animals include, but are not limited to, fish, amphibians, birds, and mammals. Mammals include, but are not limited to, rats, mice, cats, dogs, horses, sheep, cattle, cows, pigs, rabbits, non-human primates, and humans. In a preferred embodiment, the mammal is human.

Also disclosed are the following embodiments:

Embodiment 1. A double-stranded polyribonucleotide comprising a sense strand with 24 to 30 nucleotides in length and an antisense strand with 24 to 30 nucleotides in length, wherein the sense strand and the antisense strand form a fully complementary region of at least 24 base pairs with a blunt end at the 5'-end of the sense strand and the 3'-end of the antisense strand; and wherein the first 24 nucleotides at the 5'-end of the sense strand are ribonucleotides and have at least one 2'-o-methyl modification at a purine ribonucleotide at a position selected from the group consisting of position number 12, 15, and 20, and no 2'-o-methyl modification at a ribonucleotide at a position selected from the group consisting of position number 1, 7, 8, 9, and 14, and/or wherein the last 24 nucleotides at 3'-end of the antisense strand are ribonucleotides and have at least one 2'-o-methyl modification at a purine ribonucleotide at a position selected from the group consisting of position number 3, and 22, and no 2'-o-methyl modification at a ribonucleotide at a position selected from the group consisting of position 18, 20, and 23.

Embodiment 2. The double-stranded polyribonucleotide of embodiment 1, wherein the first 24 ribonucleotides at 5'-end of the sense strand further have at least one 2'-flourine modification at a ribonucleotide at a position selected from the group consisting of position number 2, 4, 6, 9, 10, 16, 21, 22, and 24, and no 2'-flourine modification at a ribonucleotide at a position selected from the group consisting of position number 1, 3, 8, and 14, and/or wherein the last 24 ribonucleotides at 3'-end of the antisense strand have at least one 2'-flourine modification at a ribonucleotide at a position selected from the group consisting of position number 5 and 13, and no 2'-flourine modification at a ribonucleotide at a position selected from the group consisting of position 18 and 23;

wherein all positions are counted from 5' to 3'.

Embodiment 3. The double-stranded polyribonucleotide of embodiment 1 or 2, wherein the remaining ribonucleotides at the other positions in the first 24 ribonucleotides at 5'-end of the sense strand and the last 24 ribonucleotides at 3'-end of the antisense strand are not modified at the ribose; wherein all positions are counted from 5' to 3'.

Embodiment 4. The double-stranded polyribonucleotide of any one of embodiments 1-3, wherein the double-stranded ribonucleotide has 2'-o-methylated purine at position 12, 15, and 20 in the first 24 ribonucleotides at 5'-end of the sense strand, and position 3 in the last 24 ribonucleotides at the 3'-end of the antisense strand; wherein all positions are counted from 5' to 3'.

Embodiment 5. The double-stranded polyribonucleotide of any one of embodiments 1-4, wherein the double-stranded ribonucleotide has a 2'-fluorinated pyrimidine at position 10 at the 5'-end of the sense strand; counted from 5' to 3'.

Embodiment 6. The double-stranded polyribonucleotide of any one of embodiments 1-5, wherein the double-stranded ribonucleotide has a 2'-fluorinated purine at position 9 of the sense strand and a 2'-o-methylated purine at position 3 of the antisense strand; counted from 5' to 3'.

Embodiment 7. The double-stranded polyribonucleotide of any one of embodiments 1-6, wherein the sense strand has a length of at most 29 nucleotides, preferably at most 28 nucleotides, such as 27 nucleotides, more preferably at most 26 nucleotides, such as 25 nucleotides, and most preferably 24 nucleotides.

Embodiment 8. The double-stranded polyribonucleotide of any one of embodiments 1-7, wherein the antisense strand has a length of at most 29 nucleotides, more preferably at most 28 nucleotides, such as 27 nucleotides, more preferably at most 26 nucleotides, such as 25 nucleotides, and most preferably 24 nucleotides.

Embodiment 9. The double-stranded polyribonucleotide of any one of embodiments 1-8, wherein the fully complementary region has a length of at most 250 base pairs, preferably at most 200 base pairs, more preferably at most 30 base pairs, such as 29 base pairs, more preferably at most 28 base pairs, such as 27 base pairs, more preferably at most 26 base pairs, such as 25 base pairs, and most preferably 24 base pairs.

Embodiment 10. The double-stranded polyribonucleotide of any one of embodiments 1-9, wherein the antisense strand has at most 2 nucleotides more in length than the sense strand; preferably at most 1 nucleotide more in length; and most preferably both strands have the same length.

Embodiment 11. The double-stranded polyribonucleotide of any one of embodiments 1-10, wherein the antisense strand has 26 ribonucleotides, and the sense strand has 24 ribonucleotides.

Embodiment 12. The double-stranded polyribonucleotide of embodiment 11, wherein the antisense strand has an overhang of two adenine at the 5'-end, and a 2'-fluorinated ribonucleotide at position 1 or 2, or in both position 1 and 2, in the last 24 ribonucleotides at the 3'-end of the antisense strand; wherein the positions are counted from 5' to 3'.

Embodiment 13. The double-stranded polyribonucleotide of any one of embodiments 1-10, wherein both strands have a length of 24 ribonucleotides, and form two blunt ends.

Embodiment 14. The double-stranded polyribonucleotide of any one of embodiments 1-13, wherein the sense strand starts at the 5' end with a sequence selected from

```
                                    (SEQ ID NO: 170)
5'-gbucndnwnnnnnnnnwnsnn-3',

                                    (SEQ ID NO: 171)
5'-gucuadnwnnnnnnnnwnsnn-3',

                                    (SEQ ID NO: 172)
5'-guagudnwnnnnnnnnwnsnn-3',
```

-continued (SEQ ID NO: 173)
5'-gguaadnwnnnnnnnnwnsnn-3', (SEQ ID NO: 174)
5'-ggcagdnwnnnnnnnnwnsnn-3', (SEQ ID NO: 175)
5'-gcuucdnwnnnnnnnnwnsnn-3', (SEQ ID NO: 176)
5'-gcccadnwnnnnnnnnwnsnn-3',
and (SEQ ID NO: 177)
5'-gcgcudnwnnnnnnnnwnsnn-3'.

Embodiment 15. The double-stranded polyribonucleotide of embodiment 14, wherein in the sense strand the ribonucleotide at position 6 is u.

Embodiment 16. The double-stranded polyribonucleotide of embodiment 14 or 15, wherein in the sense strand the ribonucleotide at position 7 is g.

Embodiment 17. The double-stranded polyribonucleotide of embodiment 14, wherein in the sense strand the ribonucleotide at position 6 is g, and the ribonucleotide at position 7 is c.

Embodiment 18. The double-stranded polyribonucleotide of any one of embodiments 14-17, wherein in the sense strand the ribonucleotide at position 8 is a.

Embodiment 19. The double-stranded polyribonucleotide of any one of embodiments 14-18, wherein in the sense strand the ribonucleotide at position 9 is a.

Embodiment 20. The double-stranded polyribonucleotide of any one of embodiments 14-19, wherein in the sense strand the ribonucleotide at position 17 is u.

Embodiment 21. The double-stranded polyribonucleotide of any one of embodiments 14-19, wherein in the sense strand the ribonucleotide at position 17 is a.

Embodiment 22. The double-stranded polyribonucleotide of any one of embodiments 14-21, wherein the sequence at the 5'-end of the sense strand is selected from (SEQ ID NO: 178)
5'-gbucndnwnnnnnnnnunsnn-3', (SEQ ID NO: 210)
5'-gbucndnwnnnnnnnnansnn-3', (SEQ ID NO: 179)
5'-gucuadnwnnnnnnnnunsnn-3', (SEQ ID NO: 180)
5'-guagudnwnnnnnnnnunsnn-3', (SEQ ID NO: 181)
5'-gguaadnwnnnnnnnnunsnn-3', (SEQ ID NO: 182)
5'-ggcagdnwnnnnnnnnunsnn-3', (SEQ ID NO: 183)
5'-gcuucdnwnnnnnnnnunsnn-3', (SEQ ID NO: 184)
5'-gcccadnwnnnnnnnnunsnn-3',
and (SEQ ID NO: 185)
5'-gcgcudnwnnnnnnnnunsnn-3'.

Embodiment 23. The double-stranded polyribonucleotide of any one of embodiments 14-22, wherein in the sequence of the sense strand the ribonucleotide at position 18 is u.

Embodiment 24. The double-stranded polyribonucleotide of any one of embodiments 14-22, wherein in the sequence of the sense strand the ribonucleotide at position 18 is a.

Embodiment 25. The double-stranded polyribonucleotide of any one of embodiments 14-24, wherein in the sequence of the sense strand the ribonucleotide at position 19 is c.

Embodiment 26. The double-stranded polyribonucleotide of embodiment 13, wherein the sequence at the 5'-end of the sense strand is selected from (SEQ ID NO: 186)
5'-gbucnugaannnnnnnnuucnn-3', (SEQ ID NO: 211)
5'-gbucngcaannnnnnnnaacnn-3', (SEQ ID NO: 187)
5'-gucuaugaannnnnnnnuucnn-3', (SEQ ID NO: 188)
5'-guaguugaannnnnnnnuucnn-3', (SEQ ID NO: 189)
5'-gguaaugaannnnnnnnuucnn-3', (SEQ ID NO: 190)
5'-ggcagugaannnnnnnnuucnn-3', (SEQ ID NO: 191)
5'-gcuucugaannnnnnnnuucnn-3', (SEQ ID NO: 192)
5'-gcccaugaannnnnnnnuucnn-3',
and (SEQ ID NO: 193)
5'-gcgcuugaannnnnnnnuucnn-3';

preferably wherein the sequence at the 5'-end of the sense strand is 5'-gbucnugaannnnnnnnuucnn-3' (SEQ ID NO: 186) or 5'-gbucngcaannnnnnnnaacnn-3' (SEQ ID NO: 211), more preferably wherein the sequence at the 5'-end of the sense strand is 5'-gbucnugaaannnnn-uuucnn-3' (SEQ ID NO: 194) or 5'-gbucngcaaunnnn-naaacnn-3' (SEQ ID NO: 212).

Embodiment 27. The double-stranded polyribonucleotide of any one of embodiments 11-26, wherein in the sense strand the ribonucleotide sequence at positions 20-24 is selected from 5'-ngavc-3', 5'-uagac-3', 5'-acuac-3', 5'-uuacc-3', 5'-cugcc-3', 5'-gaagc-3', 5'-ugggc-3', 5'-guuau-3' and 5'-agcgc-3'; preferably wherein the ribonucleotide sequence at positions 20-24 is 5'-ngavc-3'.

Embodiment 28. The double-stranded polyribonucleotide of any one of embodiments 11-27, wherein in the sequence of the sense strand the ribonucleotide at position 6 is g, the ribonucleotide at position 7 is a or c, and the ribonucleotide at position 8 is a; in particular wherein the ribonucleotide at position 9 is a.

Embodiment 29. The double-stranded polyribonucleotide of any one of embodiments 11-28, wherein in the sequence of the sense strand the ribonucleotide at position 16 is u or a.

Embodiment 30. The double-stranded polyribonucleotide of any one of embodiments 11-28, wherein in the sequence of the sense strand the ribonucleotide at position 17 is u or a, the ribonucleotide at position 18 is g or a, and the ribonucleotide at position 19 is c.

Embodiment 31. The double-stranded polyribonucleotide of any one of embodiments 1-13, wherein in the sequence of the sense strand the sequence at position 6-24 is 5'-ugaannnnnnnuucngavc-3' (SEQ ID NO: 195).

Embodiment 32. The double-stranded polyribonucleotide of embodiment 31, wherein in the sequence of the sense strand the sequence at position 6-24 is 5'-ugaannnnnnuuucngavc-3' (SEQ ID NO: 196).

Embodiment 33. The double-stranded polyribonucleotide of any one of embodiments 1-13, wherein in the sequence of the sense strand the sequence at position 6-24 is 5'-gaaannnnnnnuucngavc-3' (SEQ ID NO: 197), in particular 5'-gaaannnnnnuuucngavc-3' (SEQ ID NO: 198).

Embodiment 34. The double-stranded polyribonucleotide of any one of embodiments 1-13, wherein the sequence of the sense strand is 5'-gbucnugaannnnnnnuucnnnnn-3' (SEQ ID NO: 199), in particular wherein the first RNA sequence of the sense strand is 5'-gbucnugaannnnnnnuucngavc-3' (SEQ ID NO: 200).

Embodiment 35. The double-stranded polyribonucleotide of any one of embodiments 1-13, wherein the sequence of the sense strand is 5'-gbucngcaannnnnnnaacnnnnn-3' (SEQ ID NO: 213), in particular wherein the sequence of the sense strand is 5'-gbucngcaannnnnnnaacguuau-3' (SEQ ID NO: 214).

Embodiment 36. The double-stranded polyribonucleotide of any one of embodiments 1-13, wherein the sequence of the sense strand is 5'-gbucnugaannnnnnnuucngavc-3' (SEQ ID NO: 201).

Embodiment 37. The double-stranded polyribonucleotide of any one of embodiments 1-13, wherein the sequence of the sense strand is 5'-gbucnugaannnnnnuuungavc-3' (SEQ ID NO: 202).

Embodiment 38. The double-stranded polyribonucleotide of any one of embodiments 1-13, wherein the sequence of the sense strand is 5'-gbucngaaannnnnnnuucngavc-3' (SEQ ID NO: 203).

Embodiment 39. The double-stranded polyribonucleotide of embodiment 38, wherein the sequence of the sense strand is 5'-gbucngaaannnnnnnuucngavc-3' (SEQ ID NO: 204).

Embodiment 40. The double-stranded polyribonucleotide of embodiment 39, wherein the sequence of the sense strand is 5'-gbucngaaannnnnnuuucngavc-3' (SEQ ID NO: 205).

Embodiment 41. The double-stranded polyribonucleotide of any one of embodiments 1-40, wherein the sense strand has a mono-, di-, or triphosphate or respective analogue attached to its 5' end; preferably a tri-phosphate.

Embodiment 42. The double-stranded polyribonucleotide of any one of embodiments 1-41, wherein the antisense strand has a mono-, di-, or triphosphate or respective analogue attached to its 5' end; preferably a triphosphate.

Embodiment 43. The double-stranded polyribonucleotide of any one of embodiments 1-42, wherein the polyribonucleotide is made up of the ribonucleotides a, g, c, u, and optionally inosine only; in particular wherein the polyribonucleotide does not contain m6A, Ψ, mΨ, 5mC, 5moC, and 5hmC.

Embodiment 44. The double-stranded polyribonucleotide of any one of embodiments 1-43, wherein the polyribonucleotide comprises at least one synthetic or modified internucleoside linkage such as phosphodiester, phosphorothioate, $N_3$ phosphoramidate, boranophosphate, 2,5-phosphodiester, amide-linked, phosphonoacetate (PACE), morpholino, peptide nucleic acid (PNA), or a mixture thereof, provided the linkage(s) do not compromise the type I IFN-inducing activity of the polyribonucleotide.

Embodiment 45. The double-stranded polyribonucleotide of any one of embodiments 1-44, wherein the polyribonucleotide comprises phosphorothioate linkage(s).

Embodiment 46. The double-stranded polyribonucleotide of embodiment 45, wherein the phosphorothioate linkage(s) are located (i) between position 1 and 2, and position 2 and 3 of the sense strand;

(ii) between position 22 and 23, and position 23 and 24 of the antisense strand;

(iii) between position 22 and 23, and position 23 and 24 of the sense strand; and/or (iv) between position 1 and 2, and position 2 and 3 of the antisense strand.

Embodiment 47. The double-stranded polyribonucleotide of embodiment 1, wherein the sense strand, or the antisense strand, or both the sense strand and the antisense strand are selected from SEQ ID NO: 7-64, 69-72, 77-80, 85-88, 92-99, 104-107, 112-115, 120-123, 127-169, 206-209; in particular wherein the double-stranded polyribonucleotide is selected from the double-stranded polyribonucleotides DR2-102 to DR2-117, DR2-119 to DR2-150, DR2-152 to DR2-175, DR2-213 to DR2-223, DR2-225 to DR2-235, DR2-237 to DR2-247, DR2-254 to DR2-265 and DR2-269-270 shown in Table 1.

Embodiment 48. The double-stranded polyribonucleotide of any one of embodiments 1-47, wherein the polyribonucleotide is an agonist of RIG-I.

Embodiment 49. A pharmaceutical composition comprising at least one polyribonucleotide according to any one of embodiments 1-48, and a pharmaceutically acceptable carrier.

Embodiment 50. The pharmaceutical composition of embodiment 49, further comprising at least one agent selected from an anti-tumor agent, an immunostimulatory agent, an anti-viral agent, an anti-bacterial agent, a checkpoint-inhibitor, retinoic acid, IFN-α, and IFN-β.

Embodiment 51. The pharmaceutical composition of embodiment 49 or 50, wherein said composition is a vaccine composition.

Embodiment 52. A polyribonucleotide according to any one of embodiments 1-48, or a pharmaceutical composition according to any one of embodiments 49-51 for use in medicine or veterinary medicine.

Embodiment 53. A polyribonucleotide according to any one of embodiments 1-48, or a pharmaceutical composition according to any one of embodiments 49-51 for use in preventing and/or treating a disease or condition selected from a tumor, an infection, an allergic condition, and an immune disorder.

Embodiment 54. The pharmaceutical composition for use of embodiment 53, wherein the composition is prepared for administration in combination with at least one treatment selected from a prophylactic and/or a therapeutic treatment of a tumor, an infection, an allergic condition, and an immune disorder.

Embodiment 55. A polyribonucleotide according to any one of embodiments 1-48, or a pharmaceutical composition according to any one of embodiments 49-51 for use as a vaccine adjuvant.

Embodiment 56. An ex vivo method for inducing type I IFN production in a cell, comprising the step of contacting a cell expressing RIG-I with at least one polyribonucleotide according to any one of embodiments 1-48, optionally in mixture with a complexation agent.

Embodiment 57. A method for producing a RIG-I agonist, comprising the step of (a) preparing a sense strand as defined in any one of embodiments 1-47;

(b) preparing a fully complementary antisense strand as defined in any one of embodiments 1-47; and (c) annealing the sense strand with the antisense strand, thereby obtaining a RIG-I agonist.

Embodiment 58. A method for increasing the selectivity for RIG-I of a RIG-I agonist, comprising the steps of (a) providing a double-stranded polyribonucleotide comprising a sense strand with 24 to 30 nucleotides in length and an antisense strand with 24 to 30 nucleotides in length, wherein the sense strand and the antisense strand form a fully complementary region of at least 24 base pairs with a blunt end at the 5'-end of the sense strand and the 3'-end of the antisense strand; and wherein the first 24 nucleotides at the 5'-end of the sense strand are ribonucleotides; and wherein the sense strand has no 2'-o-methyl modification at a ribonucleotide at a position selected from the group consisting of position number 1, 7, 8, 9, and 14, and wherein the last 24 nucleotides at 3'-end of the antisense strand are ribonucleotides and wherein the antisense strand has in its last 24 nucleotides no 2'-o-methyl modification at a ribonucleotide at a position selected from the group consisting of position 18, 20, and 23; wherein all positions are counted from 5' to 3';

(b) identifying whether the polyribonucleotide of step (a) comprises a purine ribonucleotide at a position selected from the group consisting of position number 12, 15, and 20 in the sense strand, and position number 3 and 10 of the antisense strand, and (c) introducing at least one 2'-o-methyl modification at a purine ribonucleotide identified in step (b).

Embodiment 59. The method of embodiment 58, wherein the double-stranded ribonucleotide provided in step (a) has a purine at a position selected from the group of positions consisting of position 12, 15, and 20 in the first 24 ribonucleotides at 5'-end of the sense strand, and position 3 in the last 24 ribonucleotides at the 3'-end of the antisense strand.

Embodiment 60. The method of embodiment 58 or 59, further comprising introducing a 2'-o-methyl modification at the ribonucleotide at position 22 in the last 24 ribonucleotides at the 3'-end of the antisense strand.

Embodiment 61. The method of any one of embodiments 58-60, wherein the polyribonucleotide provided in step (a) is further defined as in any one of embodiments 2, 3, or 5-46.

Embodiment 62. A method for increasing the type I IFN response of a RIG-I agonist, comprising the steps of (a) providing a double-stranded polyribonucleotide comprising a sense strand with 24 to 30 nucleotides in length and an antisense strand with 24 to 30 nucleotides in length, wherein the sense strand and the antisense strand form a fully complementary region of at least 24 base pairs with a blunt end at the 5'-end of the sense strand and the 3'-end of the antisense strand; and wherein the first 24 nucleotides at the 5'-end of the sense strand are ribonucleotides; and wherein the sense strand has no 2'-fluorine modification at a ribonucleotide at a position selected from the group consisting of position number 1, 3, 8, and 14, and wherein the last 24 nucleotides at 3'-end of the antisense strand are ribonucleotides and wherein the antisense strand has in its last 24 nucleotides no 2'-fluorine modification at a ribonucleotide at a position selected from the group consisting of position 18 and 23; wherein all positions are counted from 5' to 3'; and (b) introducing at least one 2'-fluorine modification at a ribonucleotide at a position selected from the group consisting of position number 2, 4, 6, 9, 10, 16, 21, 22, and 24 of the sense strand, and position number 5, and 13 of the last 24 ribonucleotides of the antisense strand; wherein all positions are counted from 5' to 3'.

Embodiment 63. The method of embodiment 62, wherein a 2'-fluorine modification is introduced at position 10 at the 5'-end of the sense strand; counted from 5' to 3'.

Embodiment 64. The method of embodiment 62 or 63, wherein the method further comprises the step of identifying whether the polyribonucleotide of step (a) comprises a pyrimidine ribonucleotide at position 10 at the 5'-end of the sense strand, and introducing a 2'-fluorine modification at position 10 at the 5'-end of the sense strand in case said ribonucleotide is a pyrimidine ribonucleotide.

Embodiment 65. A method for increasing the type I IFN response of a RIG-I agonist, comprising the steps of (a) providing a double-stranded polyribonucleotide comprising a sense strand with 24 nucleotides in length and an antisense strand with 26 nucleotides in length, wherein the sense strand and the antisense strand form a fully complementary region with a blunt end at the 5'-end of the sense strand and the 3'-end of the antisense strand, and wherein the antisense strand has an overhang of two adenine at the 5'-end; and wherein the first 24 nucleotides at the 5'-end of the sense strand are ribonucleotides; and wherein the sense strand has no 2'-fluorine modification at a ribonucleotide at a position selected from the group consisting of position number 1, 3, 8, and 14, and wherein the last 24 nucleotides at 3'-end of the antisense strand are ribonucleotides and wherein the antisense strand has in its last 24 nucleotides no 2'-fluorine modification at a ribonucleotide at a position selected from the group consisting of position 18 and 23; wherein all positions are counted from 5' to 3'; and (b) introducing a 2'-fluorine modification at a ribonucleotide at a position selected from the group consisting of position number 1, 2, or in both positions 1 and 2 of the last 24 ribonucleotides of the antisense strand; wherein all positions are counted from 5' to 3'.

Embodiment 66. A method for increasing the type I IFN response of a RIG-I agonist, comprising the steps of (a) providing a double-stranded polyribonucleotide comprising a sense strand with 24 nucleotides in length and an antisense strand with 24 nucleotides in length, wherein the sense strand and the antisense strand form a fully complementary region with two blunt ends; and wherein the nucleotides of the sense strand are ribonucleotides; and wherein the sense strand has no 2'-fluorine modification at a ribonucleotide at a position selected from the group consisting of position number 1, 3, 8, and 14, and wherein the nucleotides of the antisense strand are ribonucleotides and wherein the antisense strand has no 2'-fluorine modification at a ribonucleotide at a position selected from the group consisting of position 18 and 23; wherein all positions are counted from 5' to 3'; and (b) introducing an overhang of two adenine at the 5'-end of the antisense strand; and (c) introducing a 2'-fluorine modification at a ribonucleotide at a position selected from the group consisting of position number 1, 2, or in both positions 1 and 2 of the last 24 ribonucleotides of the antisense strand; wherein all positions are counted from 5' to 3'.

Embodiment 67. The method of any one of embodiments 62-66, wherein the polyribonucleotide provided in step (a) is further defined as in any one of embodiments 1, 3, 4, 7, 8 or 12-46.

DESCRIPTION OF THE FIGURES

The present invention is also illustrated by the Figures and following Examples. The Figures and Examples are for illustration purposes only and are by no means to be construed to limit the scope of the invention.

FIG. 1: Detrimental effects of single 2'-oMe modifications. Four independent basis sequences (Seq 1-4; SEQ ID NOs: 1-8) were permuted for 2'-o-methylation of single nucleotides and transfected into PBMCs. On basis of the IFNα levels released (data not shown) each single 2'-o-methylation position was classified as being detrimental (decrease≥20%) or being tolerated.

In Seq1, the 2'-oMe modifications that promote RIG-I agonism, that are tolerated or decrease RIG-I activation by less than 20% are at positions 3, 10, 11, 12, 13, 15, 16, 17, 18, 19, 20, 21, 22, 23, 24 of the sense strand and at positions 2, 3, 4, 5, 7, 8, 9, 10, 11, 15, 16, 22 of the antisense strand (counted from 5' to 3'). The indicated 2'-oMe positions that compromise RIG-I agonism (decrease>20%) are at position 1, 2, 4, 5, 6, 7, 8, 9, 14 of the sense strand and at position 1, 6, 12, 13, 14, 17, 18, 19, 20, 21, 23, 24 of the antisense strand (counted from 5' to 3');

In Seq2, the 2'-oMe modifications that promote RIG-I agonism, that are tolerated or decrease RIG-I activation by less than 20% are at position 2, 3, 4, 5, 6, 10, 11, 12, 13, 15, 17, 19, 20, 21, 22, 23 of the sense strand and at position 1, 2, 3, 4, 5, 6, 8, 9, 10, 12, 13, 14, 16, 17, 19, 20, 21, 22, 24 of the antisense strand (counted from 5' to 3' of the complementary region, i.e., not counting the 5' AA overhang); the indicated 2'-oMe positions that compromise RIG-I agonism (decrease>20%) are at position 1, 7, 8, 9, 14, 16, 18, 24 of the sense strand and at position 7, 11, 15, 18, 23 of the antisense strand (counted from 5' to 3' of the complementary region, i.e., not counting the 5' AA overhang).

In Seq3, the 2'-oMe modifications that promote RIG-I agonism, that are tolerated or decrease RIG-I activation by less than 20% are at position 2, 4, 5, 6, 7, 10, 12, 13, 15, 16, 17, 21, 22, 23, and 24 of the sense strand and at position 1, 2, 3, 5, 6, 7, 8, 10, 11, 12, 13, 14, 15, 16, 17, 19, 21, 22, and 24 of the antisense strand (counted from 5' to 3'). The indicated 2'-oMe positions that compromise RIG-I agonism (decrease>20%) are at position 1, 3, 8, 9, 11, 14, 18, 19, and 20 of the sense strand and at position 4, 9, 18, 20, and 23 of the antisense strand (counted from 5' to 3').

In Seq4, the 2'-oMe modifications that promote RIG-I agonism, that are tolerated or decrease RIG-I activation by less than 20% are at position 2, 3, 9, 10, 11, 12, 13, 15, 16, 17, 18, 19, 20, 21, 22, and 24 of the sense strand and at position 1, 3, 10, 12, 14, 15, 16, 21, 22, and 24 of the antisense strand (counted from 5' to 3' of the complementary region, i.e., not counting the 5' AA overhang). The indicated 2'-oMe positions that compromise RIG-I agonism (decrease>20%) are at position 1, 4, 5, 6, 7, 8, 14, and 23 of the sense strand, and at position 2, 4, 5, 6, 7, 8, 9, 11, 13, 17, 18, 19, 20, and 23 of the antisense strand (counted from 5' to 3' of the complementary region, i.e., not counting the 5' AA overhang).

Accordingly, allowed consensus 2'-oMe positions (in 3 out of 4 polyribonucleotides) in FIG. 1 are at position 2, 3, 10, 11, 12, 13, 15, 16, 17, 19, 20, 21, 22, 23, and 24 of the sense strand and at position 1, 2, 3, 5, 8, 10, 12, 14, 15, 16, 21, 22, and 24 of the antisense stand (counted from 5' to 3'). The prohibited consensus 2'-oMe position sites (3 out of 4) are at position 1, 7, 8, 9, and 14 of the sense strand and at position 18, 20, and 23 of the antisense strand (counted from 5' to 3'). All nucleotide positions in the allowed 2'oME consensus are counted from 5' to 3' of the region of complementation (i.e., not including any 5' overhang of antisense strand, if present).

FIG. 2: 2'-o-methylation of selected nucleotide positions mediating RIG-I selectivity. Four independent basis sequences (Seq1-4) were permuted for 2'-o-methylation of single nucleotides and transfected into PBMCs to either target RIG-I (cytosolic delivery) or TLR7/8 (endosomal delivery). The activation of RIG-I, TLR7 and TLR8 was monitored by means of IFNα and IL12p70 release, respectively.

In Seq1, the 2'-oMe modifications without (w/o) adverse effect on RIG-I agonism that establish receptor selectivity are at position 15 and 20 of the sense strand and at position 4 and 5 of the antisense strand (counted from 5' to 3').

In Seq2, the 2'-oMe modifications without adverse effect on RIG-I agonism that establish receptor selectivity are at position 5, 12, 17, and 20 of the sense strand and at position 2, 3, 10, 17, and 20 of the antisense strand (counted from 5' to 3' of the complementary region, i.e., not counting the 5' AA overhang).

In Seq3, the 2'-oMe modifications without adverse effect on RIG-I agonism that establish receptor selectivity are at position 6, 7, 12, 15, and 21 of the sense strand and at position 3, 5, 6, 13, and 21 of the antisense strand (counted from 5' to 3').

In Seq4, the 2'-oMe modifications without adverse effect on RIG-I agonism that establish receptor selectivity are at position 10, 11, 12, 17, and 20 of the sense strand and at position 3, 10, 12, 15, and 21 of the antisense strand (counted from 5' to 3' of the complementary region, i.e., not counting the 5' AA overhang).

FIG. 3: Overview showing 2'-o-methyl modifications that are detrimental for RIG-I or TLR7/8.

FIG. 4: Detrimental effects of single 2'-F modifications. Four independent basis sequences (Seq1-4) were permuted for 2'-fluorine of single nucleotides and transfected into PBMCs. On basis of the IFN-α levels released (data not shown) each RNA single 2'-o-fluorine position was classified as being detrimental (decrease≥20%) or being tolerated.

In Seq1, the 2'-F modifications that promote RIG-I agonism, are tolerated or decrease RIGI activation by less than 20% are at position 2, 4, 6, 7, 9, 10, 11, 12, 13, 16, 18, 19, 20, 21, 22, 23, 24 of the sense strand and at position 2, 3, 4, 7, 11, 12, 19, 20, 21 of the antisense strand (counted from 5' to 3'). The indicated 2'-F positions that compromise RIG-I agonism (decrease>20%) are at position 1, 3, 5, 8, 14, 15, 17 of the sense strand and at position 1, 5, 6, 8, 9, 10, 13, 14, 15, 16, 17, 18, 22, 23, 24 of the antisense strand (counted from 5' to 3').

In Seq2, the 2'-F modifications that promote RIG-I agonism, are tolerated or decrease RIGI activation by less than 20% are at position 2, 3, 4, 5, 6, 8, 9, 10, 11, 12, 13, 16, 17, 18, 19, 20, 21, and 24 of the sense strand and at position 1, 2, 3, 4, 5, 6, 7, 8, 9, 10, 11, 12, 13, 14, 16, 17, 18, 19, 20, 21, 22, and 24 of the antisense strand (counted from 5' to 3' of the complementary region, i.e., not counting the 5' AA overhang). The indicated 2'-F positions that compromise RIG-I agonism (decrease>20%) are at position 1, 7, 14, 15, 22, and 23 of the sense strand and at position 15 and 23 of the antisense strand (counted from 5' to 3' of the complementary region, i.e., not counting the 5' AA overhang).

In Seq3, the 2'-F modifications that promote RIG-I agonism, are tolerated or decrease RIGI activation by less than 20% are at position 2, 4, 5, 6, 7, 9, 10, 11, 12, 13, 15, 16, 17, 18, 19, 21, 22, 23, and 24 of the sense strand, and at position 1, 2, 3, 4, 5, 6, 7, 8, 9, 10, 11, 12, 13, 14, 15, 16, 17, 19 20,21, 22, 23, and 24 of the antisense strand (counted from 5' to 3'). The indicated 2'-F positions that compromise RIG-I agonism (decrease>20%) are at position 1, 3, 8, 14, and 20 of the sense strand and at position 18 of the antisense strand (counted from 5' to 3').

In Seq4, the 2'-F modifications that promote RIG-I agonism, are tolerated or decrease RIGI activation by less than 20% are at position 4, 6, 9, 10, 12, 13, 14, 15, 16, 18, 20, 21, 22, 23, and 24 of the sense strand, and at position 1, 2, 3, 4, 5, 6, 7, 8, 9, 10, 11, 12, 13, 14, 15, 16, 17, 19, 20, 21, and 22 of the antisense strand (counted from 5' to 3' of the complementary region, i.e., not counting the 5' AA overhang). The indicated 2'-F positions that compromise RIG-I agonism (decrease>20%) are at position 1, 2, 3, 5, 7, 8, 11, 17, and 19 of the sense strand, and at position 18, 23, and 24 of the antisense strand (counted from 5' to 3' of the complementary region, i.e., not counting the 5' AA overhang).

Accordingly, the allowed consensus 2'-F positions (3 out of 4) in FIG. 4 are at position 2, 4, 6, 9, 10, 11, 12, 13, 16, 18, 19, 20, 21, 22, 23, and 24 of the sense strand and at position 1, 2, 3, 4, 5, 6, 7, 8, 9, 10, 11, 12, 13, 14, 16, 17, 19, 20, 21, and 22 of the antisense stand (counted from 5' to 3'). The prohibited consensus 2'-F positions sites (3 out of 4) are at position 1, 3, 8, and 14 of the sense strand and at position 18 and 23 of the antisense strand (counted from 5' to 3'). All nucleotide positions in the allowed 2'-F consensus are counted from 5' to 3' of the region of complementation (i.e., not including any 5' overhang of antisense strand, if present).

FIG. 5: Defined 2'-fluorination elevates the RIG-I activation. Four independent basis sequences (Seq1-4) were permuted for 2'-fluorine of single nucleotides and transfected into PBMCs. On basis of the IFN-α levels released (data not shown) one single 2'-o-fluorine position was found to increase RIG-I-related IFNα secretion independent of the RNA end configuration. Moreover, 2 more 2'-fluorine positions were identified promoting RIG-I agonism in proximity to a 5'-AA overhang.

In Seq1, the indicated RIG-I activation above parent was found for 2'-fluorine modifications at position 2, 4, 7, 10, 22, and 23 of the sense strand and at position 11 and 12 of the antisense strand (counted from 5' to 3').

In Seq2, the indicated RIG-I activation above parent was found for 2'-fluorine modifications at position 2, 5, 9, 10, 11, 16, 17, 18, and 24 of the sense strand and at position 1, 2, 8, 9, 10, and 17 of the antisense strand (counted from 5' to 3' of the complementary region, i.e., not counting the 5' AA overhang).

In Seq4, the indicated RIG-I activation above parent was found for 2'-fluorine modifications at position 10 and 21 of the sense strand and at position 1, 2, 3, 4, 5, 6, 7, 10, 12, 14, 15, 19, 20, 21, and 22 of the antisense strand (counted from 5' to 3' of the complementary region, i.e., not counting the 5' AA overhang).

In summary, the 2'-fluorine mediated boost over parent in at least 3 out of 4 polyribonucleotides is found at position 10 of the sense strand and at position 1 and 2 of the antisense strand in case of the presence of an AA overhang (>10%) (with positions counted from 5' to 3' of the complementary region, i.e., not counting the 5' AA overhang).

FIG. 6: Schematic overview of 2'-modifications and their contribution to selectivity, elevated RIG-I agonism and abrogation of RIG-I activation.

FIG. 6 shows that neither 2'-oMe nor 2'-F modification are allowed at position 1, 8, and 14 of the sense strand and at position 18 and 23 of the antisense strand (counted from 5' to 3'). FIG. 6 further shows that the 2'-oMe is not allowed at position 7 and 9 of the sense strand and at position 20 of the antisense strand (counted from 5' to 3'). FIG. 6 also shows that a 2'-F modification is not allowed at position 3 of the sense strand (counted from 5' to 3').

Additionally, FIG. 6 shows that the 2'-F modification at position 10 of the sense strand strengthens the RIG-I response; and that the 2'-F modification at position 1 and/or 2 of the antisense strand strengthens the RIG-I response in the presence of an AA overhang at the 5'-end of the antisense strand. Moreover, FIG. 6 shows that a 2'-oMe modification of purines at position 12, 15 and/or 20 of the sense strand, and/or at position 3, 10 and 22 of the antisense strand (counted from 5' to 3') establish RIG-I selectivity. It is showed that a 2'-oMe modification at position 3 and 22 of the anti-sense strand (counted from 5' to 3') prevents TLR8 agonism by this single stranded RNA.

FIG. 7: Evaluation of the identified 2'-o-methylation sites to achieve receptor selectivity in 3 novel and independent basis sequences harboring the indicated modifications at the indicated positions (pos) in the sense(s) or antisense (as) strands (compare Table 1). RNAs were transfected into PBMCs to either target RIG-I (cytosolic delivery) or TLR7/8 (endosomal delivery). The activation of RIG-I, TLR7 and TLR8 was monitored by means of IFNα and IL12p70 release, respectively (A-C). The presence of a purine at the identified 2'-o-methylation positions appears to be crucial to establish receptor selectivity (D). Sense(s) and antisense (as) strands for DR-151 are SEQ ID NOs: 23 and 24 respectively. Sense(s) and antisense (as) strands for DR-118 are SEQ ID NOs: 16 and 17 respectively. Sense(s) and antisense (as) strands for DR-101 are SEQ ID NOs: 9 and 10 respectively.

FIG. 8: Identification of a broad range 2'-modification pattern promoting receptor selectivity and ligand stabilization. Three independent basis sequences were heavily modified with 2'-methyl and 2'-fluorine according to the modification pattern (compare Table 1). RNAs were transfected into PBMCs to either target RIG-I (cytosolic delivery) or TLR7/8 (endosomal delivery). The activation of RIG-I, TLR7 and TLR8 was monitored by means of IFNα and IL12p70 release, respectively. Application of the modification pattern led to receptor selectivity without having any detrimental effect on RIG-I agonism itself. (B) gives a schematic overview about the broad range modification pattern in conjunction with the proposed positional modification pattern.

FIG. 9: Evaluation of 2'-o-methyl modification pattern in NRDR1 backbone. TLR8 agonization was tested at 50 nM agonist concentration. Sequences at bottom are the sense(s) and antisense (as) strands of DR2-101 (SEQ ID NOs: 9 and 10 respectively).

FIG. 10: Evaluation of 2'-o-methyl modification pattern in NRDR2 backbone. TLR8 agonization was tested at 50 nM agonist concentration. Sequences at bottom are the sense(s) and antisense (as) strands of DR2-118 (SEQ ID NOs: 16 and 17 respectively).

FIG. 11: Evaluation of 2'-o-methyl modification pattern in NRDR3 backbone. TLR8 agonization was tested at 50 nM agonist concentration. Sequences at bottom are the sense(s) and antisense (as) strands of DR2-151 (SEQ ID NOs: 23 and 24 respectively).

FIG. 12: Evaluation of 2'-o-methyl modification pattern in $24R^{80\ \#1.5}$ backbone with truncations or extensions to evaluate length independency. TLR7 and TLR8 agonization was tested at 50 nM agonist concentration. Sense(s) strand of 24R80 #1.5 shown at bottom (SEQ ID NO: 7).

FIG. 13: Evaluation of all identified nucleotide positions that can confer receptor selectivity in NRDR1 backbone and their purine dependency. Sequences at bottom are the sense(s) and antisense (as) strands of DR2-101 (SEQ ID NOs: 9 and 10 respectively).

FIG. 14: Evaluation of all identified nucleotide positions that can confer receptor selectivity in NRDR2 backbone and their purine dependency. Sequences at bottom are the sense(s) and antisense (as) strands of DR2-118 (SEQ ID NOs: 16 and 17 respectively).

FIG. 15: Evaluation of all identified nucleotide positions that can confer receptor selectivity in NRDR3 backbone and their purine dependency. Sequences at bottom are the sense(s) and antisense (as) strands of DR2-151 (SEQ ID NOs: 23 and 24 respectively).

FIG. 16: Evaluation how exchanging pyrimidine nucleotides at positions 12 and 20 in the sense strand of NRDR3 base sequence for purines affects oligonucleotide's preferences for the RIG-I receptor and selectivity. TLR7/8 engagement was assessed at an agonist concentration of 50 nM.

FIG. 17: Schematic overview about the broad range modification pattern, summarizing the results of Example 3 shown in FIGS. 9-16 and Tables 6-10.

DESCRIPTION OF THE SEQUENCES

TABLE 1

DESCRIPTION OF THE SEQUENCES
RNA Sequence Table.

| Ref | Internal ref | Sequence | SEQ ID NO |
|---|---|---|---|
| Seq1 | 121212 s | 5'-GACGCUGACCCUGAAGUUCAUCUU-3' | 1 |
| Seq1 | 121212 as | 5'-AAGAUGAACUUCAGGGUCAGCGUC-3' | 2 |
| Seq2 | 24R40#5.4 s | 5'-GUUCUGCAAUCAGCUAAACGUUAU-3' | 3 |
| Seq2 | 24R40#5.4 as | 5'-AAAUAACGUUUAGCUGAUUGCAGAAC-3' | 4 |
| Seq3 | biHPV16E6#003 s | 5'-GUUCUAAAAGCAAAGAUUCCAUAA-3' | 5 |
| Seq3 | biHPV16E6#003 as | 5'-UUAUGGAAUCUUUGCUUUUAGAAC-3' | 6 |
| Seq4 | 24R80#1.5 s | 5'-GGUCCGCUGUGAUUUUUGGAUUUG-3' | 7 |
| Seq4 | 24R80#1.5 as | 5'-AACAAAUCCAAAAAUCACAGCGGACC-3' | 8 |
| Seq5 | DR2-101 s | 5'-GCUCCUGAAUGCUUGCUUCAUCUU-3' | 9 |
| Seq5 | DR2-101 as | 5'-AAGAUGAAGCAAGCAUUCAGGAGC-3' | 10 |
| Seq6 | DR2-135 s | 5'-GCUCCUGAAUGC$_m$UUGCUUCAUCUU-3' | 11 |
| Seq6 | DR2-135 as | 5'-AAGAUGAAGCAAGCAUUCAGGAGC-3' | 10 |
| Seq7 | DR2-106 s | 5'-GCUCCUGAAUGC$_m$UUGCUUCAUCUU-3' | 11 |
| Seq7 | DR2-106 as | 5'-AAGAUGAAGCAAGCAUUCAGGAGC-3' | 12 |
| Seq8 | DR2-107 s | 5'-GCUCCUGAAUGC$_m$UUGCUUCAUCUU-3' | 11 |
| Seq8 | DR2-107 as | 5'-AAGAUGAAGCAAG$_f$CAUUCAGGA$_m$GC-3' | 13 |
| Seq9 | DR2-108 s | 5'-GCUCCUGAAUGC$_m$UUGCUUCAUCUU-3' | 11 |
| Seq9 | DR2-108 as | 5'-AAGAU$_f$GAAGCAAGCAUUCAGGA$_m$GC-3' | 14 |
| Seq10 | DR2-139 s | 5'-GCUCCUGAAUGCUUGCUUCAUCUU-3' | 15 |
| Seq10 | DR2-139 as | 5'-AAGAUGAAGCAAGCAUUCAGGAGC-3' | 10 |

TABLE 1-continued

DESCRIPTION OF THE SEQUENCES
RNA Sequence Table.

| Ref | Internal ref | Sequence | SEQ ID NO |
|---|---|---|---|
| Seq11 | DR2-112 s | 5'-GCUCCUGAAUGCUUGCUUCA$_m$UCUU-3' | 15 |
| Seq11 | DR2-112 as | 5'-AAGAUGAAGCAAGCAUUCAGGA$_m$GC-3' | 12 |
| Seq12 | DR2-113 s | 5'-GCUCCUGAAUGCUUGCUUCA$_m$UCUU-3' | 15 |
| Seq12 | DR2-113 as | 5'-AAGAUGAAGCAAG$_f$CAUUCAGGA$_m$GC-3' | 13 |
| Seq13 | DR2-114 s | 5'-GCUCCUGAAUGCUUGCUUCA$_m$UCUU-3' | 15 |
| Seq13 | DR2-114 as | 5'-AAGAU$_f$GAAGCAAGCAUUCAGGA$_m$GC-3' | 14 |
| Seq14 | DR2-118 s | 5'-GUUCCAAUAGUAGUCAUAGCUAUU-3' | 16 |
| Seq14 | DR2-118 as | 5'-AAUAGCUAUGACUACUAUUGGAAC-3' | 17 |
| Seq15 | DR2-143 s | 5'-GUUCCAAUAGUAGUCAUAGCUAUU-3' | 18 |
| Seq15 | DR2-143 as | 5'-AAUAGCUAUGACUACUAUUGGAAC-3' | 17 |
| Seq16 | DR2-123 s | 5'-GUUCCAAUAGUAGUCAUAGCUAUU-3' | 18 |
| Seq16 | DR2-123 as | 5'-AAUAGCUAUGACUACUAUUGGAAC-3' | 19 |
| Seq17 | DR2-124 s | 5'-GUUCCAAUAGUAGUCAUAGCUAUU-3' | 18 |
| Seq17 | DR2-124 as | 5'-AAUAGCUAUGACU$_f$ACUAUUGGA$_m$AC-3' | 20 |
| Seq18 | DR2-125 s | 5'-GUUCCAAUAGUAGUCAUAGCUAUU-3' | 18 |
| Seq18 | DR2-125 as | 5'-AAUAGCUAUGACUACUAUUGGAAC-3' | 21 |
| Seq19 | DR2-147 s | 5'-GUUCCAAUAGUAGUCAUAGC$_m$UAUU-3' | 22 |
| Seq19 | DR2-147 as | 5'-AAUAGCUAUGACUACUAUUGGAAC-3' | 17 |
| Seq20 | DR2-129 s | 5'-GUUCCAAUAGUAGUCAUAGC$_m$UAUU-3' | 22 |
| Seq20 | DR2-129 as | 5'-AAUAGCUAUGACUACUAUUGGAAC-3' | 19 |
| Seq21 | DR2-130 s | 5'-GUUCCAAUAGUAGUCAUAGC$_m$UAUU-3' | 22 |
| Seq21 | DR2-130 as | 5'-AAUAGCUAUGACU$_F$ACUAUUGGAAC-3' | 20 |
| Seq22 | DR2-131 s | 5'-GUUCCAAUAGUAGUCAUAGC$_m$UAUU-3' | 22 |
| Seq22 | DR2-131 as | 5'-AAUAGCUAUGACUACUAUUGGAAC-3' | 21 |
| Seq23 | DR2-151 s | 5'-GUUCUGCAACUCAAAGUGCUAUUG-3' | 23 |
| Seq23 | DR2-151 as | 5'-CAAUAGCACUUUGAGUUGCAGAAC-3' | 24 |
| Seq24 | DR2-156 s | 5'-GUUCUGCAACUC$_m$AAAGUGCUAUUG-3' | 25 |
| Seq24 | DR2-156 as | 5'-CAAUAGCACUUUGAGUUGCAGAAC-3' | 24 |
| Seq25 | DR2-157 s | 5'-GUUCUGCAACUC$_m$AAAGUGCUAUUG-3' | 25 |
| Seq25 | DR2-157 as | 5'-CAAUAGCACUUUGAGUUGCAGAAC-3' | 26 |
| Seq26 | DR2-158 s | 5'-GUUCUGCAACUC$_m$AAAGUGCUAUUG-3' | 25 |
| Seq26 | DR2-158 as | 5'-CAAUAGCACUUUG$_f$AGUUGCAGA$_m$AC-3' | 27 |
| Seq27 | DR2-159 s | 5'-GUUCUGCAACUC$_m$AAAGUGCUAUUG-3' | 25 |
| Seq27 | DR2-159 as | 5'-CAAUA$_f$GCACUUUGAGUUGCAGA$_m$AC-3' | 28 |
| Seq28 | DR2-166 s | 5'-GUUCUGCAACUCAAAGUGCU$_m$AUUG-3' | 29 |
| Seq28 | DR2-166 as | 5'-CAAUAGCACUUUGAGUUGCAGAAC-3' | 24 |

TABLE 1-continued

DESCRIPTION OF THE SEQUENCES
RNA Sequence Table.

| Ref | Internal ref | Sequence | SEQ ID NO |
|---|---|---|---|
| Seq29 | DR2-167 s | 5'-GUUCUGCAACUCAAAGUGCU$_m$AUUG-3' | 29 |
| Seq29 | DR2-167 as | 5'-CAAUAGCACUUUGAGUUGCAGAAC-3' | 26 |
| Seq30 | DR2-168 s | 5'-GUUCUGCAACUCAAAGUGCU$_m$AUUG-3' | 29 |
| Seq30 | DR2-168 as | 5'-CAAUAGCACUUUG$_f$AGUUGCAGA$_m$AC-3' | 27 |
| Seq31 | DR2-169 s | 5'-GUUCUGCAACUCAAAGUGCU$_m$AUUG-3' | 29 |
| Seq31 | DR2-169 as | 5'-CAAUA$_f$GCACUUUGAGUUGCAGA$_m$AC-3' | 28 |
| Seq32 | DR2-105 s | 5'-GC$_f$UC$_f$CUGAA$_f$U$_f$GC$_m$UUG$_m$C$_f$UUCAU$_f$C$_f$UU$_f$-3' | 30 |
| Seq32 | DR2-105 as | 5'-AAGAU$_f$GAAGCAAG$_f$CAUUCAGGA$_m$GC-3' | 31 |
| Seq33 | DR2-122 s | 5'-GU$_f$UC$_f$CAAUA$_f$G$_f$UA$_m$GUC$_m$A$_f$UAGC$_m$U$_f$A$_f$UU$_f$-3' | 32 |
| Seq33 | DR2-122 as | 5'-AAUAG$_f$CUAUGACU$_f$ACUAUUGGA$_m$AC-3' | 33 |
| Seq34 | DR2-155 s | 5'-GU$_f$UC$_f$UGCAA$_f$C$_f$UC$_m$AAA$_m$G$_f$UGCU$_m$A$_f$U$_f$UG$_f$-3' | 34 |
| Seq34 | DR2-155 as | 5'-CAAUA$_f$GCACUUUG$_f$AGUUGCAGA$_m$AC-3' | 35 |
| Seq35 | 122212 s | 5'-3P-GACGCUGACCCUGAAGUUCAUCUU-3' | 36 |
| Seq35 | 122212 as | 5'-AAGAUGAACUUCAGGGUCAGCGUC-3' | 2 |
| Seq36 | 123212 s | 5'-GACGCUG$_f$ACCCUGAA$_m$GUUCAUC*U$_f$*U-3' | 37 |
| Seq36 | 123212 as | 5'-A*A*GAUGAACUUC$_f$AGGGUCAGCG$_m$UC-3' | 38 |
| | DR2-102 s | 5'-GC$_f$UC$_f$CU$_f$GAA$_f$U$_f$GC$_m$UUG$_m$C$_f$UUCA$_m$U$_f$C$_f$UU$_f$-3' | 39 |
| | DR2-102 as | 5'-AAGAU$_f$GAAGCAAG$_f$CAUUC$_f$AGGA$_m$GC-3' | 40 |
| | DR2-103 s | 5'-GCUCCUGAAUGC$_m$UUG$_m$CUUCA$_m$UCUU-3' | 41 |
| | DR2-103 as | 5'-AAGAUGAAGCAAGCAUUCAGGA$_m$GC-3' | 12 |
| | DR2-104 s | 5'-GC$_f$UC$_f$CU$_f$GAA$_f$U$_f$GCUUGC$_f$UUCAU$_f$C$_f$UU$_f$-3' | 42 |
| | DR2-104 as | 5'-AAGAU$_f$GAAGCAAG$_f$CAUUC$_f$AGGAGC-3' | 43 |
| | DR2-109 s | 5'-GCUC$_f$CUGAAUGC$_m$UUGCUUCAU$_f$CUU-3' | 44 |
| | DR2-109 as | 5'-AAGAUGAAGCAAGCAUUCAGGA$_m$GC-3' | 12 |
| | DR2-110 s | 5'-GCUC$_f$CUGAAUGC$_m$UUGCUUCAU$_f$CUU-3' | 44 |
| | DR2-110 as | 5'-AAGAUGAAGCAAG$_f$CAUUCAGGA$_m$GC-3' | 13 |
| | DR2-111 s | 5'-GCUC$_f$CUGAAUGC$_m$UUGCUUCAU$_f$CUU-3' | 44 |
| | DR2-111 as | 5'-AAGAU$_f$GAAGCAAGCAUUCAGGA$_m$GC-3' | 14 |
| | DR2-115 s | 5'-GCUC$_f$CUGAAUGCUUGCUUCA$_m$U$_f$CUU-3' | 45 |
| | DR2-115 as | 5'-AAGAUGAAGCAAGCAUUCAGGA$_m$GC-3' | 12 |
| | DR2-116 s | 5'-GCUC$_f$CUGAAUGCUUGCUUCA$_m$U$_f$CUU-3' | 45 |
| | DR2-116 as | 5'-AAGAUGAAGCAAG$_m$CAUUCAGGA$_m$GC-3' | 13 |
| | DR2-117 s | 5'-GCUCCUGAAUGCUUGCUUCA$_m$UCUU-3' | 45 |
| | DR2-117 as | 5'-AAGAU$_m$GAAGCAAGCAUUCAGGA$_m$GC-3' | 14 |
| | DR2-119 s | 5'-GU$_f$UC$_f$CA$_f$AUA$_f$G$_f$UA$_m$GUC$_m$A$_f$UAGC$_m$U$_f$A$_f$UU$_f$-3' | 46 |
| | DR2-119 as | 5'-AAUAG$_f$CUAUGACU$_f$ACUAU$_f$UGGA$_m$AC-3' | 47 |
| | DR2-120 s | 5'-GUUCCAAUAGUA$_m$GUC$_m$AUAGC$_m$UAUU-3' | 48 |

TABLE 1-continued

DESCRIPTION OF THE SEQUENCES
RNA Sequence Table.

| Ref | Internal ref | Sequence | SEQ ID NO |
|---|---|---|---|
| | DR2-120 as | 5'-AAUAGCUAUGACUACUAUUGG$A_m$AC-3' | 19 |
| | DR2-121 s | 5'-G$U_f$U$C_f$C$A_f$AU$A_f$$G_f$UAGUC$A_f$UAGC$U_f$$A_f$U$U_f$-3' | 49 |
| | DR2-121 as | 5'-AAUA$G_f$CUAUGAC$U_f$ACUAUUGGAAC-3' | 50 |
| | DR2-126 s | 5'-GUU$C_f$CAAUAGU$A_m$GUCAUAGC$U_f$AUU-3' | 51 |
| | DR2-126 as | 5'-AAUAGCUAUGACUACUAUUGG$A_m$AC-3' | 19 |
| | DR2-127 s | 5'-GUU$C_f$CAAUAGU$A_m$GUCAUAGC$U_f$AUU-3' | 51 |
| | DR2-127 as | 5'-AAUAGCUAUGAC$U_f$ACUAUUGG$A_m$AC-3' | 20 |
| | DR2-128 s | 5'-GUU$C_f$CAAUAGU$A_m$GUCAUAGC$U_f$AUU-3' | 51 |
| | DR2-128 as | 5'-AAUA$G_f$CUAUGACUACUAUUGG$A_m$AC-3' | 21 |
| | DR2-132 s | 5'-GUU$C_f$CAAUAGUAGUCAUAG$C_m$$U_f$AUU-3' | 52 |
| | DR2-132 as | 5'-AAUAGCUAUGACUACUAUUGG$A_m$AC-3' | 19 |
| | DR2-133 s | 5'-GUU$C_f$CAAUAGUAGUCAUAG$C_m$$U_f$AUU-3' | 52 |
| | DR2-133 as | 5'-AAUAGCUAUGAC$U_f$ACUAUUGG$A_m$AC-3' | 20 |
| | DR2-134 s | 5'-GUU$C_f$CAAUAGUAGUCAUAG$C_m$$U_f$AUU-3' | 52 |
| | DR2-134 as | 5'-AAUA$G_f$CUAUGACUACUAUUGG$A_m$AC-3' | 21 |
| | DR2-136 s | 5'-GCUCCUGAAUG$C_m$UUGCUUCAUCUU-3' | 11 |
| | DR2-136 as | 5'-AAGA$U_f$GAAGCAA$G_f$CAUUCAGG$A_m$GC-3' | 53 |
| | DR2-137 s | 5'-GCUCCUGAAUG$C_m$UUGCUUCA$U_f$CUU-3' | 44 |
| | DR2-137 as | 5'-AAGAUGAAGCAAGCAUUCAGGAGC-3' | 10 |
| | DR2-138 s | 5'-GCU$C_f$CUGAAUG$C_m$UUGCUUCA$U_f$CUU-3' | 44 |
| | DR2-138 as | 5'-AAGA$U_f$GAAGCAA$G_f$CAUUCAGG$A_m$GC-3' | 53 |
| | DR2-140 s | 5'-GCUCCUGAAUGCUUGCUUC$A_m$UCUU-3' | 15 |
| | DR2-140 as | 5'-AAGA$U_f$GAAGCAA$G_f$CAUUCAGG$A_m$GC-3' | 53 |
| | DR2-141 s | 5'-GCU$C_f$CUGAAUGCUUGCUUC$A_m$$U_f$CUU-3' | 45 |
| | DR2-141 as | 5'-AAGAUGAAGCAAGCAUUCAGGAGC-3' | 10 |
| | DR2-142 s | 5'-GCU$C_f$CUGAAUGCUUGCUUC$A_m$$U_f$CUU-3' | 45 |
| | DR2-142 as | 5'-AAGA$U_f$GAAGCAA$G_f$CAUUCAGG$A_m$GC-3' | 53 |
| | DR2-144 s | 5'-GUUCCAAUAGU$A_m$GUCAUAGCUAUU-3' | 18 |
| | DR2-144 as | 5'-AAUA$G_f$CUAUGAC$U_f$ACUAUUGG$A_m$AC-3' | 54 |
| | DR2-145 s | 5'-GUU$C_f$CAAUAGU$A_m$GUCAUAGC$U_f$AUU-3' | 51 |
| | DR2-145 as | 5'-AAUAGCUAUGACUACUAUUGGAAC-3' | 17 |
| | DR2-146 s | 5'-GUU$C_f$CAAUAGU$A_m$GUCAUAGC$U_f$AUU-3' | 51 |
| | DR2-146 as | 5'-AAUA$G_f$CUAUGAC$U_f$ACUAUUGG$A_m$AC-3' | 54 |
| | DR2-148 s | 5'-GUUCCAAUAGUAGUCAUAG$C_m$UAUU-3' | 22 |
| | DR2-148 as | 5'-AAUA$G_f$CUAUGAC$U_f$ACUAUUGG$A_m$AC-3' | 54 |
| | DR2-149 s | 5'-GUU$C_f$CAAUAGUAGUCAUAG$C_m$$U_f$AUU-3' | 45 |

TABLE 1-continued

DESCRIPTION OF THE SEQUENCES
RNA Sequence Table.

| Ref | Internal ref | Sequence | SEQ ID NO |
|---|---|---|---|
| | DR2-149 as | 5'-AAUAGCUAUGACUACUAUUGGAAC-3' | 17 |
| | DR2-150 s | 5'-GUUC$_f$CAAUAGUAGUCAUAGC$_m$U$_f$AUU-3' | 45 |
| | DR2-150 as | 5'-AAUAG$_f$CUAUGACU$_f$ACUAUUGGA$_m$AC-3' | 54 |
| | DR2-152 s | 5'-GU$_f$UC$_f$UG$_f$CAA$_f$C$_f$UC$_m$AAA$_m$G$_f$UGCU$_m$A$_f$U$_f$UG$_f$-3' | 55 |
| | DR2-152 as | 5'-CAAUA$_f$GCACUUUG$_f$AGUUG$_f$CAGA$_m$AC-3' | 56 |
| | DR2-153 s | 5'-GUUCUGCAACUC$_m$AAA$_m$GUGCU$_m$AUUG-3' | 57 |
| | DR2-153 as | 5'-CAAUAGCACUUUGAGUUGCAGA$_m$AC-3' | 26 |
| | DR2-154 s | 5'-GU$_f$UC$_f$UG$_f$CAA$_f$C$_f$UCAAAG$_f$UGCUA$_f$U$_f$UG$_f$-3' | 58 |
| | DR2-154 as | 5'-CAAUA$_f$GCACUUUG$_f$AGUUG$_f$CAGAAC-3' | 59 |
| | DR2-160 s | 5'-GUUCUGCAACUC$_m$AAAGUGCUAUUG-3' | 25 |
| | DR2-160 as | 5'-CAAUA$_f$GCACUUUG$_f$AGUUGCAGA$_m$AC-3' | 60 |
| | DR2-161 s | 5'-GUUC$_f$UGCAACUC$_m$AAAGUGCUA$_f$UUG-3' | 61 |
| | DR2-161 as | 5'-CAAUAGCACUUUGAGUUGCAGAAC-3' | 24 |
| | DR2-162 s | 5'-GUUC$_f$UGCAACUC$_m$AAAGUGCUA$_f$UUG-3' | 61 |
| | DR2-162 as | 5'-CAAUAGCACUUUGAGUUGCAGA$_m$AC-3' | 26 |
| | DR2-163 s | 5'-GUUC$_f$UGCAACUC$_m$AAAGUGCUA$_f$UUG-3' | 61 |
| | DR2-163 as | 5'-CAAUAGCACUUUG$_f$AGUUGCAGA$_m$AC-3' | 27 |
| | DR2-164 s | 5'-GUUC$_f$UGCAACUC$_m$AAAGUGCUA$_f$UUG-3' | 61 |
| | DR2-164 as | 5'-CAAUA$_f$GCACUUUGAGUUGCAGA$_m$AC-3' | 28 |
| | DR2-165 s | 5'-GUUC$_f$UGCAACUC$_m$AAAGUGCUA$_f$UUG-3' | 61 |
| | DR2-165 as | 5'-CAAUA$_f$GCACUUUG$_f$AGUUGCAGA$_m$AC-3' | 60 |
| | DR2-170 s | 5'-GUUCUGCAACUCAAAGUGCU$_m$AUUG-3' | 29 |
| | DR2-170 as | 5'-CAAUA$_f$GCACUUUG$_f$AGUUGCAGA$_m$AC-3' | 60 |
| | DR2-171 s | 5'-GUUC$_f$UGCAACUCAAAGUGCU$_m$A$_f$UUG-3' | 62 |
| | DR2-171 as | 5'-CAAUAGCACUUUGAGUUGCAGAAC-3' | 24 |
| | DR2-172 s | 5'-GUUC$_f$UGCAACUCAAAGUGCU$_m$A$_f$UUG-3' | 62 |
| | DR2-172 as | 5'-CAAUAGCACUUUGAGUUGCAGAAC-3' | 26 |
| | DR2-173 s | 5'-GUUCUGCAACUCAAAGUGCU$_m$A{UUG-3' | 62 |
| | DR2-173 as | 5'-CAAUAGCACUUUGAGUUGCAGA$_m$AC-3' | 27 |
| | DR2-174 s | 5'-GUUCUGCAACUCAAAGUGCU$_m$A{UUG-3' | 62 |
| | DR2-174 as | 5'-CAAUA$_m$GCACUUUGAGUUGCAGA$_m$AC-3' | 28 |
| | DR2-175 s | 5'-GUUCUGCAACUCAAAGUGCU$_m$A{UUG-3' | 62 |
| | DR2-175 as | 5'-CAAUA$_m$GCACUUUG$_m$AGUUGCAGA$_m$AC-3' | 60 |
| | DR2-176 s | 5'-GGUCCGCUGUGAUUUUUGGAUUUG-3' | 7 |
| | DR2-176 as | 5'-CAAAUCCAAAAAUCACAGCGGACC-3' | 8 |
| | DR2-177 s | 5'-GGUCCGCUGUGA$_m$UUU$_m$UUGGA$_m$UUUG-3' | 63 |
| | DR2-177 as | 5'-CAAAUCCAAAAAUCACAGCGGA$_m$CC-3' | 64 |

TABLE 1-continued

DESCRIPTION OF THE SEQUENCES
RNA Sequence Table.

| Ref | Internal ref | Sequence | SEQ ID NO |
|---|---|---|---|
| | DR2-178 s | 5'-GGUCCGCUGUGA$_m$UUU$_m$UUGGA$_m$UU-3' | 65 |
| | DR2-178 as | 5'-AAUCCAAAAAUCACAGCGGA$_m$CC-3' | 66 |
| | DR2-179 s | 5'-GGUCCGCUGUGA$_m$UUU$_m$UUGGA$_m$-3' | 67 |
| | DR2-179 as | 5'-UCCAAAAAUCACAGCGGA$_m$CC-3' | 68 |
| | DR2-180 s | 5'-GGUCCGCUGUGA$_m$UUU$_m$UUGGA$_m$UUUGAA-3' | 69 |
| | DR2-180 as | 5'-UUCAAAUCCAAAAAUCACAGCGGA$_m$CC-3' | 70 |
| | DR2-181 s | 5'-GGUCCGCUGUGA$_m$UUU$_m$UUGGA$_m$UUUGAAAA-3' | 71 |
| | DR2-181 as | 5'-UUUUCAAAUCCAAAAAUCACAGCGGA$_m$CC-3' | 72 |
| | DR2-182 s | 5'-UCCGCUGUGA$_m$UUU$_m$UUGGA$_m$UUUG-3' | 73 |
| | DR2-182 as | 5'-CAAAUCCAAAAAUCACAGCGGA$_m$-3' | 74 |
| | DR2-183 s | 5'-CGCUGUGA$_m$UUU$_m$UUGGA$_m$UUUG-3' | 75 |
| | DR2-183 as | 5'-CAAAUCCAAAAAUCACAGCG-3' | 76 |
| | DR2-184 s | 5'-GAGGUCCGCUGUGA$_m$UUU$_m$UUGGA$_m$UUUG-3' | 77 |
| | DR2-184 as | 5'-CAAAUCCAAAAAUCACAGCGGACCUC-3' | 78 |
| | DR2-185 s | 5'-GAGAGGUCCGCUGUGA$_m$UUU$_m$UUGGA$_m$UUUG-3' | 79 |
| | DR2-185 as | 5'-CAAAUCCAAAAAUCACAGCGGACCUCUC-3' | 80 |
| | DR2-186 s | 5'-GGUCCGCUGUGAUUUUUGGAUU-3' | 81 |
| | DR2-186 as | 5'-AAUCCAAAAAUCACAGCGGACC-3' | 82 |
| | DR2-187 s | 5'-GGUCCGCUGUGAUUUUUGGA-3' | 83 |
| | DR2-187 as | 5'-UCCAAAAAUCACAGCGGACC-3' | 84 |
| | DR2-188 s | 5'-GGUCCGCUGUGAUUUUUGGAUUUGAA-3' | 85 |
| | DR2-188 as | 5'-UUCAAAUCCAAAAAUCACAGCGGACC-3' | 86 |
| | DR2-189 s | 5'-GGUCCGCUGUGAUUUUUGGAUUUGAAAA-3' | 87 |
| | DR2-189 as | 5'-UUUUCAAAUCCAAAAAUCACAGCGGACC-3' | 88 |
| | DR2-190 s | 5'-UCCGCUGUGAUUUUUGGAUUUG-3' | 89 |
| | DR2-190 as | 5'-CAAAUCCAAAAAUCACAGCGGA-3' | 90 |
| | DR2-191 s | 5'-CGCUGUGAUUUUUGGAUUUG-3' | 91 |
| | DR2-191 as | 5'-CAAAUCCAAAAAUCACAGCG-3' | 76 |
| | DR2-192 s | 5'-GAGGUCCGCUGUGAUUUUUGGAUUUG-3' | 92 |
| | DR2-192 as | 5'-CAAAUCCAAAAAUCACAGCGGACCUC-3' | 93 |
| | DR2-193 s | 5'-GAGAGGUCCGCUGUGAUUUUUGGAUUUG-3' | 94 |
| | DR2-193 as | 5'-CAAAUCCAAAAAUCACAGCGGACCUCUC-3' | 95 |
| | DR2-194 s | 5'-GGUCCUGGGUGAUUUUCUAAUUUG-3' | 96 |
| | DR2-194 as | 5'-CAAAUUAGAAAAUCACCCAGGACC-3' | 97 |
| | DR2-195 s | 5'-GGUCCUGGGUGA$_m$UUU$_m$UCUAA$_m$UUUG-3' | 98 |
| | DR2-195 as | 5'-CAAAUUAGAAAAUCACCCAGGA$_m$CC-3' | 99 |

TABLE 1-continued

DESCRIPTION OF THE SEQUENCES
RNA Sequence Table.

| Ref | Internal ref | Sequence | SEQ ID NO |
|---|---|---|---|
| | DR2-196 s | 5'-GGUCCUGGGUGA$_m$UUU$_m$UCUAA$_m$UU-3' | 100 |
| | DR2-196 as | 5'-AAUUAGAAAAUCACCCAGGACC-3' | 101 |
| | DR2-197 s | 5'-GGUCCUGGGUGA$_m$UUU$_m$UCUAA$_m$-3' | 102 |
| | DR2-197 as | 5'-UUAGAAAAUCACCCAGGACC-3' | 103 |
| | DR2-198 s | 5'-GGUCCUGGGUGA$_m$UUU$_m$UCUAA$_m$UUUGAA-3' | 104 |
| | DR2-198 as | 5'-UUCAAAUUAGAAAAUCACCCAGGACC-3' | 105 |
| | DR2-199 s | 5'-GGUCCUGGGUGA$_m$UUU$_m$UCUAA$_m$UUUGAAAA-3' | 106 |
| | DR2-199 as | 5'-UUUUCAAAUUAGAAAAUCACCCAGGA$_m$CC-3' | 107 |
| | DR2-200 s | 5'-UCCUGGGUGAUUU$_m$UCUAA$_m$UUUG-3' | 108 |
| | DR2-200 as | 5'-CAAAUUAGAAAAUCACCCAGGAn-3' | 109 |
| | DR2-201 s | 5'-CUGGGUGA$_m$UUU$_m$UCUAA$_m$UUUG-3' | 110 |
| | DR2-201 as | 5'-CAAAUUAGAAAAUCACCCAG-3' | ill |
| | DR2-202 s | 5'-GAGGUCCUGGGUGA$_m$UUU$_m$UCUAA$_m$UUUG-3' | 112 |
| | DR2-202 as | 5'-CAAAUUAGAAAAUCACCCAGGA$_m$CCUC-3' | 113 |
| | DR2-203 s | 5'-GAGAGGUCCUGGGUGA$_m$UUU$_m$UCUAA$_m$UUUG-3' | 114 |
| | DR2-203 as | 5'-CAAAUUAGAAAAUCACCCAGGA$_m$CCUCUC-3' | 115 |
| | DR2-204 s | 5'-GGUCCUGGGUGAUUUUCUAAUU-3' | 116 |
| | DR2-204 as | 5'-AAUUAGAAAAUCACCCAGGACC-3' | 117 |
| | DR2-205 s | 5'-GGUCCUGGGUGAUUUUCUAA-3' | 118 |
| | DR2-205 as | 5'-UUAGAAAAUCACCCAGGACC-3' | 119 |
| | DR2-206 s | 5'-GGUCCUGGGUGAUUUUCUAAUUUGAA-3' | 120 |
| | DR2-206 as | 5'-UUCAAAUUAGAAAAUCACCCAGGACC-3' | 121 |
| | DR2-207 s | 5'-GGUCCUGGGUGAUUUUCUAAUUUGAAAA-3' | 122 |
| | DR2-207 as | 5'-UUUUCAAAUUAGAAAAUCACCCAGGACC-3' | 123 |
| | DR2-208 s | 5'-UCCUGGGUGAUUUUCUAAUUUG-3' | 124 |
| | DR2-208 as | 5'-CAAAUUAGAAAAUCACCCAGGA-3' | 125 |
| | DR2-209 s | 5'-CUGGGUGAUUUUCUAAUUUG-3' | 126 |
| | DR2-209 as | 5'-CAAAUUAGAAAAUCACCCAG-3' | ill |
| | DR2-210 s | 5'-GAGGUCCUGGGUGAUUUUCUAAUUUG-3' | 127 |
| | DR2-210 as | 5'-CAAAUUAGAAAAUCACCCAGGACCUC-3' | 128 |
| | DR2-211 s | 5'-GAGAGGUCCUGGGUGAUUUUCUAAUUUG-3' | 129 |
| | DR2-211 as | 5'-CAAAUUAGAAAAUCACCCAGGACCUCUC-3' | 130 |
| | DR2-212 s | 5'-GCUCCUGAAUGCUUGCUUCAUCUU-3' | 9 |
| | DR2-212 as | 5'-AAGAUGAAGCAAGCAUUCAGGAGC-3' | 10 |
| | DR2-213 s | 5'-GCUCCUGAAUGC$_m$UUGCUUCAUCUU-3' | 11 |
| | DR2-213 as | 5'-AAGAUGAAGCAAGCAUUCAGGAGC-3' | 10 |
| | DR2-214 s | 5'-GCUCCUGAAUGCUUG$_m$CUUCAUCUU-3' | 131 |

TABLE 1-continued

DESCRIPTION OF THE SEQUENCES
RNA Sequence Table.

| Ref | Internal ref | Sequence | SEQ ID NO |
|---|---|---|---|
| | DR2-214 as | 5'-AAGAUGAAGCAAGCAUUCAGGAGC-3' | 10 |
| | DR2-215 s | 5'-GCUCCUGAAUGCUUGCUUCA$_m$UCUU-3' | 15 |
| | DR2-215 as | 5'-AAGAUGAAGCAAGCAUUCAGGAGC-3' | 10 |
| | DR2-216 s | 5'-GCUCCUGAAUGCUUGCUUCAUCUU-3' | 9 |
| | DR2-216 as | 5'-AAG$_m$AUGAAGCAAGCAUUCAGGAGC-3' | 132 |
| | DR2-217 s | 5'-GCUCCUGAAUGC$_m$UUGCUUCAUCUU-3' | 11 |
| | DR2-217 as | 5'-AAG$_m$AUGAAGCAAGCAUUCAGGAGC-3' | 132 |
| | DR2-218 s | 5'-GCUCCUGAAUGCUUG$_m$CUUCAUCUU-3' | 131 |
| | DR2-218 as | 5'-AAG$_m$AUGAAGCAAGCAUUCAGGAGC-3' | 132 |
| | DR2-219 s | 5'-GCUCCUGAAUGCUUGCUUCA$_m$UCUU-3' | 15 |
| | DR2-219 as | 5'-AAG$_m$AUGAAGCAAGCAUUCAGGAGC-3' | 132 |
| | DR2-220 s | 5'-GCUCCUGAAUGCUUGCUUCAUCUU-3' | 9 |
| | DR2-220 as | 5'-AAGAUGAAGC$_m$AAGCAUUCAGGAGC-3' | 133 |
| | DR2-221 s | 5'-GCUCCUGAAUGC$_m$UUGCUUCAUCUU-3' | 11 |
| | DR2-221 as | 5'-AAGAUGAAGC$_m$AAGCAUUCAGGAGC-3' | 133 |
| | DR2-222 s | 5'-GCUCCUGAAUGCUUGCUUCAUCUU-3' | 131 |
| | DR2-222 as | 5'-AAGAUGAAGC$_m$AAGCAUUCAGGAGC-3' | 133 |
| | DR2-223 s | 5'-GCUCCUGAAUGCUUGCUUCA$_m$UCUU-3' | 15 |
| | DR2-223 as | 5'-AAGAUGAAGC$_m$AAGCAUUCAGGAGC-3' | 133 |
| | DR2-224 s | 5'-GUUCCAAUAGUAGUCAUAGCUAUU-3' | 16 |
| | DR2-224 as | 5'-AAUAGCUAUGACUACUAUUGGAAC-3' | 17 |
| | DR2-225 s | 5'-GUUCCAAUAGUA$_m$GUCAUAGCUAUU-3' | 18 |
| | DR2-225 as | 5'-AAUAGCUAUGACUACUAUUGGAAC-3' | 17 |
| | DR2-226 s | 5'-GUUCCAAUAGUAGUC$_m$AUAGCUAUU-3' | 134 |
| | DR2-226 as | 5'-AAUAGCUAUGACUACUAUUGGAAC-3' | 17 |
| | DR2-227 s | 5'-GUUCCAAUAGUAGUCAUAGC$_m$UAUU-3' | 22 |
| | DR2-227 as | 5'-AAUAGCUAUGACUACUAUUGGAAC-3' | 17 |
| | DR2-228 s | 5'-GUUCCAAUAGUAGUCAUAGCUAUU-3' | 16 |
| | DR2-228 as | 5'-AAU$_m$AGCUAUGACUACUAUUGGAAC-3' | 135 |
| | DR2-229 s | 5'-GUUCCAAUAGUAGUCAUAGCUAUU-3' | 18 |
| | DR2-229 as | 5'-AAU$_m$AGCUAUGACUACUAUUGGAAC-3' | 135 |
| | DR2-230 s | 5'-GUUCCAAUAGUAGUCAUAGCUAUU-3' | 134 |
| | DR2-230 as | 5'-AAUAGCUAUGACUACUAUUGGAAC-3' | 135 |
| | DR2-231 s | 5'-GUUCCAAUAGUAGUCAUAGC$_m$UAUU-3' | 22 |
| | DR2-231 as | 5'-AAUAGCUAUGACUACUAUUGGAAC-3' | 135 |
| | DR2-232 s | 5'-GUUCCAAUAGUAGUCAUAGCUAUU-3' | 16 |

TABLE 1-continued

DESCRIPTION OF THE SEQUENCES
RNA Sequence Table.

| Ref | Internal ref | Sequence | SEQ ID NO |
|---|---|---|---|
| | DR2-232 as | 5'-AAUAGCUAUGACUACUAUUGGAAC-3' | 136 |
| | DR2-233 s | 5'-GUUCCAAUAGUA$_m$GUCAUAGCUAUU-3' | 18 |
| | DR2-233 as | 5'-AAUAGCUAUGACUACUAUUGGAAC-3' | 136 |
| | DR2-234 s | 5'-GUUCCAAUAGUAGUCAUAGCUAUU-3' | 134 |
| | DR2-234 as | 5'-AAUAGCUAUGACUACUAUUGGAAC-3' | 136 |
| | DR2-235 s | 5'-GUUCCAAUAGUAGUCAUAGC$_m$UAUU-3' | 22 |
| | DR2-235 as | 5'-AAUAGCUAUGACUACUAUUGGAAC-3' | 136 |
| | DR2-236 s | 5'-GUUCUGCAACUCAAAGUGCUAUUG-3' | 23 |
| | DR2-236 as | 5'-CAAUAGCACUUUGAGUUGCAGAAC-3' | 24 |
| | DR2-237 s | 5'-GUUCUGCAACUC$_m$AAAGUGCUAUUG-3' | 25 |
| | DR2-237 as | 5'-CAAUAGCACUUUGAGUUGCAGAAC-3' | 24 |
| | DR2-238 s | 5'-GUUCUGCAACUCAAA$_m$GUGCUAUUG-3' | 137 |
| | DR2-238 as | 5'-CAAUAGCACUUUGAGUUGCAGAAC-3' | 24 |
| | DR2-239 s | 5'-GUUCUGCAACUCAAAGUGCU$_m$AUUG-3' | 29 |
| | DR2-239 as | 5'-CAAUAGCACUUUGAGUUGCAGAAC-3' | 24 |
| | DR2-240 s | 5'-GUUCUGCAACUCAAAGUGCUAUUG-3' | 23 |
| | DR2-240 as | 5'-CAA$_m$UAGCACUUUGAGUUGCAGAAC-3' | 138 |
| | DR2-241 s | 5'-GUUCUGCAACUCAAAGUGCUAUUG-3' | 25 |
| | DR2-241 as | 5'-CAA$_m$UAGCACUUUGAGUUGCAGAAC-3' | 138 |
| | DR2-242 s | 5'-GUUCUGCAACUCAAAGUGCUAUUG-3' | 137 |
| | DR2-242 as | 5'-CAA$_m$UAGCACUUUGAGUUGCAGAAC-3' | 138 |
| | DR2-243 s | 5'-GUUCUGCAACUCAAAGUGCUAUUG-3' | 29 |
| | DR2-243 as | 5'-CAA$_m$UAGCACUUUGAGUUGCAGAAC-3' | 138 |
| | DR2-244 s | 5'-GUUCUGCAACUCAAAGUGCUAUUG-3' | 23 |
| | DR2-244 as | 5'-CAAUAGCACU$_m$UUGAGUUGCAGAAC-3' | 139 |
| | DR2-245 s | 5'-GUUCUGCAACUC$_m$AAAGUGCUAUUG-3' | 25 |
| | DR2-245 as | 5'-CAAUAGCACU$_m$UUGAGUUGCAGAAC-3' | 139 |
| | DR2-246 s | 5'-GUUCUGCAACUCAAAGUGCUAUUG-3' | 137 |
| | DR2-246 as | 5'-CAAUAGCACU$_m$UUGAGUUGCAGAAC-3' | 139 |
| | DR2-247 s | 5'-GUUCUGCAACUCAAAGUGCUAUUG-3' | 29 |
| | DR2-247 as | 5'-CAAUAGCACU$_m$UUGAGUUGCAGAAC-3' | 139 |
| | DR2-248 s | 5'-GUUCUGCAACUGAAAGUGCUAUUG-3' | 140 |
| | DR2-248 as | 5'-CAAUAGCACUUUCAGUUGCAGAAC-3' | 141 |
| | DR2-249 s | 5'-GUUCUGCAACUAAAAGUGCUAUUG-3' | 142 |
| | DR2-249 as | 5'-CAAUAGCACUUUUAGUUGCAGAAC-3' | 143 |
| | DR2-250 s | 5'-GUUCUGCAACUCAAAGUGCGAUUG-3' | 144 |
| | DR2-250 as | 5'-CAAUCGCACUUUGAGUUGCAGAAC-3' | 145 |

TABLE 1-continued

DESCRIPTION OF THE SEQUENCES
RNA Sequence Table.

| Ref | Internal ref | Sequence | SEQ ID NO |
|---|---|---|---|
| | DR2-251 s | 5'-GUUCUGCAACUCAAAGUGCAAUUG-3' | 146 |
| | DR2-251 as | 5'-CAAUUGCACUUUGAGUUGCAGAAC-3' | 147 |
| | DR2-252 s | 5'-GUUCUGCAACUGAAAGUGCGAUUG-3' | 148 |
| | DR2-252 as | 5'-CAAUCGCACUUUCAGUUGCAGAAC-3' | 149 |
| | DR2-253 s | 5'-GUUCUGCAACUAAAAGUGCAAUUG-3' | 150 |
| | DR2-253 as | 5'-CAAUUGCACUUUUAGUUGCAGAAC-3' | 151 |
| | DR2-254 s | 5'-GUUCUGCAACUGAAAGUGCUAUUG-3' | 152 |
| | DR2-254 as | 5'-CAAUAGCACUUUCAGUUGCAGAAC-3' | 141 |
| | DR2-255 s | 5'-GUUCUGCAACUAAAAGUGCUAUUG-3' | 153 |
| | DR2-255 as | 5'-CAAUAGCACUUUUAGUUGCAGAAC-3' | 143 |
| | DR2-256 s | 5'-GUUCUGCAACUCAAAGUGCGAUUG-3' | 154 |
| | DR2-256 as | 5'-CAAUCGCACUUUGAGUUGCAGAAC-3' | 145 |
| | DR2-257 s | 5'-GUUCUGCAACUCAAAGUGCAAUUG-3' | 155 |
| | DR2-257 as | 5'-CAAUUGCACUUUGAGUUGCAGAAC-3' | 147 |
| | DR2-258 s | 5'-GUUCUGCAACUG$_m$AAAGUGCGAUUG-3' | 156 |
| | DR2-258 as | 5'-CAAUCGCACUUUCAGUUGCAGAAC-3' | 149 |
| | DR2-259 s | 5'-GUUCUGCAACUA$_m$AAAGUGCAAUUG-3' | 157 |
| | DR2-259 as | 5'-CAAUUGCACUUUUAGUUGCAGAAC-3' | 151 |
| | DR2-260 s | 3P-5'-<br>GC$_f$UC$_f$CUGAA$_f$U$_f$GC$_m$UUG$_m$C$_f$UUCA$_m$U$_f$C$_f$*U*U$_f$-3' | 158 |
| | DR2-260 as | 5'-AAA*A*GAU$_f$GAAGCAAG$_f$CAUUCAGGA$_m$GC-3' | 159 |
| | DR2-261 s | 3P-5'-<br>G*C$_f$*UC$_f$CUGAA$_f$U$_f$GC$_m$UUG$_m$C$_f$UUCA$_m$U$_f$C$_f$ *U*U$_f$-3' | 160 |
| | DR2-261 as | 5'-AAA*A*GAU$_f$GAAGCAAG$_f$CAUUCAGGA$_m$GC-3' | 159 |
| | DR2-262 s | 3P-5'-<br>GU$_f$UC$_f$CAAUA$_f$G$_f$UA$_m$GUC$_m$A$_f$UAGC$_m$U$_f$A$_f$*U*U$_f$-3' | 161 |
| | DR2-262 as | 5'-AAA*A*UAG$_f$CUAUGACU$_f$ACUAUUGGA$_m$AC-3' | 162 |
| | DR2-263 s | 3P-5'-<br>G*U$_f$ *UC$_f$CAAUA$_f$G$_f$UA$_m$GUC$_m$A$_f$UAGC$_m$U$_f$A$_f$*U*U$_f$-3' | 163 |
| | DR2-263 as | 5'-AAA*A*UAGCUAUGACUACUAUUGGA$_m$AC-3' | 162 |
| | DR2-264 s | 3P-5'-<br>GU$_f$UC$_f$UGCAA$_f$C$_f$UC$_m$AAA$_m$G$_f$UGCU$_m$A$_f$U$_f$*U*G$_f$-3' | 164 |
| | DR2-264 as | 5'-AAC*A*AUA$_f$GCACUUUG$_f$AGUUGCAGA$_m$AC-3' | 165 |
| | DR2-265 s | 3P-5'-<br>G*U$_f$*UC$_f$UGCAA$_f$C$_f$UC$_m$AAA$_m$G$_f$UGCU$_m$A$_f$U$_f$*U*G$_f$-3' | 166 |
| | DR2-265 as | 5'-AAC*A*AUA$_f$GCACUUUG$_f$AGUUGCAGA$_m$AC-3' | 165 |
| | DR2-266 s | 3P-5'-GCUCCUGAAUGCUUGCUUCAUCUU-3' | 167 |
| | DR2-266 as | 5'-AAGAUGAAGCAAGCAUUCAGGAGC-3' | 10 |
| | DR2-267 s | 3P-5'-GUUCCAAUAGUAGUCAUAGCUAUU-3' | 168 |

TABLE 1-continued

DESCRIPTION OF THE SEQUENCES
RNA Sequence Table.

| Ref | Internal ref | Sequence | SEQ ID NO |
|---|---|---|---|
| | DR2-267 as | 5'-AAUAGCUAUGACUACUAUUGGAAC-3' | 17 |
| | DR2-268 s | 3P-5'-GUUCUGCAACUCAAAGUGCUAUUG-3' | 169 |
| | DR2-268 as | 5'-CAAUAGCACUUUGAGUUGCAGAAC-3' | 24 |
| | DR2-269 s | 3P-5'-G*U*UCU$_m$GCAA$_f$UCAG$_f$CUAAACGUU*A*U-3' | 206 |
| | DR2-269 as | 5'-A*U*A$_m$ACGUU$_f$UAGC$_f$UGAUUGCAGAAC-3' | 207 |
| | DR2-270 s | 5'-G*U*UCU$_m$GCAA$_f$UCAG$_f$CUAAACGUU*A*U-3' | 208 |
| | DR2-270 as | 5'-A*U*A$_m$ACGUU$_f$UAGC$_f$UGAUUGCAGAAC-3' | 209 |
| | | 5'-gbucndnwnnnnnnnnnwnsnn-3' | 170 |
| | | 5'-gucuadnwnnnnnnnnnwnsnn-3' | 171 |
| | | 5'-guagudnwnnnnnnnnnwnsnn-3' | 172 |
| | | 5'-gguaadnwnnnnnnnnnwnsnn-3' | 173 |
| | | 5'-ggcagdnwnnnnnnnnnwnsnn-3' | 174 |
| | | 5'-gcuucdnwnnnnnnnnnwnsnn-3' | 175 |
| | | 5'-gcccadnwnnnnnnnnnwnsnn-3' | 176 |
| | | 5'-gcgcudnwnnnnnnnnnwnsnn-3' | 177 |
| | | 5'-gbucndnwnnnnnnnnnunsnn-3' | 178 |
| | | 5'-gbucndnwnnnnnnnnnansnn-3' | 210 |
| | | 5'-gucuadnwnnnnnnnnnunsnn-3' | 179 |
| | | 5'-guagudnwnnnnnnnnnunsnn-3' | 180 |
| | | 5'-gguaadnwnnnnnnnnnunsnn-3' | 181 |
| | | 5'-ggcagdnwnnnnnnnnnunsnn-3' | 182 |
| | | 5'-gcuucdnwnnnnnnnnnunsnn-3' | 183 |
| | | 5'-gcccadnwnnnnnnnnnunsnn-3' | 184 |
| | | 5'-gcgcudnwnnnnnnnnnunsnn-3' | 185 |
| | | 5'-gbucnugaannnnnnnnuucnn-3' | 186 |
| | | 5'-gbucngcaannnnnnnnaacnn-3' | 211 |
| | | 5'-gucuaugaannnnnnnnuucnn-3' | 187 |
| | | 5'-guaguugaannnnnnnnuucnn-3' | 188 |
| | | 5'-gguaaugaannnnnnnnuucnn-3' | 189 |
| | | 5'-ggcagugaannnnnnnnuucnn-3' | 190 |
| | | 5'-gcuucugaannnnnnnnuucnn-3' | 191 |
| | | 5'-gcccaugaannnnnnnnuucnn-3' | 192 |
| | | 5'-gcgcuugaannnnnnnnuucnn-3' | 193 |
| | | 5'-gbucnugaaannnnnnuuucnn-3' | 194 |
| | | 5'-gbucngcaaunnnnnnaaacnn-3' | 212 |
| | | 5'-ugaannnnnnnnuucngavc-3' | 195 |

TABLE 1-continued

DESCRIPTION OF THE SEQUENCES
RNA Sequence Table.

| Ref | Internal ref | Sequence | SEQ ID NO |
|---|---|---|---|
| | | 5'-ugaannnnnnuuucngavc-3' | 196 |
| | | 5'-gaaannnnnnnuucngavc-3' | 197 |
| | | 5'-gaaannnnnnuuucngavc-3' | 198 |
| | | 5'-gbucnugaannnnnnnuucnnnnn-3' | 199 |
| | | 5'-gbucngcaannnnnnnaacnnnnn-3' | 213 |
| | | 5'-gbucngcaannnnnnnaacguuau-3' | 214 |
| | | 5'-gbucnugaannnnnnnuucngavc-3' | 200 |
| | | 5'-gbucnugaannnnnnnuucngavc-3' | 201 |
| | | 5'-gbucnugaannnnnnuuucngavc-3' | 202 |
| | | 5'-gbucngaaannnnnnnuucngavc-3' | 203 |
| | | 5'-gbucngaaannnnnnnuucngavc-3' | 204 |
| | | 5'-gbucngaaannnnnnuuucngavc-3' | 205 |

An indexed 'm' indicates 2'-O-methyl, an indexed 'f' indicates 2'- fluoro, '*' indicates a phosphorothioate linkage, and '3P-5'-indicates a 5'-triphosphate.
RNAs were used either as dsRNA duplexes or as ssRNAs depending on the receptor to be activated.

EXAMPLES

Material and Methods

Cell Culture

Human primary peripheral blood mononuclear cells (PBMCs) were isolated from fresh buffy coats obtained from healthy volunteers according to standard protocols (Schuberth-Wagner et al., Immunity. 2015; 43 (1): 41-51). PBMCs ($2\times10^6$ cells/ml) were seeded in 96-well plates and maintained in RPMI1640 supplemented with 10% FCS, 1.5 mM L-glutamine and 1× penicillin/streptomycin. In some experiments, PBMCs were pre-treated with 2.5 mg/ml chloroquine (Sigma Aldrich) for at least 1 hour to prevent endosomal TLR activation. All cell culture reagents were obtained from Gibco.

Cell Stimulation

Chemically synthesized RNA oligonucleotides were synthesized or purchased from Biomers (Ulm, Germany) and Axolabs (Kulmbach, Germany). RNA (dsRNA or ssRNA) was transfected into cells using Lipofectamine 2000 according to manufacturer's instructions (Invitrogen) or poly-L-arginine (Sigma Aldrich) at the indicated concentration (e.g., 50 or 5 nM). The chosen complexing conditions ensure specific targeting of RIG-I or TLR7 or TLR8. TLR8 was activated using both single strands in separate reactions. PBMCs were stimulated and conditioned medium was harvested after 17 hrs.

ELISA-Based Quantitation of Cytokines

Conditioned PBMC supernatant was collected after 17 hrs. Quantitation of IFN-α levels in cell culture supernatant was performed using the human IFN-α matched antibody pairs ELISA (eBioscience). TLR8-related IL-12p70 levels were measured applying the human IL-12 (p70) ELISA set (BD Biosciences).

Example 1—Regional 2'-O-Methylation Promotes RIG-I Selectivity or Abrogates RIG-I Agonism Current approaches to identify positions suitable for 2'-o-methylation base on whole sequence permutations and are time-consuming, laborious and costly. To diminish the number of nucleotides to be modified it is worth to identify sensitive 2'-modification sites that are detrimental following 2'-o-methylation. Thus, four independent RNA basis sequences (SEQ ID NOs: 1&2, 3&4, 5&6, 7&8) were applied and their 2'-o-methylation pattern analyzed in terms of adverse effects and selectivity promoting effects. PBMCs were treated with RNAs containing single modified 2'-o-methylated nucleotides and compared to the non-modified parent RNA. An adverse effect was considered when the immune activation by means of IFN-α release was reduced by at least 20%.

Comparison of the four different sequences revealed 5 sites (positions 1, 7, 8, 9 and 14 counted from 5'-3') in the sense strand and 3 sites (positions 18, 20 and 23 counted from 5'-3') in the anti-sense strand that reduce IFN-α release by at least 20% in 3 out of 4 sequences (FIG. 1; red squares). Moreover, also found was 2'-o-methylation sites that were considered being tolerated (FIG. 1; purple squares).

RIG-I selectivity is of great interest to avoid unwanted stimulation of TLRs. Although 2'-o-methylation is currently a widely-accepted approach to establish receptor selectivity, a systematic approach was not applied yet to identify selectivity for RIG-I activation promoting 2'-o-methylation sites independent of the overall RNA sequence. Thus, the data set was analyzed with regard to 2'-o-methylation sites that would not compromise RIG-I agonism by more than 20% of the non-modified parent RNA, and where no associated increased TLR7 and TLR8 activation was observed. Among the sequences investigated, found were 2 positions (positions 12 and 20 counted from 5'-3') in the sense strand and one (position 3 counted from 5'-3') in the anti-sense strand (FIG. 2) to prevent TLR7/8 activation. Moreover, selectivity appeared to depend on the availability of a purine (A or G) at the positions described above (FIG. 2). Interestingly, if only a pyrimidine (U or C) is available, the 2'-o-methylation will not result in RIG-I selectivity. This is further corroborated by position 15 (FIG. 2, highlighted by the light green square). The RIG-I selectivity establishing 2'-o-methylation was either in the sense or the anti-sense strand depending on where the purine sat (FIG. 2).

The role of defined 2'-o-methylation sites and characterized their functional consequences (FIG. 3) were systematically determined.

Example 2—Positional Effects of 2'-Fluorine Substitutions

Classically, 2'-fluorine modifications are a versatile tool to enhance RNA stability. However, as for 2'-o-methylation, a systematic approach was not conducted yet to classify functional consequences of 2'-fluorination in terms of RIG-I agonism. Here, four independent RNA basis sequences were applied and their 2'-o-fluorination pattern was analyzed in terms of adverse effects and boosting effects. PBMCs were treated with RNAs containing single modified 2'-o-fluorinated nucleotides and compared to the non-modified parent RNA. An adverse or boosting effect was considered when the immune activation by means of IFN-α release was reduced by at least 20% or enhanced by 10%, respectively.

Four sites (1, 3, 15 and 8 counted from 5'-3') within the sense strand and 2 sites (18 and 23 counted from 5'-3') within the anti-sense strand were identified showing an adverse effect on RIGI activation (FIG. 4, blue boxes). Moreover, a bunch of different 2'-fluorination sites that are tolerated and have no influence on RIG-I agonism (FIG. 4, green boxes) was found. Furthermore, a 2'-fluorine modification at position 10 in the sense strand conferred a boosting effect on RIG-I. Interestingly, this effect was related to pyrimidines (C or U) at this particular position (FIG. 5, blue boxes). In addition, 2'-fluorination of 2 nucleotides at the end of a double stranded RNA next to a 5'-AA overhang seemed to promote RIG-I agonism (FIG. 5, yellow boxes).

FIG. 6 integrates all findings described for 2'-fluorination and 2'-o-methylation and gives an overview on how the 2'-modification strategy can be streamlined.

Example 3—2'-o-Methylation-Dependent RIG-I Selectivity Depends on the Presence of Purines The findings described above indicate that particular 2'-o-methyl sites establish receptor selectivity and that this effect depends on the availability of purines (A or G). To address this in further detail, 3 additional RNA sequences with or without purines at position 12 or 20 in the sense strand were used. The basis sequence DR2-101 had a pyrimidine at position 12, but a purine at position 20 (compare table 1). Non-modified DR2-101 activated RIG-I, TLR7 and TLR8. 2'-o-methylation of position 12 (DR2-135) did not prevent TLR7 and TLR8 activation. However, 2'-omethylation of position 20 in the sense strand abrogated TLR7 activation (FIG. 7A, Table 2). Moreover, the sense strand carrying a 2'-o-methyl at position 20 did not induce TLR8 (FIG. 7A, Table 2). The second sequence analyzed had at position 12 a purine and at position 20 a pyrimidine (compare Table 1). 2'-o-methylation at position 12 only prevented TLR7 activation (FIG. 7B, Table 3). Moreover, the sense strand carrying a 2'-o-methyl at position 12 did not induce TLR8 (FIG. 7B, Table 3). The third sequence tested lacked purines at both positions 12 and 20 (compare Table 1). 2'-o-methylation at both positions did not prevent TLR7 or TLR8 activation (FIG. 7C, Table 4).

It was also observed that a dsRNA duplex the combination of 2'-o-methylation of an appropriate purine in the sense strand and concomitant 2'-o-methylation of position 22 in the antisense strand (counted from 5'-3') established RIG-I selectivity and abolished TLR7 activation completely (FIG. 7A/B, Tables 2/3; sequences DR2-112 and DR2-123). Moreover, 2-o-methylation of the anti-sense strand at position 22 circumvented TLR8 activation (FIG. 7).

FIG. 7D summarizes the findings pertaining to the prerequisite of purine modification.

FIG. 9 shows the evaluation of 2'-o-methyl modification pattern in the NRDR1 backbone. TLR8 agonization was also tested at 50 nM agonist concentration, the results of which are shown in Table 6.

FIG. 10 shows the evaluation of 2'-o-methyl modification pattern in the NRDR2 backbone. TLR8 agonization was also tested at 50 nM agonist concentration, the results of which are shown in Table 7.

FIG. 11 shows the evaluation of 2'-o-methyl modification pattern in the NRDR3 backbone. TLR8 agonization was also tested at 50 nM agonist concentration, the results of which are shown in Table 8.

FIG. 12 shows the evaluation of 2'-o-methyl modification pattern in the $24R^{80\ \#1.5}$ backbone with truncations or extensions to evaluate length independency. TLR8 agonization was also tested at 50 nM agonist concentration, the results of which are shown in Table 9.

FIG. 13 shows an evaluation of all identified nucleotide positions that can confer receptor selectivity in NRDR1 backbone and their purine dependency.

| ID | Sense strand | Anti-sense strand |
|---|---|---|
| DR2-223 | NRDR1_2'oMe pos20_s | NRDR1_2'oMe pos10 (5'-3)_as |
| DR2-222 | NRDR1_2'oMe pos15_s | NRDR1_2'oMe pos10 (5'-3)_as |
| DR2-221 | NRDR1_2'oMe pos12_s | NRDR1_2'oMe pos10 (5'-3)_as |
| DR2-220 | NRDR1_non modified_s | NRDR1_2'oMe pos10 (5'-3)_as |
| DR2-219 | NRDR1_2'oMe pos20_s | NRDR1_2'oMe pos3 (5'-3')_as |
| DR2-218 | NRDR1_2'oMe pos15_s | NRDR1_2'oMe pos3 (5'-3')_as |
| DR2-217 | NRDR1_2'oMe pos12_s | NRDR1_2'oMe pos3 (5'-3')_as |
| DR2-216 | NRDR1_non modified_s | NRDR1_2'oMe pos3 (5'-3')_as |
| DR2-215 | NRDR1_2'oMe pos20_s | NRDR1_non modified_as |
| DR2-214 | NRDR1_2'oMe pos15_s | NRDR1_non modified_as |
| DR2-213 | NRDR1_2'oMe pos12_s | NRDR1_non modified_as |
| DR2-212 | NRDR1_non modified_s | NRDR1_non modified_as |

FIG. 14 shows an evaluation of all identified nucleotide positions that can confer receptor selectivity in NRDR2 backbone and their purine dependency.

| ID | Sense strand | Anti-sense strand |
|---|---|---|
| DR2-235 | NRDR2_2'oMe pos20_s | NRDR2_2'oMe pos10 (5'-3')_as |
| DR2-234 | NRDR2_2'oMe pos15_s | NRDR2_2'oMe pos10 (5'-3')_as |
| DR2-233 | NRDR2_2'oMe pos12_s | NRDR2_2'oMe pos10 (5'-3')_as |
| DR2-232 | NRDR2_non modified_s | NRDR2_2'oMe pos10 (5'-3')_as |
| DR2-231 | NRDR2_2'oMe pos20_s | NRDR2_2'oMe pos3 (5'-3')_as |
| DR2-230 | NRDR2_2'oMe pos15_s | NRDR2_2'oMe pos3 (5'-3')_as |
| DR2-229 | NRDR2_2'oMe pos12_s | NRDR2_2'oMe pos3 (5'-3')_as |
| DR2-228 | NRDR2_non modified_s | NRDR2_2'oMe pos3 (5'-3')_as |
| DR2-227 | NRDR2_2'oMe pos20_s | NRDR2_non modified_as |
| DR2-226 | NRDR2_2'oMe pos15_s | NRDR2_non modified_as |
| DR2-225 | NRDR2_2'oMe pos12_s | NRDR2_non modified_as |
| DR2-224 | NRDR2_non modified_s | NRDR2_non modified_as |

FIG. 15 shows an evaluation of all identified nucleotide positions that can confer receptor selectivity in NRDR4 backbone and their purine dependency.

| ID | Sense strand | Anti-sense strand |
|---|---|---|
| DR2-247 | NRDR3_2'oMe pos20_s | NRDR3_2'oMe pos10 (5'-3')_as |
| DR2-246 | NRDR3_2'oMe pos15_s | NRDR3_2'oMe pos10 (5'-3')_as |
| DR2-245 | NRDR3_2'oMe pos12_s | NRDR3_2'oMe pos10 (5'-3')_as |
| DR2-244 | NRDR3_non modified_s | NRDR3_2'oMe pos10 (5'-3')_as |
| DR2-243 | NRDR3_2'oMe pos20_s | NRDR3_2'oMe pos3 (5'-3')_as |
| DR2-242 | NRDR3_2'oMe pos15_s | NRDR3_2'oMe pos3 (5'-3')_as |
| DR2-241 | NRDR3_2'oMe pos12_s | NRDR3_2'oMe pos3 (5'-3')_as |
| DR2-240 | NRDR3_non modified_s | NRDR3_2'oMe pos3 (5'-3')_as |
| DR2-239 | NRDR3_2'oMe pos20_s | NRDR3_non modified_as |
| DR2-238 | NRDR3_2'oMe pos15_s | NRDR3_non modified_as |
| DR2-237 | NRDR3_2'oMe pos12_s | NRDR3_non modified_as |
| DR2-236 | NRDR3_non modified_s | NRDR3_non modified_as |

FIG. 16 shows an evaluation how exchanging pyrimidine nucleotides at positions 12 and 20 in the sense strand of NRDR3 base sequence for purines affects oligonucleotide's preferences for the RIG-I receptor and selectivity. TLR7/8 engagement was assessed at an agonist concentration of 50 nM. Further information is provided in Table 10.

A schematic overview about the broad range modification pattern, summarizing the results of Example 3 shown in FIGS. 9-16 and Tables 6-10 is shown in FIG. 17.

TABLE 2

Tabular view of FIG. 7A data

| | RIG-I agonism | TLR7 agonism | TLR8 agonism | |
|---|---|---|---|---|
| | Duplex | Duplex | Sense strand | Antisense strand |
| DR2-114 | RIG-I activation | No TLR7 signal | No TLR8 signal | No TLR8 signal |
| DR2-113 | RIG-I activation (<80% of parent at 50 nM) | No TLR7 signal | No TLR8 signal | No TLR8 signal |
| DR2-112 | RIG-I activation | No TLR7 signal | No TLR8 signal | No TLR8 signal |
| DR2-139 | RIG-I activation | Very low TLR7 signal | No TLR8 signal | TLR8 activation |
| DR2-108 | RIG-I activation | No TLR7 signal | TLR8 activation | No TLR8 signal |
| DR2-107 | RIG-I activation (<80% of parent at 50 nM) | No TLR7 signal | TLR8 activation | No TLR8 signal |
| DR2-106 | RIG-I activation | No TLR7 signal | TLR8 activation | No TLR8 signal |
| DR2-135 | RIG-I activation | TLR7 activation | TLR8 activation | TLR8 activation |
| DR2-101 | RIG-I activation | TLR7 activation | TLR8 activation | TLR8 activation |

TABLE 3

Tabular view of FIG. 7B data

| | RIG-I agonism | TLR7 agonism | TLR8 agonism | |
|---|---|---|---|---|
| | Duplex | Duplex | Sense strand | Antisense strand |
| DR2-131 | RIG-I activation | TLR7 activation | TLR8 activation | No TLR8 signal |
| DR2-130 | RIG-I activation (<80% of parent at 50 nM) | TLR7 activation | TLR8 activation | No TLR8 signal |
| DR2-129 | RIG-I activation | TLR7 activation | TLR8 activation | No TLR8 signal |
| DR2-147 | RIG-I activation | TLR7 activation | TLR8 activation | TLR8 activation |
| DR2-125 | RIG-I activation | No TLR7 signal | No TLR8 signal | No TLR8 signal |
| DR2-124 | RIG-I activation (<80% of parent at 50 nM) | No TLR7 signal | No TLR8 signal | No TLR8 signal |
| DR2-123 | RIG-I activation | No TLR7 signal | No TLR8 signal | No TLR8 signal |
| DR2-143 | RIG-I activation (<80% of parent at 50 nM) | No TLR7 signal | No TLR8 signal | TLR8 activation |
| DR2-118 | RIG-I activation | TLR7 activation | TLR8 activation | TLR8 activation |

TABLE 4

Tabular view of FIG. 7C data

| | RIG-I agonism | TLR7 agonism | TLR8 agonism | |
|---|---|---|---|---|
| | Duplex | Duplex | Sense strand | Antisense strand |
| DR2-169 | RIG-I activation | TLR7 activation | TLR8 activation | No TLR8 signal |
| DR2-168 | RIG-I activation | TLR7 activation | TLR8 activation | TLR8 activation |
| DR2-167 | RIG-I activation | TLR7 activation | TLR8 activation | No TLR8 signal |
| DR2-166 | RIG-I activation | TLR7 activation | TLR8 activation | TLR8 activation |
| DR2-159 | RIG-I activation | TLR7 activation | TLR8 activation | No TLR8 signal |
| DR2-158 | RIG-I activation | TLR7 activation | TLR8 activation | TLR8 activation |
| DR2-157 | RIG-I activation | TLR7 activation | TLR8 activation | No TLR8 signal |
| DR2-156 | RIG-I activation | TLR7 activation | TLR8 activation | TLR8 activation |
| DR2-151 | RIG-I activation | TLR7 activation | TLR8 activation | TLR8 activation |

TABLE 5

Tabular view of FIG. 8A data

| | RIG-I agonism | TLR7 agonism | TLR8 agonism | |
|---|---|---|---|---|
| | Duplex | Duplex | Sense strand | Antisense strand |
| DR2-105 | RIG-I activation | No TLR7 signal | No TLR8 signal | No TLR8 signal |
| DR2-101 | RIG-I activation | TLR7 activation | TLR8 activation | TLR8 activation |
| DR2-122 | RIG-I activation | No TLR7 signal | No TLR8 signal | No TLR8 signal |
| DR2-118 | RIG-I activation | TLR7 activation | TLR8 activation | TLR8 activation |
| DR2-155 | RIG-I activation | No TLR7 signal | No TLR8 signal | No TLR8 signal |
| DR2-151 | RIG-I activation | TLR7 activation | TLR8 activation | TLR8 activation |

TABLE 6

Evaluation of 2'-o-methyl modification pattern in the NRDR1 backbone. TLR8 agonization was tested at 50 nM agonist concentration.

| | ID | Sense strand | TLR8 activation | Anti-sense strand * | TLR8 activation |
|---|---|---|---|---|---|
| Selectivity | DR2-142 | NRDR1_2'oMe pos20, 2'Fpos4/21_s | No TLR8 signal | NRDR1_Box1/2 w/o mods_as | No TLR8 signal |
| | DR2-117 | NRDR1_2'oMe pos20, 2'Fpos4/21_s | No TLR8 signal | NRDR1_2'oMe pos3, 2Fpos20_as | No TLR8 signal |
| | DR2-116 | NRDR1_2'oMe pos20, 2'Fpos4/21_s | No TLR8 signal | NRDR1_2'oMe pos3, 2Fpos12_as | No TLR8 signal |
| | DR2-115 | NRDR1_2'oMe pos20, 2'Fpos4/21_s | No TLR8 signal | NRDR1_2'oMe pos3_as | No TLR8 signal |
| | DR2-141 | NRDR1_2'oMe pos20, 2'Fpos4/21_s | No TLR8 signal | NRDR1_non modified_as | TLR8 activation |
| | DR2-140 | NRDR1_2'oMe pos20_s | No TLR8 signal | NRDR1_Box1/2 w/o mods_as | No TLR8 signal |
| | DR2-114 | NRDR1_2'oMe pos20_s | No TLR8 signal | NRDR1_2'oMe pos3, 2Fpos20_as | No TLR8 signal |
| | DR2-113 | NRDR1_2'oMe pos20_s | No TLR8 signal | NRDR1_2'oMe pos3, 2Fpos12_as | No TLR8 signal |
| | DR2-112 | NRDR1_2'oMe pos20_s | No TLR8 signal | NRDR1_2'oMe pos3_as | No TLR8 signal |
| | DR2-139 | NRDR1_2'oMe pos20_s | No TLR8 signal | NRDR1_non modified_as | TLR8 activation |
| No selectivity | DR2-138 | NRDR1_2'oMe pos12, 2'Fpos4/21_s | TLR8 activation | NRDR1_Box1/2 w/o mods_as | No TLR8 signal |
| | DR2-111 | NRDR1_2'oMe pos12, 2'Fpos4/21_s | TLR8 activation | NRDR1_2'oMe pos3, 2Fpos20_as | No TLR8 signal |
| | DR2-110 | NRDR1_2'oMe pos12, 2'Fpos4/21_s | TLR8 activation | NRDR1_2'oMe pos3, 2Fpos12_as | No TLR8 signal |
| | DR2-109 | NRDR1_2'oMe pos12, 2'Fpos4/21_s | TLR8 activation | NRDR1_2'oMe pos3_as | No TLR8 signal |
| | DR2-137 | NRDR1_2'oMe pos12, 2'Fpos4/21_s | TLR8 activation | NRDR1_non modified_as | TLR8 activation |
| | DR2-136 | NRDR1_2'oMe pos12_s | TLR8 activation | NRDR1_Box1/2 w/o mods_as | No TLR8 signal |
| | DR2-108 | NRDR1_2'oMe pos12_s | TLR8 activation | NRDR1_2'oMe pos3, 2Fpos20_as | No TLR8 signal |
| | DR2-107 | NRDR1_2'oMe pos12_s | TLR8 activation | NRDR1_2'oMe pos3, 2Fpos12_as | No TLR8 signal |
| | DR2-106 | NRDR1_2'oMe pos12_s | TLR8 activation | NRDR1_2'oMe pos3_as | No TLR8 signal |
| | DR2-135 | NRDR1_2'oMe pos12_s | TLR8 activation | NRDR1_non modified_as | TLR8 activation |
| | DR2-105 | NRDR1 Box1/2 w/o modss | No TLR8 signal | NRDR1_Box1/2 w/o mods_as | No TLR8 signal |
| | DR2-101 | NRDR1 non modified s | TLR8 activation | NRDR1_non modified_as | TLR8 activation |

* The numbering in 'As' is counted from 3'-5'. 'As' contains only mods that are allowed, no selectivity.

TABLE 7

Evaluation of 2'-o-methyl modification pattern in the NRDR2 backbone. TLR8 agonization was tested at 50 nM agonist concentration.

| | ID | Sense strand | TLR8 activation | Anti-sense strand * | TLR8 activation |
|---|---|---|---|---|---|
| No Selectivity | DR2-150 | NRDR2_2'oMe pos20, 2'Fpos4/21_s | TLR8 activation | NRDR2_Box1/2 w/o mods_as | No TLR8 signal |
| | DR2-134 | NRDR2_2'oMe pos20, 2'Fpos4/21_s | TLR8 activation | NRDR2_2'oMe pos3, 2Fpos20_as | No TLR8 signal |
| | DR2-133 | NRDR2_2'oMe pos20, 2'Fpos4/21_s | TLR8 activation | NRDR2_2'oMe pos3, 2Fpos12_as | No TLR8 signal |
| | DR2-132 | NRDR2_2'oMe pos20, 2'Fpos4/21_s | TLR8 activation | NRDR2_2'oMe pos3_as | No TLR8 signal |
| | DR2-149 | NRDR2_2'oMe pos20, 2'Fpos4/21_s | TLR8 activation | NRDR2_non modified_as | TLR8 activation |
| | DR2-148 | NRDR2_2'oMe pos20_s | TLR8 activation | NRDR2_Box1/2 w/o mods_as | No TLR8 signal |
| | DR2-131 | NRDR2_2'oMe pos20_s | TLR8 activation | NRDR2_2'oMe pos3, 2Fpos20_as | No TLR8 signal |
| | DR2-130 | NRDR2_2'oMe pos20_s | TLR8 activation | NRDR2_2'oMe pos3, 2Fpos12_as | No TLR8 signal |

TABLE 7-continued

Evaluation of 2'-o-methyl modification pattern in the NRDR2 backbone. TLR8 agonization was tested at 50 nM agonist concentration.

| | ID | Sense strand | TLR8 activation | Anti-sense strand * | TLR8 activation |
|---|---|---|---|---|---|
| | DR2-129 | NRDR2_2'oMe pos20_s | TLR8 activation | NRDR2_2'oMe pos3_as | No TLR8 signal |
| | DR2-147 | NRDR2_2'oMe pos20_s | TLR8 activation | NRDR2_non modified_as | TLR8 activation |
| Selectivity | DR2-146 | NRDR2_2'oMe pos12, 2'Fpos4/21_s | No TLR8 signal | NRDR2_Box1/2 w/o mods_as | No TLR8 signal |
| | DR2-128 | NRDR2_2'oMe pos12, 2'Fpos4/21_s | No TLR8 signal | NRDR2_2'oMe pos3, 2Fpos20_as | No TLR8 signal |
| | DR2-127 | NRDR2_2'oMe pos12, 2'Fpos4/21_s | No TLR8 signal | NRDR2_2'oMe pos3, 2Fpos12_as | No TLR8 signal |
| | DR2-126 | NRDR2_2'oMe pos12, 2'Fpos4/21_s | No TLR8 signal | NRDR2_2'oMe pos3_as | No TLR8 signal |
| | DR2-145 | NRDR2_2'oMe pos12, 2'Fpos4/21_s | No TLR8 signal | NRDR2_non modified_as | TLR8 activation |
| | DR2-144 | NRDR2_2'oMe pos12_s | No TLR8 signal | NRDR2_Box1/2 w/o mods_as | No TLR8 signal |
| | DR2-125 | NRDR2_2'oMe pos12_s | No TLR8 signal | NRDR2_2'oMe pos3, 2Fpos20_as | No TLR8 signal |
| | DR2-124 | NRDR2_2'oMe pos12_s | No TLR8 signal | NRDR2_2'oMe pos3, 2Fpos12_as | No TLR8 signal |
| | DR2-123 | NRDR2_2'oMe pos12_s | No TLR8 signal | NRDR2_2'oMe pos3_as | No TLR8 signal |
| | DR2-143 | NRDR2_2'oMe pos12_s | No TLR8 signal | NRDR2_non modified_as | TLR8 activation |
| | DR2-122 | NRDR2_Box 1/2 w/o mod_ss | No TLR8 signal | NRDR2_Box1/2 w/o mods_as | No TLR8 signal |
| | DR2-118 | NRDR2_non modified_s | TLR8 activation | NRDR2_non modified_as | TLR8 activation |

* The numbering in 'As' is counted from 3'-5'. 'As' contains only mods that are allowed, no selectivity.

TABLE 8

Evaluation of 2'-o-methyl modification pattern in the NRDR3 backbone. TLR8 agonization was tested at 50 nM agonist concentration.

| | ID | Sense strand | TLR8 activation | Anti-sense strand * | TLR8 activation |
|---|---|---|---|---|---|
| No Selectivity | DR2-175 | NRDR3_2'oMe pos20, 2'Fpos4/21_s | No TLR8 signal | NRDR3_Box1/2 w/o mods_as | No TLR8 signal |
| | DR2-174 | NRDR3_2'oMe pos20, 2'Fpos4/21_s | No TLR8 signal | NRDR3_2'oMe pos3, 2Fpos20_as | No TLR8 signal |
| | DR2-173 | NRDR3_2'oMe pos20, 2'Fpos4/21_s | No TLR8 signal | NRDR3_2'oMe pos3, 2Fpos12_as | TLR8 activation |
| | DR2-172 | NRDR3_2'oMe pos20, 2'Fpos4/21_s | No TLR8 signal | NRDR3_2'oMe pos3_as | No TLR8 signal |
| | DR2-171 | NRDR3_2'oMe pos20, 2'Fpos4/21_s | No TLR8 signal | NRDR3_non modified_as | TLR8 activation |
| | DR2-170 | NRDR3_2'oMe pos20_s | TLR8 activation | NRDR3_Box1/2 w/o mods_as | No TLR8 signal |
| | DR2-169 | NRDR3_2'oMe pos20_s | TLR8 activation | NRDR3_2'oMe pos3, 2Fpos20_as | No TLR8 signal |
| | DR2-168 | NRDR3_2'oMe pos20_s | TLR8 activation | NRDR3_2'oMe pos3, 2Fpos12_as | TLR8 activation |
| | DR2-167 | NRDR3_2'oMe pos20_s | TLR8 activation | NRDR3_2'oMe pos3_as | No TLR8 signal |
| | DR2-166 | NRDR3_2'oMe pos20_s | TLR8 activation | NRDR3_non modified_as | TLR8 activation |
| No Selectivity | DR2-165 | NRDR3_2'oMe pos12, 2'Fpos4/21_s | No TLR8 signal | NRDR3_Box1/2 w/o mods_as | No TLR8 signal |
| | DR2-164 | NRDR3_2'oMe pos12, 2'Fpos4/21_s | No TLR8 signal | NRDR3_2'oMe pos3, 2Fpos20_as | No TLR8 signal |
| | DR2-163 | NRDR3_2'oMe pos12, 2'Fpos4/21_s | No TLR8 signal | NRDR3_2'oMe pos3, 2Fpos12_as | TLR8 activation |
| | DR2-162 | NRDR3_2'oMe pos12, 2'Fpos4/21_s | No TLR8 signal | NRDR3_2'oMe pos3_as | No TLR8 signal |
| | DR2-161 | NRDR3_2'oMe pos12, 2'Fpos4/21_s | No TLR8 signal | NRDR3_non modified_as | TLR8 activation |
| | DR2-160 | NRDR3_2'oMe pos12_s | TLR8 activation | NRDR3_Box1/2 w/o mods_as | No TLR8 signal |

TABLE 8-continued

Evaluation of 2'-o-methyl modification pattern in the NRDR3 backbone. TLR8 agonization was tested at 50 nM agonist concentration.

| ID | Sense strand | TLR8 activation | Anti-sense strand * | TLR8 activation |
|---|---|---|---|---|
| DR2-159 | NRDR3_2'oMe pos12_s | TLR8 activation | NRDR3_2'oMe pos3, 2Fpos20_as | No TLR8 signal |
| DR2-158 | NRDR3_2'oMe pos12_s | TLR8 activation | NRDR3_2'oMe pos3, 2Fpos12_as | No TLR8 activation |
| DR2-157 | NRDR3_2'oMe pos12_s | TLR8 activation | NRDR3_2'oMe pos3_as | No TLR8 signal |
| DR2-156 | NRDR3_2'oMe pos12_s | TLR8 activation | NRDR3_non modified_as | TLR8 activation |
| DR2-155 | NRDR3_Box1/2 w/o mods_s | No TLR8 signal | NRDR3_Box1/2 w/o mods_as | No TLR8 signal |
| DR2-154 | NRDR3_2'F modified_s | No TLR8 signal | NRDR3_2'F modified_as | TLR8 activation |
| DR2-153 | NRDR3_2'oMe modified_s | No TLR8 signal | NRDR3_2'oMe modified_as | No TLR8 signal |
| DR2-152 | NRDR3_fully modified_s | No TLR8 signal | NRDR3_fully modified_as | No TLR8 signal |
| DR2-151 | NRDR3_non modified_s | TLR8 activation | NRDR3_non modified_as | TLR8 activation |

* The numbering in 'As' is counted from 3'-5'. 'As' contains only mods that are allowed, no selectivity.

TABLE 9

Evaluation of 2'-o-methyl modification pattern in the 24R80#1.5 backbone TLR8 agonization was tested at 50 nM agonist concentration.

| ID | Sense strand | IL12p70 (pg/ml) | Anti-sense strand * | IL12p70 (pg/ml) |
|---|---|---|---|---|
| DR2-176 | 24R80#1.5blunt_s | 324.4 | 24R80#1.5blunt_as | 8.0 |
| DR2-177 | 24R80#1.5blunt_DR2 oMe full_s | 0.2 | 24R80#1.5blunt_DR2 oMe full_as | 0 |
| DR2-178 | 24R80#1.5blunt_DR2 oMe full − 2r_s | 0 | 24R80#1.5blunt_DR2 oMe full − 2r_as | 1.9 |
| DR2-179 | 24R80#1.5blunt_DR2 oMe full − 4r_s | 0 | 24R80#1.5blunt_DR2 oMe full − 4r_as | 0 |
| DR2-180 | 24R80#1.5blunt_DR2 oMe full + 2r_s | 1.5 | 24R80#1.5blunt_DR2 oMe full + 2r_as | 40.4 |
| DR2-181 | 24R80#1.5blunt_DR2 oMe full + 4r_s | 17.1 | 24R80#1.5blunt_DR2 oMe full + 4r_as | 128.5 |
| DR2-182 | 24R80#1.5blunt_DR2 oMe full − 2l_s | 0 | 24R80#1.5blunt_DR2 oMe full − 2l_as | 33.8 |
| DR2-183 | 24R80#1.5blunt_DR2 oMe full − 4l_s | 0.7 | 24R80#1.5blunt_DR2 oMe full − 4l_as | 3.6 |
| DR2-184 | 24R80#1.5blunt_DR2 oMe full + 2l_s | 3.6 | 24R80#1.5blunt_DR2 oMe full + 2l_as | 1.5 |
| DR2-185 | 24R80#1.5blunt_DR2 oMe full + 4l_s | 0.7 | 24R80#1.5blunt_DR2 oMe full + 4l_as | 68.1 |
| DR2-186 | 24R80#1.5blunt_DR2 − 2r_s | 154.4 | 24R80#1.5blunt_DR2 − 2r_as | 36.1 |
| DR2-187 | 24R80#1.5blunt_DR2 − 4r_s | 346.9 | 24R80#1.5blunt_DR2 − 4r_as | 11.8 |
| DR2-188 | 24R80#1.5blunt_DR2 + 2r_s | 930.6 | 24R80#1.5blunt_DR2 + 2r_as | 120.5 |
| DR2-189 | 24R80#1.5blunt_DR2 + 4r_s | 992.9 | 24R80#1.5blunt_DR2 + 4r_as | 125.1 |
| DR2-190 | 24R80#1.5blunt_DR2 − 2l_s | 427.9 | 24R80#1.5blunt_DR2 − 2l_as | 56.0 |
| DR2-191 | 24R80#1.5blunt_DR2 − 4l_s | 520.7 | 24R80#1.5blunt_DR2 − 4l_as | 23.9 |
| DR2-192 | 24R80#1.5blunt_DR2 + 2l_s | 563.2 | 24R80#1.5blunt_DR2 + 2l_as | 15.7 |
| DR2-193 | 24R80#1.5blunt_DR2 + 4l_s | 610.0 | 24R80#1.5blunt_DR2 + 4l_as | 128.9 |

* The numbering in 'As' is counted from 3'-5'. 'As' contains only mods that are allowed, no selectivity.

TABLE 10

Tabular view of FIG. 16 data.

| ID | Sense strand | IL12p70 (pg/ml) | Anti-sense strand | IL12p70 (pg/ml) |
|---|---|---|---|---|
| DR2-259 | NRDR3_2'oMe modified_p12sA/p20sA_s | 0.8 | NRDR3_non modified_p12sA/p20sA_as | |
| DR2-258 | NRDR3_2'oMe modified_p12sG/p20sG_s | 30.9 | NRDR3_non modified_p12sG/p20sG_as | |
| DR2-257 | NRDR3_2'oMe modified_p20sA_s | 1.1 | NRDR3_non modified_p20sA_as | |
| DR2-256 | NRDR3_2'oMe modified_p20sG_s | 26.2 | NRDR3_non modified_p20sG_as | |
| DR2-255 | NRDR3_2'oMe modified_p12sA_s | 10.8 | NRDR3_non modified_p12sA_as | |
| DR2-254 | NRDR3_2'oMe modified_p12sG_s | 339.7 | NRDR3_non modified_p12sG_as | |
| DR2-253 | NRDR3_non modified_p12sA/p20sA_s | 514.7 | NRDR3_non modified_P12sA/p20sA_as | 1522.5 |
| DR2-252 | NRDR3_non modified_p12sG/p20sG_s | 903.1 | NRDR3_non modified_p12sG/p20sG_as | 341.6 |
| DR2-251 | NRDR3_non modified_p20sA_s | 584.0 | NRDR3_non modified_p20sA_as | 1314.7 |
| DR2-250 | NRDR3_non modified_p20sG_s | 1030.3 | NRDR3_non modified_p20sG_as | 520.3 |
| DR2-249 | NRDR3_non modified_p12sA_s | 933.9 | NRDR3_non modified_p12sA_as | 287.3 |
| DR2-248 | NRDR3_non modified_p12sG_s | 720.2 | NRDR3_non modified_p12sG_as | 326.0 |
| DR2-239 | NRDR3_2'oMe pos20_s | 48.1 | NRDR3_non modified_as | |

TABLE 10-continued

Tabular view of FIG. 16 data.

| ID | Sense strand | IL12p70 (pg/ml) | Anti-sense strand | IL12p70 (pg/ml) |
|---|---|---|---|---|
| DR2-238 | NRDR3_2'oMe pos15_s | 132.1 | NRDR3_non modified_as | |
| DR2-237 | NRDR3_2'oMe pos12_s | 471.5 | NRDR3_non modified_as | |
| DR2-236 | NRDR3_non modified_s | 726.7 | NRDR3_non modified_as | 424.2 |

Example 4-Identification of a Broad Range Modification Pattern

The RNA basis sequences of DR2-101, DR2-118 and DR2-151 were modified (2'-o-methyl at positions 12, 15 and 20 in the sense and position 22 in the anti-sense strand from 5' to 3'; 2'-fluorine at positions 2, 4, 9, 10, 16, 21, 22 and 24 in the sense and positions 5 and 13 in the antisense strand from 5' to 3'). All three RNAs affected RIG-I agonism by less than 20%, but established RIG-I selectivity as compared to the parent non-modified RNA (FIG. 8A). FIG. 8B shows the schematic modification pattern.

Moreover, whether the defined 2'-modification pattern shown in FIG. 8B confers receptor selectivity in tri-phosphorylated RNAs was investigated. The results are shown in the following Table 11. As an outcome, it was demonstrated that the 2'-modification pattern promotes receptor selectivity. Moreover, tri-phosphorylation elevates the RIG-I response in 2 out of 3 base sequences tested.

TABLE 11

Investigation whether the defined 2'-modification pattern confers receptor selectivity in tri-phosphorylated RNAs.

| | Sense strand | Anti-sense strand | EC50 (duplex; nM) | TLR7 (IFNα; pg/ml) | TLR8 Sense (IL12p70; pg/ml) | TLR8 Anti-sense (IL12p70; pg/ml) |
|---|---|---|---|---|---|---|
| DR2-101 | NRDR1__non modified__s | NRDR1__non modified__as | 2.3 | 2167.54 | 553.25 | 806.22 |
| DR2-105 | NRDR1__Box1/2 w/o mods__s | NRDR1__Box1/2 w/o mods__as | 3.7 | 10.71 | 3.53 | 1.42 |
| DR2-260 | 3P-NRDR1__Box1/2 w/o mods__+3'-PTO__s | NRDR1__Box1/2 w/o mods__+5'-AA OH__+5'-PTO__as | 1.4 | 7.59 | 0.79 | 4.10 |
| DR2-261 | 3P-NRDR1__Box1/2 w/o mods__+5'+3'-PTO__s | NRDR1__Box1/2 w/o mods__+5'-AA OH__+5'-PTO__as | 1.0 | 10.34 | 0.81 | |
| DR2-118 | NRDR2__non modified__s | NRDR2__non modified__as | 1.3 | 2375.34 | 378.63 | 724.18 |
| DR2-122 | NRDR2__Box1/2 w/o mods__s | NRDR2__Box1/2 w/o mods__as | 1.4 | 5 | 0.94 | 2.81 |
| DR2-262 | 3P-NRDR2__Box1/2 w/o mods__+3'-PTO__s | NRDR2__Box1/2 w/o mods__+5'-AA OH__+5'-PTO__as | 0.3 | 7.89 | 0.79 | 4.35 |
| DR2-263 | 3P-NRDR2__Box1/2 w/o mods__+5'+3'-PTO__s | NRDR2__Box1/2 w/o mods__+5'-AA OH__+5'-PTO__as | 0.3 | 14.60 | 1.00 | |
| DR2-151 | NRDR3__non modified__s | NRDR3__non modified__as | 0.5 | 1927.21 | 576.37 | 262.66 |
| DR2-155 | NRDR3__Box1/2 w/o mods__s | NRDR3__Box1/2 w/o mods__as | 0.3 | 2.84 | 0.15 | 0.83 |
| DR2-264 | 3P-NRDR3__Box1/2 w/o mods__+3'-PTO__s | NRDR3__Box1/2 w/o mods__+5'-AA OH__+5'-PTO__as | 0.6 | 7.14 | 3.08 | 53.03 |
| DR2-265 | 3P-NRDR3__Box1/2 w/o mods__+5'+3'-PTO__s | NRDR3__Box1/2 w/o mods__+5'-AA OH__+5'-PTO__as | 0.5 | 5.59 | 3.97 | |

What is claimed is:

1. A method for increasing the selectivity for RIG-I of a RIG-I agonist, comprising the steps of:

(a) providing a double-stranded polyribonucleotide comprising a sense strand with 24 to 30 nucleotides in length and an antisense strand with 24 to 30 nucleotides in length, wherein the sense strand, or the antisense strand, or both the sense strand and the antisense strand are selected from SEQ ID NO: 10-15, 18-22, 24-35, 44-45, 49-54, 60-62, 159-166, and 206-209, wherein the sense strand and the antisense strand form a fully complementary region of at least 24 base pairs with a blunt end at the 5'-end of the sense strand and the 3'-end of the antisense strand; and wherein the first 24 nucleotides at the 5'-end of the sense strand are ribonucleotides; and wherein the sense strand has no 2'-o-methyl modification at a ribonucleotide at a position selected from the group consisting of position number 1, 7, 8, 9, and 14, and wherein the last 24 nucleotides at 3'-end of the antisense strand are ribonucleotides and wherein the antisense strand has in its last 24 nucleotides no 2'-o-methyl modification at a ribonucleotide at a position selected from the group consisting of position 18, 20, and 23; wherein all positions are counted from 5' to 3';

(b) identifying whether the polyribonucleotide of step (a) comprises a purine ribonucleotide at a position selected from the group consisting of position number 12, 15, and 20 in the sense strand, and position number 3 and 10 of the antisense strand, and (c) introducing at least one 2'-o-methyl modification at a purine ribonucleotide identified in step (b).

2. The method of claim 1, wherein the double-stranded ribonucleotide provided in step (a) has a purine at a position selected from the group of positions consisting of position 12, 15, and 20 in the first 24 ribonucleotides at 5'-end of the sense strand, and position 3 in the last 24 ribonucleotides at the 3'-end of the antisense strand.

3. The method of claim 1, further comprising introducing a 2'-o-methyl modification at the ribonucleotide at position 22 in the last 24 ribonucleotides at the 3'-end of the antisense strand.

4. The method of claim 1, wherein the polyribonucleotide provided in step (a) is further defined by: the remaining ribonucleotides at the other positions in the first 24 ribonucleotides at 5'-end of the sense strand and the last 24 ribonucleotides at 3'-end of the antisense strand are not modified at the ribose; wherein all positions are counted from 5' to 3'.

* * * * *

SEQUENCE LISTING

```
<160> NUMBER OF SEQ ID NOS: 214

<210> SEQ ID NO 1
<211> LENGTH: 24
<212> TYPE: RNA
<213> ORGANISM: Artificial Sequence
<220> FEATURE:
<223> OTHER INFORMATION: Description of Artificial Sequence: Synthetic
```

oligonucleotide
<220> FEATURE:
<223> OTHER INFORMATION: 121212 s

<400> SEQUENCE: 1
gacgcugacc cugaaguuca ucuu 24

<210> SEQ ID NO 2
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: 121212 as

<400> SEQUENCE: 2
aagaugaacu ucagggucag cguc 24

<210> SEQ ID NO 3
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: 24R40#5.4 s

<400> SEQUENCE: 3
guucugcaau cagcuaaacg uuau 24

<210> SEQ ID NO 4
<211> LENGTH: 26
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: 24R40#5.4 as

<400> SEQUENCE: 4
aaauaacguu uagcugauug cagaac 26

<210> SEQ ID NO 5
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: biHPV16E6#003 s

<400> SEQUENCE: 5
guucuaaaag caaagauucc auaa 24

<210> SEQ ID NO 6
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: biHPV16E6#003 as

<400> SEQUENCE: 6
uuauggaauc uuugcuuuua gaac 24

<210> SEQ ID NO 7
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: 24R80#1.5 s

<400> SEQUENCE: 7
gguccgcugu gauuuuugga uuug 24

<210> SEQ ID NO 8
<211> LENGTH: 26
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: 24R80#1.5 as

<400> SEQUENCE: 8
aacaaaucca aaaaucacag cggacc 26

<210> SEQ ID NO 9
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: DR2-101 s

<400> SEQUENCE: 9
gcuccugaau gcuugcuuca ucuu 24

<210> SEQ ID NO 10
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: DR2-101 as

<400> SEQUENCE: 10
aagaugaagc aagcauucag gagc 24

<210> SEQ ID NO 11
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: DR2-135 s
<220> FEATURE:
<221> NAME/KEY: misc_feature
<222> LOCATION: (12)..(12)
<223> OTHER INFORMATION: 2'-o-methyl -continued

<400> SEQUENCE: 11
gcuccugaau gcuugcuuca ucuu 24

<210> SEQ ID NO 12
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-106 as
<220> FEATURE:
<221> NAME/KEY: misc_feature
<222> LOCATION: (22)..(22)
<223> OTHER INFORMATION: 2'-o-methyl

<400> SEQUENCE: 12
aagaugaagc aagcauucag gagc 24

<210> SEQ ID NO 13
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-107 as
<220> FEATURE:
<221> NAME/KEY: misc_feature
<222> LOCATION: (13)..(13)
<223> OTHER INFORMATION: 2'-fluoro
<220> FEATURE:
<221> NAME/KEY: misc_feature
<222> LOCATION: (22)..(22)
<223> OTHER INFORMATION: 2'-o-methyl

<400> SEQUENCE: 13
aagaugaagc aagcauucag gagc 24

<210> SEQ ID NO 14
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-108 as
<220> FEATURE:
<221> NAME/KEY: misc_feature
<222> LOCATION: (5)..(5)
<223> OTHER INFORMATION: 2'-fluoro
<220> FEATURE:
<221> NAME/KEY: misc_feature
<222> LOCATION: (22)..(22)
<223> OTHER INFORMATION: 2'-o-methyl

<400> SEQUENCE: 14
aagaugaagc aagcauucag gagc 24

<210> SEQ ID NO 15
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-139 s

```
<220> FEATURE:
<221> NAME/KEY: misc_feature
<222> LOCATION: (20)..(20)
<223> OTHER INFORMATION: 2'-o-methyl

<400> SEQUENCE: 15

gcuccugaau gcuugcuuca ucuu                                            24


<210> SEQ ID NO 16
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DR2-118 s

<400> SEQUENCE: 16

guuccaauag uagucauagc uauu                                            24


<210> SEQ ID NO 17
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DR2-118 as

<400> SEQUENCE: 17

aauagcuaug acuacuauug gaac                                            24


<210> SEQ ID NO 18
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DR2-143 s
<220> FEATURE:
<221> NAME/KEY: misc_feature
<222> LOCATION: (12)..(12)
<223> OTHER INFORMATION: 2'-o-methyl

<400> SEQUENCE: 18

guuccaauag uagucauagc uauu                                            24


<210> SEQ ID NO 19
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DR2-123 as
<220> FEATURE:
<221> NAME/KEY: misc_feature
<222> LOCATION: (22)..(22)
<223> OTHER INFORMATION: 2'-o-methyl

<400> SEQUENCE: 19

aauagcuaug acuacuauug gaac                                            24


<210> SEQ ID NO 20
```

-continued

```
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DR2-124 as
<220> FEATURE:
<221> NAME/KEY: misc_feature
<222> LOCATION: (13)..(13)
<223> OTHER INFORMATION: 2'-fluoro
<220> FEATURE:
<221> NAME/KEY: misc_feature
<222> LOCATION: (22)..(22)
<223> OTHER INFORMATION: 2'-o-methyl

<400> SEQUENCE: 20

aauagcuaug acuacuauug gaac                                            24


<210> SEQ ID NO 21
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DR2-125 as
<220> FEATURE:
<221> NAME/KEY: misc_feature
<222> LOCATION: (5)..(5)
<223> OTHER INFORMATION: 2'-fluoro
<220> FEATURE:
<221> NAME/KEY: misc_feature
<222> LOCATION: (22)..(22)
<223> OTHER INFORMATION: 2'-o-methyl

<400> SEQUENCE: 21

aauagcuaug acuacuauug gaac                                            24


<210> SEQ ID NO 22
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DR2-147 s
<220> FEATURE:
<221> NAME/KEY: misc_feature
<222> LOCATION: (20)..(20)
<223> OTHER INFORMATION: 2'-o-methyl

<400> SEQUENCE: 22

guuccaauag uagucauagc uauu                                            24


<210> SEQ ID NO 23
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DR2-151 s

<400> SEQUENCE: 23

guucugcaac ucaaagugcu auug                                            24
```

-continued

<210> SEQ ID NO 24
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-151 as

<400> SEQUENCE: 24
caauagcacu uugaguugca gaac 24

<210> SEQ ID NO 25
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-156 s
<220> FEATURE:
<221> NAME/KEY: misc_feature
<222> LOCATION: (12)..(12)
<223> OTHER INFORMATION: 2'-o-methyl

<400> SEQUENCE: 25
guucugcaac ucaaagugcu auug 24

<210> SEQ ID NO 26
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-157 as
<220> FEATURE:
<221> NAME/KEY: misc_feature
<222> LOCATION: (22)..(22)
<223> OTHER INFORMATION: 2'-o-methyl

<400> SEQUENCE: 26
caauagcacu uugaguugca gaac 24

<210> SEQ ID NO 27
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-158 as
<220> FEATURE:
<221> NAME/KEY: misc_feature
<222> LOCATION: (13)..(13)
<223> OTHER INFORMATION: 2'-fluoro
<220> FEATURE:
<221> NAME/KEY: misc_feature
<222> LOCATION: (22)..(22)
<223> OTHER INFORMATION: 2'-o-methyl

<400> SEQUENCE: 27
caauagcacu uugaguugca gaac 24

<210> SEQ ID NO 28
<211> LENGTH: 24
<212> TYPE: RNA

-continued

<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DR2-159 as
<220> FEATURE:
<221> NAME/KEY: misc_feature
<222> LOCATION: (5)..(5)
<223> OTHER INFORMATION: 2'-fluoro
<220> FEATURE:
<221> NAME/KEY: misc_feature
<222> LOCATION: (22)..(22)
<223> OTHER INFORMATION: 2'-o-methyl

<400> SEQUENCE: 28
caauagcacu uugaguugca gaac 24

<210> SEQ ID NO 29
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DR2-166 s
<220> FEATURE:
<221> NAME/KEY: misc_feature
<222> LOCATION: (20)..(20)
<223> OTHER INFORMATION: 2'-o-methyl

<400> SEQUENCE: 29
guucugcaac ucaaagugcu auug 24

<210> SEQ ID NO 30
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DR2-105 s
<220> FEATURE:
<221> NAME/KEY: misc_feature
<222> LOCATION: (2)..(2)
<223> OTHER INFORMATION: 2'-fluoro
<220> FEATURE:
<221> NAME/KEY: misc_feature
<222> LOCATION: (4)..(4)
<223> OTHER INFORMATION: 2'-fluoro
<220> FEATURE:
<221> NAME/KEY: misc_feature
<222> LOCATION: (9)..(9)
<223> OTHER INFORMATION: 2'-fluoro
<220> FEATURE:
<221> NAME/KEY: misc_feature
<222> LOCATION: (10)..(10)
<223> OTHER INFORMATION: 2'-fluoro
<220> FEATURE:
<221> NAME/KEY: misc_feature
<222> LOCATION: (12)..(12)
<223> OTHER INFORMATION: 2'-o-methyl
<220> FEATURE:
<221> NAME/KEY: misc_feature
<222> LOCATION: (15)..(15)
<223> OTHER INFORMATION: 2'-o-methyl
<220> FEATURE:
<221> NAME/KEY: misc_feature
<222> LOCATION: (16)..(16)
<223> OTHER INFORMATION: 2'-fluoro
<220> FEATURE:
<221> NAME/KEY: misc_feature
<222> LOCATION: (21)..(21)

<223> OTHER INFORMATION: 2'-fluoro
<220> FEATURE:
<221> NAME/KEY: misc_feature
<222> LOCATION: (22)..(22)
<223> OTHER INFORMATION: 2'-fluoro
<220> FEATURE:
<221> NAME/KEY: misc_feature
<222> LOCATION: (24)..(24)
<223> OTHER INFORMATION: 2'-fluoro

<400> SEQUENCE: 30
gcuccugaau gcuugcuuca ucuu 24

<210> SEQ ID NO 31
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-105 as
<220> FEATURE:
<221> NAME/KEY: misc_feature
<222> LOCATION: (5)..(5)
<223> OTHER INFORMATION: 2'-fluoro
<220> FEATURE:
<221> NAME/KEY: misc_feature
<222> LOCATION: (13)..(13)
<223> OTHER INFORMATION: 2'-fluoro
<220> FEATURE:
<221> NAME/KEY: misc_feature
<222> LOCATION: (22)..(22)
<223> OTHER INFORMATION: 2'-o-methyl

<400> SEQUENCE: 31
aagaugaagc aagcauucag gagc 24

<210> SEQ ID NO 32
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-122 s
<220> FEATURE:
<221> NAME/KEY: misc_feature
<222> LOCATION: (2)..(2)
<223> OTHER INFORMATION: 2'-fluoro
<220> FEATURE:
<221> NAME/KEY: misc_feature
<222> LOCATION: (4)..(4)
<223> OTHER INFORMATION: 2'-fluoro
<220> FEATURE:
<221> NAME/KEY: misc_feature
<222> LOCATION: (9)..(9)
<223> OTHER INFORMATION: 2'-fluoro
<220> FEATURE:
<221> NAME/KEY: misc_feature
<222> LOCATION: (10)..(10)
<223> OTHER INFORMATION: 2'-fluoro
<220> FEATURE:
<221> NAME/KEY: misc_feature
<222> LOCATION: (12)..(12)
<223> OTHER INFORMATION: 2'-o-methyl
<220> FEATURE:
<221> NAME/KEY: misc_feature
<222> LOCATION: (15)..(15)
<223> OTHER INFORMATION: 2'-o-methyl
<220> FEATURE:
<221> NAME/KEY: misc_feature
<222> LOCATION: (16)..(16)
<223> OTHER INFORMATION: 2'-fluoro

```
<220> FEATURE:
<221> NAME/KEY: misc_feature
<222> LOCATION: (20)..(20)
<223> OTHER INFORMATION: 2'-o-methyl
<220> FEATURE:
<221> NAME/KEY: misc_feature
<222> LOCATION: (21)..(21)
<223> OTHER INFORMATION: 2'-fluoro
<220> FEATURE:
<221> NAME/KEY: misc_feature
<222> LOCATION: (22)..(22)
<223> OTHER INFORMATION: 2'-fluoro
<220> FEATURE:
<221> NAME/KEY: misc_feature
<222> LOCATION: (24)..(24)
<223> OTHER INFORMATION: 2'-fluoro

<400> SEQUENCE: 32

guuccaauag uagucauagc uauu                                            24


<210> SEQ ID NO 33
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DR2-122 as
<220> FEATURE:
<221> NAME/KEY: misc_feature
<222> LOCATION: (5)..(5)
<223> OTHER INFORMATION: 2'-fluoro
<220> FEATURE:
<221> NAME/KEY: misc_feature
<222> LOCATION: (13)..(13)
<223> OTHER INFORMATION: 2'-fluoro
<220> FEATURE:
<221> NAME/KEY: misc_feature
<222> LOCATION: (22)..(22)
<223> OTHER INFORMATION: 2'-o-methyl

<400> SEQUENCE: 33

aauagcuaug acuacuauug gaac                                            24


<210> SEQ ID NO 34
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DR2-155 s
<220> FEATURE:
<221> NAME/KEY: misc_feature
<222> LOCATION: (2)..(2)
<223> OTHER INFORMATION: 2'-fluoro
<220> FEATURE:
<221> NAME/KEY: misc_feature
<222> LOCATION: (4)..(4)
<223> OTHER INFORMATION: 2'-fluoro
<220> FEATURE:
<221> NAME/KEY: misc_feature
<222> LOCATION: (9)..(9)
<223> OTHER INFORMATION: 2'-fluoro
<220> FEATURE:
<221> NAME/KEY: misc_feature
<222> LOCATION: (10)..(10)
<223> OTHER INFORMATION: 2'-fluoro
<220> FEATURE:
<221> NAME/KEY: misc_feature
<222> LOCATION: (12)..(12)
<223> OTHER INFORMATION: 2'-o-methyl
<220> FEATURE:
```

```
<221> NAME/KEY: misc_feature
<222> LOCATION: (15)..(15)
<223> OTHER INFORMATION: 2'-o-methyl
<220> FEATURE:
<221> NAME/KEY: misc_feature
<222> LOCATION: (16)..(16)
<223> OTHER INFORMATION: 2'-fluoro
<220> FEATURE:
<221> NAME/KEY: misc_feature
<222> LOCATION: (20)..(20)
<223> OTHER INFORMATION: 2'-o-methyl
<220> FEATURE:
<221> NAME/KEY: misc_feature
<222> LOCATION: (21)..(21)
<223> OTHER INFORMATION: 2'-fluoro
<220> FEATURE:
<221> NAME/KEY: misc_feature
<222> LOCATION: (22)..(22)
<223> OTHER INFORMATION: 2'-fluoro
<220> FEATURE:
<221> NAME/KEY: misc_feature
<222> LOCATION: (24)..(24)
<223> OTHER INFORMATION: 2'-fluoro

<400> SEQUENCE: 34

guucugcaac ucaaagugcu auug                                              24


<210> SEQ ID NO 35
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DR2-155 as
<220> FEATURE:
<221> NAME/KEY: misc_feature
<222> LOCATION: (5)..(5)
<223> OTHER INFORMATION: 2'-fluoro
<220> FEATURE:
<221> NAME/KEY: misc_feature
<222> LOCATION: (13)..(13)
<223> OTHER INFORMATION: 2'-fluoro
<220> FEATURE:
<221> NAME/KEY: misc_feature
<222> LOCATION: (22)..(22)
<223> OTHER INFORMATION: 2'-o-methyl

<400> SEQUENCE: 35

caauagcacu uugaguugca gaac                                              24


<210> SEQ ID NO 36
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 122212 s
<220> FEATURE:
<221> NAME/KEY: misc_feature
<222> LOCATION: (1)..(1)
<223> OTHER INFORMATION: 5'-triphosphate

<400> SEQUENCE: 36

gacgcugacc cugaaguuca ucuu                                              24


<210> SEQ ID NO 37
<211> LENGTH: 24
<212> TYPE: RNA
<213> ORGANISM: Artificial Sequence
```

```
<220> FEATURE:
<223> OTHER INFORMATION: Description of Artificial Sequence: Synthetic
      oligonucleotide
<220> FEATURE:
<223> OTHER INFORMATION: 123212 s
<220> FEATURE:
<221> NAME/KEY: misc_feature
<222> LOCATION: (7)..(7)
<223> OTHER INFORMATION: 2'-fluoro
<220> FEATURE:
<221> NAME/KEY: misc_feature
<222> LOCATION: (15)..(15)
<223> OTHER INFORMATION: 2'-o-methyl
<220> FEATURE:
<221> NAME/KEY: misc_feature
<222> LOCATION: (22)..(24)
<223> OTHER INFORMATION: phosphorothioate linkages between residues 22
      and 23, and 23 and 24
<220> FEATURE:
<221> NAME/KEY: misc_feature
<222> LOCATION: (23)..(23)
<223> OTHER INFORMATION: 2'-fluoro

<400> SEQUENCE: 37

gacgcugacc cugaaguuca ucuu                                            24


<210> SEQ ID NO 38
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 123212 as
<220> FEATURE:
<221> NAME/KEY: misc_feature
<222> LOCATION: (1)..(3)
<223> OTHER INFORMATION: phosphorothioate linkages between residues 1
      and 2, and residues 2 and 3
<220> FEATURE:
<221> NAME/KEY: misc_feature
<222> LOCATION: (12)..(12)
<223> OTHER INFORMATION: 2'-fluoro
<220> FEATURE:
<221> NAME/KEY: misc_feature
<222> LOCATION: (22)..(22)
<223> OTHER INFORMATION: 2'-o-methyl

<400> SEQUENCE: 38

aagaugaacu ucagggucag cguc                                            24


<210> SEQ ID NO 39
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DR2-102s
<220> FEATURE:
<221> NAME/KEY: misc_feature
<222> LOCATION: (2)..(2)
<223> OTHER INFORMATION: 2'-fluoro
<220> FEATURE:
<221> NAME/KEY: misc_feature
<222> LOCATION: (4)..(4)
<223> OTHER INFORMATION: 2'-fluoro
<220> FEATURE:
<221> NAME/KEY: misc_feature
<222> LOCATION: (6)..(6)
<223> OTHER INFORMATION: 2'-fluoro
<220> FEATURE:
<221> NAME/KEY: misc_feature
```

<222> LOCATION: (9)..(9)
<223> OTHER INFORMATION: 2'-fluoro
<220> FEATURE:
<221> NAME/KEY: misc_feature
<222> LOCATION: (10)..(10)
<223> OTHER INFORMATION: 2'-fluoro
<220> FEATURE:
<221> NAME/KEY: misc_feature
<222> LOCATION: (12)..(12)
<223> OTHER INFORMATION: 2'-o-methyl
<220> FEATURE:
<221> NAME/KEY: misc_feature
<222> LOCATION: (15)..(15)
<223> OTHER INFORMATION: 2'-o-methyl
<220> FEATURE:
<221> NAME/KEY: misc_feature
<222> LOCATION: (16)..(16)
<223> OTHER INFORMATION: 2'-fluoro
<220> FEATURE:
<221> NAME/KEY: misc_feature
<222> LOCATION: (20)..(20)
<223> OTHER INFORMATION: 2'-o-methyl
<220> FEATURE:
<221> NAME/KEY: misc_feature
<222> LOCATION: (21)..(21)
<223> OTHER INFORMATION: 2'-fluoro
<220> FEATURE:
<221> NAME/KEY: misc_feature
<222> LOCATION: (22)..(22)
<223> OTHER INFORMATION: 2'-fluoro
<220> FEATURE:
<221> NAME/KEY: misc_feature
<222> LOCATION: (24)..(24)
<223> OTHER INFORMATION: 2'-fluoro

<400> SEQUENCE: 39
gcuccugaau gcuugcuuca ucuu 24

<210> SEQ ID NO 40
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-102as
<220> FEATURE:
<221> NAME/KEY: misc_feature
<222> LOCATION: (5)..(5)
<223> OTHER INFORMATION: 2'-fluoro
<220> FEATURE:
<221> NAME/KEY: misc_feature
<222> LOCATION: (13)..(13)
<223> OTHER INFORMATION: 2'-fluoro
<220> FEATURE:
<221> NAME/KEY: misc_feature
<222> LOCATION: (18)..(18)
<223> OTHER INFORMATION: 2'-fluoro
<220> FEATURE:
<221> NAME/KEY: misc_feature
<222> LOCATION: (22)..(22)
<223> OTHER INFORMATION: 2'-o-methyl

<400> SEQUENCE: 40
aagaugaagc aagcauucag gagc 24

<210> SEQ ID NO 41
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:

<223> OTHER INFORMATION: DR2-103s
<220> FEATURE:
<221> NAME/KEY: misc_feature
<222> LOCATION: (12)..(12)
<223> OTHER INFORMATION: 2'-o-methyl
<220> FEATURE:
<221> NAME/KEY: misc_feature
<222> LOCATION: (15)..(15)
<223> OTHER INFORMATION: 2'-o-methyl
<220> FEATURE:
<221> NAME/KEY: misc_feature
<222> LOCATION: (20)..(20)
<223> OTHER INFORMATION: 2'-o-methyl

<400> SEQUENCE: 41
gcuccugaau gcuugcuuca ucuu 24

<210> SEQ ID NO 42
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-104s
<220> FEATURE:
<221> NAME/KEY: misc_feature
<222> LOCATION: (2)..(2)
<223> OTHER INFORMATION: 2'-fluoro
<220> FEATURE:
<221> NAME/KEY: misc_feature
<222> LOCATION: (4)..(4)
<223> OTHER INFORMATION: 2'-fluoro
<220> FEATURE:
<221> NAME/KEY: misc_feature
<222> LOCATION: (6)..(6)
<223> OTHER INFORMATION: 2'-fluoro
<220> FEATURE:
<221> NAME/KEY: misc_feature
<222> LOCATION: (9)..(9)
<223> OTHER INFORMATION: 2'-fluoro
<220> FEATURE:
<221> NAME/KEY: misc_feature
<222> LOCATION: (10)..(10)
<223> OTHER INFORMATION: 2'-fluoro
<220> FEATURE:
<221> NAME/KEY: misc_feature
<222> LOCATION: (16)..(16)
<223> OTHER INFORMATION: 2'-fluoro
<220> FEATURE:
<221> NAME/KEY: misc_feature
<222> LOCATION: (21)..(21)
<223> OTHER INFORMATION: 2'-fluoro
<220> FEATURE:
<221> NAME/KEY: misc_feature
<222> LOCATION: (22)..(22)
<223> OTHER INFORMATION: 2'-fluoro
<220> FEATURE:
<221> NAME/KEY: misc_feature
<222> LOCATION: (24)..(24)
<223> OTHER INFORMATION: 2'-fluoro

<400> SEQUENCE: 42
gcuccugaau gcuugcuuca ucuu 24

<210> SEQ ID NO 43
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-104as
<220> FEATURE:
<221> NAME/KEY: misc_feature
<222> LOCATION: (5)..(5)
<223> OTHER INFORMATION: 2'-fluoro
<220> FEATURE:
<221> NAME/KEY: misc_feature
<222> LOCATION: (13)..(13)
<223> OTHER INFORMATION: 2'-fluoro
<220> FEATURE:
<221> NAME/KEY: misc_feature
<222> LOCATION: (18)..(18)
<223> OTHER INFORMATION: 2'-fluoro

<400> SEQUENCE: 43
aagaugaagc aagcauucag gagc 24

<210> SEQ ID NO 44
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-109s
<220> FEATURE:
<221> NAME/KEY: misc_feature
<222> LOCATION: (4)..(4)
<223> OTHER INFORMATION: 2'-fluoro
<220> FEATURE:
<221> NAME/KEY: misc_feature
<222> LOCATION: (12)..(12)
<223> OTHER INFORMATION: 2'-o-methyl
<220> FEATURE:
<221> NAME/KEY: misc_feature
<222> LOCATION: (21)..(21)
<223> OTHER INFORMATION: 2'-fluoro

<400> SEQUENCE: 44
gcuccugaau gcuugcuuca ucuu 24

<210> SEQ ID NO 45
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-115s
<220> FEATURE:
<221> NAME/KEY: misc_feature
<222> LOCATION: (4)..(4)
<223> OTHER INFORMATION: 2'-fluoro
<220> FEATURE:
<221> NAME/KEY: misc_feature
<222> LOCATION: (20)..(20)
<223> OTHER INFORMATION: 2'-o-methyl
<220> FEATURE:
<221> NAME/KEY: misc_feature
<222> LOCATION: (21)..(21)
<223> OTHER INFORMATION: 2'-fluoro

<400> SEQUENCE: 45
gcuccugaau gcuugcuuca ucuu 24

<210> SEQ ID NO 46
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide <220> FEATURE:
<223> OTHER INFORMATION: DR2-119s
<220> FEATURE:
<221> NAME/KEY: misc_feature
<222> LOCATION: (2)..(2)
<223> OTHER INFORMATION: 2'-fluoro
<220> FEATURE:
<221> NAME/KEY: misc_feature
<222> LOCATION: (4)..(4)
<223> OTHER INFORMATION: 2'-fluoro
<220> FEATURE:
<221> NAME/KEY: misc_feature
<222> LOCATION: (6)..(6)
<223> OTHER INFORMATION: 2'-fluoro
<220> FEATURE:
<221> NAME/KEY: misc_feature
<222> LOCATION: (9)..(9)
<223> OTHER INFORMATION: 2'-fluoro
<220> FEATURE:
<221> NAME/KEY: misc_feature
<222> LOCATION: (10)..(10)
<223> OTHER INFORMATION: 2'-fluoro
<220> FEATURE:
<221> NAME/KEY: misc_feature
<222> LOCATION: (12)..(12)
<223> OTHER INFORMATION: 2'-o-methyl
<220> FEATURE:
<221> NAME/KEY: misc_feature
<222> LOCATION: (15)..(15)
<223> OTHER INFORMATION: 2'-o-methyl
<220> FEATURE:
<221> NAME/KEY: misc_feature
<222> LOCATION: (16)..(16)
<223> OTHER INFORMATION: 2'-fluoro
<220> FEATURE:
<221> NAME/KEY: misc_feature
<222> LOCATION: (20)..(20)
<223> OTHER INFORMATION: 2'-o-methyl
<220> FEATURE:
<221> NAME/KEY: misc_feature
<222> LOCATION: (21)..(21)
<223> OTHER INFORMATION: 2'-fluoro
<220> FEATURE:
<221> NAME/KEY: misc_feature
<222> LOCATION: (22)..(22)
<223> OTHER INFORMATION: 2'-fluoro
<220> FEATURE:
<221> NAME/KEY: misc_feature
<222> LOCATION: (24)..(24)
<223> OTHER INFORMATION: 2'-fluoro

<400> SEQUENCE: 46
guuccaauag uagucauagc uauu 24

<210> SEQ ID NO 47
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-119as
<220> FEATURE:
<221> NAME/KEY: misc_feature
<222> LOCATION: (5)..(5)
<223> OTHER INFORMATION: 2'-fluoro
<220> FEATURE:
<221> NAME/KEY: misc_feature
<222> LOCATION: (13)..(13)
<223> OTHER INFORMATION: 2'-fluoro
<220> FEATURE:
<221> NAME/KEY: misc_feature
<222> LOCATION: (18)..(18)
<223> OTHER INFORMATION: 2'-fluoro
<220> FEATURE:
<221> NAME/KEY: misc_feature
<222> LOCATION: (22)..(22)
<223> OTHER INFORMATION: 2'-o-methyl

<400> SEQUENCE: 47
aauagcuaug acuacuauug gaac 24

<210> SEQ ID NO 48
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-120s
<220> FEATURE:
<221> NAME/KEY: misc_feature
<222> LOCATION: (12)..(12)
<223> OTHER INFORMATION: 2'-o-methyl
<220> FEATURE:
<221> NAME/KEY: misc_feature
<222> LOCATION: (15)..(15)
<223> OTHER INFORMATION: 2'-o-methyl
<220> FEATURE:
<221> NAME/KEY: misc_feature
<222> LOCATION: (20)..(20)
<223> OTHER INFORMATION: 2'-o-methyl

<400> SEQUENCE: 48
guuccaauag uagucauagc uauu 24

<210> SEQ ID NO 49
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-121s
<220> FEATURE:
<221> NAME/KEY: misc_feature
<222> LOCATION: (2)..(2)
<223> OTHER INFORMATION: 2'-fluoro
<220> FEATURE:
<221> NAME/KEY: misc_feature
<222> LOCATION: (4)..(4)
<223> OTHER INFORMATION: 2'-fluoro
<220> FEATURE:
<221> NAME/KEY: misc_feature
<222> LOCATION: (6)..(6)
<223> OTHER INFORMATION: 2'-fluoro
<220> FEATURE:
<221> NAME/KEY: misc_feature
<222> LOCATION: (9)..(9)
<223> OTHER INFORMATION: 2'-fluoro
<220> FEATURE:
<221> NAME/KEY: misc_feature
<222> LOCATION: (10)..(10)
<223> OTHER INFORMATION: 2'-fluoro
<220> FEATURE:
<221> NAME/KEY: misc_feature
<222> LOCATION: (16)..(16)
<223> OTHER INFORMATION: 2'-fluoro
<220> FEATURE:
<221> NAME/KEY: misc_feature
<222> LOCATION: (21)..(21)
<223> OTHER INFORMATION: 2'-fluoro
<220> FEATURE:
<221> NAME/KEY: misc_feature
<222> LOCATION: (22)..(22)
<223> OTHER INFORMATION: 2'-fluoro
<220> FEATURE:
<221> NAME/KEY: misc_feature
<222> LOCATION: (24)..(24)

<223> OTHER INFORMATION: 2'-fluoro

<400> SEQUENCE: 49
guuccaauag uagucauagc uauu 24

<210> SEQ ID NO 50
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-121as
<220> FEATURE:
<221> NAME/KEY: misc_feature
<222> LOCATION: (5)..(5)
<223> OTHER INFORMATION: 2'-fluoro
<220> FEATURE:
<221> NAME/KEY: misc_feature
<222> LOCATION: (13)..(13)
<223> OTHER INFORMATION: 2'-fluoro

<400> SEQUENCE: 50
aauagcuaug acuacuauug gaac 24

<210> SEQ ID NO 51
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-126s
<220> FEATURE:
<221> NAME/KEY: misc_feature
<222> LOCATION: (4)..(4)
<223> OTHER INFORMATION: 2'-fluoro
<220> FEATURE:
<221> NAME/KEY: misc_feature
<222> LOCATION: (12)..(12)
<223> OTHER INFORMATION: 2'-o-methyl
<220> FEATURE:
<221> NAME/KEY: misc_feature
<222> LOCATION: (21)..(21)
<223> OTHER INFORMATION: 2'-fluoro

<400> SEQUENCE: 51
guuccaauag uagucauagc uauu 24

<210> SEQ ID NO 52
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-132s
<220> FEATURE:
<221> NAME/KEY: misc_feature
<222> LOCATION: (4)..(4)
<223> OTHER INFORMATION: 2'-fluoro
<220> FEATURE:
<221> NAME/KEY: misc_feature
<222> LOCATION: (20)..(20)
<223> OTHER INFORMATION: 2'-o-methyl
<220> FEATURE:
<221> NAME/KEY: misc_feature
<222> LOCATION: (21)..(21)
<223> OTHER INFORMATION: 2'-fluoro -continued

<400> SEQUENCE: 52
guuccaauag uagucauagc uauu 24

<210> SEQ ID NO 53
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: DR2-136as
<220> FEATURE:
<221> NAME/KEY: misc_feature
<222> LOCATION: (5)..(5)
<223> OTHER INFORMATION: 2'-fluoro
<220> FEATURE:
<221> NAME/KEY: misc_feature
<222> LOCATION: (13)..(13)
<223> OTHER INFORMATION: 2'-fluoro
<220> FEATURE:
<221> NAME/KEY: misc_feature
<222> LOCATION: (22)..(22)
<223> OTHER INFORMATION: 2'-o-methyl

<400> SEQUENCE: 53
aagaugaagc aagcauucag gagc 24

<210> SEQ ID NO 54
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: DR2-144as
<220> FEATURE:
<221> NAME/KEY: misc_feature
<222> LOCATION: (5)..(5)
<223> OTHER INFORMATION: 2'-fluoro
<220> FEATURE:
<221> NAME/KEY: misc_feature
<222> LOCATION: (13)..(13)
<223> OTHER INFORMATION: 2'-fluoro
<220> FEATURE:
<221> NAME/KEY: misc_feature
<222> LOCATION: (22)..(22)
<223> OTHER INFORMATION: 2'-o-methyl

<400> SEQUENCE: 54
aauagcuaug acuacuauug gaac 24

<210> SEQ ID NO 55
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: DR2-152s
<220> FEATURE:
<221> NAME/KEY: misc_feature
<222> LOCATION: (2)..(2)
<223> OTHER INFORMATION: 2'-fluoro
<220> FEATURE:
<221> NAME/KEY: misc_feature
<222> LOCATION: (4)..(4)
<223> OTHER INFORMATION: 2'-fluoro
<220> FEATURE:
<221> NAME/KEY: misc_feature
<222> LOCATION: (6)..(6)

<223> OTHER INFORMATION: 2'-fluoro
<220> FEATURE:
<221> NAME/KEY: misc_feature
<222> LOCATION: (9)..(9)
<223> OTHER INFORMATION: 2'-fluoro
<220> FEATURE:
<221> NAME/KEY: misc_feature
<222> LOCATION: (10)..(10)
<223> OTHER INFORMATION: 2'-fluoro
<220> FEATURE:
<221> NAME/KEY: misc_feature
<222> LOCATION: (12)..(12)
<223> OTHER INFORMATION: 2'-o-methyl
<220> FEATURE:
<221> NAME/KEY: misc_feature
<222> LOCATION: (15)..(15)
<223> OTHER INFORMATION: 2'-o-methyl
<220> FEATURE:
<221> NAME/KEY: misc_feature
<222> LOCATION: (16)..(16)
<223> OTHER INFORMATION: 2'-fluoro
<220> FEATURE:
<221> NAME/KEY: misc_feature
<222> LOCATION: (20)..(20)
<223> OTHER INFORMATION: 2'-o-methyl
<220> FEATURE:
<221> NAME/KEY: misc_feature
<222> LOCATION: (21)..(21)
<223> OTHER INFORMATION: 2'-fluoro
<220> FEATURE:
<221> NAME/KEY: misc_feature
<222> LOCATION: (22)..(22)
<223> OTHER INFORMATION: 2'-fluoro
<220> FEATURE:
<221> NAME/KEY: misc_feature
<222> LOCATION: (24)..(24)
<223> OTHER INFORMATION: 2'-fluoro

<400> SEQUENCE: 55
guucugcaac ucaaagugcu auug 24

<210> SEQ ID NO 56
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-152as
<220> FEATURE:
<221> NAME/KEY: misc_feature
<222> LOCATION: (5)..(5)
<223> OTHER INFORMATION: 2'-fluoro
<220> FEATURE:
<221> NAME/KEY: misc_feature
<222> LOCATION: (13)..(13)
<223> OTHER INFORMATION: 2'-fluoro
<220> FEATURE:
<221> NAME/KEY: misc_feature
<222> LOCATION: (18)..(18)
<223> OTHER INFORMATION: 2'-fluoro
<220> FEATURE:
<221> NAME/KEY: misc_feature
<222> LOCATION: (22)..(22)
<223> OTHER INFORMATION: 2'-o-methyl

<400> SEQUENCE: 56
caauagcacu uugaguugca gaac 24

<210> SEQ ID NO 57
<211> LENGTH: 24
<212> TYPE: RNA
<213> ORGANISM: Artificial Sequence
<220> FEATURE:

```
<223> OTHER INFORMATION: Description of Artificial Sequence: Synthetic
      oligonucleotide
<220> FEATURE:
<223> OTHER INFORMATION: DR2-153s
<220> FEATURE:
<221> NAME/KEY: misc_feature
<222> LOCATION: (12)..(12)
<223> OTHER INFORMATION: 2'-o-methyl
<220> FEATURE:
<221> NAME/KEY: misc_feature
<222> LOCATION: (15)..(15)
<223> OTHER INFORMATION: 2'-o-methyl
<220> FEATURE:
<221> NAME/KEY: misc_feature
<222> LOCATION: (20)..(20)
<223> OTHER INFORMATION: 2'-o-methyl

<400> SEQUENCE: 57

guucugcaac ucaaagugcu auug                                            24


<210> SEQ ID NO 58
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DR2-154s
<220> FEATURE:
<221> NAME/KEY: misc_feature
<222> LOCATION: (2)..(2)
<223> OTHER INFORMATION: 2'-fluoro
<220> FEATURE:
<221> NAME/KEY: misc_feature
<222> LOCATION: (4)..(4)
<223> OTHER INFORMATION: 2'-fluoro
<220> FEATURE:
<221> NAME/KEY: misc_feature
<222> LOCATION: (6)..(6)
<223> OTHER INFORMATION: 2'-fluoro
<220> FEATURE:
<221> NAME/KEY: misc_feature
<222> LOCATION: (9)..(9)
<223> OTHER INFORMATION: 2'-fluoro
<220> FEATURE:
<221> NAME/KEY: misc_feature
<222> LOCATION: (10)..(10)
<223> OTHER INFORMATION: 2'-fluoro
<220> FEATURE:
<221> NAME/KEY: misc_feature
<222> LOCATION: (16)..(16)
<223> OTHER INFORMATION: 2'-fluoro
<220> FEATURE:
<221> NAME/KEY: misc_feature
<222> LOCATION: (21)..(21)
<223> OTHER INFORMATION: 2'-fluoro
<220> FEATURE:
<221> NAME/KEY: misc_feature
<222> LOCATION: (22)..(22)
<223> OTHER INFORMATION: 2'-fluoro
<220> FEATURE:
<221> NAME/KEY: misc_feature
<222> LOCATION: (24)..(24)
<223> OTHER INFORMATION: 2'-fluoro

<400> SEQUENCE: 58

guucugcaac ucaaagugcu auug                                            24


<210> SEQ ID NO 59
<211> LENGTH: 24
<212> TYPE: RNA
<213> ORGANISM: Artificial Sequence
<220> FEATURE:
<223> OTHER INFORMATION: Description of Artificial Sequence: Synthetic
```

oligonucleotide
<220> FEATURE:
<223> OTHER INFORMATION: DR2-154as
<220> FEATURE:
<221> NAME/KEY: misc_feature
<222> LOCATION: (5)..(5)
<223> OTHER INFORMATION: 2'-fluoro
<220> FEATURE:
<221> NAME/KEY: misc_feature
<222> LOCATION: (13)..(13)
<223> OTHER INFORMATION: 2'-fluoro
<220> FEATURE:
<221> NAME/KEY: misc_feature
<222> LOCATION: (18)..(18)
<223> OTHER INFORMATION: 2'-fluoro

<400> SEQUENCE: 59
caauagcacu uugaguugca gaac 24

<210> SEQ ID NO 60
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-160as
<220> FEATURE:
<221> NAME/KEY: misc_feature
<222> LOCATION: (5)..(5)
<223> OTHER INFORMATION: 2'-fluoro
<220> FEATURE:
<221> NAME/KEY: misc_feature
<222> LOCATION: (13)..(13)
<223> OTHER INFORMATION: 2'-fluoro
<220> FEATURE:
<221> NAME/KEY: misc_feature
<222> LOCATION: (22)..(22)
<223> OTHER INFORMATION: 2'-o-methyl

<400> SEQUENCE: 60
caauagcacu uugaguugca gaac 24

<210> SEQ ID NO 61
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-161s
<220> FEATURE:
<221> NAME/KEY: misc_feature
<222> LOCATION: (4)..(4)
<223> OTHER INFORMATION: 2'-fluoro
<220> FEATURE:
<221> NAME/KEY: misc_feature
<222> LOCATION: (12)..(12)
<223> OTHER INFORMATION: 2'-o-methyl
<220> FEATURE:
<221> NAME/KEY: misc_feature
<222> LOCATION: (21)..(21)
<223> OTHER INFORMATION: 2'-fluoro

<400> SEQUENCE: 61
guucugcaac ucaaagugcu auug 24

<210> SEQ ID NO 62
<211> LENGTH: 24
<212> TYPE: RNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: DR2-171s
<220> FEATURE:
<221> NAME/KEY: misc_feature
<222> LOCATION: (4)..(4)
<223> OTHER INFORMATION: 2'-fluoro
<220> FEATURE:
<221> NAME/KEY: misc_feature
<222> LOCATION: (20)..(20)
<223> OTHER INFORMATION: 2'-o-methyl
<220> FEATURE:
<221> NAME/KEY: misc_feature
<222> LOCATION: (21)..(21)
<223> OTHER INFORMATION: 2'-fluoro

<400> SEQUENCE: 62

guucugcaac ucaaagugcu auug                                            24


<210> SEQ ID NO 63
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DR2-177s
<220> FEATURE:
<221> NAME/KEY: misc_feature
<222> LOCATION: (12)..(12)
<223> OTHER INFORMATION: 2'-o-methyl
<220> FEATURE:
<221> NAME/KEY: misc_feature
<222> LOCATION: (15)..(15)
<223> OTHER INFORMATION: 2'-o-methyl
<220> FEATURE:
<221> NAME/KEY: misc_feature
<222> LOCATION: (20)..(20)
<223> OTHER INFORMATION: 2'-o-methyl

<400> SEQUENCE: 63

gguccgcugu gauuuuugga uuug                                            24


<210> SEQ ID NO 64
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DR2-177as
<220> FEATURE:
<221> NAME/KEY: misc_feature
<222> LOCATION: (22)..(22)
<223> OTHER INFORMATION: 2'-o-methyl

<400> SEQUENCE: 64

caaauccaaa aaucacagcg gacc                                            24


<210> SEQ ID NO 65
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DR2-178s
<220> FEATURE:
```

<221> NAME/KEY: misc_feature
<222> LOCATION: (12)..(12)
<223> OTHER INFORMATION: 2'-o-methyl
<220> FEATURE:
<221> NAME/KEY: misc_feature
<222> LOCATION: (15)..(15)
<223> OTHER INFORMATION: 2'-o-methyl
<220> FEATURE:
<221> NAME/KEY: misc_feature
<222> LOCATION: (20)..(20)
<223> OTHER INFORMATION: 2'-o-methyl

<400> SEQUENCE: 65
gguccgcugu gauuuuugga uu 22

<210> SEQ ID NO 66
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-178as
<220> FEATURE:
<221> NAME/KEY: misc_feature
<222> LOCATION: (20)..(20)
<223> OTHER INFORMATION: 2'-o-methyl

<400> SEQUENCE: 66
aauccaaaaa ucacagcgga cc 22

<210> SEQ ID NO 67
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-179s
<220> FEATURE:
<221> NAME/KEY: misc_feature
<222> LOCATION: (12)..(12)
<223> OTHER INFORMATION: 2'-o-methyl
<220> FEATURE:
<221> NAME/KEY: misc_feature
<222> LOCATION: (15)..(15)
<223> OTHER INFORMATION: 2'-o-methyl
<220> FEATURE:
<221> NAME/KEY: misc_feature
<222> LOCATION: (20)..(20)
<223> OTHER INFORMATION: 2'-o-methyl

<400> SEQUENCE: 67
gguccgcugu gauuuuugga 20

<210> SEQ ID NO 68
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-179as
<220> FEATURE:
<221> NAME/KEY: misc_feature
<222> LOCATION: (18)..(18)
<223> OTHER INFORMATION: 2'-o-methyl

<400> SEQUENCE: 68

-continued uccaaaaauc acagcggacc 20

<210> SEQ ID NO 69
<211> LENGTH: 26
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-180s
<220> FEATURE:
<221> NAME/KEY: misc_feature
<222> LOCATION: (12)..(12)
<223> OTHER INFORMATION: 2'-o-methyl
<220> FEATURE:
<221> NAME/KEY: misc_feature
<222> LOCATION: (15)..(15)
<223> OTHER INFORMATION: 2'-o-methyl
<220> FEATURE:
<221> NAME/KEY: misc_feature
<222> LOCATION: (20)..(20)
<223> OTHER INFORMATION: 2'-o-methyl

<400> SEQUENCE: 69
gguccgcugu gauuuuugga uuugaa 26

<210> SEQ ID NO 70
<211> LENGTH: 26
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-180as
<220> FEATURE:
<221> NAME/KEY: misc_feature
<222> LOCATION: (24)..(24)
<223> OTHER INFORMATION: 2'-o-methyl

<400> SEQUENCE: 70
uucaaaucca aaaaucacag cggacc 26

<210> SEQ ID NO 71
<211> LENGTH: 28
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-181s
<220> FEATURE:
<221> NAME/KEY: misc_feature
<222> LOCATION: (12)..(12)
<223> OTHER INFORMATION: 2'-o-methyl
<220> FEATURE:
<221> NAME/KEY: misc_feature
<222> LOCATION: (15)..(15)
<223> OTHER INFORMATION: 2'-o-methyl
<220> FEATURE:
<221> NAME/KEY: misc_feature
<222> LOCATION: (20)..(20)
<223> OTHER INFORMATION: 2'-o-methyl

<400> SEQUENCE: 71
gguccgcugu gauuuuugga uuugaaaa 28

<210> SEQ ID NO 72
<211> LENGTH: 28
<212> TYPE: RNA

<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-181as
<220> FEATURE:
<221> NAME/KEY: misc_feature
<222> LOCATION: (26)..(26)
<223> OTHER INFORMATION: 2'-o-methyl

<400> SEQUENCE: 72
uuuucaaauc caaaaaucac agcggacc 28

<210> SEQ ID NO 73
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-182s
<220> FEATURE:
<221> NAME/KEY: misc_feature
<222> LOCATION: (10)..(10)
<223> OTHER INFORMATION: 2'-o-methyl
<220> FEATURE:
<221> NAME/KEY: misc_feature
<222> LOCATION: (13)..(13)
<223> OTHER INFORMATION: 2'-o-methyl
<220> FEATURE:
<221> NAME/KEY: misc_feature
<222> LOCATION: (18)..(18)
<223> OTHER INFORMATION: 2'-o-methyl

<400> SEQUENCE: 73
uccgcuguga uuuuuggauu ug 22

<210> SEQ ID NO 74
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-182as
<220> FEATURE:
<221> NAME/KEY: misc_feature
<222> LOCATION: (22)..(22)
<223> OTHER INFORMATION: 2'-o-methyl

<400> SEQUENCE: 74
caaauccaaa aaucacagcg ga 22

<210> SEQ ID NO 75
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-183s
<220> FEATURE:
<221> NAME/KEY: misc_feature
<222> LOCATION: (8)..(8)
<223> OTHER INFORMATION: 2'-o-methyl
<220> FEATURE:
<221> NAME/KEY: misc_feature
<222> LOCATION: (11)..(11)
<223> OTHER INFORMATION: 2'-o-methyl -continued
<220> FEATURE:
<221> NAME/KEY: misc_feature
<222> LOCATION: (16)..(16)
<223> OTHER INFORMATION: 2'-o-methyl

<400> SEQUENCE: 75
cgcugugauu uuuggauuug 20

<210> SEQ ID NO 76
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-183as

<400> SEQUENCE: 76
caaauccaaa aaucacagcg 20

<210> SEQ ID NO 77
<211> LENGTH: 26
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-184s
<220> FEATURE:
<221> NAME/KEY: misc_feature
<222> LOCATION: (14)..(14)
<223> OTHER INFORMATION: 2'-o-methyl
<220> FEATURE:
<221> NAME/KEY: misc_feature
<222> LOCATION: (17)..(17)
<223> OTHER INFORMATION: 2'-o-methyl
<220> FEATURE:
<221> NAME/KEY: misc_feature
<222> LOCATION: (22)..(22)
<223> OTHER INFORMATION: 2'-o-methyl

<400> SEQUENCE: 77
gagguccgcu gugauuuuug gauuug 26

<210> SEQ ID NO 78
<211> LENGTH: 26
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-184as
<220> FEATURE:
<221> NAME/KEY: misc_feature
<222> LOCATION: (22)..(22)
<223> OTHER INFORMATION: 2'-o-methyl

<400> SEQUENCE: 78
caaauccaaa aaucacagcg gaccuc 26

<210> SEQ ID NO 79
<211> LENGTH: 28
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:

-continued

<223> OTHER INFORMATION: DR2-185s
<220> FEATURE:
<221> NAME/KEY: misc_feature
<222> LOCATION: (16)..(16)
<223> OTHER INFORMATION: 2'-o-methyl
<220> FEATURE:
<221> NAME/KEY: misc_feature
<222> LOCATION: (19)..(19)
<223> OTHER INFORMATION: 2'-o-methyl
<220> FEATURE:
<221> NAME/KEY: misc_feature
<222> LOCATION: (24)..(24)
<223> OTHER INFORMATION: 2'-o-methyl

<400> SEQUENCE: 79
gagagguccg cugugauuuu uggauuug 28

<210> SEQ ID NO 80
<211> LENGTH: 28
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-185as
<220> FEATURE:
<221> NAME/KEY: misc_feature
<222> LOCATION: (22)..(22)
<223> OTHER INFORMATION: 2'-o-methyl

<400> SEQUENCE: 80
caaauccaaa aaucacagcg gaccucuc 28

<210> SEQ ID NO 81
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-186s

<400> SEQUENCE: 81
gguccgcugu gauuuuugga uu 22

<210> SEQ ID NO 82
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-186as

<400> SEQUENCE: 82
aauccaaaaa ucacagcgga cc 22

<210> SEQ ID NO 83
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-187s

<400> SEQUENCE: 83 ggucc gcugu gauuuuugga 20

<210> SEQ ID NO 84
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: DR2-187as

<400> SEQUENCE: 84
uccaaaaauc acagcggacc 20

<210> SEQ ID NO 85
<211> LENGTH: 26
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: DR2-188s

<400> SEQUENCE: 85
gguccgcugu gauuuuugga uuugaa 26

<210> SEQ ID NO 86
<211> LENGTH: 26
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: DR2-188as

<400> SEQUENCE: 86
uucaaaucca aaaaucacag cggacc 26

<210> SEQ ID NO 87
<211> LENGTH: 28
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: DR2-189s

<400> SEQUENCE: 87
gguccgcugu gauuuuugga uuugaaaa 28

<210> SEQ ID NO 88
<211> LENGTH: 28
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: DR2-189as

<400> SEQUENCE: 88
uuuucaaauc caaaaaucac agcggacc 28

<210> SEQ ID NO 89
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-190s

<400> SEQUENCE: 89
uccgcuguga uuuuuggauu ug 22

<210> SEQ ID NO 90
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-190as

<400> SEQUENCE: 90
caaauccaaa aaucacagcg ga 22

<210> SEQ ID NO 91
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-191s

<400> SEQUENCE: 91
cgcugugauu uuuggauuug 20

<210> SEQ ID NO 92
<211> LENGTH: 26
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-192s

<400> SEQUENCE: 92
gagguccgcu gugauuuuug gauuug 26

<210> SEQ ID NO 93
<211> LENGTH: 26
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-192as

<400> SEQUENCE: 93
caaauccaaa aaucacagcg gaccuc 26

<210> SEQ ID NO 94
<211> LENGTH: 28
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: DR2-193s

<400> SEQUENCE: 94
gagagguccg cugugauuuu uggauuug 28

<210> SEQ ID NO 95
<211> LENGTH: 28
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: DR2-193as

<400> SEQUENCE: 95
caaauccaaa aaucacagcg gaccucuc 28

<210> SEQ ID NO 96
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: DR2-194s

<400> SEQUENCE: 96
gguccugggu gauuuucuaa uuug 24

<210> SEQ ID NO 97
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: DR2-194as

<400> SEQUENCE: 97
caaauuagaa aaucacccag gacc 24

<210> SEQ ID NO 98
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: DR2-195s
<220> FEATURE:
<221> NAME/KEY: misc_feature
<222> LOCATION: (12)..(12)
<223> OTHER INFORMATION: 2'-o-methyl
<220> FEATURE:
<221> NAME/KEY: misc_feature
<222> LOCATION: (15)..(15)
<223> OTHER INFORMATION: 2'-o-methyl
<220> FEATURE:
<221> NAME/KEY: misc_feature
<222> LOCATION: (20)..(20)
<223> OTHER INFORMATION: 2'-o-methyl

<400> SEQUENCE: 98
gguccugggu gauuuucuaa uuug 24

<210> SEQ ID NO 99
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: DR2-195as
<220> FEATURE:
<221> NAME/KEY: misc_feature
<222> LOCATION: (22)..(22)
<223> OTHER INFORMATION: 2'-o-methyl

<400> SEQUENCE: 99
caaauuagaa aaucacccag gacc 24

<210> SEQ ID NO 100
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: DR2-196s
<220> FEATURE:
<221> NAME/KEY: misc_feature
<222> LOCATION: (12)..(12)
<223> OTHER INFORMATION: 2'-o-methyl
<220> FEATURE:
<221> NAME/KEY: misc_feature
<222> LOCATION: (15)..(15)
<223> OTHER INFORMATION: 2'-o-methyl
<220> FEATURE:
<221> NAME/KEY: misc_feature
<222> LOCATION: (20)..(20)
<223> OTHER INFORMATION: 2'-o-methyl

<400> SEQUENCE: 100
gguccugggu gauuuucuaa uu 22

<210> SEQ ID NO 101
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: DR2-196as
<220> FEATURE:
<221> NAME/KEY: misc_feature
<222> LOCATION: (20)..(20)
<223> OTHER INFORMATION: 2'-o-methyl

<400> SEQUENCE: 101
aauuagaaaa ucacccagga cc 22

<210> SEQ ID NO 102
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: DR2-197s
<220> FEATURE:

<221> NAME/KEY: misc_feature
<222> LOCATION: (12)..(12)
<223> OTHER INFORMATION: 2'-o-methyl
<220> FEATURE:
<221> NAME/KEY: misc_feature
<222> LOCATION: (15)..(15)
<223> OTHER INFORMATION: 2'-o-methyl
<220> FEATURE:
<221> NAME/KEY: misc_feature
<222> LOCATION: (20)..(20)
<223> OTHER INFORMATION: 2'-o-methyl

<400> SEQUENCE: 102 ggucugggu gauuuucuaa 20

<210> SEQ ID NO 103
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-197as
<220> FEATURE:
<221> NAME/KEY: misc_feature
<222> LOCATION: (18)..(18)
<223> OTHER INFORMATION: 2'-o-methyl

<400> SEQUENCE: 103
uuagaaaauc acccaggacc 20

<210> SEQ ID NO 104
<211> LENGTH: 26
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-198s
<220> FEATURE:
<221> NAME/KEY: misc_feature
<222> LOCATION: (12)..(12)
<223> OTHER INFORMATION: 2'-o-methyl
<220> FEATURE:
<221> NAME/KEY: misc_feature
<222> LOCATION: (15)..(15)
<223> OTHER INFORMATION: 2'-o-methyl
<220> FEATURE:
<221> NAME/KEY: misc_feature
<222> LOCATION: (20)..(20)
<223> OTHER INFORMATION: 2'-o-methyl

<400> SEQUENCE: 104
gguccugggu gauuuucuaa uuugaa 26

<210> SEQ ID NO 105
<211> LENGTH: 26
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-198as
<220> FEATURE:
<221> NAME/KEY: misc_feature
<222> LOCATION: (24)..(24)
<223> OTHER INFORMATION: 2'-o-methyl

<400> SEQUENCE: 105

-continued uucaaauuag aaaaucaccc aggacc 26

<210> SEQ ID NO 106
<211> LENGTH: 28
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: DR2-199s
<220> FEATURE:
<221> NAME/KEY: misc_feature
<222> LOCATION: (12)..(12)
<223> OTHER INFORMATION: 2'-o-methyl
<220> FEATURE:
<221> NAME/KEY: misc_feature
<222> LOCATION: (15)..(15)
<223> OTHER INFORMATION: 2'-o-methyl
<220> FEATURE:
<221> NAME/KEY: misc_feature
<222> LOCATION: (20)..(20)
<223> OTHER INFORMATION: 2'-o-methyl

<400> SEQUENCE: 106
gguccugggu gauuuucuaa uuugaaaa 28

<210> SEQ ID NO 107
<211> LENGTH: 28
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: DR2-199as
<220> FEATURE:
<221> NAME/KEY: misc_feature
<222> LOCATION: (26)..(26)
<223> OTHER INFORMATION: 2'-o-methyl

<400> SEQUENCE: 107 uuucaaauu agaaaaucac ccaggacc 28

<210> SEQ ID NO 108
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: DR2-200s
<220> FEATURE:
<221> NAME/KEY: misc_feature
<222> LOCATION: (10)..(10)
<223> OTHER INFORMATION: 2'-o-methyl
<220> FEATURE:
<221> NAME/KEY: misc_feature
<222> LOCATION: (13)..(13)
<223> OTHER INFORMATION: 2'-o-methyl
<220> FEATURE:
<221> NAME/KEY: misc_feature
<222> LOCATION: (18)..(18)
<223> OTHER INFORMATION: 2'-o-methyl

<400> SEQUENCE: 108
uccuggguga uuuucuaauu ug 22

<210> SEQ ID NO 109
<211> LENGTH: 22
<212> TYPE: RNA

<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-200as
<220> FEATURE:
<221> NAME/KEY: misc_feature
<222> LOCATION: (22)..(22)
<223> OTHER INFORMATION: 2'-o-methyl

<400> SEQUENCE: 109
caaauuagaa aaucacccag ga 22

<210> SEQ ID NO 110
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-201s
<220> FEATURE:
<221> NAME/KEY: misc_feature
<222> LOCATION: (8)..(8)
<223> OTHER INFORMATION: 2'-o-methyl
<220> FEATURE:
<221> NAME/KEY: misc_feature
<222> LOCATION: (11)..(11)
<223> OTHER INFORMATION: 2'-o-methyl
<220> FEATURE:
<221> NAME/KEY: misc_feature
<222> LOCATION: (16)..(16)
<223> OTHER INFORMATION: 2'-o-methyl

<400> SEQUENCE: 110
cugggugauu uucuaauuug 20

<210> SEQ ID NO 111
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-201as

<400> SEQUENCE: 111
caaauuagaa aaucacccag 20

<210> SEQ ID NO 112
<211> LENGTH: 26
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-202s
<220> FEATURE:
<221> NAME/KEY: misc_feature
<222> LOCATION: (14)..(14)
<223> OTHER INFORMATION: 2'-o-methyl
<220> FEATURE:
<221> NAME/KEY: misc_feature
<222> LOCATION: (17)..(17)
<223> OTHER INFORMATION: 2'-o-methyl
<220> FEATURE:
<221> NAME/KEY: misc_feature
<222> LOCATION: (22)..(22)
<223> OTHER INFORMATION: 2'-o-methyl

<400> SEQUENCE: 112
gagguccugg gugauuuucu aauuug 26

<210> SEQ ID NO 113
<211> LENGTH: 26
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: DR2-202as
<220> FEATURE:
<221> NAME/KEY: misc_feature
<222> LOCATION: (22)..(22)
<223> OTHER INFORMATION: 2'-o-methyl

<400> SEQUENCE: 113
caaauuagaa aaucacccag gaccuc 26

<210> SEQ ID NO 114
<211> LENGTH: 28
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: DR2-203s
<220> FEATURE:
<221> NAME/KEY: misc_feature
<222> LOCATION: (16)..(16)
<223> OTHER INFORMATION: 2'-o-methyl
<220> FEATURE:
<221> NAME/KEY: misc_feature
<222> LOCATION: (19)..(19)
<223> OTHER INFORMATION: 2'-o-methyl
<220> FEATURE:
<221> NAME/KEY: misc_feature
<222> LOCATION: (24)..(24)
<223> OTHER INFORMATION: 2'-o-methyl

<400> SEQUENCE: 114
gagagguccu gggugauuuu cuaauuug 28

<210> SEQ ID NO 115
<211> LENGTH: 28
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: DR2-203as
<220> FEATURE:
<221> NAME/KEY: misc_feature
<222> LOCATION: (22)..(22)
<223> OTHER INFORMATION: 2'-o-methyl

<400> SEQUENCE: 115
caaauuagaa aaucacccag gaccucuc 28

<210> SEQ ID NO 116
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:

<223> OTHER INFORMATION: DR2-204s

<400> SEQUENCE: 116
gguccugggu gauuuucuaa uu 22

<210> SEQ ID NO 117
<211> LENGTH: 22
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-204as

<400> SEQUENCE: 117
aauuagaaaa ucacccagga cc 22

<210> SEQ ID NO 118
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-205s

<400> SEQUENCE: 118
gguccugggu gauuuucuaa 20

<210> SEQ ID NO 119
<211> LENGTH: 20
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-205as

<400> SEQUENCE: 119
uuagaaaauc acccaggacc 20

<210> SEQ ID NO 120
<211> LENGTH: 26
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-206s

<400> SEQUENCE: 120
gguccugggu gauuuucuaa uuugaa 26

<210> SEQ ID NO 121
<211> LENGTH: 26
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-206as

<400> SEQUENCE: 121

-continued uucaaauuag aaaaucaccc aggacc 26

<210> SEQ ID NO 122
<211> LENGTH: 28
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: DR2-207s

<400> SEQUENCE: 122
gguccugggu gauuuucuaa uuugaaaa 28

<210> SEQ ID NO 123
<211> LENGTH: 28
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: DR2-207as

<400> SEQUENCE: 123
uuuucaaauu agaaaaucac ccaggacc 28

<210> SEQ ID NO 124
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: DR2-208s

<400> SEQUENCE: 124
uccuggguga uuuucuaauu ug 22

<210> SEQ ID NO 125
<211> LENGTH: 22
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: DR2-208as

<400> SEQUENCE: 125
caaauuagaa aaucacccag ga 22

<210> SEQ ID NO 126
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: DR2-209s

<400> SEQUENCE: 126
cugggugauu uucuaauuug 20

<210> SEQ ID NO 127

<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DR2-210s

<400> SEQUENCE: 127
gagguccugg gugauuuucu aauuug 26

<210> SEQ ID NO 128
<211> LENGTH: 26
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DR2-210as

<400> SEQUENCE: 128
caaauuagaa aaucacccag gaccuc 26

<210> SEQ ID NO 129
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DR2-211s

<400> SEQUENCE: 129
gagagguccu gggugauuuu cuaauuug 28

<210> SEQ ID NO 130
<211> LENGTH: 28
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DR2-211as

<400> SEQUENCE: 130
caaauuagaa aaucacccag gaccucuc 28

<210> SEQ ID NO 131
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DR2-214s
<220> FEATURE:
<221> NAME/KEY: misc_feature
<222> LOCATION: (15)..(15)
<223> OTHER INFORMATION: 2'-o-methyl

<400> SEQUENCE: 131
gcuccugaau gcuugcuuca ucuu 24

<210> SEQ ID NO 132

-continued

<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-216as
<220> FEATURE:
<221> NAME/KEY: misc_feature
<222> LOCATION: (3)..()
<223> OTHER INFORMATION: 2'-o-methyl

<400> SEQUENCE: 132
aagaugaagc aagcauucag gagc 24

<210> SEQ ID NO 133
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-220as
<220> FEATURE:
<221> NAME/KEY: misc_feature
<222> LOCATION: (10)..()
<223> OTHER INFORMATION: 2'-o-methyl

<400> SEQUENCE: 133
aagaugaagc aagcauucag gagc 24

<210> SEQ ID NO 134
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-226s
<220> FEATURE:
<221> NAME/KEY: misc_feature
<222> LOCATION: (15)..(15)
<223> OTHER INFORMATION: 2'-o-methyl

<400> SEQUENCE: 134
guuccaauag uagucauagc uauu 24

<210> SEQ ID NO 135
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-228as
<220> FEATURE:
<221> NAME/KEY: misc_feature
<222> LOCATION: (3)..()
<223> OTHER INFORMATION: 2'-o-methyl

<400> SEQUENCE: 135
aauagcuaug acuacuauug gaac 24

<210> SEQ ID NO 136
<211> LENGTH: 24
<212> TYPE: RNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: DR2-232as
<220> FEATURE:
<221> NAME/KEY: misc_feature
<222> LOCATION: (10)..(10)
<223> OTHER INFORMATION: 2'-o-methyl

<400> SEQUENCE: 136

aauagcuaug acuacuauug gaac                                              24


<210> SEQ ID NO 137
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DR2-238s
<220> FEATURE:
<221> NAME/KEY: misc_feature
<222> LOCATION: (15)..(15)
<223> OTHER INFORMATION: 2'-o-methyl

<400> SEQUENCE: 137

guucugcaac ucaaagugcu auug                                              24


<210> SEQ ID NO 138
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DR2-240as
<220> FEATURE:
<221> NAME/KEY: misc_feature
<222> LOCATION: (3)..(3)
<223> OTHER INFORMATION: 2'-o-methyl

<400> SEQUENCE: 138

caauagcacu uugaguugca gaac                                              24


<210> SEQ ID NO 139
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DR2-244as
<220> FEATURE:
<221> NAME/KEY: misc_feature
<222> LOCATION: (10)..(10)
<223> OTHER INFORMATION: 2'-o-methyl

<400> SEQUENCE: 139

caauagcacu uugaguugca gaac                                              24


<210> SEQ ID NO 140
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
```

<220> FEATURE:
<223> OTHER INFORMATION: DR2-248s

<400> SEQUENCE: 140
guucugcaac ugaaagugcu auug 24

<210> SEQ ID NO 141
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: DR2-248as

<400> SEQUENCE: 141
caauagcacu uucaguugca gaac 24

<210> SEQ ID NO 142
<211> LENGTH: 23
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: DR2-249s

<400> SEQUENCE: 142
guucugcaac uaaaagugcu auu 23

<210> SEQ ID NO 143
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: DR2-249as

<400> SEQUENCE: 143
caauagcacu uuuaguugca gaac 24

<210> SEQ ID NO 144
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: DR2-250s

<400> SEQUENCE: 144
guucugcaac ucaaagugcg auug 24

<210> SEQ ID NO 145
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: DR2-250as

<400> SEQUENCE: 145
caaucgcacu uugaguugca gaac 24

<210> SEQ ID NO 146
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-251s

<400> SEQUENCE: 146
guucugcaac ucaaagugca auug 24

<210> SEQ ID NO 147
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-251as

<400> SEQUENCE: 147
caauugcacu uugaguugca gaac 24

<210> SEQ ID NO 148
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-252s

<400> SEQUENCE: 148
guucugcaac ugaaagugcg auug 24

<210> SEQ ID NO 149
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-252as

<400> SEQUENCE: 149
caaucgcacu uucaguugca gaac 24

<210> SEQ ID NO 150
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-253s

<400> SEQUENCE: 150
guucugcaac uaaaagugca auug 24

<210> SEQ ID NO 151
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-253as

<400> SEQUENCE: 151
caauugcacu uuuaguugca gaac 24

<210> SEQ ID NO 152
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-254s
<220> FEATURE:
<221> NAME/KEY: misc_feature
<222> LOCATION: (12)..(12)
<223> OTHER INFORMATION: 2'-o-methyl

<400> SEQUENCE: 152
guucugcaac ugaaagugcu auug 24

<210> SEQ ID NO 153
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-255s
<220> FEATURE:
<221> NAME/KEY: misc_feature
<222> LOCATION: (12)..(12)
<223> OTHER INFORMATION: 2'-o-methyl

<400> SEQUENCE: 153
guucugcaac uaaaagugcu auug 24

<210> SEQ ID NO 154
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-256s
<220> FEATURE:
<221> NAME/KEY: misc_feature
<222> LOCATION: (20)..(20)
<223> OTHER INFORMATION: 2'-o-methyl

<400> SEQUENCE: 154
guucugcaac ucaaagugcg auug 24

<210> SEQ ID NO 155
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide -continued <220> FEATURE:
<223> OTHER INFORMATION: DR2-257s
<220> FEATURE:
<221> NAME/KEY: misc_feature
<222> LOCATION: (20)..(20)
<223> OTHER INFORMATION: 2'-o-methyl

<400> SEQUENCE: 155
guucugcaac ucaaagugca auug 24

<210> SEQ ID NO 156
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-258s
<220> FEATURE:
<221> NAME/KEY: misc_feature
<222> LOCATION: (12)..(12)
<223> OTHER INFORMATION: 2'-o-methyl
<220> FEATURE:
<221> NAME/KEY: misc_feature
<222> LOCATION: (20)..(20)
<223> OTHER INFORMATION: 2'-o-methyl

<400> SEQUENCE: 156
guucugcaac ugaaagugcg auug 24

<210> SEQ ID NO 157
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-259s
<220> FEATURE:
<221> NAME/KEY: misc_feature
<222> LOCATION: (12)..(12)
<223> OTHER INFORMATION: 2'-o-methyl
<220> FEATURE:
<221> NAME/KEY: misc_feature
<222> LOCATION: (20)..(20)
<223> OTHER INFORMATION: 2'-o-methyl

<400> SEQUENCE: 157
guucugcaac uaaaagugca auug 24

<210> SEQ ID NO 158
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-260s
<220> FEATURE:
<221> NAME/KEY: misc_feature
<222> LOCATION: (1)..(1)
<223> OTHER INFORMATION: 5'-triphosphate
<220> FEATURE:
<221> NAME/KEY: misc_feature
<222> LOCATION: (2)..(2)
<223> OTHER INFORMATION: 2'-fluoro
<220> FEATURE:
<221> NAME/KEY: misc_feature
<222> LOCATION: (4)..(4)
<223> OTHER INFORMATION: 2'-fluoro
<220> FEATURE:
<221> NAME/KEY: misc_feature
<222> LOCATION: (9)..(9)
<223> OTHER INFORMATION: 2'-fluoro
<220> FEATURE:
<221> NAME/KEY: misc_feature
<222> LOCATION: (10)..(10)
<223> OTHER INFORMATION: 2'-fluoro
<220> FEATURE:
<221> NAME/KEY: misc_feature
<222> LOCATION: (12)..(12)
<223> OTHER INFORMATION: 2'-o-methyl
<220> FEATURE:
<221> NAME/KEY: misc_feature
<222> LOCATION: (15)..(15)
<223> OTHER INFORMATION: 2'-o-methyl
<220> FEATURE:
<221> NAME/KEY: misc_feature
<222> LOCATION: (16)..(16)
<223> OTHER INFORMATION: 2'-fluoro
<220> FEATURE:
<221> NAME/KEY: misc_feature
<222> LOCATION: (20)..(20)
<223> OTHER INFORMATION: 2'-o-methyl
<220> FEATURE:
<221> NAME/KEY: misc_feature
<222> LOCATION: (21)..(21)
<223> OTHER INFORMATION: 2'-fluoro
<220> FEATURE:
<221> NAME/KEY: misc_feature
<222> LOCATION: (22)..(22)
<223> OTHER INFORMATION: 2'-fluoro
<220> FEATURE:
<221> NAME/KEY: misc_feature
<222> LOCATION: (22)..(24)
<223> OTHER INFORMATION: phosphorothioate linkages between position 22
and 23, and between position 23 and 24
<220> FEATURE:
<221> NAME/KEY: misc_feature
<222> LOCATION: (24)..(24)
<223> OTHER INFORMATION: 2'-fluoro

<400> SEQUENCE: 158
gcuccugaau gcuugcuuca ucuu 24

<210> SEQ ID NO 159
<211> LENGTH: 26
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-260as
<220> FEATURE:
<221> NAME/KEY: misc_feature
<222> LOCATION: (3)..(5)
<223> OTHER INFORMATION: phosphorothioate linkages between position 3
and 4 and between position 4 and 5
<220> FEATURE:
<221> NAME/KEY: misc_feature
<222> LOCATION: (7)..(7)
<223> OTHER INFORMATION: 2'-fluoro
<220> FEATURE:
<221> NAME/KEY: misc_feature
<222> LOCATION: (15)..(15)
<223> OTHER INFORMATION: 2'-fluoro
<220> FEATURE:
<221> NAME/KEY: misc_feature
<222> LOCATION: (24)..(24)
<223> OTHER INFORMATION: 2'-o-methyl

<400> SEQUENCE: 159
aaaagaugaa gcaagcauuc aggagc 26

-continued

<210> SEQ ID NO 160
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: DR2-261s
<220> FEATURE:
<221> NAME/KEY: misc_feature
<222> LOCATION: (1)..(1)
<223> OTHER INFORMATION: 5'-triphosphate
<220> FEATURE:
<221> NAME/KEY: misc_feature
<222> LOCATION: (1)..(3)
<223> OTHER INFORMATION: phosphorothioate linkages between position 1 and 2 and between position 2 and 3
<220> FEATURE:
<221> NAME/KEY: misc_feature
<222> LOCATION: (2)..(2)
<223> OTHER INFORMATION: 2'-fluoro
<220> FEATURE:
<221> NAME/KEY: misc_feature
<222> LOCATION: (4)..(4)
<223> OTHER INFORMATION: 2'-fluoro
<220> FEATURE:
<221> NAME/KEY: misc_feature
<222> LOCATION: (9)..(9)
<223> OTHER INFORMATION: 2'-fluoro
<220> FEATURE:
<221> NAME/KEY: misc_feature
<222> LOCATION: (10)..(10)
<223> OTHER INFORMATION: 2'-fluoro
<220> FEATURE:
<221> NAME/KEY: misc_feature
<222> LOCATION: (12)..(12)
<223> OTHER INFORMATION: 2'-o-methyl
<220> FEATURE:
<221> NAME/KEY: misc_feature
<222> LOCATION: (15)..(15)
<223> OTHER INFORMATION: 2'-o-methyl
<220> FEATURE:
<221> NAME/KEY: misc_feature
<222> LOCATION: (16)..(16)
<223> OTHER INFORMATION: 2'-fluoro
<220> FEATURE:
<221> NAME/KEY: misc_feature
<222> LOCATION: (20)..(20)
<223> OTHER INFORMATION: 2'-o-methyl
<220> FEATURE:
<221> NAME/KEY: misc_feature
<222> LOCATION: (21)..(21)
<223> OTHER INFORMATION: 2'-fluoro
<220> FEATURE:
<221> NAME/KEY: misc_feature
<222> LOCATION: (22)..(22)
<223> OTHER INFORMATION: 2'-fluoro
<220> FEATURE:
<221> NAME/KEY: misc_feature
<222> LOCATION: (22)..(24)
<223> OTHER INFORMATION: phosphorothioate linkages between position 22 and 23 and between position 23 and 24
<220> FEATURE:
<221> NAME/KEY: misc_feature
<222> LOCATION: (24)..(24)
<223> OTHER INFORMATION: 2'-fluoro

<400> SEQUENCE: 160
gcuccugaau gcuugcuuca ucuu 24

<210> SEQ ID NO 161
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: DR2-262s
<220> FEATURE:
<221> NAME/KEY: misc_feature
<222> LOCATION: (1)..()
<223> OTHER INFORMATION: 5'-triphosphate
<220> FEATURE:
<221> NAME/KEY: misc_feature
<222> LOCATION: (2)..(2)
<223> OTHER INFORMATION: 2'-fluoro
<220> FEATURE:
<221> NAME/KEY: misc_feature
<222> LOCATION: (4)..(4)
<223> OTHER INFORMATION: 2'-fluoro
<220> FEATURE:
<221> NAME/KEY: misc_feature
<222> LOCATION: (9)..(9)
<223> OTHER INFORMATION: 2'-fluoro
<220> FEATURE:
<221> NAME/KEY: misc_feature
<222> LOCATION: (10)..(10)
<223> OTHER INFORMATION: 2'-fluoro
<220> FEATURE:
<221> NAME/KEY: misc_feature
<222> LOCATION: (12)..(12)
<223> OTHER INFORMATION: 2'-o-methyl
<220> FEATURE:
<221> NAME/KEY: misc_feature
<222> LOCATION: (15)..(15)
<223> OTHER INFORMATION: 2'-o-methyl
<220> FEATURE:
<221> NAME/KEY: misc_feature
<222> LOCATION: (16)..(16)
<223> OTHER INFORMATION: 2'-fluoro
<220> FEATURE:
<221> NAME/KEY: misc_feature
<222> LOCATION: (20)..(20)
<223> OTHER INFORMATION: 2'-o-methyl
<220> FEATURE:
<221> NAME/KEY: misc_feature
<222> LOCATION: (21)..(21)
<223> OTHER INFORMATION: 2'-fluoro
<220> FEATURE:
<221> NAME/KEY: misc_feature
<222> LOCATION: (22)..(22)
<223> OTHER INFORMATION: 2'-fluoro
<220> FEATURE:
<221> NAME/KEY: misc_feature
<222> LOCATION: (22)..(24)
<223> OTHER INFORMATION: phosphorothioate linkages between position 22
and 23 and between position 23 and 24
<220> FEATURE:
<221> NAME/KEY: misc_feature
<222> LOCATION: (24)..(24)
<223> OTHER INFORMATION: 2'-fluoro

<400> SEQUENCE: 161
guuccaauag uagucauagc uauu 24

<210> SEQ ID NO 162
<211> LENGTH: 26
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: DR2-262as
<220> FEATURE:
<221> NAME/KEY: misc_feature
<222> LOCATION: (3)..(5)
<223> OTHER INFORMATION: phosphorothioate linkages between position 3
and 4 and between position 4 and 5
<220> FEATURE:
<221> NAME/KEY: misc_feature
<222> LOCATION: (7)..(7)

<223> OTHER INFORMATION: 2'-fluoro
<220> FEATURE:
<221> NAME/KEY: misc_feature
<222> LOCATION: (15)..(15)
<223> OTHER INFORMATION: 2'-fluoro
<220> FEATURE:
<221> NAME/KEY: misc_feature
<222> LOCATION: (24)..(24)
<223> OTHER INFORMATION: 2'-o-methyl

<400> SEQUENCE: 162
aaaauagcua ugacuacuau uggaac 26

<210> SEQ ID NO 163
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: DR2-263s
<220> FEATURE:
<221> NAME/KEY: misc_feature
<222> LOCATION: (1)..(1)
<223> OTHER INFORMATION: 5'-triphosphate
<220> FEATURE:
<221> NAME/KEY: misc_feature
<222> LOCATION: (1)..(3)
<223> OTHER INFORMATION: phosphorothioate linkages between position 1 and 2 and between position 2 and 3
<220> FEATURE:
<221> NAME/KEY: misc_feature
<222> LOCATION: (2)..(2)
<223> OTHER INFORMATION: 2'-fluoro
<220> FEATURE:
<221> NAME/KEY: misc_feature
<222> LOCATION: (4)..(4)
<223> OTHER INFORMATION: 2'-fluoro
<220> FEATURE:
<221> NAME/KEY: misc_feature
<222> LOCATION: (9)..(9)
<223> OTHER INFORMATION: 2'-fluoro
<220> FEATURE:
<221> NAME/KEY: misc_feature
<222> LOCATION: (10)..(10)
<223> OTHER INFORMATION: 2'-fluoro
<220> FEATURE:
<221> NAME/KEY: misc_feature
<222> LOCATION: (12)..(12)
<223> OTHER INFORMATION: 2'-o-methyl
<220> FEATURE:
<221> NAME/KEY: misc_feature
<222> LOCATION: (15)..(15)
<223> OTHER INFORMATION: 2'-o-methyl
<220> FEATURE:
<221> NAME/KEY: misc_feature
<222> LOCATION: (16)..(16)
<223> OTHER INFORMATION: 2'-fluoro
<220> FEATURE:
<221> NAME/KEY: misc_feature
<222> LOCATION: (20)..(20)
<223> OTHER INFORMATION: 2'-o-methyl
<220> FEATURE:
<221> NAME/KEY: misc_feature
<222> LOCATION: (21)..(21)
<223> OTHER INFORMATION: 2'-fluoro
<220> FEATURE:
<221> NAME/KEY: misc_feature
<222> LOCATION: (22)..(22)
<223> OTHER INFORMATION: 2'-fluoro
<220> FEATURE:
<221> NAME/KEY: misc_feature
<222> LOCATION: (22)..(24)
<223> OTHER INFORMATION: phosphorothioate linkages between position 22 and 23 and between position 23 and 24
<220> FEATURE:

<221> NAME/KEY: misc_feature
<222> LOCATION: (24)..(24)
<223> OTHER INFORMATION: 2'-fluoro

<400> SEQUENCE: 163
guuccaauag uagucauagc uauu 24

<210> SEQ ID NO 164
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: DR2-264s
<220> FEATURE:
<221> NAME/KEY: misc_feature
<222> LOCATION: (1)..(1)
<223> OTHER INFORMATION: 5'-triphosphate
<220> FEATURE:
<221> NAME/KEY: misc_feature
<222> LOCATION: (2)..(2)
<223> OTHER INFORMATION: 2'-fluoro
<220> FEATURE:
<221> NAME/KEY: misc_feature
<222> LOCATION: (4)..(4)
<223> OTHER INFORMATION: 2'-fluoro
<220> FEATURE:
<221> NAME/KEY: misc_feature
<222> LOCATION: (9)..(9)
<223> OTHER INFORMATION: 2'-fluoro
<220> FEATURE:
<221> NAME/KEY: misc_feature
<222> LOCATION: (10)..(10)
<223> OTHER INFORMATION: 2'-fluoro
<220> FEATURE:
<221> NAME/KEY: misc_feature
<222> LOCATION: (12)..(12)
<223> OTHER INFORMATION: 2'-o-methyl
<220> FEATURE:
<221> NAME/KEY: misc_feature
<222> LOCATION: (15)..(15)
<223> OTHER INFORMATION: 2'-o-methyl
<220> FEATURE:
<221> NAME/KEY: misc_feature
<222> LOCATION: (16)..(16)
<223> OTHER INFORMATION: 2'-fluoro
<220> FEATURE:
<221> NAME/KEY: misc_feature
<222> LOCATION: (20)..(20)
<223> OTHER INFORMATION: 2'-o-methyl
<220> FEATURE:
<221> NAME/KEY: misc_feature
<222> LOCATION: (21)..(21)
<223> OTHER INFORMATION: 2'-fluoro
<220> FEATURE:
<221> NAME/KEY: misc_feature
<222> LOCATION: (22)..(22)
<223> OTHER INFORMATION: 2'-fluoro
<220> FEATURE:
<221> NAME/KEY: misc_feature
<222> LOCATION: (22)..(24)
<223> OTHER INFORMATION: phosphorothioate linkages between position 22 and 23 and between position 23 and 24
<220> FEATURE:
<221> NAME/KEY: misc_feature
<222> LOCATION: (24)..(24)
<223> OTHER INFORMATION: 2'-fluoro

<400> SEQUENCE: 164
guucugcaac ucaaagugcu auug 24

<210> SEQ ID NO 165
<211> LENGTH: 26

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DR2-264as
<220> FEATURE:
<221> NAME/KEY: misc_feature
<222> LOCATION: (3)..(5)
<223> OTHER INFORMATION: phosphorothioate linkages between psition 3 and
      4 and between position 4 and 5
<220> FEATURE:
<221> NAME/KEY: misc_feature
<222> LOCATION: (7)..(7)
<223> OTHER INFORMATION: 2'-fluoro
<220> FEATURE:
<221> NAME/KEY: misc_feature
<222> LOCATION: (15)..(15)
<223> OTHER INFORMATION: 2'-fluoro
<220> FEATURE:
<221> NAME/KEY: misc_feature
<222> LOCATION: (24)..(24)
<223> OTHER INFORMATION: 2'-o-methyl

<400> SEQUENCE: 165

aacaauagca cuuugaguug cagaac                                          26


<210> SEQ ID NO 166
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DR2-265s
<220> FEATURE:
<221> NAME/KEY: misc_feature
<222> LOCATION: (1)..(1)
<223> OTHER INFORMATION: 5'-triphosphate
<220> FEATURE:
<221> NAME/KEY: misc_feature
<222> LOCATION: (1)..(3)
<223> OTHER INFORMATION: phosphorothioate linkages between position 1
      and 2 and between position 2 and 3
<220> FEATURE:
<221> NAME/KEY: misc_feature
<222> LOCATION: (2)..(2)
<223> OTHER INFORMATION: 2'-fluoro
<220> FEATURE:
<221> NAME/KEY: misc_feature
<222> LOCATION: (4)..(4)
<223> OTHER INFORMATION: 2'-fluoro
<220> FEATURE:
<221> NAME/KEY: misc_feature
<222> LOCATION: (9)..(9)
<223> OTHER INFORMATION: 2'-fluoro
<220> FEATURE:
<221> NAME/KEY: misc_feature
<222> LOCATION: (10)..(10)
<223> OTHER INFORMATION: 2'-fluoro
<220> FEATURE:
<221> NAME/KEY: misc_feature
<222> LOCATION: (12)..(12)
<223> OTHER INFORMATION: 2'-o-methyl
<220> FEATURE:
<221> NAME/KEY: misc_feature
<222> LOCATION: (15)..(15)
<223> OTHER INFORMATION: 2'-o-methyl
<220> FEATURE:
<221> NAME/KEY: misc_feature
<222> LOCATION: (16)..(16)
<223> OTHER INFORMATION: 2'-fluoro
<220> FEATURE:
<221> NAME/KEY: misc_feature
<222> LOCATION: (20)..(20)
```

-continued

<223> OTHER INFORMATION: 2'-o-methyl
<220> FEATURE:
<221> NAME/KEY: misc_feature
<222> LOCATION: (21)..(21)
<223> OTHER INFORMATION: 2'-fluoro
<220> FEATURE:
<221> NAME/KEY: misc_feature
<222> LOCATION: (22)..(22)
<223> OTHER INFORMATION: 2'-fluoro
<220> FEATURE:
<221> NAME/KEY: misc_feature
<222> LOCATION: (22)..(24)
<223> OTHER INFORMATION: phosphorothioate linkages between position 22
      and 23 and between position 23 and 24
<220> FEATURE:
<221> NAME/KEY: misc_feature
<222> LOCATION: (24)..(24)
<223> OTHER INFORMATION: 2'-fluoro

<400> SEQUENCE: 166
guucugcaac ucaaagugcu auug 24

<210> SEQ ID NO 167
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DR2-266s
<220> FEATURE:
<221> NAME/KEY: misc_feature
<222> LOCATION: (1)..(1)
<223> OTHER INFORMATION: 5'-triphosphate

<400> SEQUENCE: 167
gcuccugaau gcuugcuuca ucuu 24

<210> SEQ ID NO 168
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DR2-267s
<220> FEATURE:
<221> NAME/KEY: misc_feature
<222> LOCATION: (1)..(1)
<223> OTHER INFORMATION: 5'-triphosphate

<400> SEQUENCE: 168
guuccaauag uagucauagc uauu 24

<210> SEQ ID NO 169
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DR2-268s
<220> FEATURE:
<221> NAME/KEY: misc_feature
<222> LOCATION: (1)..(1)
<223> OTHER INFORMATION: 5'-triphosphate

<400> SEQUENCE: 169
guucugcaac ucaaagugcu auug 24

<210> SEQ ID NO 170
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Consensus sequence
<220> FEATURE:
<221> NAME/KEY: misc_feature
<222> LOCATION: (5)..(5)
<223> OTHER INFORMATION: n is a, c, g, or u
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (9)..(16)
<223> OTHER INFORMATION: n is a, c, g, or u
<220> FEATURE:
<221> NAME/KEY: misc_feature
<222> LOCATION: (18)..(18)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 170
gbucndnwnn nnnnnnwnsn n 21

<210> SEQ ID NO 171
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Consensus sequence
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (9)..(16)
<223> OTHER INFORMATION: n is a, c, g, or u
<220> FEATURE:
<221> NAME/KEY: misc_feature
<222> LOCATION: (18)..(18)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 171
gucuadnwnn nnnnnnwnsn n 21

<210> SEQ ID NO 172
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Consensus sequence
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (9)..(16)
<223> OTHER INFORMATION: n is a, c, g, or u
<220> FEATURE:
<221> NAME/KEY: misc_feature
<222> LOCATION: (18)..(18)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 172
guagudnwnn nnnnnnwnsn n 21

<210> SEQ ID NO 173
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Consensus sequence
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (9)..(16)
<223> OTHER INFORMATION: n is a, c, g, or u
<220> FEATURE:
<221> NAME/KEY: misc_feature
<222> LOCATION: (18)..(18)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 173
gguaadnwnn nnnnnnwnsn n 21

<210> SEQ ID NO 174
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Consensus sequence
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (9)..(16)
<223> OTHER INFORMATION: n is a, c, g, or u
<220> FEATURE:
<221> NAME/KEY: misc_feature
<222> LOCATION: (18)..(18)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 174

```
ggcagdnwnn nnnnnnwnsn n                                               21


<210> SEQ ID NO 175
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Consensus sequence
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (9)..(16)
<223> OTHER INFORMATION: n is a, c, g, or u
<220> FEATURE:
<221> NAME/KEY: misc_feature
<222> LOCATION: (18)..(18)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 175

gcuucdnwnn nnnnnnwnsn n                                               21


<210> SEQ ID NO 176
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Consensus sequence
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (9)..(16)
<223> OTHER INFORMATION: n is a, c, g, or u
<220> FEATURE:
<221> NAME/KEY: misc_feature
<222> LOCATION: (18)..(18)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 176

gcccadnwnn nnnnnnwnsn n                                               21


<210> SEQ ID NO 177
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Consensus sequence
<220> FEATURE:
<221> NAME/KEY: misc_feature
<222> LOCATION: (7)..(7)
<223> OTHER INFORMATION: n is a, c, g, or u
<220> FEATURE:
```

<221> NAME/KEY: misc_feature
<222> LOCATION: (9)..(16)
<223> OTHER INFORMATION: n is a, c, g, or u
<220> FEATURE:
<221> NAME/KEY: misc_feature
<222> LOCATION: (18)..(18)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 177
gcgcudnwnn nnnnnnwnsn n 21

<210> SEQ ID NO 178
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Consensus sequence
<220> FEATURE:
<221> NAME/KEY: misc_feature
<222> LOCATION: (5)..(5)
<223> OTHER INFORMATION: n is a, c, g, or u
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (9)..(16)
<223> OTHER INFORMATION: n is a, c, g, or u
<220> FEATURE:
<221> NAME/KEY: misc_feature
<222> LOCATION: (18)..(18)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 178
gbucndnwnn nnnnnnunsn n 21

<210> SEQ ID NO 179
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Consensus sequence
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (9)..(16)
<223> OTHER INFORMATION: n is a, c, g, or u
<220> FEATURE:
<221> NAME/KEY: misc_feature
<222> LOCATION: (18)..(18)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 179
gucuadnwnn nnnnnnunsn n 21

<210> SEQ ID NO 180
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Consensus sequence
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (9)..(16)
<223> OTHER INFORMATION: n is a, c, g, or u
<220> FEATURE:
<221> NAME/KEY: misc_feature
<222> LOCATION: (18)..(18)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 180
guagudnwnn nnnnnnunsn n 21

<210> SEQ ID NO 181
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Consensus sequence
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (9)..(16)
<223> OTHER INFORMATION: n is a, c, g, or u
<220> FEATURE:
<221> NAME/KEY: misc_feature
<222> LOCATION: (18)..(18)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 181
gguaadnwnn nnnnnnunsn n 21

<210> SEQ ID NO 182
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Consensus sequence
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (9)..(16)
<223> OTHER INFORMATION: n is a, c, g, or u
<220> FEATURE:
<221> NAME/KEY: misc_feature
<222> LOCATION: (18)..(18)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 182
ggcagdnwnn nnnnnnunsn n 21

<210> SEQ ID NO 183
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Consensus sequence
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (9)..(16)
<223> OTHER INFORMATION: n is a, c, g, or u
<220> FEATURE:
<221> NAME/KEY: misc_feature
<222> LOCATION: (18)..(18)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 183
gcuucdnwnn nnnnnnunsn n 21

<210> SEQ ID NO 184
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Consensus sequence
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (9)..(16)
<223> OTHER INFORMATION: n is a, c, g, or u
<220> FEATURE:
<221> NAME/KEY: misc_feature
<222> LOCATION: (18)..(18)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 184
gcccadnwnn nnnnnnunsn n 21

<210> SEQ ID NO 185
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Consensus sequence
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (9)..(16)
<223> OTHER INFORMATION: n is a, c, g, or u
<220> FEATURE:
<221> NAME/KEY: misc_feature
<222> LOCATION: (18)..(18)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 185
gcgcudnwnn nnnnnnunsn n 21

<210> SEQ ID NO 186
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Consensus sequence
<220> FEATURE:
<221> NAME/KEY: misc_feature
<222> LOCATION: (5)..(5)
<223> OTHER INFORMATION: n is a, c, g, or u
<220> FEATURE:
<221> NAME/KEY: misc_feature
<222> LOCATION: (10)..(16)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 186
gbucnugaan nnnnnnuucn n 21

<210> SEQ ID NO 187
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Consensus sequence
<220> FEATURE:
<221> NAME/KEY: misc_feature
<222> LOCATION: (10)..(16)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 187

-continued gucuaugaan nnnnnnuucn n 21

<210> SEQ ID NO 188
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Consensus sequence
<220> FEATURE:
<221> NAME/KEY: misc_feature
<222> LOCATION: (10)..(16)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 188
guaguugaan nnnnnnuucn n 21

<210> SEQ ID NO 189
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Consensus sequence
<220> FEATURE:
<221> NAME/KEY: misc_feature
<222> LOCATION: (10)..(16)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 189
gguaaugaan nnnnnnuucn n 21

<210> SEQ ID NO 190
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Consensus sequence
<220> FEATURE:
<221> NAME/KEY: misc_feature
<222> LOCATION: (10)..(16)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 190
ggcagugaan nnnnnnuucn n 21

<210> SEQ ID NO 191
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide <220> FEATURE:
<223> OTHER INFORMATION: Consensus sequence
<220> FEATURE:
<221> NAME/KEY: misc_feature
<222> LOCATION: (10)..(16)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 191
gcuucugaan nnnnnnuucn n 21

<210> SEQ ID NO 192
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Consensus sequence
<220> FEATURE:
<221> NAME/KEY: misc_feature
<222> LOCATION: (10)..(16)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 192
gcccaugaan nnnnnnuucn n 21

<210> SEQ ID NO 193
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Consensus sequence
<220> FEATURE:
<221> NAME/KEY: misc_feature
<222> LOCATION: (10)..(16)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 193
gcgcuugaan nnnnnnuucn n 21

<210> SEQ ID NO 194
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Consensus sequence
<220> FEATURE:
<221> NAME/KEY: misc_feature
<222> LOCATION: (5)..(5)
<223> OTHER INFORMATION: n is a, c, g, or u
<220> FEATURE:
<221> NAME/KEY: misc_feature
<222> LOCATION: (11)..(15)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 194
gbucnugaaa nnnnnuuucn n 21

<210> SEQ ID NO 195
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Consensus sequence
<220> FEATURE:
<221> NAME/KEY: misc_feature
<222> LOCATION: (5)..(11)
<223> OTHER INFORMATION: n is a, c, g, or u
<220> FEATURE:
<221> NAME/KEY: misc_feature
<222> LOCATION: (15)..(15)
<223> OTHER INFORMATION: n is a, c, g, or u

<400> SEQUENCE: 195
ugaannnnnn nuucngavc 19

<210> SEQ ID NO 196
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Consensus sequence
<220> FEATURE:
<221> NAME/KEY: misc_feature
<222> LOCATION: (5)..(10)
<223> OTHER INFORMATION: n is a, c, g, or u
<220> FEATURE:
<221> NAME/KEY: misc_feature
<222> LOCATION: (15)..(15)
<223> OTHER INFORMATION: n is a, c, g, or u

<400> SEQUENCE: 196
ugaannnnnn uuucngavc 19

<210> SEQ ID NO 197
<211> LENGTH: 19
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Consensus sequence
<220> FEATURE:
<221> NAME/KEY: misc_feature
<222> LOCATION: (5)..(11)
<223> OTHER INFORMATION: n is a, c, g, or u
<220> FEATURE:
<221> NAME/KEY: misc_feature
<222> LOCATION: (15)..(15)
<223> OTHER INFORMATION: n is a, c, g, or u

<400> SEQUENCE: 197
gaaannnnnn nuucngavc 19

<210> SEQ ID NO 198
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Consensus sequence
<220> FEATURE:
<221> NAME/KEY: misc_feature
<222> LOCATION: (5)..(10)
<223> OTHER INFORMATION: n is a, c, g, or u
<220> FEATURE:
<221> NAME/KEY: misc_feature
<222> LOCATION: (15)..(15)
<223> OTHER INFORMATION: n is a, c, g, or u

<400> SEQUENCE: 198
gaaannnnnn uuucngavc 19

<210> SEQ ID NO 199
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Consensus sequence
<220> FEATURE:
<221> NAME/KEY: misc_feature
<222> LOCATION: (5)..(5)
<223> OTHER INFORMATION: n is a, c, g, or u
<220> FEATURE:
<221> NAME/KEY: misc_feature
<222> LOCATION: (10)..(16)
<223> OTHER INFORMATION: n is a, c, g, or u
<220> FEATURE:
<221> NAME/KEY: misc_feature
<222> LOCATION: (20)..(24)
<223> OTHER INFORMATION: n is a, c, g, or u

<400> SEQUENCE: 199
gbucnugaan nnnnnnuucn nnnn 24

<210> SEQ ID NO 200
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Consensus sequence
<220> FEATURE:
<221> NAME/KEY: misc_feature
<222> LOCATION: (5)..(5)
<223> OTHER INFORMATION: n is a, c, g, or u
<220> FEATURE:
<221> NAME/KEY: misc_feature
<222> LOCATION: (10)..(16)
<223> OTHER INFORMATION: n is a, c, g, or u
<220> FEATURE:
<221> NAME/KEY: misc_feature
<222> LOCATION: (20)..(20)
<223> OTHER INFORMATION: n is a, c, g, or u

<400> SEQUENCE: 200
gbucnugaan nnnnnnuucn gavc 24

<210> SEQ ID NO 201
<211> LENGTH: 24

<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Consensus sequence
<220> FEATURE:
<221> NAME/KEY: misc_feature
<222> LOCATION: (5)..(5)
<223> OTHER INFORMATION: n is a, c, g, or u
<220> FEATURE:
<221> NAME/KEY: misc_feature
<222> LOCATION: (10)..(16)
<223> OTHER INFORMATION: n is a, c, g, or u
<220> FEATURE:
<221> NAME/KEY: misc_feature
<222> LOCATION: (20)..(20)
<223> OTHER INFORMATION: n is a, c, g, or u

<400> SEQUENCE: 201
gbucnugaan nnnnnnuucn gavc 24

<210> SEQ ID NO 202
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Consensus sequence
<220> FEATURE:
<221> NAME/KEY: misc_feature
<222> LOCATION: (5)..(5)
<223> OTHER INFORMATION: n is a, c, g, or u
<220> FEATURE:
<221> NAME/KEY: misc_feature
<222> LOCATION: (10)..(15)
<223> OTHER INFORMATION: n is a, c, g, or u
<220> FEATURE:
<221> NAME/KEY: misc_feature
<222> LOCATION: (20)..(20)
<223> OTHER INFORMATION: n is a, c, g, or u

<400> SEQUENCE: 202
gbucnugaan nnnnnuuucn gavc 24

<210> SEQ ID NO 203
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Consensus sequence
<220> FEATURE:
<221> NAME/KEY: misc_feature
<222> LOCATION: (5)..(5)
<223> OTHER INFORMATION: n is a, c, g, or u
<220> FEATURE:
<221> NAME/KEY: misc_feature
<222> LOCATION: (10)..(16)
<223> OTHER INFORMATION: n is a, c, g, or u
<220> FEATURE:
<221> NAME/KEY: misc_feature
<222> LOCATION: (20)..(20)
<223> OTHER INFORMATION: n is a, c, g, or u

<400> SEQUENCE: 203
gbucngaaan nnnnnnuucn gavc 24

```
<210> SEQ ID NO 204
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Consensus sequence
<220> FEATURE:
<221> NAME/KEY: misc_feature
<222> LOCATION: (5)..(5)
<223> OTHER INFORMATION: n is a, c, g, or u
<220> FEATURE:
<221> NAME/KEY: misc_feature
<222> LOCATION: (10)..(16)
<223> OTHER INFORMATION: n is a, c, g, or u
<220> FEATURE:
<221> NAME/KEY: misc_feature
<222> LOCATION: (20)..(20)
<223> OTHER INFORMATION: n is a, c, g, or u

<400> SEQUENCE: 204

gbucngaaan nnnnnnuucn gavc                                              24


<210> SEQ ID NO 205
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Consensus sequence
<220> FEATURE:
<221> NAME/KEY: misc_feature
<222> LOCATION: (5)..(5)
<223> OTHER INFORMATION: n is a, c, g, or u
<220> FEATURE:
<221> NAME/KEY: misc_feature
<222> LOCATION: (10)..(15)
<223> OTHER INFORMATION: n is a, c, g, or u
<220> FEATURE:
<221> NAME/KEY: misc_feature
<222> LOCATION: (20)..(20)
<223> OTHER INFORMATION: n is a, c, g, or u

<400> SEQUENCE: 205

gbucngaaan nnnnnuuucn gavc                                              24


<210> SEQ ID NO 206
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DR2-269 s
<220> FEATURE:
<221> NAME/KEY: misc_feature
<222> LOCATION: (1)..(1)
<223> OTHER INFORMATION: 5'-triphosphate
<220> FEATURE:
<221> NAME/KEY: misc_feature
<222> LOCATION: (1)..(3)
<223> OTHER INFORMATION: phosphorothioate linkages between residues 1
      and 2, and 2 and 3
<220> FEATURE:
<221> NAME/KEY: misc_feature
<222> LOCATION: (5)..(5)
<223> OTHER INFORMATION: 2'-o-methyl
<220> FEATURE:
<221> NAME/KEY: misc_feature
<222> LOCATION: (9)..(9)
```

```
<223> OTHER INFORMATION: 2'-fluoro
<220> FEATURE:
<221> NAME/KEY: misc_feature
<222> LOCATION: (13)..(13)
<223> OTHER INFORMATION: 2'-fluoro
<220> FEATURE:
<221> NAME/KEY: misc_feature
<222> LOCATION: (22)..(24)
<223> OTHER INFORMATION: phosphorothioate linkages between residues 22
      and 23, and 23 and 24

<400> SEQUENCE: 206

guucugcaau cagcuaaacg uuau                                            24


<210> SEQ ID NO 207
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DR2-269 as
<220> FEATURE:
<221> NAME/KEY: misc_feature
<222> LOCATION: (1)..(3)
<223> OTHER INFORMATION: phosphorothioate linkages between residues 1
      and 2, and 2 and 3
<220> FEATURE:
<221> NAME/KEY: misc_feature
<222> LOCATION: (3)..(3)
<223> OTHER INFORMATION: 2'-o-methyl
<220> FEATURE:
<221> NAME/KEY: misc_feature
<222> LOCATION: (8)..(8)
<223> OTHER INFORMATION: 2'-fluoro
<220> FEATURE:
<221> NAME/KEY: misc_feature
<222> LOCATION: (12)..(12)
<223> OTHER INFORMATION: 2'-fluoro

<400> SEQUENCE: 207

auaacguuua gcugauugca gaac                                            24


<210> SEQ ID NO 208
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: DR2-270 s
<220> FEATURE:
<221> NAME/KEY: misc_feature
<222> LOCATION: (1)..(3)
<223> OTHER INFORMATION: phosphorothioate linkages between residues 1
      and 2, and 2 and 3
<220> FEATURE:
<221> NAME/KEY: misc_feature
<222> LOCATION: (5)..(5)
<223> OTHER INFORMATION: 2'-o-methyl
<220> FEATURE:
<221> NAME/KEY: misc_feature
<222> LOCATION: (9)..(9)
<223> OTHER INFORMATION: 2'-fluoro
<220> FEATURE:
<221> NAME/KEY: misc_feature
<222> LOCATION: (13)..(13)
<223> OTHER INFORMATION: 2'-fluoro
<220> FEATURE:
<221> NAME/KEY: misc_feature
<222> LOCATION: (22)..(24)
<223> OTHER INFORMATION: phosphorothioate linkages between residues 22
      and 23, and 23 and 24
```

<400> SEQUENCE: 208
guucugcaau cagcuaaacg uuau 24

<210> SEQ ID NO 209
<211> LENGTH: 24
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: DR2-270 as
<220> FEATURE:
<221> NAME/KEY: misc_feature
<222> LOCATION: (1)..(3)
<223> OTHER INFORMATION: phosphorothioate linkages between residues 1 and 2, and 2 and 3
<220> FEATURE:
<221> NAME/KEY: misc_feature
<222> LOCATION: (3)..(3)
<223> OTHER INFORMATION: 2'-o-methyl
<220> FEATURE:
<221> NAME/KEY: misc_feature
<222> LOCATION: (8)..(8)
<223> OTHER INFORMATION: 2'-fluoro
<220> FEATURE:
<221> NAME/KEY: misc_feature
<222> LOCATION: (12)..(12)
<223> OTHER INFORMATION: 2'-fluoro

<400> SEQUENCE: 209
auaacguuua gcugauugca gaac 24

<210> SEQ ID NO 210
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Consensus sequence
<220> FEATURE:
<221> NAME/KEY: misc_feature
<222> LOCATION: (5)..(5)
<223> OTHER INFORMATION: n is a, c, g, or u
<220> FEATURE:
<221> NAME/KEY: misc_feature
<222> LOCATION: (7)..(7)
<223> OTHER INFORMATION: n is a, c, g, or u
<220> FEATURE:
<221> NAME/KEY: misc_feature
<222> LOCATION: (9)..(16)
<223> OTHER INFORMATION: n is a, c, g, or u
<220> FEATURE:
<221> NAME/KEY: misc_feature
<222> LOCATION: (18)..(18)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 210
gbucndnwnn nnnnnnansn n 21

<210> SEQ ID NO 211
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: Consensus sequence
<220> FEATURE:
<221> NAME/KEY: misc_feature
<222> LOCATION: (5)..(5)
<223> OTHER INFORMATION: n is a, c, g, or u
<220> FEATURE:
<221> NAME/KEY: misc_feature
<222> LOCATION: (10)..(16)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 211
gbucngcaan nnnnnnaacn n 21

<210> SEQ ID NO 212
<211> LENGTH: 21
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Consensus sequence
<220> FEATURE:
<221> NAME/KEY: misc_feature
<222> LOCATION: (5)..(5)
<223> OTHER INFORMATION: n is a, c, g, or u
<220> FEATURE:
<221> NAME/KEY: misc_feature
<222> LOCATION: (11)..(15)
<223> OTHER INFORMATION: n is a, c, g, or u
<220> FEATURE:
<221> NAME/KEY: misc_feature
<222> LOCATION: (20)..(21)
<223> OTHER INFORMATION: n is a, c, g, or u

<400> SEQUENCE: 212
gbucngcaau nnnnnaaacn n 21

<210> SEQ ID NO 213
<211> LENGTH: 24
<212> TYPE: RNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Consensus sequence
<220> FEATURE:
<221> NAME/KEY: misc_feature
<222> LOCATION: (5)..(5)
<223> OTHER INFORMATION: n is a, c, g, or u
<220> FEATURE:
<221> NAME/KEY: misc_feature
<222> LOCATION: (10)..(16)
<223> OTHER INFORMATION: n is a, c, g, or u
<220> FEATURE:
<221> NAME/KEY: misc_feature
<222> LOCATION: (20)..(24)
<223> OTHER INFORMATION: n is a, c, g, or u

<400> SEQUENCE: 213
gbucngcaan nnnnnnaacn nnnn 24

<210> SEQ ID NO 214
<211> LENGTH: 24
<212> TYPE: RNA
<213> ORGANISM: Artificial Sequence -continued

```
<220> FEATURE:
<223> OTHER INFORMATION: Description of Artificial Sequence: Synthetic
      oligonucleotide
<220> FEATURE:
<221> NAME/KEY: misc_feature
<222> LOCATION: (5)..(5)
<223> OTHER INFORMATION: n is a, c, g, or u
<220> FEATURE:
<221> NAME/KEY: misc_feature
<222> LOCATION: (10)..(16)
<223> OTHER INFORMATION: n is a, c, g, or u

<400> SEQUENCE: 214

gbucngcaan nnnnnnaacg uuau                                        24
```